(12) United States Patent
Brown et al.

(10) Patent No.: US 10,383,847 B2
(45) Date of Patent: Aug. 20, 2019

(54) COMPOSITIONS AND METHODS TO IMPROVE THE THERAPEUTIC BENEFIT OF INDIRUBIN AND ANALOGS THEREOF, INCLUDING MEISOINDIGO

(71) Applicants: Dennis M. Brown, Menlo Park, CA (US); Ian Nisbet, Victoria (AU)

(72) Inventors: Dennis M. Brown, Menlo Park, CA (US); Ian Nisbet, Victoria (AU)

( * ) Notice: Subject to any disclaimer, the term of this patent is extended or adjusted under 35 U.S.C. 154(b) by 0 days.

(21) Appl. No.: 14/250,958

(22) Filed: Apr. 11, 2014

(65) Prior Publication Data

US 2016/0243077 A1    Aug. 25, 2016

Related U.S. Application Data

(63) Continuation-in-part of application No. PCT/US2013/033556, filed on Mar. 22, 2013.

(60) Provisional application No. 61/614,724, filed on Mar. 23, 2012.

(51) Int. Cl.
| | |
|---|---|
| *A61K 31/404* | (2006.01) |
| *A61K 45/06* | (2006.01) |
| *C07K 16/40* | (2006.01) |
| *C12N 15/113* | (2010.01) |
| *A61K 31/7056* | (2006.01) |
| *A61K 39/395* | (2006.01) |
| *C07D 209/34* | (2006.01) |

(52) U.S. Cl.
CPC ........ *A61K 31/404* (2013.01); *A61K 31/7056* (2013.01); *A61K 39/3955* (2013.01); *A61K 45/06* (2013.01); *C07D 209/34* (2013.01); *C07K 16/40* (2013.01); *C12N 15/1137* (2013.01); *C12N 2310/141* (2013.01); *C12N 2320/31* (2013.01)

(58) Field of Classification Search
CPC .................................................. A61K 31/404
USPC ........................................................ 514/176
See application file for complete search history.

(56) References Cited

U.S. PATENT DOCUMENTS

| | | | |
|---|---|---|---|
| 5,972,640 A | 10/1999 | Drubin et al. | |
| 6,566,341 B1 | 5/2003 | Wang et al. | |
| 6,573,292 B1 | 6/2003 | Nardella | |
| 6,593,098 B1 | 7/2003 | Yen et al. | |
| 6,664,285 B1 | 12/2003 | Eisenbrand et al. | |
| 6,921,772 B2 | 7/2005 | Nardella | |
| 6,933,315 B2 * | 8/2005 | Wang | C07H 19/23 514/25 |
| 6,987,092 B1 | 1/2006 | Eisenbrand et al. | |
| 6,989,362 B1 | 1/2006 | Bibb et al. | |
| 7,101,576 B2 | 9/2006 | Hovey et al. | |
| 7,196,090 B2 | 3/2007 | Connonlly et al. | |
| 7,314,886 B2 | 1/2008 | Chao et al. | |
| 7,318,931 B2 | 1/2008 | Okumu et al. | |
| 7,446,122 B2 | 11/2008 | Chao et al. | |
| 7,572,784 B2 | 8/2009 | Claiborne et al. | |
| 7,572,923 B2 | 8/2009 | Kim et al. | |
| 7,582,670 B2 | 9/2009 | Wang et al. | |
| 7,619,005 B2 | 11/2009 | Epstein et al. | |
| 7,718,648 B2 | 5/2010 | Claiborne et al. | |
| 7,723,336 B2 | 5/2010 | Vaccaro et al. | |
| 7,781,580 B2 | 8/2010 | Lee et al. | |
| 7,897,568 B2 | 3/2011 | Jia et al. | |
| 7,906,134 B2 | 3/2011 | Hauenstein | |
| 7,943,629 B2 | 5/2011 | Luecking et al. | |
| 8,026,355 B2 | 9/2011 | Hansen et al. | |
| 8,076,375 B2 | 12/2011 | Sefton et al. | |
| 8,084,457 B2 | 12/2011 | Choidas et al. | |
| 8,106,069 B2 | 1/2012 | Salom et al. | |
| 8,207,165 B2 | 6/2012 | Cervi et al. | |

(Continued)

FOREIGN PATENT DOCUMENTS

| | | |
|---|---|---|
| EP | 1332755 A1 | 8/2003 |
| WO | 99/62503 A2 | 12/1999 |

(Continued)

OTHER PUBLICATIONS

Wikipedia, Leukemia (2016).*

(Continued)

*Primary Examiner* — Yong L Chu
(74) *Attorney, Agent, or Firm* — Ditthavong & Steiner, P.C.

(57) ABSTRACT

The present invention describes methods and compositions for improving the therapeutic efficacy of therapeutically active agents previously limited by suboptimal therapeutic performance by either improving efficacy as monotherapy or reducing side effects. Such methods and compositions are particularly applicable to therapeutically active agents selected from the group consisting of: (i) indirubin; (ii) an analog of indirubin; (iii) a derivative of indirubin or of an analog of indirubin; and (iv) a pharmaceutical composition comprising indirubin, an analog of indirubin, or a derivative of indirubin or of an analog of indirubin, especially meisoindigo. In particular, the therapeutically active agents selected from the group consisting of: (i) indirubin; (ii) an analog of indirubin; (iii) a derivative of indirubin or of an analog of indirubin; and (iv) a pharmaceutical composition comprising indirubin, an analog of indirubin, or a derivative of indirubin or of an analog of indirubin, especially meisoindigo, are effective Nek9 inhibitors. The active agent, such as meisoindigo, can act as a Nek9 inhibitor. The active agent can be used together with Nek9 inhibitors or agents that inhibit the expression of Nek9.

2 Claims, 15 Drawing Sheets

Specification includes a Sequence Listing.

(56) References Cited

U.S. PATENT DOCUMENTS

| | | |
|---|---|---|
| 8,242,270 B2 | 8/2012 | Lajeunesse et al. |
| 8,252,795 B2 | 8/2012 | Fink et al. |
| 8,344,162 B2 | 1/2013 | Jung et al. |
| 8,349,822 B2 | 1/2013 | Yu |
| 8,354,386 B2 | 1/2013 | Lee et al. |
| 8,354,408 B2 | 1/2013 | Bourke et al. |
| 8,389,527 B2 | 3/2013 | Fink et al. |
| 8,394,802 B2 | 3/2013 | Mirizzi et al. |
| 8,399,659 B2 | 3/2013 | Claiborne et al. |
| 8,470,798 B2 | 6/2013 | Takagi et al. |
| 8,476,255 B2 | 7/2013 | Rajagopal et al. |
| 8,491,927 B2 | 7/2013 | Epner et al. |
| 8,492,401 B2 | 7/2013 | Oalmann et al. |
| 8,501,737 B2 | 8/2013 | Van Emelen |
| 8,513,237 B2 | 8/2013 | Van Emelen et al. |
| 8,513,241 B2 | 8/2013 | Cervi et al. |
| 8,524,711 B2 | 9/2013 | Angibaud et al. |
| 8,541,576 B2 | 9/2013 | Casuscelli et al. |
| 8,546,588 B2 | 10/2013 | Blackburn et al. |
| 8,551,980 B2 | 10/2013 | Schulze et al. |
| 8,557,825 B2 | 10/2013 | Van Emelen et al. |
| 8,586,297 B2 | 11/2013 | Pagano et al. |
| 8,586,719 B2 | 11/2013 | Chan et al. |
| 8,591,943 B2 | 11/2013 | Deng et al. |
| 8,592,441 B2 | 11/2013 | Verdonck et al. |
| 8,592,444 B2 | 11/2013 | Varasi et al. |
| 8,598,168 B2 | 12/2013 | Moradei et al. |
| 8,603,521 B2 | 12/2013 | Loury et al. |
| 8,609,678 B2 | 12/2013 | Duzer et al. |
| 8,614,223 B2 | 12/2013 | Van Duzer et al. |
| 8,629,118 B2 | 1/2014 | Pellman |
| 8,637,547 B2 | 1/2014 | Davidson et al. |
| 8,648,092 B2 | 2/2014 | Lee et al. |
| 2002/0107404 A1 | 8/2002 | Prien et al. |
| 2002/0132792 A1 | 9/2002 | Prien et al. |
| 2004/0096436 A1 | 5/2004 | Carson et al. |
| 2004/0225002 A1 | 11/2004 | Wang et al. |
| 2005/0080020 A1 | 4/2005 | Eisenbrand et al. |
| 2006/0204980 A1 | 9/2006 | Altieri et al. |
| 2006/0217368 A1 | 9/2006 | Morishita et al. |
| 2007/0207952 A1 | 9/2007 | Silva et al. |
| 2007/0276025 A1 | 11/2007 | Meijer et al. |
| 2008/0194021 A1 | 8/2008 | Mays |
| 2008/0207594 A1 | 8/2008 | Mussmann et al. |
| 2009/0196912 A1 | 8/2009 | Eickhoff et al. |
| 2009/0227533 A1 | 9/2009 | Bader et al. |
| 2010/0004190 A1 | 1/2010 | Chan et al. |
| 2010/0016252 A1 | 1/2010 | Keana et al. |
| 2010/0068303 A1 | 3/2010 | Yu |
| 2010/0069458 A1 | 3/2010 | Atadja et al. |
| 2010/0137356 A1 | 6/2010 | Cheng et al. |
| 2010/0152434 A1 | 6/2010 | Peterson |
| 2010/0160318 A1 | 6/2010 | Tang et al. |
| 2010/0173954 A1 | 7/2010 | Wilhelm et al. |
| 2010/0190749 A1 | 7/2010 | Ren et al. |
| 2010/0239631 A1 | 9/2010 | Bourke et al. |
| 2010/0272717 A1 | 10/2010 | Evans et al. |
| 2010/0291025 A1 | 11/2010 | Rao et al. |
| 2010/0331327 A1 | 12/2010 | Meijer et al. |
| 2011/0034459 A1 | 2/2011 | Adibhatla Kali Satya et al. |
| 2011/0053968 A1 | 3/2011 | Zhang |
| 2011/0136808 A1 | 6/2011 | Meijer et al. |
| 2011/0195066 A1 | 8/2011 | Zhang |
| 2011/0206661 A1 | 8/2011 | Zhang et al. |
| 2011/0229484 A1 | 9/2011 | Baumert et al. |
| 2011/0230481 A2 | 9/2011 | Brzozka et al. |
| 2011/0268658 A1 | 11/2011 | Crawford et al. |
| 2012/0040961 A1 | 2/2012 | Gray et al. |
| 2012/0053208 A1 | 3/2012 | Li et al. |
| 2012/0101042 A1 | 4/2012 | Duffield et al. |
| 2012/0283241 A1 | 11/2012 | Fink et al. |
| 2012/0295948 A1 | 11/2012 | Kim et al. |
| 2013/0023514 A1 | 1/2013 | Markwalder et al. |
| 2013/0040949 A1 | 2/2013 | Gray et al. |
| 2013/0090336 A1 | 4/2013 | Bourke et al. |
| 2013/0184221 A9 | 7/2013 | Panitch et al. |
| 2013/0331359 A1 | 12/2013 | Yun et al. |
| 2014/0005183 A1 | 1/2014 | Galatsis et al. |

FOREIGN PATENT DOCUMENTS

| | | |
|---|---|---|
| WO | 03/070823 A2 | 8/2003 |
| WO | 2005/107760 A1 | 11/2005 |
| WO | 2006/128063 A2 | 11/2006 |
| WO | 2009/017795 A1 | 2/2009 |
| WO | 2009/032694 A1 | 3/2009 |
| WO | 2011/070150 A1 | 6/2011 |
| WO | 2011/126882 A2 | 10/2011 |
| WO | 2011/153553 A2 | 12/2011 |
| WO | 2012/109075 A1 | 8/2012 |
| WO | 2012/158843 A2 | 11/2012 |
| WO | 2013/006758 A1 | 1/2013 |
| WO | 2013/040286 A2 | 3/2013 |
| WO | 2013/074986 A1 | 5/2013 |
| WO | 2013/147711 A1 | 10/2013 |
| WO | 2013/148864 A1 | 10/2013 |

OTHER PUBLICATIONS

Cormack et al. Leukemia (2005), 19, p. 687-706.*
Chen et al., Leukemia Research, (2010), v34, e75-e77.*
Han et al. Drug Development Research, (2010), v71, p. 221-227.*
B. Calabretta et al., "Altered Expression of G1-Specific Genes in Human Malignant Myeloid Cells," Proc. Natl. Acad. Sci. 83: 1495-1498 (1986).
S.B. Vuyyuri et al., "Evaluation of D-Methionine as a Novel Oral Radiation Protector for Prevention of Mucositis," Clin. Cancer Res. 14: 2161-2170 (2008).
C. Aghajanian et al., "A Phase I Trial of the Novel Proteasome Inhibitor PS341 in Advanced Solid Tumor Malignancies," Clin. Cancer Res. 8: 2505-2511 (2002).
A.M. Martelli et al., "Phosphoinositide Signaling in Nuclei of Friend Cells: Phospholipase C [BETA] Down-Regulation is Related to Cell Differentiation," Cancer Res. 54: 2536-2540 (1994).
T. Hideshima et al., "The Proteasome Inhibitor PS-341 Inhibits Growth, Induces Apoptosis, and Overcomes Drug Resistance in Human Multiple Myeloma Cells," Cancer Res. 61: 3071-3076 (2001).
M. Guo et al., "Differential and Antagonistic Effects of v-Jun and c-Jun," Cancer Res. 56: 4229-4235 (1996).
A.L.B. Seynhaeve et al., "Tumor Necrosis Factor [ALPHA] Mediates Homogeneous Distribution of Liposomes in Murine Melanoma that Contributes to a Better Tumor Response," Cancer Res. 67: 9455-9462 (2007).
M. Hingorani et al., "Inhibition of Repair of Radiation-Induced DNA Damage Enhances Gene Expression from Replication-Defective Adenoviral Vectors," Cancer Res. 68: 9771-9778 (2008).
M.T. Bertran et al., "Nek9 is a Plk1-Activated Kinase that Controls Early Centrosome Separation Through Nek6/7 and Eg5," EMBO J. 30: 2634-2647 (2011).
B.J. Druker & N.B. Lydon, "Lessons Learned from the Development of an Abl Tyrosine Kinase Inhibitor for Chronic Myelogenous Leukemia," J. Clin. Invest. 105: 3-7 (2000).
J. Du et al., "Critical Role of CDK2 for Melanoma Growth Linked to Its Melanocyte-Specific Transcriptional Regulation by MITF," Cancer Cell 6: 565-576 (2004).
F. Canova et al., "Intrathecal Chemotherapy in Lymphomatous Meningitis," Crit. Rev. Oncol. 79: 127-134 (2011).
B. C.-M. Tan and S.-C. Lee, "Nek9, a Novel FACT-Associated Protein, Modulates Interphase Progression," J. Biol. Chem. 279: 9321-9330 (2004).
K. Polyak et al., "p27Kip1, a Cyclin-Cdk Inhibitor, Links Transforming Growth Factor-B and Contact Inhibition to Cell Cycle Arrest," Genes Develop. 8: 9-22 (1994).
T. Ikezoe et al., "Oridonin, a Diterpenoid Purified from Rabdosia rubescens, Inhibits the Proliferation of Cells from Lymphoid Malignancies in Association with Blockade of the NF-κB Signal Pathways," Mol. Cancer Ther. 4: 578-586 (2005).

(56) References Cited

OTHER PUBLICATIONS

W.D. Figg et al., "A Randomized Phase II Trial of Thalidomide, an Angiogenesis Inhibitor, in Patients with Androgen-Independent Prostate Cancer," Clin. Cancer Res. 7: 1888-1893 (2001).

M. Faber et al., "Overexpression of the Rabies Virus Glycoprotein Results in Enhancement of Apoptosis and Antiviral Immune Response," J. Virol. 76: 3374-3381 (2002).

Y. Kaneta & A. Ullrich "NEK9 Depletion Induces Catastrophic Mitosis by Impairment of Mitotic Checkpoint Control and Spindle Dynamics," Biochem. Biophys. Res. Commun. 442: 139-146 (2013).

Chan et al., "An Indirubin Derivative, E804, Exhibits Potent Angiosuppressive Activity," Biochemical Pharmacology, vol. 83, dated Dec. 9, 2011, pp. 598-607.

Notification of Transmittal of the International Search Report and the Written Opinion of the International Searching Authority, or the Declaration, International Search Report, and Written Opinion, for corresponding International Application No. PCT/US2013/033556, dated Jun. 4, 2014, 11 pages.

"Phase II Clinical Trial on Meisoindigo in the Treatment of Chronic Myelogenous Leukemia", published in Zhonghua Xueyexue Zazhi 18: 69-72 (1997).

Xiujuan et al., "Pharmacological Studies of Meisoindigo: Absorption and Mechanism of Action", published in Biochem. Environ. Sci. 4: 332-337 (1991).

Xiao et al., "Anti-Angiogenesis Effects of Meisoindigo on Chronic Myelogenous Leukemia in Vitro", published in Leukemia Res. 30: 54-59 (2006).

Xiao et al., "Meisoindigo for the Treatment of Chronic Myelogenous Leukemia", published in Br. J. Haematol. 111: 711-715(2000).

L. Chin-Cheng et al., "Meisoindigo is a Promising Agent with in Vitro and in Vivo Activity Against Human Acute Myeloid Leukemia", published in Leukemia & Lymphoma 51: 897-905 (2010).

* cited by examiner

| KINASE TARGET | MEISOINDIGO |
|---|---|
| AMBIT GENE SYBMBOL | %CTRL @ 50000nM |
| AAK1 | 91 |
| ABL1(E255K)-PHOSPHORYLATED | 100 |
| ABL1(F317I)-NONPHOSPHORYLATED | 100 |
| ABL1(F317I)-PHOSPHORYLATED | 100 |
| ABL1(F317L)-NONPHOSPHORYLATED | 100 |
| ABL1(F317L)-PHOSPHORYLATED | 81 |
| ABL1(H396P)-NONPHOSPHORYLATED | 100 |
| ABL1(H396P)-PHOSPHORYLATED | 94 |
| ABL1(M351T)-PHOSPHORYLATED | 73 |
| ABL1(Q252H)-NONPHOSPHORYLATED | 100 |
| ABL1(Q252H)-PHOSPHORYLATED | 100 |
| ABL1(T315I)-NONPHOSPHORYLATED | 98 |
| ABL1(T315I)-PHOSPHORYLATED | 94 |
| ABL1(Y253F)-PHOSPHORYLATED | 100 |
| ABL1-NONPHOSPHORYLATED | 100 |
| ABL1-PHOSPHORYLATED | 96 |
| ABL2 | 89 |
| ACVR1 | 99 |
| ACVR1B | 100 |
| ACVR2A | 99 |
| ACVR2B | 100 |
| ACVRL1 | 100 |

| KINASE TARGET | MEISOINDIGO |
|---|---|
| AMBIT GENE SYBMBOL | %CTRL @ 50000nM |
| BRSK2 | 100 |
| BTK | 82 |
| CAMK1 | 88 |
| CAMK1D | 100 |
| CAMK1G | 85 |
| CAMK2A | 99 |
| CAMK2B | 86 |
| CAMK2D | 80 |
| CAMK2G | 90 |
| CAMK4 | 88 |
| CAMKK1 | 86 |
| CAMKK2 | 100 |
| CASK | 100 |
| CDC2L1 | 87 |
| CDC2L2 | 100 |
| CDC2L5 | 100 |
| CDK11 | 98 |
| CDK2 | 100 |
| CDK3 | 78 |
| CDK4-CYCLIND1 | 81 |
| CDK4-CYCLIND3 | 100 |
| CDK5 | 100 |
| CDK7 | 100 |

FIG. 6A

| KINASE TARGET AMBIT GENE SYBMBOL | MEISOINDIGO %CTRL @ 50000nM | KINASE TARGET AMBIT GENE SYBMBOL | MEISOINDIGO %CTRL @ 50000nM |
|---|---|---|---|
| ADCK3 | 74 | CDK8 | 100 |
| ADCK4 | 78 | CDK9 | 84 |
| AKT1 | 100 | CDKL1 | 79 |
| AKT2 | 82 | CDKL2 | 100 |
| AKT3 | 92 | CDKL3 | 100 |
| ALK | 97 | CDKL5 | 91 |
| AMPK-ALPHA1 | 100 | CHEK1 | 100 |
| AMPK-ALPHA2 | 100 | CHEK2 | 100 |
| ANKK1 | 81 | CIT | 78 |
| ARK5 | 85 | CLK1 | 100 |
| ASK1 | 100 | CLK2 | 75 |
| ASK2 | 100 | CLK3 | 100 |
| AURKA | 100 | CLK4 | 100 |
| AURKB | 100 | CSF1R | 98 |
| AURKC | 94 | CSK | 100 |
| AXL | 90 | CSNK1A1 | 100 |
| BIKE | 95 | CSNK1A1L | 97 |
| BLK | 100 | CSNK1D | 83 |
| BMPR1A | 100 | CSNK1E | 91 |
| BMPR1B | 89 | CSNK1G1 | 95 |
| BMPR2 | 96 | CSNK1G2 | 93 |
| BMX | 89 | CSNK1G3 | 90 |
| BRAF | 84 | CSNK2A1 | 79 |
| BRAF (V600E) | 72 | CSNK2A2 | 82 |
| BRK | 100 | CTK | 56 |
| BRSK1 | 94 | DAPK1 | 86 |

FIG. 6B

| KINASE TARGET | MEISOINDIGO | | KINASE TARGET | MEISOINDIGO |
|---|---|---|---|---|
| AMBIT GENE SYBMBOL | %CTRL @ 50000nM | | AMBIT GENE SYBMBOL | %CTRL @ 50000nM |
| DAPK2 | 85 | | ERK8 | 96 |
| DAPK3 | 93 | | ERN1 | 83 |
| DCAMKL1 | 100 | | FAK | 83 |
| DCAMKL2 | 93 | | FER | 88 |
| DCAMKL3 | 99 | | FES | 95 |
| DDR1 | 84 | | FGFR1 | 100 |
| DDR2 | 86 | | FGFR2 | 89 |
| DLK | 100 | | FGFR3 | 100 |
| DMPK | 84 | | FGFR3(G697C) | 100 |
| DMPK2 | 92 | | FGFR4 | 100 |
| DRAK1 | 100 | | FGR | 95 |
| DRAK2 | 100 | | FLT1 | 93 |
| DYRK1A | 100 | | FLT3 | 79 |
| DYRK1B | 92 | | FLT3(D835H) | 100 |
| DYRK2 | 84 | | FLT3(D835Y) | 75 |
| EGFR | 100 | | FLT3(ITD) | 76 |
| EGFR(E746-A750DEL) | 83 | | FLT3(K663Q) | 91 |
| EGFR(G719C) | 89 | | FLT3(N841I) | 100 |
| EGFR(G719S) | 94 | | FLT3(R834Q) | 100 |
| EGFR(L747-E749DEL, A750P) | 83 | | FLT4 | 100 |
| EGFR(L747-S863DEL, P753S) | 64 | | FRK | 96 |
| EGFR(L747-T751DEL, SINS) | 87 | | FYN | 100 |
| EGFR(L858R) | 89 | | GAK | 98 |

FIG. 6C

| KINASE TARGET AMBIT GENE SYBMBOL | MEISOINDIGO %CTRL @ 50000nM |
|---|---|
| EGFR(L858R, T790M) | 98 |
| EGFR(L861Q) | 83 |
| EGFR(S752-I759DEL) | 88 |
| EGFR(T790M) | 96 |
| EIF2AK1 | 64 |
| EPHA1 | 100 |
| EPHA2 | 97 |
| EPHA3 | 91 |
| EPHA4 | 100 |
| EPHA5 | 96 |
| EPHA6 | 95 |
| EPHA7 | 100 |
| EPHA8 | 94 |
| EPHB1 | 97 |
| EPHB2 | 100 |
| EPHB3 | 90 |
| EPHB4 | 98 |
| EPHB6 | 89 |
| ERBB2 | 100 |
| ERBB3 | 51 |
| ERBB4 | 88 |
| ERK1 | 100 |
| ERK2 | 100 |
| ERK3 | 100 |
| ERK4 | 86 |
| ERK5 | 97 |

| KINASE TARGET AMBIT GENE SYBMBOL | MEISOINDIGO %CTRL @ 50000nM |
|---|---|
| GCN2(KIN.DOM.2,S808G) | 88 |
| GRK1 | 100 |
| GRK4 | 100 |
| GRK7 | 100 |
| GSK3A | 85 |
| GSK3B | 90 |
| HCK | 100 |
| HIPK1 | 83 |
| HIPK2 | 66 |
| HIPK3 | 80 |
| HIPK4 | 100 |
| HPK1 | 93 |
| HUNK | 98 |
| ICK | 92 |
| IGF1R | 100 |
| IKK-ALPHA | 85 |
| IKK-BETA | 77 |
| IKK-EPSILON | 100 |
| INSR | 91 |
| INSRR | 84 |
| IRAK1 | 64 |
| IRAK3 | 90 |
| IRAK4 | 75 |
| ITK | 78 |
| JAK1(JH1DOMAIN-CATALYTIC) | 94 |
| JAK1(JH2DOMAIN-PSEUDOKINASE) | 100 |

FIG. 6D

| KINASE TARGET | MEISOINDIGO | KINASE TARGET | MEISOINDIGO |
|---|---|---|---|
| AMBIT GENE SYBMBOL | %CTRL @ 50000nM | AMBIT GENE SYBMBOL | %CTRL @ 50000nM |
| JAK2(JH1DOMAIN-CATALYTIC) | 73 | MERTK | 100 |
| JAK3(JH1DOMAIN-CATALYTIC) | 74 | MET | 100 |
| JNK1 | 77 | MET(M1250T) | 80 |
| JNK2 | 76 | MET(Y1235D) | 99 |
| JNK3 | 77 | MINK | 75 |
| KIT | 94 | MKK7 | 75 |
| KIT(A829P) | 63 | MKNK1 | 98 |
| KIT(D816H) | 75 | MKNK2 | 68 |
| KIT(D816V) | 100 | MLCK | 100 |
| KIT(L576P) | 98 | MLK1 | 100 |
| KIT(V559D) | 91 | MLK2 | 100 |
| KIT(V559D, T670I) | 93 | MLK3 | 71 |
| KIT(V559D, V654A) | 100 | MRCKA | 92 |
| LATS1 | 100 | MRCKB | 83 |
| LATS2 | 90 | MST1 | 95 |
| LCK | 96 | MST1R | 92 |
| LIMK1 | 84 | MST2 | 99 |
| LIMK2 | 100 | MST3 | 88 |
| LKB1 | 100 | MST4 | 100 |
| LOK | 100 | MTOR | 100 |
| LRRK2 | 96 | MUSK | 86 |
| LRRK2(G2019S) | 74 | MYLK | 82 |
| LTK | 92 | MYLK2 | 94 |

FIG. 6E

| KINASE TARGET | MEISOINDIGO | KINASE TARGET | MEISOINDIGO |
|---|---|---|---|
| AMBIT GENE SYBMBOL | %CTRL @ 50000nM | AMBIT GENE SYBMBOL | %CTRL @ 50000nM |
| LYN | 100 | MYLK4 | 87 |
| LZK | 63 | MYO3A | 100 |
| MAK | 71 | MYO3B | 100 |
| MAP3K1 | 83 | NDR1 | 87 |
| MAP3K15 | 69 | NDR2 | 100 |
| MAP3K2 | 99 | NEK1 | 92 |
| MAP3K3 | 94 | NEK11 | 100 |
| MAP3K4 | 100 | NEK2 | 92 |
| MAP4K2 | 92 | NEK3 | 100 |
| MAP4K3 | 90 | NEK4 | 86 |
| MAP4K4 | 100 | NEK5 | 96 |
| MAP4K5 | 100 | NEK6 | 81 |
| MAPKAPK2 | 100 | NEK7 | 59 |
| MAPKAPK5 | 100 | NEK9 | 33 |
| MARK1 | 92 | NIM1 | 86 |
| MARK2 | 75 | NLK | 100 |
| MARK3 | 98 | OSR1 | 83 |
| MARK4 | 77 | P38-ALPHA | 100 |
| MAST1 | 85 | P38-BETA | 100 |
| MEK1 | 81 | P38-DELTA | 100 |
| MEK2 | 89 | P38-GAMMA | 92 |
| MEK3 | 72 | PAK1 | 43 |
| MEK4 | 100 | PAK2 | 47 |
| MEK5 | 97 | PAK3 | 93 |
| MEK6 | 100 | PAK4 | 84 |
| MELK | 83 | PAK6 | 100 |

FIG. 6F

| KINASE TARGET AMBIT GENE SYBMBOL | MEISOINDIGO %CTRL @ 50000nM |
|---|---|
| PAK7 | 98 |
| PCTK1 | 92 |
| PCTK2 | 96 |
| PCTK3 | 84 |
| PDGFRA | 85 |
| PDGFRB | 100 |
| PDPK1 | 100 |
| PFCDPK1(P.FALCIPARUM) | 87 |
| PFPK5(P.FALCIPARUM) | 72 |
| PFTAIRE2 | 88 |
| PFTK1 | 94 |
| PHKG1 | 97 |
| PHKG2 | 100 |
| PIK3C2B | 100 |
| PIK3C2G | 99 |
| PIK3CA | 92 |
| PIK3CA(C420R) | 85 |
| PIK3CA(E542K) | 91 |
| PIK3CA(E545A) | 71 |
| PIK3CA(E545K) | 81 |
| PIK3CA(H1047L) | 99 |
| PIK3CA(H1047Y) | 74 |
| PIK3CA(I800L) | 69 |

| KINASE TARGET AMBIT GENE SYBMBOL | MEISOINDIGO %CTRL @ 50000nM |
|---|---|
| PRKCQ | 99 |
| PRKD1 | 97 |
| PRKD2 | 87 |
| PRKD3 | 94 |
| PRKG1 | 95 |
| PRKG2 | 94 |
| PRKR | 80 |
| PRKX | 100 |
| PRP4 | 89 |
| PYK2 | 100 |
| QSK | 100 |
| RAF1 | 100 |
| RET | 89 |
| RET(M918T) | 100 |
| RET(V804L) | 100 |
| RET(V804M) | 100 |
| RIOK1 | 87 |
| RIOK2 | 84 |
| RIOK3 | 89 |
| RIPK1 | 95 |
| RIPK2 | 100 |
| RIPK4 | 98 |
| RIPK5 | 92 |

FIG. 6G

| KINASE TARGET | MEISOINDIGO | KINASE TARGET | MEISOINDIGO |
|---|---|---|---|
| AMBIT GENE SYBMBOL | %CTRL @ 50000nM | AMBIT GENE SYBMBOL | %CTRL @ 50000nM |
| PIK3CA(M1043I) | 76 | ROCK1 | 87 |
| PIK3CA(Q546K) | 92 | ROCK2 | 77 |
| PIK3CD | 95 | ROS1 | 81 |
| PIK3CG | 100 | RPS6KA4(KIN.DOM.1-N-TERMINAL) | 82 |
| PIK4CB | 100 | RPS6KA4(KIN.DOM.2-C-TERMINAL) | 89 |
| PIM1 | 83 | RPS6KA5(KIN.DOM.1-N-TERMINAL) | 100 |
| PIM2 | 100 | RPS6KA5(KIN.DOM.2-C-TERMINAL) | 100 |
| PIM3 | 79 | RSK1(KIN.DOM.1-N-TERMINAL) | 96 |
| PIP5K1A | 100 | RSK1(KIN.DOM.2-C-TERMINAL) | 84 |
| PIP5K1C | 81 | RSK2(KIN.DOM.1-N-TERMINAL) | 94 |
| PIP5K2B | 100 | RSK3(KIN.DOM.1-N-TERMINAL) | 100 |
| PIP5K2C | 55 | RSK3(KIN.DOM.2-C-TERMINAL) | 92 |
| PKAC-ALPHA | 93 | RSK4(KIN.DOM.1-N-TERMINAL) | 99 |
| PKAC-BETA | 91 | RSK4(KIN.DOM.2-C-TERMINAL) | 71 |
| PKMYT1 | 100 | S6K1 | 85 |
| PKN1 | 100 | SBK1 | 100 |
| PKN2 | 99 | SGK110 | 100 |
| PKNB(M.TUBERCULOSIS) | 100 | SGK3 | 68 |
| PLK1 | 100 | SIK | 93 |
| PLK2 | 94 | SIK2 | 95 |
| PLK3 | 100 | SLK | 100 |
| PLK4 | 79 | SNARK | 89 |
| PRKCD | 100 | SNRK | 81 |
| PRKCE | 75 | SRC | 100 |
| PRKCH | 100 | SRMS | 88 |
| PRKCI | 100 | SRPK1 | 100 |

FIG. 6H

| KINASE TARGET | MEISOINDIGO |
| --- | --- |
| AMBIT GENE SYBMBOL | %CTRL @ 50000nM |
| SRPK2 | 100 |
| SRPK3 | 100 |
| STK16 | 89 |
| STK33 | 100 |
| STK35 | 89 |
| STK36 | 90 |
| STK39 | 78 |
| SYK | 85 |
| TAK1 | 76 |
| TAOK1 | 87 |
| TAOK2 | 84 |
| TAOK3 | 85 |
| TBK1 | 80 |
| TEC | 100 |
| TESK1 | 100 |
| TGFBR1 | 100 |
| TGFBR2 | 94 |
| TIE1 | 83 |
| TIE2 | 100 |
| TLK1 | 81 |
| TLK2 | 86 |
| TNIK | 100 |
| TNK1 | 98 |

FIG. 6I

| KINASE TARGET | MEISOINDIGO |
| --- | --- |
| AMBIT GENE SYBMBOL | %CTRL @ 50000nM |
| TNK2 | 93 |
| TNNI3K | 95 |
| TRKA | 65 |
| TRKB | 68 |
| TRKC | 66 |
| TRPM6 | 78 |
| TSSK1B | 45 |
| TTK | 86 |
| TXK | 100 |
| TYK2(JH1DOMAIN-CATALYTIC) | 77 |
| TYK2(JH1DOMAIN-PSEUDOKINASE) | 88 |
| TYRO3 | 77 |
| ULK1 | 68 |
| ULK2 | 98 |
| ULK3 | 85 |
| VEGFR2 | 100 |
| VRK2 | 79 |
| WEE1 | 91 |
| WEE2 | 95 |
| YANK1 | 89 |
| YANK2 | 100 |
| YANK3 | 76 |
| YES | 86 |
| YSK1 | 40 |
| YSK4 | 91 |
| ZAK | 90 |

FIG. 6J

COMPOSITIONS AND METHODS TO IMPROVE THE THERAPEUTIC BENEFIT OF INDIRUBIN AND ANALOGS THEREOF, INCLUDING MEISOINDIGO

CROSS-REFERENCES

This application is a continuation-in-part of PCT Patent Application Serial No. PCT/US2013/033556 by D. M. Brown, filed Mar. 22, 2013 and entitled "Compositions and Methods to Improve the Therapeutic Benefit of Indirubin and Analogs Thereof, Including Meisoindigo," which PCT application in turn claimed the benefit of U.S. Provisional Application Ser. No. 61/614,724 by D. M. Brown, filed Mar. 23, 2012 and entitled "Compositions and Methods to Improve the Therapeutic Benefit of Indirubin and Analogs Thereof, Including Meisoindigo." *The contents of both PCT Patent Application Serial No. PCT/US*2013/033556 and U.S. Provisional Application Ser. No. 61/614,724 are incorporated herein in their entirety by this reference.

SEQUENCE LISTING

The instant application contains a Sequence Listing which has been filed electronically in ASCII format and is hereby incorporated by reference in its entirety. Said ASCII copy, created on May 13, 2019, is named P6669US01_SL.txt and is 10,275 bytes in size.

FIELD OF THE INVENTION

The present invention relates to the general field of hyperproliferative diseases including oncology with a focus on novel methods and compositions for the improved utility of chemical agents, compounds, and dosage forms previously limited by suboptimal human therapeutic performance including indirubin and analogs thereof, such as meisoindigo, particularly use to inhibit the kinase Nek9.

BACKGROUND OF THE INVENTION

The search for and identification of cures for many life-threatening diseases that plague humans still remains an empirical and sometimes serendipitous process. While many advances have been made from basic scientific research to improvements in practical patient management, there still remains tremendous frustration in the rational and successful discovery of useful therapies particularly for life-threatening diseases such as cancer, inflammatory conditions, infection, and other conditions.

Since the "War on Cancer" began in the early 1970's by the United States National Cancer Institute (NCI) of the National Institutes of Health (NIH), a wide variety of strategies and programs have been created and implemented to prevent, diagnose, treat and cure cancer. One of the oldest and arguably most successful programs has been the synthesis and screening of small chemical entities (<1500 MW) for biological activity against cancer. This program was organized to improve and streamline the progression of events from chemical synthesis and biological screening to preclinical studies for the logical progression into human clinical trials with the hope of finding cures for the many types of life-threatening malignant tumors. The synthesis and screening of hundreds of thousands of chemical compounds from academic and industrial sources, in addition to the screening of natural products and extracts from prokaryotes, invertebrate animals, plant collections, and other sources from all over the world has been and continues to be a major approach for the identification of novel lead structures as potential new and useful medicines. This is in addition to other programs including biotherapeutics designed to stimulate the human immune system with vaccines, therapeutic antibodies, cytokines, lymphokines, inhibitors of tumor blood vessel development (angiogenesis) or gene and antisense therapies to alter the genetic make-up of cancer cells, and other biological response modifiers.

The work supported by the NCI, other governmental agencies both domestic and foreign in academic or industrial research and development laboratories has resulted in an extraordinary body of biological, chemical and clinical information. In addition, large chemical libraries have been created, as well as highly characterized in vitro and in vivo biological screening systems that have been successfully used. However, from the tens of billions of dollars spent over the past thirty years supporting these programs both preclinically and clinically, only a small number of compounds have been identified or discovered that have resulted in the successful development of useful therapeutic products. Nevertheless, the biological systems both in vitro and in vivo and the "decision trees" used to warrant further animal studies leading to clinical studies have been validated. These programs, biological models, clinical trial protocols, and other information developed by this work remain critical for the discovery and development of any new therapeutic agent.

Unfortunately, many of the compounds that have successfully met the preclinical testing and federal regulatory requirements for clinical evaluation were either unsuccessful or disappointing in human clinical trials. Many compounds were found to have untoward or idiosyncratic side-effects that were discovered during human clinical Phase I dose-escalation studies used to determine the maximum tolerated dose (MTD) and side-effect profile. In some cases, these toxicities or the magnitude of their toxicity were not identified or predicted in preclinical toxicology studies. In other cases, chemical agents where in vitro and in vivo studies suggested a potentially unique activity against a particular tumor type, molecular target or biological pathway were not successful in human Phase II clinical trials where specific examination of particular cancer indications/types were evaluated in government sanctioned (e.g., U.S. FDA), IRB approved clinical trials. In addition, there are those cases where potential new agents were evaluated in randomized Phase III clinical trials where a significant clinical benefit could not be demonstrated; such cases have also been the cause of great frustration and disappointment. Finally, a number of compounds have reached commercialization but their ultimate clinical utility has been limited by poor efficacy as monotherapy (<25% response rates) and untoward dose-limiting side-effects (Grade III and IV) (e.g., myelosuppression, neurotoxicity, cardiotoxicity, gastrointestinal toxicities, or other significant side effects).

In many cases, after the great time and expense of developing and moving an investigational compound into human clinical trials and where clinical failure has occurred, the tendency has been to return to the laboratory to create a better analog, look for agents with different structures but potentially related mechanisms of action, or try other modifications of the drug. In some cases, efforts have been made to try additional Phase I or II clinical trials in an attempt to make some improvement with the side-effect profile or therapeutic effect in selected patients or cancer indications. In many of those cases, the results did not realize a significant enough improvement to warrant further clinical development toward product registration. Even for commercialized products, their ultimate use is still limited by suboptimal performance.

With so few therapeutics approved for cancer patients and the realization that cancer is a collection of diseases with a multitude of etiologies and that a patient's response and survival from therapeutic intervention is complex with many factors playing a role in the success or failure of treatment including disease indication, stage of invasion and metastatic spread, patient gender, age, health conditions, previous therapies or other illnesses, genetic markers that can either promote or retard therapeutic efficacy, and other factors, the opportunity for cures in the near term remains elusive. Moreover, the incidence of cancer continues to rise with an approximate 4% increase predicted for 2003 in the United States by the American Cancer Society such that over 1.3 million new cancer cases are estimated. In addition, with advances in diagnosis such as mammography for breast cancer and PSA tests for prostate cancer, more patients are being diagnosed at a younger age. For difficult to treat cancers, a patient's treatment options are often exhausted quickly resulting in a desperate need for additional treatment regimens. Even for the most limited of patient populations, any additional treatment opportunities would be of considerable value. This invention focuses on inventive compositions and methods for improving the therapeutic benefit of suboptimally administered chemical compounds including indirubin and analogs thereof.

Relevant literature includes Foye, W. O., "Cancer Chemotherapeutic Agents," American Chemical Society, 1995, and Dorr, R. T., and Von Hoff, D. D., "Cancer Chemotherapy Handbook," Appleton and Lange, 1994.

Therefore, there is a need for compositions and methods that improve the therapeutic benefit of suboptimally administered chemical compounds and therapeutic compositions, particularly with respect to the inhibition of the kinase NEK9.

SUMMARY OF THE INVENTION

This invention meets the needs described above for compositions and methods that improve the therapeutic benefit of suboptimally administered chemical compounds and therapeutic compositions. Specifically, this invention relates to novel compositions and methods to improve the utility of chemical agents with suboptimal performance in patients suffering with cancer. The invention describes novel improvements, pharmaceutical ingredients, dosage forms, excipients, solvents, diluents, drug delivery systems, preservatives, more accurate drug administrations, improved dose determination and schedules, toxicity monitoring and amelioration, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches. The invention also relates to the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some case, the use of these suboptimal therapeutics in conjunction with radiation or other conventional chemotherapeutic agents or biotherapeutic agents such as antibodies, vaccines, cytokines, lymphokines, gene and antisense therapies, or other chemotherapeutic or biotherapeutic agents, would provide novel approaches and significant improvement. In particular, the present invention provides novel approaches for the inhibition of the kinase Nek9.

In the inventive compositions and methods, the term suboptimal therapy includes agents where Phase I toxicity precluded further human clinical evaluation. It also includes those agents from Phase II trials where limited (<25% response rates) or no significant tumor responses were identified. Also, suboptimal therapy includes those agents, the subject of Phase III clinical trials the outcome of which was either medically or statistically not significant to warrant regulatory submission or approval by government agencies for commercialization or commercialized agents whose clinical performance (i.e. response rates) as a monotherapy are less than 25%, or whose side-effects are severe enough to limit wide utility. Agents with suboptimal clinical activity include but are not limited to the following: indirubin and analogs thereof, including meisoindigo.

One aspect of the invention is a method to improve the efficacy and/or reduce the side effects of suboptimally administered drug therapy comprising the steps of:

(i) identifying at least one factor or parameter associated with the efficacy and/or occurrence of side effects of the drug therapy; and (ii) modifying the factor or parameter to improve the efficacy and/or reduce the side effects of the drug therapy.

In this method, the factor or parameter can be selected from the group consisting of:

(i) dose modification;
(ii) route of administration;
(iii) schedule of administration;
(iv) indications for use;
(v) selection of disease stage;
(vi) other indications;
(vii) patient selection;
(viii) patient/disease phenotype;
(ix) patient/disease genotype;
(x) pre/post-treatment preparation
(xi) toxicity management;
(xii) pharmacokinetic/pharmacodynamic monitoring;
(xiii) drug combinations;
(xiv) chemosensitization;
(xv) chemopotentiation;
(xvi) post-treatment patient management;
(xvii) alternative medicine/therapeutic support;
(xviii) bulk drug product improvements;
(xix) diluent systems;
(xx) solvent systems;
(xxi) excipients;
(xxii) dosage forms;
(xxiii) dosage kits and packaging;
(xxiv) drug delivery systems;
(xxv) drug conjugate forms;
(xxvi) compound analogs;
(xxvii) prodrugs;
(xxvii) multiple drug systems;
(xxviii) biotherapeutic enhancement;
(xxix) biotherapeutic resistance modulation;
(xxx) radiation therapy enhancement;
(xxxi) novel mechanisms of action; and
(xxxii) selective target cell population therapeutics.

The drug therapy can be administered to treat a hyperproliferative disease, such as cancer.

Typically, the suboptimally administered drug therapy comprises administration of a therapeutically active agent selected from the group consisting of: (i) indirubin; (ii) an analog of indirubin; (iii) a derivative of indirubin or of an analog of indirubin; and (iv) a pharmaceutical composition comprising indirubin, an analog of indirubin, or a derivative of indirubin or of an analog of indirubin, including meisoindigo.

Another aspect of the present invention is a composition to improve the efficacy and/or reduce the side effects of suboptimally administered drug therapy comprising an alternative selected from the group consisting of:

(1) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;

(2) a composition comprising:
   (a) a therapeutically effective quantity of a therapeutic agent, a modified therapeutic agent or a derivative, analog, or prodrug of a therapeutic agent or modified therapeutic agent; and
   (b) at least one additional therapeutic agent, therapeutic agent subject to chemosensitization, therapeutic agent subject to chemopotentiation, diluent, excipient, solvent system, or drug delivery system, wherein the composition possesses increased therapeutic efficacy or reduced side effects as compared with an unmodified therapeutic agent;

(3) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;

(4) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and (5) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent;

wherein the therapeutic agent, the modified therapeutic agent or the derivative, analog, or prodrug of a therapeutic agent or modified therapeutic agent is selected from the group consisting of: (i) indirubin; (ii) an analog of indirubin; and (iii) a derivative of indirubin or of an analog of indirubin.

Typically, the composition possesses increased efficacy or reduced side effects for cancer therapy. Typically, the unmodified therapeutic agent is indirubin or an analog thereof, particularly meisoindigo.

In one alternative, the invention provides methods and compositions for the treatment of malignancies by the inhibition of the kinase Nek9.

BRIEF DESCRIPTION OF THE DRAWINGS

The following invention will become better understood with reference to the specification, appended claims, and accompanying drawings, where:

FIG. 6, shown as FIG. 6A, FIG. 6B, FIG. 6C, FIG. 6D, FIG. 6E, FIG. 6F, FIG. 6G, FIG. 6H, FIG. 6I, and FIG. 6A, is a table showing the results of a screen for kinase inhibition by meisoindigo, wherein meisoindigo shows significant inhibition of the kinase Nek9. FIG. 6A shows results for AAK1 to CDK7. FIG. 6B shows results for ADCK3 to DADK1. FIG. 6C shows results for DAPK2 to GAK. FIG. 6D shows results for EGFR (L858R, T790M) to JAK1 (JH2DOMAIN-PSEUDOKINASE). FIG. 6E shows results for JAK2 (JH1 DOMAIN-CATALYTIC) to MYLK2. FIG. 6F shows results for LYN to PAK6. FIG. 6G shows results for PAK7 to RIPK5. FIG. 6H shows results from PIK3A (M1043I) to SRPK1. FIG. 6I shows results for SRPK2 to TNK1. FIG. 6J shows results for TNK2 to ZAK.

DETAILED DESCRIPTION OF THE INVENTION

Figure 1:
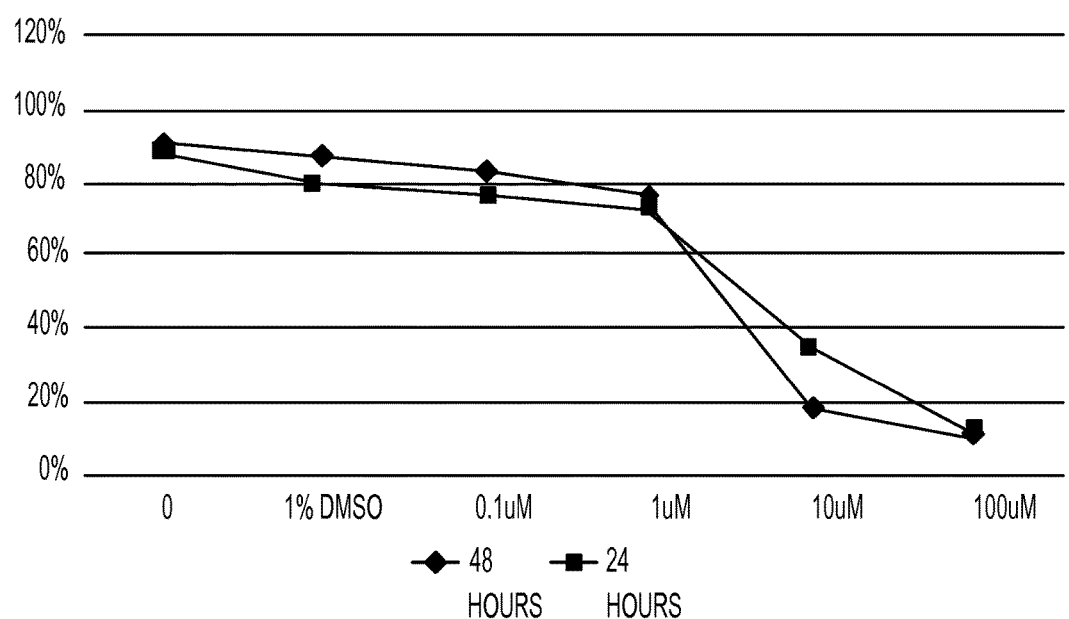
FIG. 1 shows the viability of the AML cell line MV 4-11 (FLT-3 ITD) after meisoindigo treatments. Viability at 48 hours is shown by (♦); viability at 24 hours is shown by (■). Results are shown for a control, 1% DMSO without meisoindigo, 0.1 µM meisoindigo, 1 µM meisoindigo, 10 µM meisoindigo, and 100 µM meisoindigo.

This invention relates to novel compositions and methods to improve the utility of chemical agents including indirubin and analogs and derivatives thereof with suboptimal performance for patients with cancer, as well as additional therapeutic agents or agents capable of therapeutic application. The invention describes the novel development of improved pharmaceutical ingredients, dosage forms, excipients, solvents, diluents, drug delivery systems, preservatives, more accurate drug administrations, improved dose determination and schedules, toxicity monitoring and ameliorization, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches, the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some cases, the inventive examples include the use of these sub-optimal therapeutics in conjunction with radiation or other conventional chemotherapeutic agents or biotherapeutic agents such as antibodies, vaccines, cytokines, lymphokines, gene and antisense therapies, or other chemotherapeutic or biotherapeutic agents.

By definition, the term "suboptimal therapy" includes agents where Phase I toxicity precluded further human clinical evaluation. It also includes those agents from Phase II trials where limited or no significant tumor responses were identified. In addition, it also includes those agents, the subject of Phase III clinical trials, whose outcome was either medically or statistically not significant to warrant submission or approval by regulatory agencies for commercialization or commercialized agents whose response rates as a monotherapy are less than 25% or whose side-effects are severe enough to limit wider utility. Agents with suboptimal activity include but are not limited to the following: indirubin and analogs and derivatives thereof. More specifically, the inventive methods and compositions also focus on improvements for indirubin and analogs and derivatives thereof, including meisoindigo.

(I) Suboptimal Therapeutics

In general, examples of compounds with suboptimal therapeutic activity include, but are not limited to, compounds of the following classes: DNA/nucleic acid binding/reactive agents, topoisomerase inhibitors, anti-tubulin agents, signal transduction inhibitors, protein synthesis inhibitors, inhibitors of DNA transcribing enzymes, DNA/RNA intercalating agents, DNA minor groove binders, drugs that block steroid hormone action, photochemically active agents, immune modifying agents, hypoxia selective cytotoxins, chemical radiation sensitizers and protectors, antisense nucleic acids, oligonucleotides and polynucleotides therapeutic agents, immune modifying agents, antitumor antibiotics, biotherapeutics, biologic agents such as cancer vaccines, antibody therapies, cytokines, lyphokines, gene therapies, nucleic acid therapies, vascular disrupting agents, anti-angiogenic agents, and cellular therapies. In some cases, a compound may fall within more than one of these classes; such compounds are also within the scope of the invention.

In some cases, compounds or compositions may be in current clinical use for one or more indications, but yet be considered suboptimal for another indication, such as a different type of malignancy, either in terms of the cell type involved in the malignancy or in terms of the stage of the malignancy. Such compounds or compositions are within the scope of the invention.

Specific examples include indirubin analogs and derivatives thereof as described below, including, but not limited to, meisoindigo.

The structure of indirubin is shown in Formula (I), below.

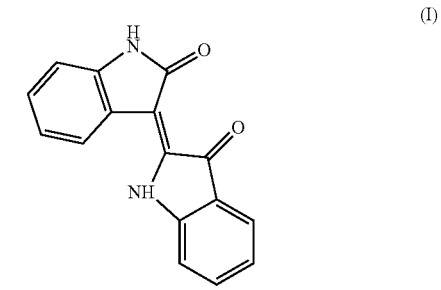 [SMILES: O=C1Nc2ccccc2/C1=C1\Nc2ccccc2C1=O]

Also within the scope of the invention are derivatives of indirubin that, for example, have the hydrogen of the benzene rings replaced with halo or lower alkyl or have the hydrogen attached to the nitrogen of the five-membered rings replaced with lower alkyl.

Analogs of indirubin include, but are not limited to, the compounds described below and derivatives thereof.

One particular analog of indirubin is a compound named meisoindigo, whose systemic name is 3-(1,2-dihydro-2-oxo-3H-indol-3-ylidene)-1,3-dihydro-1-methyl-2H-indol-2-one. Meisoindigo has the structure shown as Formula (II):

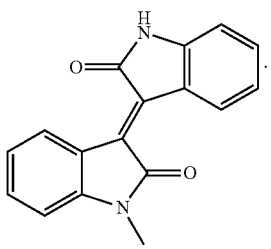

Meisoindigo is a derivative of the Chinese herb, Qing dai, Indigo naturalis. It is a second-generation synthetic derivative of indirubin and is a water-soluble small molecule. Meisoindigo is active against both cell lines and primary cancer cells. Its $IC_{50}$ is in the high-µM concentration range. It has shown activity against AML (acute myelogenous leukemia) (NB4, HL-60, U937), CML (chronic myelogenous leukemia (K562), colorectal cancer (HT29), HUVEC, ECV304, as well as against primary AML. Meisoindigo is metabolized by cytochrome P450 1A2 and 2C19 by oxidation. Meisoindigo is also metabolized by uridine glucuronyltransferases (UGT) via direct conjugation (i.e., without initial cytochrome P450 oxidation) to produce more polar metabolites. Meisoindigo also inhibits cytochrome P450 1A2 and 2C8 at low micromolar concentrations.

FIG. 1 shows the viability of the AML cell line MV 4-11 (FLT-3 ITD) after meisoindigo treatments. Viability at 48 hours is shown by (♦); viability at 24 hours is shown by (■). Results are shown for a control, 1% DMSO without meisoindigo, 0.1 µM meisoindigo, 1 µM meisoindigo, 10 µM meisoindigo, and 100 µM meisoindigo.

Figure 2:
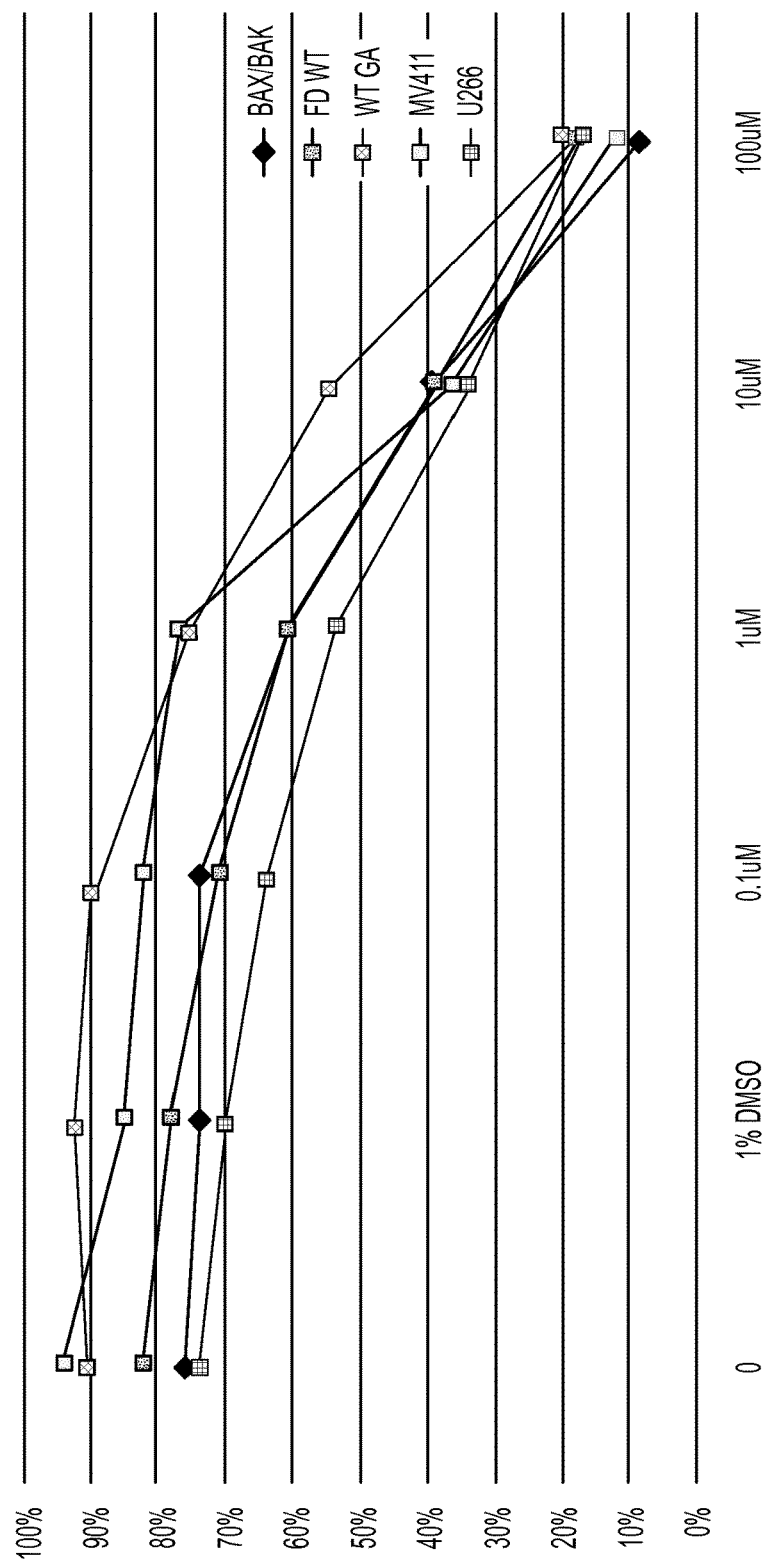
FIG. 2 shows the viability of a number of myeloid cell lines in terms of the percentage of viable cells after 24 hours of treatment with meisoindigo. Results are shown for a control, 1% DMSO without meisoindigo, 0.1 µM meisoindigo, 1 µM meisoindigo, 10 µM meisoindigo, and 100 µM meisoindigo.

FIG. 2 shows the viability of a number of myeloid cell lines in terms of the percentage of viable cells after 24 hours of treatment with meisoindigo. Results are shown for a control, 1% DMSO without meisoindigo, 0.1 µM meisoindigo, 1 µM meisoindigo, 10 µM meisoindigo, and 100 µM meisoindigo.

Figure 3:
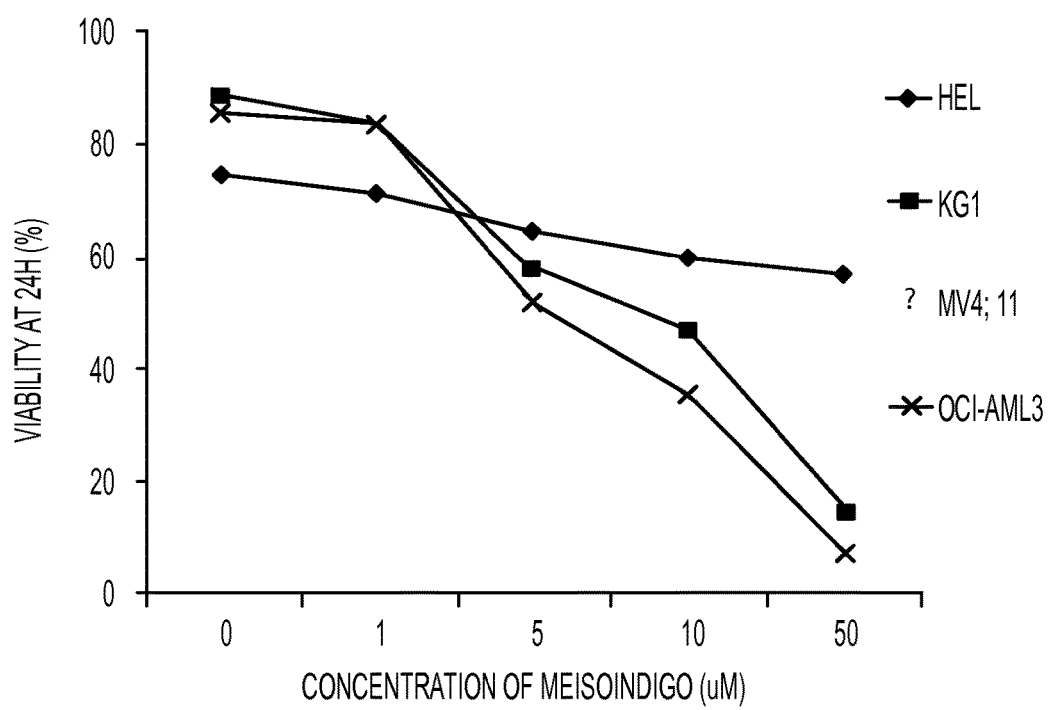
FIG. 3 shows the viability of a number of additional myeloid cell lines in terms of the percentage of viable cells after 24 hours of treatment with meisoindigo. Results are shown for a control, 1% DMSO without meisoindigo, 0.1 µM meisoindigo, 1 µM meisoindigo, 10 µM meisoindigo, and 100 µM meisoindigo.

FIG. 3 shows the viability of a number of additional myeloid cell lines in terms of the percentage of viable cells after 24 hours of treatment with meisoindigo. Results are shown for a control, 1% DMSO without meisoindigo, 0.1 µM meisoindigo, 1 µM meisoindigo, 10 µM meisoindigo, and 100 µM meisoindigo.

Meisoindigo has shown to be effective in murine cancer models. Meisoindigo has also been shown to be effective in the AML NOD/SCID model, showing dose-dependent spleen size reduction, in HT-29 colorectal xenografts, Lewis lung sarcoma, and Walker 256 carcino-sarcoma.

Meisoindigo is active via several, possibly novel mechanisms of action. It has cell cycle specific effects, including arrest in G(O)/G1 for AML cell lines and G2/M arrest for HT-29 colorectal cell lines. It also stimulates apoptosis through a number of mechanisms, including the upregulation of p21 and p27 and the downregulation of Bcl-2 in primary AML cells, as well as upregulation of Bak and Bax in AML cells (DKO insensitive to chemotherapy), and a novel caspase-dependent pathway in K562 cells. Meisoindigo also has effects on mitochondria, but with no change in Bcl-2, Bax, and Bid protein expression. Meisoindigo also stimulates the cleavage of pro-caspase 3, 8, 9 and PARP in HL-60 myeloid cells.

Meisoindigo also is directed to multiple cellular targets, which are possibly synergistic and complementary. For example, it promotes differentiation of human myeloblastic leukemic cells, accompanied by downregulation of c-myb gene expression. It also promotes inhibition of DNA and RNA synthesis in W256 cells, microtubule assembly, glycogen synthase kinase-3β (GSK-3β) (at 5-50 nM), CDK1/cyclin B, and CDK5/p25 (tau microtubule protein phosphorylation). Additionally, meisoindigo decreases β-catenin and c-myc (HL-60 cells, but not in K562), affects the Wnt pathway through inhibiting GSK-3β and downregulating β-catenin and c-myc protein expression. Meisoindigo also promotes upregulation of CD11b, promoting myeloid differentiation, and upregulation of Ahi-1 in Jurkat cells (inducing phosphorylation of c-Myb. Furthermore, meisoindigo exhibits antiangiogenic effects, including decreased VEGF protection, VCAM-1, tubule formulation in HUVEC, and ECV304 apoptosis.

Figure 4:
FIG. 4 shows the targeting of kinases by meisoindigo.

As shown in FIGS. 4 and 6, meisoindigo targets a number of kinases. The strongest binding is with NEK9, but significant binding is also shown with STK25, PAK1, TSSK1B, and ERBB3. This suggests that meisoindigo can affect a substantial number of pathways regulated by kinase activity or by proteins phosphorylated by kinase activity.

Meisoindigo is rapidly absorbed and widely distributed in the tissues. It is metabolized by hepatic cytochrome P450 (CYP)-mediated N-demethylation and mono ring hydroxylation. There are no major interspecies differences between the metabolism of meisoindigo in rats, pigs, and humans, and no sex differences in metabolism. The human hepatic internal CL is ~83 ($Cl_{int}$, mL/mg/kg). Excretion of meisoindigo is through renal and biliary routes, with renal excretion strongly predominating.

Rodent and non-rodent toxicology studies indicate a safe profile for meisoindigo. The single dose $LD_{50}$ in rats is 3.9 g/kg, an extremely high dose. In rats, up to 400 mg/kg/d p.o. for 30 days is well tolerated. In dogs, 10 mg/kg/d p.o. for 6 months is well tolerated. The target organs in rat and dog are liver and the gastrointestinal tract. Meisoindigo is not genotoxic in the Ames and Chromabs tests.

Several decades of clinical work on meisoindigo supports its safety, with clinical trials as a single agent or in combination with chemotherapy. It has been well tolerated in several patient populations. Common adverse effects include mild nausea and vomiting (30%), which spontaneously disappeared in two weeks, with no cardiac, hepatic, or renal adverse effects. However, anticipated potential side effects include marrow suppression, joint pain, skin itch, gastrointestinal symptoms including nausea, vomiting, anorexia, abdominal pain, abdominal distention, and diarrhea, edema, pigmentation of face and extremities, headache, head distention, or alterations in liver function, with slight increase in alanine transaminase (ALT).

Previous experience with meisoindigo includes several trials in chronic myelogenous leukemia (CML). The regimen was 50-200 mg/d p.o. for several days; it was used as a single agent and in combinations with other chemotherapeutic agents, including busulfan and hydroxyurea. There was a reduction of splenomegaly (median 25 d) followed by leukocyte count (median 31 d). There was a complete hematologic response in 33% of patients and a partial hematologic response in 58% of patients. A synergistic effect with hydroxyurea was seen.

Figure 5:
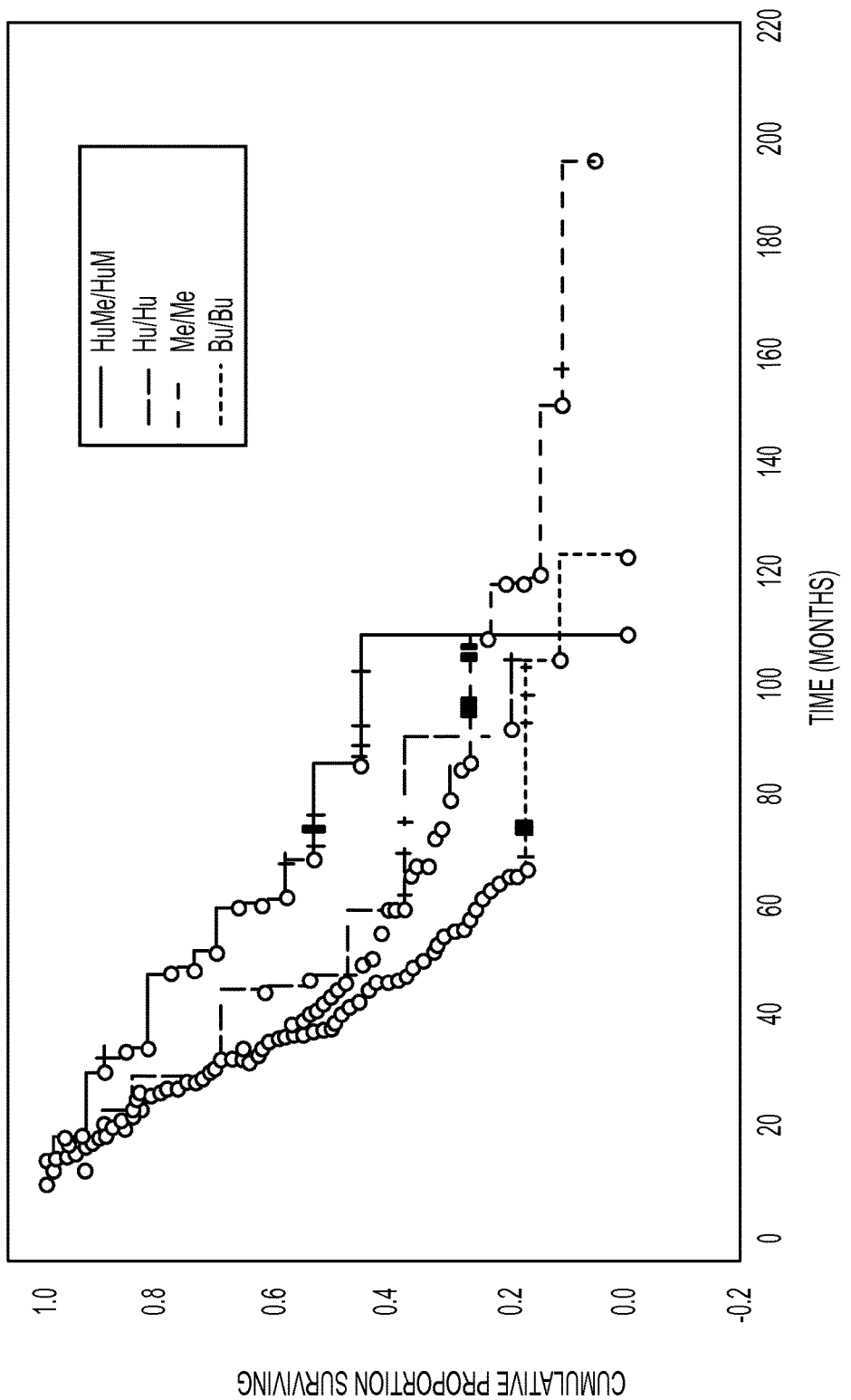
FIG. 5 shows the overall survival with meisoindigo, alone and with hydroxyurea, in chronic myelogenous leukemia, together with the results for busulfan.

The overall survival with meisoindigo, alone and with hydroxyurea, in chronic myelogenous leukemia is shown in FIG. 5. FIG. 5 also shows the results with busulfan.

One possible additional use for meisoindigo is in patients with acute myelogenous leukemia, acute promyelocytic leukemia (APL), acute lymphoblastic leukemia (ALL), or high-risk myelodysplastic syndrome (MDS) who are unsuitable for treatment with standard chemotherapy regimens (i.e., elderly, considered to be poor risk, or chemorefractory). The meisoindigo can be administered as a single agent orally in a soft gel capsule; dosing would start at 100 or 150 mg and increase. If no dose limiting toxicity (DLT) is seen after 4 weeks of treatment, the highest dose level could be used. Other dosing alternatives are described below, including use with additional agents in addition to meisoindigo.

Other indirubin analogs and derivatives are within the scope of the present invention. These include, but are not limited to, the following:

U.S. Pat. No. 6,566,341 to Wang et al. discloses indirubin (Formula I)), isoindigo (Formula (III)), indigo (Formula (IV)) and derivatives thereof, shown in Formulas (V), (VI), and (VII) along with 1-(β-D-O-triacetyl-xylopyranosyl)-isoindigo (Formula (VIII). In these indirubin, isoindigo, or indirubin derivatives, $R_1$, $R_2$, $R_3$, $R_4$, $R_5$, $R_6$, $R_7$, $R_8$, $R_9$, and $R_{10}$ are independently a hydrogen, a monosaccharide, a disaccharide, a halogen, a hydrocarbyl group, or a functional hydrocarbyl group unsubstituted or substituted with one or more hydroxyl moieties, carboxyl moieties, nitroxyl moieties, monosaccharides, disaccharides, amines, amides, thiols, sulfate groups, sulfonate groups, sulfonamide groups, or halogens, wherein a hydrocarbyl has 1 to 12 carbon atoms.

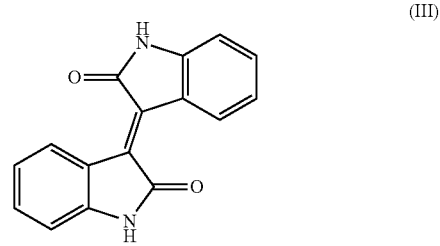

(III)

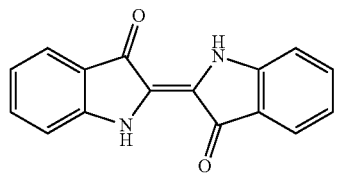

(IV)

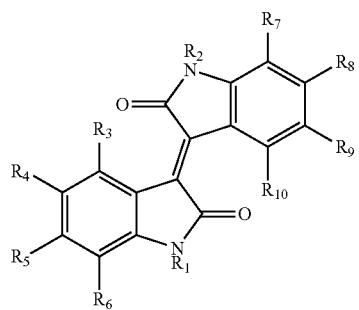

(V)

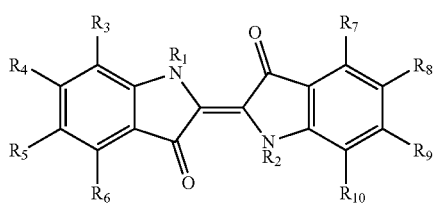

(VI)

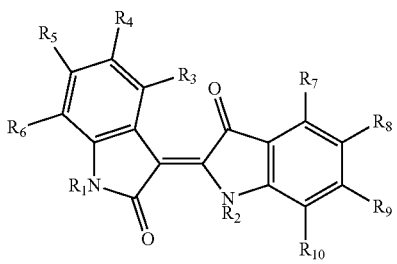

(VII)

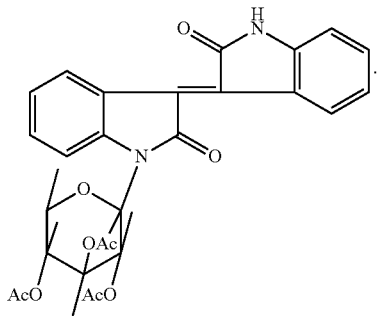

(VIII)

U.S. Pat. No. 6,664,285 to Eisenbrand et al. discloses indigoid bisindigo derivatives of Formula (IX) in which: (i) when X is an oxygen atom, $R^1$ is a hydrogen atom, a halogen atom, a —$NO_2$ group, a methyl group, a sulfonamide group, or $SO_2$—NH—$CH_2CH_2$—OH; or (ii) when X is NOH, $R^1$ is a hydrogen atom or an iodine atom.

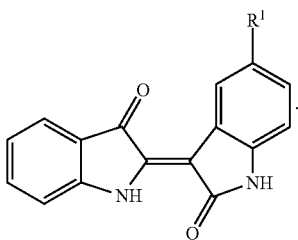

(IX)

U.S. Pat. No. 6,987,092 to Eisenbrand et al. discloses additional indigoid bisindigo derivatives of Formula (X) in which: X and Y are the same or different and are an oxygen atom; a sulfur atom; a selenium atom; a tellurium atom; a group N-A-B—$R^{14}$ in which A is a single bond or an oxygen atom, —NH— or —NH—CO—; B is a single bond or a group $[(CD_2)_nZ]_m$ wherein D has the same meaning as $R^{14}$ and Z is an oxygen atom or —NH—, n is 0 or an integer and m is an integer; and the group $R^{14}$ is a hydrogen atom, a straight-chain or branched-chain alkyl group having 1 to 18 carbon atoms which can carry one or more hydroxy and/or amino groups and can be substituted by one or more carboxyl groups and/or phosphoryl groups, a substituted or unsubstituted aryl group which can comprise one or more heteroatoms, an aralkyl group, an acyl group, a gycoside selected from monosaccharides, disaccharides or oligosaccharides, or a group selected from the group consisting of sugars, amino acids, peptides or steroid hormones; or a hydrazone group N—$NR^{15}R^{16}$, wherein $R^{15}$ and $R^{16}$ can be the same or different and represent a hydrogen atom, a straight-chain or branched-chain alkyl group having 1 to 18 carbon atoms which can be substituted by one or more carboxyl groups and/or phosphoryl groups, a substituted or unsubstituted aryl group which can comprise one or more heteroatoms, an aralkyl group, an acyl group, or a glycoside selected from monosaccharides, disaccharides or oligosaccharides, or a group selected from the group consisting of sugars, amino acids, peptides or steroid hormones; $R^2$, $R^3$, $R^4$, $R^5$, $R^7$, $R^8$, $R^9$ and $R^{10}$ can be the same or different and represent a hydrogen atom; a halogen atom; a hydroxy group; a nitroso group; a nitro group; an aryloxy group; an alkoxy group; a straight-chain or branched-chain alkyl group having 1 to 18 carbon atoms which can additionally carry one or more hydroxy and/or amino groups; a substituted or unsubstituted aryl group which can comprise one or more heteroatoms; a cycloalkyl group having 3 to 7 carbon atoms which can comprise one or more heteroatoms; an aralkyl group; a trifluoromethyl group; a —COM group; a —COOM group; a —$CH_2COOM$ group, wherein M is hydrogen, a straight-chain or branched-chain alkyl group having 1 to 18 carbon atoms which can additionally carry one or more hydroxy and/or amino groups, or an aryl group which can comprise one or more heteroatoms and can be substituted with one or more halogen atoms, one or more alkyl groups or one or more alkoxy groups; a —$NR^{11}R^{12}$ group, wherein $R^{11}$ and $R^{12}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group, or $R^{11}$ and $R^{12}$ form together a ring having 2 to 6, optionally substituted, $CH_2$ groups; a benzyl group, wherein the benzene nucleus can comprise one or more heteroatoms; a hydroxylamino group; a phosphate group; a phosphonate group; a sulfate group; a sulfonamide group, wherein the nitrogen atom can be independently substituted by a hydrogen atom, a straight-chain or branched-chain alkyl group having 1 to 18 carbon atoms which can additionally carry one or more hydroxy and/or amino groups, a substituted or unsubstituted aryl group or wherein the nitrogen atom is part of a cycloalkyl group having 3 to 7 carbon atoms which can comprise one or more heteroatoms; an azo group N=N—$R^{13}$, in which $R^{13}$ represents an aromatic system which can be substituted by one or more carboxyl groups and/or phosphoryl groups; or a O-glycoside or a N-glycoside, wherein the glycoside is selected from monosaccharides, disaccharides or oligosaccharides; or a group selected from the group consisting of sugars, amino acids, peptides or steroid hormones; or $R^1$ and $R^5$, and $R^6$ and $R^{10}$, respectively, form independently from each other a ring together having 1 to 4, optionally substituted, $CH_2$ groups; the groups $R^1$ and $R^6$ are the same or different and represent a hydrogen atom; a halogen atom; a hydroxy group; a methylenehydroxy group; a straight-chain or branched-chain alkyl group having 1 to 18 carbon atoms; a cycloalkyl group having 3 to 7 carbon atoms which can comprise one or more heteroatoms; a substituted or unsubstituted aryl group which can comprise one or more heteroatoms; a mono-, di- or trialkylsilyl group having 1 to 6 carbon atoms independently of each other in each instance in the straight-chain or branched-chain alkyl group; a mono-, di- or triarylsilyl group with substituted or unsubstituted aryl groups independently of each other in each instance; an aralkyl group; a trifluoromethyl group; a —COM group; a —COOM group; a —$CH_2COOM$ group, wherein M is hydrogen, a straight-chain or branched-chain alkyl group having 1 to 18 carbon atoms which can additionally carry one or more hydroxy and/or amino groups, or an aryl group which can comprise one or more heteroatoms and can be substituted with one or more halogen atoms, one or more alkyl groups or one or more alkoxy groups; a —$NR^{17}R^{18}$ group, wherein $R^{17}$ and $R^{18}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group; a methyleneamino group —$CH_2$—$NR^{17}R^{18}$, wherein $R^{17}$ and $R^{18}$ have the above definitions; a benzyl group, wherein the benzene nucleus can comprise one or more heteroatoms; a methylenecycloalkyl group having 3 to 7 carbon atoms which can comprise one or more heteroatoms; a physiological amino acid residue bound to the nitrogen as an amide; an O-glycoside or a N-glycoside, wherein the glycoside is selected from monosaccharides, disaccharides or oligosaccharides; or a group selected from the group consisting of sugars, amino acids, peptides or steroid hormones; or a methylene sulfonate group. The indigo derivatives have the general formula Formula (XI) wherein $R^1$ to $R^{10}$ and X and Y have the same meanings as for Formula (X). Also included are compounds of Formula (XII) wherein $R^1$ to $R^{10}$ have the same meanings as for Formula (XI) and $R^{19}$ and $R^{20}$, which may be the same or different, have the same meanings as $R^2$ for Formula (X).

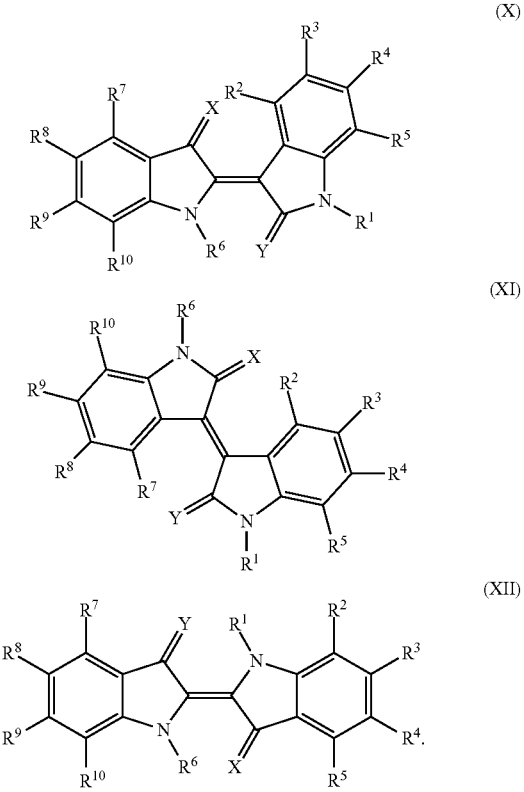

U.S. Pat. No. 7,582,670 to Wang et al. discloses derivatives and analogs of indirubin of Formulas (V), (VI), and (VII) wherein: $R_3$, $R_4$, $R_5$, $R_6$, $R_7$, $R_8$, $R_9$, and $R_{10}$ are the same or different and represent a hydrogen atom; a hydroxy group; a nitroso group; a nitro group; a monosaccharide; a disaccharide; a halogen atom; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a —$R_{11}R_{12}$ group, wherein $R_{11}$ and $R_{12}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group, or $R_{11}$ and $R_{12}$ form together a ring having 2 to 6, optionally substituted, $CH_2$ groups; an azo group —N=N—$R_{13}$, wherein $R_{13}$ represents an aromatic system which can be substituted by one or more carboxyl groups and/or phosphoryl groups, or a group selected from the group consisting of sugars, amino acids, peptides or steroid hormones; or $R_1$ and $R_6$, and $R_2$ and $R_7$, respectively, form independently from each other a ring together having 1 to 4, optionally substituted, $CH_2$ groups; and $R_1$ and $R_2$ are the same or different and represent a hydrogen atom; a halogen atom; a hydroxy group; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a mono-, di- or trialkylsilyl group having 1 to 6 carbon atoms independently of each other in each instance in the straight-chain or branched-chain alkyl group; a mono-, di- or triarylsilyl group with substituted or unsubstituted aryl groups independently of each other in each instance; a —NR$_{17}$R$_{18}$ group, wherein R$_{17}$ and R$_{18}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group; a methyleneamino group —CH$_2$—NR$_{17}$R$_{18}$, wherein R$_{17}$ and R$_{18}$ have the above definitions; a physiological amino acid residue bound to the nitrogen as an amide, substituted or unsubstituted monosaccharide, disaccharides or oligosaccharides; or a sugar, amino acid, peptide or steroid hormone. Preferably, at least R$_1$ or R$_2$ is a monosaccharide, a disaccharide unsubstituted or substituted with one or more hydroxy moieties or carboxy moieties; a halogen; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms. In another embodiment at least R$_1$ or R$_2$ is an acetylated monosaccharide. Preferably, at least R$_1$ or R$_2$ can be a methyl group. U.S. Pat. No. 7,582,670 to Wang et al. also discloses a compound that is a derivative of Formula (VIII) above in which the hydrogen bound to the nitrogen of the five-membered ring is replaced with a methyl group. This compound is shown as Formula (XIII):

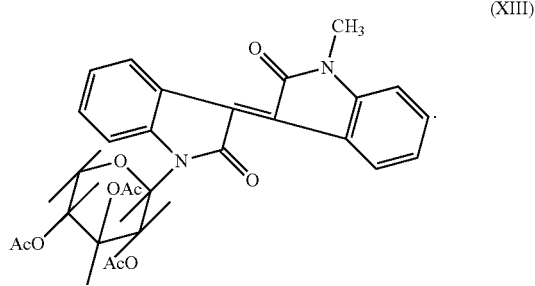

(XIII)

United States Patent Application Publication No. 2002/0107404 by Prien et al. discloses sulfur-containing indirubin derivatives of Formula (XIV), wherein R$^1$ and R$^2$ stand for hydrogen, halogen, hydroxy, nitroso, nitro, C$_1$-C$_{10}$ alkoxy optionally interrupted by one or more oxygen atoms; C$_1$-C$_{18}$ alkyl optionally substituted in one or more places with halogen, hydroxy and/or amino; aryl or heteroaryl optionally substituted in one or more places with halogen, C$_1$-C$_6$ alkyl, hydroxy, amino and/or C$_1$-C$_6$ alkoxy; or aralkyl, aryloxy, methylenearyloxy, C$_3$-C$_8$ cycloalkyl, C$_3$-C$_8$ cycloalkenyl or C$_3$-C$_7$ methylenecycloalkyl optionally substituted in one or more places with halogen, C$_1$-C$_6$ alkyl, hydroxy, amino and/or C$_1$-C$_6$ alkoxy and optionally containing one or more heteroatoms; or hydroxylamino, phosphate, phosphonate, sulfate, sulfonate, sulfonamide optionally substituted in one or more places with halogen, C$_1$-C$_6$ alkyl, hydroxy, amino and/or C$_1$-C$_6$ alkoxy; or a —COM group, —COOM group, —CH$_2$COOM group, —CONR$^{10}$R$^{11}$ group, —NR R$^{10}$R$^{11}$ group, —SO$_2$NR R$^{10}$R$^{11}$ group, —N=N—R$^8$ group or an —S(O)$_n$R$^6$ group; or an O-glycoside or N-glycoside, whereby the glycosides are selected from the group of mono- or disaccharides, R$^3$ stands for oxygen, sulfur, selenium, tellurium or the group =NOR$^7$ or =NR$^9$, R$^4$ and R$^5$ stand for hydrogen, halogen, hydroxy, nitroso, nitro, C$_1$-C$_{10}$ alkoxy optionally interrupted by one or more oxygen atoms; C$_1$-C$_{18}$ alkyl optionally substituted in one or more places with halogen, hydroxy and/or amino; aryl, benzyl, benzyloxy, or heteroaryl optionally substituted in one or more places with halogen, C$_1$-C$_6$ alkyl, hydroxy, amino and/or C$_1$-C$_6$ alkoxy; or aralkyl, aryloxy, methylenearyloxy, C$_3$-C$_8$ cycloalkyl, C$_3$-C$_8$ cycloalkenyl or C$_3$-C$_7$ methylenecycloalkyl optionally substituted in one or more places with halogen, C$_1$-C$_6$ alkyl, hydroxy, amino and/or C$_1$-C$_6$ alkoxy and optionally containing one or more heteroatoms; or hydroxylamino, phosphate, phosphonate, sulfate, sulfonate, sulfonamide optionally substituted in one or more places with halogen, C$_1$-C$_6$ alkyl, hydroxy, amino and/or C$_1$-C$_6$ alkoxy; or a —COM group, —COOM group, —CH$_2$COOM group, —CONR$^{10}$R$^{11}$ group, —NR R$^{10}$R$^{11}$ group, —SO$_2$NR R$^{10}$R$^{11}$ group, —N=N—R$^8$ group or an —S(O)$_n$R$^6$ group; or an O-glycoside or N-glycoside, whereby the glycosides are selected from the group of mono- or disaccharides, and R$^6$ stands for hydrogen, C$_1$-C$_{18}$ alkyl that is substituted in one or more places with halogen, hydroxy and/or amino; aryl, heteroaryl or C$_3$-C$_8$ cycloalkyl that is optionally substituted in one or more places with halogen, hydroxy, amino, C$_1$-C$_6$ alkyl and/or C$_1$-C$_6$ alkoxy; or R$_1$ or R$_2$, or R$_4$ or R$_5$, independently of one another, form a ring with 1 to 4-CH$_2$ groups, which, independently of one another, optionally are substituted in one or two places with halogen, hydroxy, nitroso, nitro, C$_1$-C$_{10}$ alkoxy; C$_1$-C$_{18}$ alkyl that is optionally substituted in one or more places with halogen, hydroxy and/or amino; aryl or heteroaryl that is optionally substituted in one or more places with halogen, C$_1$-C$_6$ alkyl, hydroxy, amino and/or C$_1$-C$_6$ alkoxy; or aralkyl, aryloxy, methylenearyloxy, C$_3$-C$_8$ cycloalkyl, C$_3$-C$_8$ cycloalkenyl or C$_3$-C$_7$ methylenecycloalkyl that is optionally substituted in one or more places with halogen, C$_1$-C$_6$ alkyl, hydroxy, amino and/or C$_1$-C$_6$ alkoxy and that optionally contains one or more heteroatoms; or hydroxylamino, phosphate, phosphonate, sulfate, sulfonate, sulfonamide that is optionally substituted in one or more places with halogen, C$_1$-C$_6$ alkyl, hydroxy, amino and/or C$_1$-C$_6$ alkoxy; or a —COM group, —COOM group, —CH$_2$COOM group, —CONR$^{10}$R$^{11}$ group, —NR R$^{10}$R$^{11}$ group —SO$_2$NR R$^{10}$R$^{11}$ group, —N=N—R$^8$ group or an —S(O)$_n$R$^6$ group; or an O-glycoside or N-glycoside, whereby the glycosides are selected from the group of mono- or disaccharides, R$^7$ is hydrogen, C$_1$-C$_{18}$ alkyl, C$_1$-C$_{18}$ alkenyl, C$_3$-C$_8$ cycloalkyl, or C$_3$-C$_8$ cycloalkenyl that is optionally substituted by one or more oxygen atoms, R$^8$ is aryl that is optionally substituted by one or more carboxyl, phosphoryl, or sulfonate groups, R$^9$ is hydrogen, C$_1$-C$_{18}$ alkyl that is optionally substituted in one or more places with carboxy, phosphoryl or sulfonate groups, or an aryl group with one or more heteroatoms that is optionally substituted with aralkyl or sulfonate, R$^{10}$ and R$^{11}$ are the same or different and mean hydrogen or C$_1$-C$_{18}$ alkyl, aryl, heteroaryl or acyl that is optionally substituted with hydroxy and/or amino; or C$_1$-C$_{18}$ alkyl, C$_3$-C$_8$ cycloalkyl or C$_3$-C$_8$ cycloalkenyl that is optionally interrupted by one or more oxygen atoms, or R$^{10}$ and R$^{11}$ together with the nitrogen atom of the amino group forms a C$_3$-C$_8$ cycloalkyl, which can contain one or more additional heteroatoms, M is hydrogen, C$_1$-C$_{18}$ alkyl that is optionally substituted by one or more hydroxy groups and/or amino groups, or aryl or heteroaryl that is optionally substituted in one or more places with halogen, C$_1$-C$_6$ alkyl or C$_1$-C$_6$ alkoxy, n is 0, 1, or 2, and at least one of R$^1$, R$^2$, R$^4$, or R$^5$ is substituted with an S(O)$_n$R$^6$ group, and optical isomers and salts thereof. Examples include 5-methylsulfanylindirubin, 5-methylsulfinylindirubin, 5-methylsulfinyl-3'-hydroxyiminoindirubin, and 5-methylsulfanyl-5'-N-acetylindirubin.

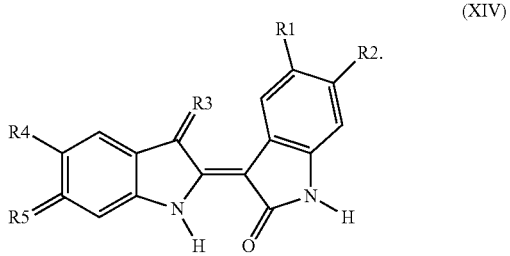

(XIV)

United States Patent Application Publication No. 2002/0132792 by Prien et al. discloses aryl-substituted indirubin derivatives of Formula (XV) in which: $R^1$, $R^2$, $R^4$ and $R^5$ are hydrogen, hydroxy, $C_1$-$C_6$ alkoxy, aryloxy, trifluoromethyl, nitro, halogen, cyano or the group —$SO_pR^6$, —$SO_2NR^7R^8$, or —$COR^9$; or is aryl or heteroaryl that is optionally substituted by the same or a different component in one or more places with hydroxy, halogen, $C_1$-$C_6$ alkyl, amino, nitro, trifluoromethyl, —O—Si($C_1$-$C_6$ alkyl)$_3$, cyano, COO$C_1$-$C_4$ alkyl, CO$_{1-4}$ alkyl, CO$_{1-4}$ aryl, SO$_2$($C_1$-$C_4$ alkyl), SO$_2$ aryl and/or $C_1$-C6 alkoxy, $R^3$ is hydrogen or —$NOR^9$, or $R^1$ and $R^2$ or $R^4$ and $R^5$ optionally form another $C_3$-$C_6$-membered ring, $R^6$ is hydrogen, $C_1$-$C_{18}$ alkyl that is optionally substituted in one or more places with halogen, hydroxy and/or amino; aryl, heteroaryl or $C_3$-$C_8$ cycloalkyl that is optionally substituted in one or more places with halogen, hydroxy, amino, $C_1$-$C_5$ alkyl and/or $C_1$-$C_6$ alkoxy, $R^7$ and $R^8$ are the same or different and are hydrogen or for $C_1$-$C_{18}$ alkyl, aryl, heteroaryl or acyl that is optionally substituted in one or more places with hydroxy, halogen and/or amino; or $C_1$-$C_{18}$ alkyl, $C_3$-$C_8$ cycloalkyl or $C_3$-$C_8$ cycloalkenyl that is optionally interrupted by one or more oxygen atoms, or $R^7$ or $R^8$ together with the nitrogen atom of the amino group form a $C_3$-$C_8$ cycloalkyl which can contain one or more additional heteroatoms, $R^9$ is hydrogen or $C_1$-$C_6$ alkyl that is optionally substituted in one or more places with hydroxy, halogen, $C_1$-$C_4$ alkoxy, amino, nitro, trifluoromethyl, cyano, COO$C_{1-4}$ alkyl, CO$_{1-4}$ alkyl, CO$_{1-4}$ aryl, SO$_2$($C_1$-$C_4$ alkyl) and/or SO$_2$-aryl; or for aryl or heteroaryl that is optionally substituted in one or more places with halogen, $C_1$-$C_6$ alkyl, hydroxy, amino, nitro, trifluoromethyl, cyano, COO$C_1$-$C_4$ alkyl, CO$_{1-4}$ alkyl, CO$_{1-4}$ aryl, SO$_2$($C_{1-4}$ alkyl), SO$_2$ arylamino and/or $C_1$-$C_6$ alkoxy, and p is 0, 1, or 2, and whereby at least of one of the two radicals $R^1$ and $R^2$ or the two radicals $R^4$ and $R^5$ is an aryl or heteroaryl radical, as well as isomers and salts thereof, with the following examples: 5-(4-methoxyphenyl)-indirubin.

United States Patent Application Publication No. 2005/0080020 by Eisenbrand et al. discloses hydroxylated indirubin derivatives of Formula (XVI) wherein R is a straight-chain or branched chain alkyl group or a straight-chain or branched chain alkoxy group each having 1 to 18 carbon atoms, preferably 1 to 4 carbon atoms, and R' represents H, a straight-chain or branched chain alkyl group having 1 to 4 carbon atoms or a glucuronide group, and X is H or OH, including 6-hydroxy-5-methylindirubin and 6,7'-dihydroxy-5-methylindirubin and their glucuronide derivatives, i.e. 3,4,5-trihydroxy-6-(5-methyl-1H,1'H-[2',3]bis-indolyliden-2,3'-dion-6-yl)-tetrahydropyran-2-carboxylic acid and 3,4,5-trihydroxy-6-(7'-hydroxy-5-methyl-1H1'H-[2',3]bisindolyliden-2,3'-dion-6-yl)-tetrahydropyran-2-carboxylic acid. 5-methylindirubin is also recited as having anticancer properties.

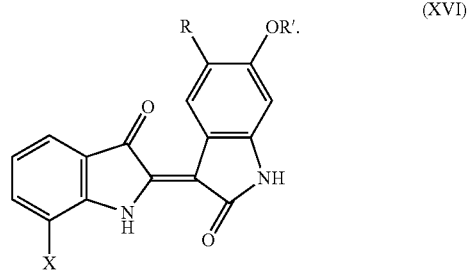

(XVI)

United States Patent Application Publication No. 2008/0194021 by Mays discloses a number of indirubin analogs and derivatives, including compounds of Formula (XVII) wherein: each X is independently O, S, N—$OR^1$, N(Z), or two groups independently selected from hydrogen, fluoro, chloro, bromo, iodo, $NO_2$, phenyl, and $C_1$-$C_6$ alkyl, wherein $R^1$ is hydrogen, $C_1$-$C_6$ alkyl, or ($C_1$-$C_6$ alkyl)C(O)—; each Y is independently hydrogen, $C_1$-$C_6$ alkyl, ($C_1$-$C_6$ alkyl)C(O)—, ($C_1$-$C_6$ alkyl)C(O)O—, phenyl, N(Z)(Z), sulfonyl, phosphonyl, fluoro, chloro, bromo, or iodo; each Z is independently hydrogen, $C_1$-$C_6$ alkyl, phenyl, benzyl, or both Z groups together with the nitrogen to which they are attached form 5-, 6-, or 7-membered heterocycloalkyl; each n is independently 0, 1, 2, 3, or 4; each R is independently hydrogen, $C_1$-$C_6$ alkyl, ($C_1$-$C_6$ alkyl)-C(O)—, phenyl, benzyl, or benzoyl; wherein alkyl is branched or straight-chain, optionally substituted with 1, 2, 3, 4, or 5 hydroxyl, N(Z)(Z), $C_1$-$C_6$ alkyl, phenyl, benzyl, fluoro, chloro, bromo, or iodo; where any phenyl, benzyl, or benzoyl is optionally substituted with 1, 2, 3, 4, or 5 hydroxyl, N(Z)(Z), $C_1$-$C_6$ alkyl, fluoro, chloro, bromo, or iodo; or a salt thereof.

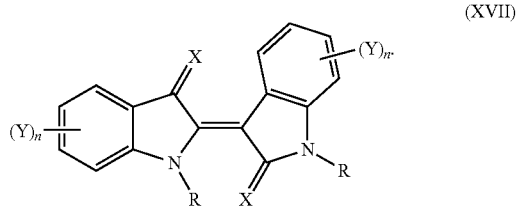

(XVII)

United States Patent Application Publication No. 2008/207594 by Mussmann et al. discloses indirubin derivatives of Formula (XVIII) wherein: $R^5$ and $R^6$ are independently hydrogen, $C_1$-$C_6$ alkyl, optionally substituted, or —CO—

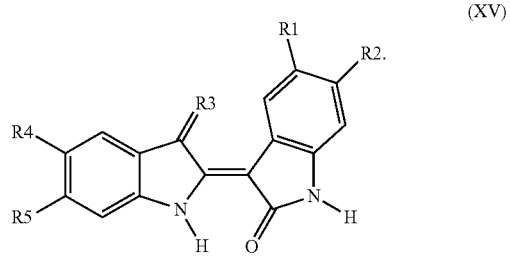

(XV)

$C_1$-$C_6$ alkyl, optionally substituted, wherein the substituents are independently selected from one or more of halo, —CN, hydroxyl, —O—$C_1$-$C_6$ alkyl, —COOH, —COO$C_1$-$C_6$ alkyl, —CONH$_2$, —CONH($C_1$-$C_6$ alkyl), —CON($C_1$-$C_6$ alkyl)$_2$, aryl, heteroaryl, or combinations thereof; each $R^7$ and $R^8$ is independently selected from $C_1$-$C_6$ alkyl, $C_2$-$C_6$ alkenyl, $C_2$-$C_6$ alkynyl, $C_3$-$C_{10}$ cycloalkyl; $C_3$-$C_{10}$ heterocyclyl, aryl with 6 to 10 carbon atoms, heteroaryl with 5 to 10 ring atoms, each optionally substituted with halo, —NO$_2$, —CN, —OR$^1$, —COOR$^1$, or NR$^1$R$^2$, where $R^1$ and $R^2$ are independently selected from one or more of halo, —CN, hydroxyl, —O—$C_1$-$C_6$ alkyl, —COOH, —COO$C_1$-$C_6$ alkyl, —CONH$_2$, —CONH($C_1$-$C_6$ alkyl), —CON($C_1$-$C_6$ alkyl)$_2$, aryl, heteroaryl, or combinations thereof; wherein alkyl, alkenyl, or alkynyl is optionally substituted with one or more of oxo, halo, —NO$_2$, —CN, —OR$^1$, —COOR$^1$, —OCOR$^1$, —NR$^1$R$^2$, —NR$^1$COR$^2$, —NR$^1$OCOR$^2$, —NR$^1$CONR$^1$R$^2$, —SR$^1$, —SOR$^1$, —SO$_2$R$^1$, —SONR$^1$R$^2$, —SO$_2$NR$^1$R$^2$, —NR$^1$SO$_2$NR$^1$R$^2$, or combinations thereof, wherein $R^1$ and $R^2$ are as defined above; wherein cycloalkyl, heterocyclyl, aryl, or heteroaryl is optionally substituted with $C_1$-$C_6$ alkyl, oxo, halo, —NO$_2$, —CN, —OR$^1$, —COOR$^1$, —OCOR$^1$, —NR$^1$R$^2$, —NR$^1$COR$^2$, —NR$^1$OCOR$^2$, —NR$^1$CONR$^1$R$^2$, —SR$^1$, —SOR$^1$, —SO$_2$R$^1$, —SONR$^1$R$^2$, —SO$_2$NR$^1$R$^2$, —NR$^1$SO$_2$NR$^1$R$^2$, or combinations thereof, wherein $R^1$ and $R^2$ are as defined above; or two $R^7$ or two $R^8$ can together form a ring; wherein n is 0, 1, 2, or 3, and wherein m is 0, 1, 2, or 3; or an optical isomer or salt thereof.

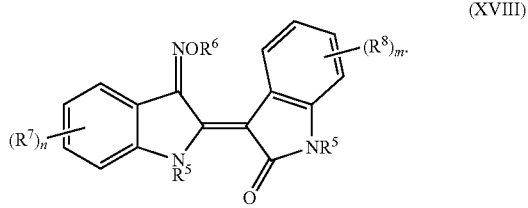

(XVIII)

United States Patent Application Publication No. 2010/0016252 by Keana et al. discloses Mannich base N-oxides or N-oxide rearrangement prodrugs of a number of indirubin derivatives, including indirubin, indirubin-3'-oxime, indirubin-5-sulfonic acid, and 5-chloroindirubin.

United States Patent Application Publication No. 2010/0137356 by Cheng et al. discloses N-1-methylisoindigo as well as azaindole-indole coupled derivatives. The compounds of United States Patent Application Publication No. 2010/0137356 by Cheng et al. include: (1) azaindole-indole coupled derivatives linked by a double bond of the general schematic formula Y=Z, in which Y is an azaindole group represented by Formula (XIX) or (XX) and Z is an indole group represented by Formula (XXI) or (XXII), wherein the double bond in "Y=Z" is located between the 3-position of the azaindole group (Y) and the 2'- or 3'-position of the indole group (Z), and in which: $R^1$ and $R^{1'}$ independently are hydrogen or the following groups which may be unsubstituted or substituted by 1 to 3 substituents: $C_1$-$C_6$ alkyl, aryl, aralkyl, acyl, aroyl, glycosyl or biosyl protected by acyl, glycosyl or biosyl; wherein said substituents are selected from: halogen, hydroxyl, $C_1$-$C_3$ alkyl, nitro or amino; $R^2$, $R^3$, $R^4$, $R^{2'}$, $R^{3'}$, $R^{4'}$ and $R^{5'}$ independently represent H, halogen, hydroxyl, sulfhydryl, or the following groups which may be unsubstituted or substituted by 1 to 3 substituents: $C_1$-$C_4$ alkyl, nitro, amino, amido, amide, $C_1$-$C_4$ alkoxy, methylthio, phenyl, phenoxy, aryl, aralkyl, trifluoromethyl, acyl, aroyl, sulfonic group, sulfamoyl, isocyanate, or alkyl isocyanate; wherein said substituents are selected from: halogen, hydroxyl, $C_1$-$C_3$ alkyl, nitro or amino; $R^2$, $R^3$, $R^4$, $R^{2'}$, $R^{3'}$, $R^{4'}$ and $R^{5'}$ independently represent H, halogen, hydroxyl, sulfhydryl, or the following groups which may be unsubstituted or substituted by 1 to 3 substituents: $C_1$-$C_4$ alkyl, nitro, amino, amido, amide, $C_1$-$C_4$ alkoxy, methylthio, phenyl, phenoxy, aryl, aralkyl, trifluoromethyl, acyl, aroyl, sulfonic group, sulfamoyl, isocyanate, or alkyl isocyanate; wherein said substituents are selected from: halogen, hydroxyl, $C_1$-$C_3$ alkyl, nitro or amino; R represents oxygen, sulfur, or selenium, or a NR$^6$ or NOR$^6$ group, wherein $R^6$ is H or the following groups which may be unsubstituted or substituted by 1 to 3 substituents: $C_1$-$C_6$ straight-chain or branched chain alkyl, aryl, aralkyl, $C_3$-$C_6$ alicyclic group, acyl, aroyl, sulfonyl, or phosphoryl, wherein the substituents are selected from halogen, hydroxyl, $C_1$-$C_3$ alkyl, nitro, or amino; (2) compounds of Formulas (XXIII), (XXIV), (XXV), and (XXVI) in which: R, $R^1$, $R^{1'}$, $R^2$, $R^3$, $R^4$, $R^{2'}$, $R^{3'}$, $R^{4'}$ and $R^{5'}$ are defined as above in compounds of the general schematic formula Y=Z; and (3) compounds of Formulas (XXIII), (XXIV), (XXV), and (XXVI) in which: $R^1$ and $R^{1'}$ independently are hydrogen, $C_1$-$C_6$ alkyl, aryl, aralkyl, acyl, aroyl, glycosyl protected by acyl, or glycosyl; $R^2$, $R^3$, $R^4$, $R^{2'}$, $R^{3'}$, $R^{4'}$ and $R^{5'}$ are hydrogen, halogen, hydroxyl, sulfhydryl, $C_1$-$C_4$ alkyl, amino, amide, $C_1$-$C_4$ alkoxy, methylthio, phenyl, phenyloxy, aryl, aralkyl, trifluoromethyl, acyl, aroyl, sulfonic group, or isocyanate; and R represents oxygen, sulfur, or selenium, or a NR$^6$ or NOR$^6$ group, wherein $R^6$ is H or the following groups which may be unsubstituted or substituted by 1 to 3 substituents: $C_1$-$C_6$ straight-chain or branched chain alkyl, aryl, aralkyl, $C_3$-$C_6$ alicyclic group, acyl, aroyl, sulfonyl, or phosphoryl, wherein the substituents are selected from halogen, hydroxyl, $C_1$-$C_3$ alkyl, nitro, or amino. In these compounds, compounds of Formula (XXIII) are 5-azaindirubin derivatives, compounds of Formula (XXIV) are 5-azaindigo derivatives, compounds of Formula (XXV) are 7-azaindirubin derivatives, and compounds of Formula (XXVI) are 7-azaindigo derivatives. Specific compounds include: 3'-oximido-7-azaindirubin; 7-azaindirubin-3'-oxime ether; 1-methyl-5-azaindirubin; 1-benzyl-5'-chloro-5-azaindirubin; 1-butyl-5-azaindirubin-3'-oxime; 1-butyl-5-azaindirubin-3'-oxime O-methyl ether; 1-isopropyl-5-azaisoindigo; 1-methyl-7-azaindirubin; 1-benzyl-5'-bromo-7-azaindirubin; 1-butyl-7-azaindirubin-3'-oxime; 1-butyl-7-azaindirubin-3'-oxime O-methyl ether; 1-isopropyl-7-azaisoindigo.

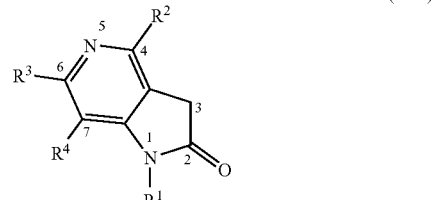

(XIX)

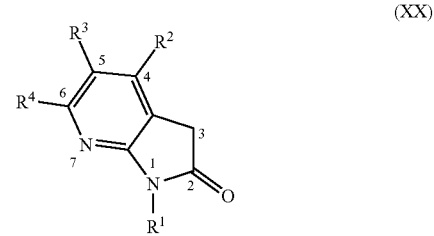

(XX)

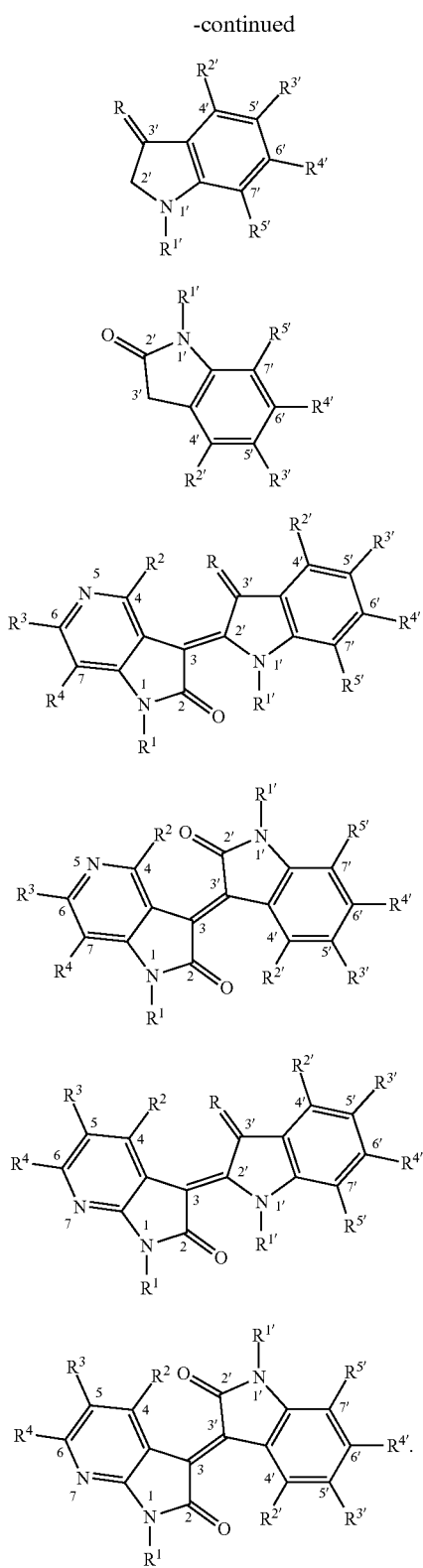

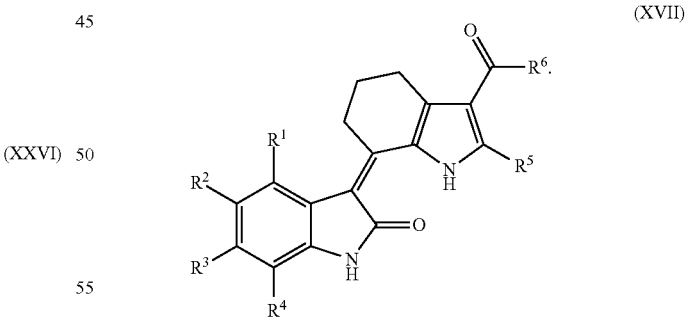

C(O)NR$^{11}$R$^{12}$; R$^2$ is selected from the group consisting of hydrogen, halo, alkyl, haloalkyl, hydroxyl, alkoxy, haloalkoxy, nitro, cyano, —NR$^8$R$^9$, —NR$^8$C(O)R$^9$, —C(O)R$^7$, aryl, heteroaryl, —C(O)NR$^{11}$R$^{12}$, —S(O)$_2$R$^8$R$^9$, and —S(O)$_2$R$^{13}$; R$^3$ is selected from the group consisting of hydrogen, alkyl, haloalkyl, hydroxy, alkoxy, —C(O)R$^7$, —NR$^8$R$^9$, aryl, heteroaryl, —S(O)$_2$R$^8$R$^9$, —NR$^8$C(O)R$^9$, —NR$^8$C(O)OR$^9$, and —NR$^8$C(O)R$^9$; R$^4$ is selected from the group consisting of hydrogen, halo, alkyl, hydroxy, alkoxy, and —NR$^8$R$^9$; R$^5$ is selected from the group consisting of hydrogen, alkyl, and C(O)R$^{14}$; R$^6$ is selected from the group consisting of hydroxy, alkoxy, aryloxy, —N(R$^{15}$)(CH$_2$)$_r$R$^{16}$, —NR$^8$R$^9$, and —N(R$^{17}$)—CH(R$^{18}$)—CR$^{19}$(OH)—CH(R$^{20}$)Z; R$^7$ is selected from the group consisting of hydrogen, hydroxy, alkoxy, and aryloxy; R$^8$ and R$^9$ are each independently selected from the group consisting of hydrogen, alkyl, cycloalkyl, aryl, and heteroaryl, or R$^8$ and R$^9$ together with the atoms to which they are attached may form a heteroalicyclic ring; R$^{10}$ is selected from the group consisting of hydroxy, —C(O)R$^7$, —NR$^8$R$^9$, and —C(O)NR$^8$R$^9$; R$^{11}$ and R$^{12}$ are each independently selected from the group consisting of hydrogen, alkyl, and aryl, or R$^{11}$ and R$^{12}$ together with the nitrogen atom to which they are attached may form a heteroalicyclic ring; R$^{13}$ is selected from the group consisting of alkyl, aryl, aralkyl, heteroaryl, and heteroaralkyl; R$^{14}$ is selected from the group consisting of hydroxy, alkoxy, aryloxy, and —NR$^8$R$^9$; R$^{15}$ is selected from the group consisting of hydrogen and alkyl; R$^{16}$ is selected from the group consisting of hydroxy, —NR$^8$R$^9$, —C(O)R$^7$, aryl, heteroaryl, —N$^+$(O$^-$)R$^8$R$^9$, N(OH)R$^8$, and NHC(O)R$^a$, wherein R$^a$ is selected from the group consisting of unsubstituted alkyl, R$^{17}$, R$^{18}$, R$^{19}$, and R$^{20}$ are each independently selected from the group consisting of hydrogen and alkyl; Z is selected from the group consisting of aryl, heteroaryl, and —NR$^8$R$^9$; and n and r are each independently an integer from 1 to 4.

United States Patent Application Publication No. 2010/0160318 by Tang et al. discloses 3-pyrrolo[b]cyclohexylene-2-dihydroindolinone derivatives of Formula (XXVII), wherein: R$^1$ is selected from the group consisting of hydrogen, halo, alkyl, cycloalkyl, aryl, heteroaryl, heteroalicyclic, hydroxy, alkoxy, —C(O)R$^7$, —NR$^8$R$^9$, —(CH$_2$)$_n$R$^{10}$, and United States Patent Application Publication No. 2010/0331327 by Meijer et al. discloses 7-substituted indirubin-3'-oximes of Formula (XXVIII) wherein R is N—OH, N—O-alkyl, or N—O—CO-alkyl, NO—(R$_a$)$_{n1}$-Het, or N—O—(Y)$_{n1}$—NR$_a$R$_b$, N—O—CO—N(R$_b$, R$_c$) radical with Het representing an aliphatic nitrogeneous heterocycle, Y is an optionally substituted —CH$_2$— radical, n1 is 1 to 3, X is a halogen atom selected from the group consisting of F, Cl, Br, or I, and Z is H or methyl, and the salts thereof.

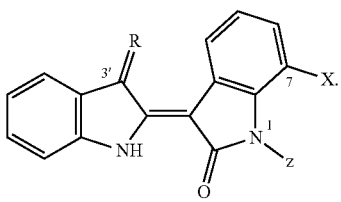

(XVIII)

United States Patent Application Publication No. 2011/0136808 by Meijer et al. discloses 3',6-substituted indirubins of Formula (XXIX) wherein R is -(A)$_n$-R$^1$ or —CO—N—(R$^2$, R$^3$) wherein A is a C$_1$-C$_5$ alkylene group, optionally substituted by one or several A$^1$ radicals, wherein A$^1$ is Br, OH, OR$^4$, or NH$_2$, wherein R$^4$ is C$_1$-C$_5$ alkyl, —R$^1$ is halogen, OH, or N(R$^2$, R$^3$) wherein R$^2$ and R$^3$ are identical or different and are C$_1$-C$_5$ alkyl optionally substituted by A$^1$ as defined above, or R$^2$ and R$^3$ are part of a cyclic structure with 5 or 6 members optionally comprising another heteroatom such as 0 or N, and n is 1 to 5.

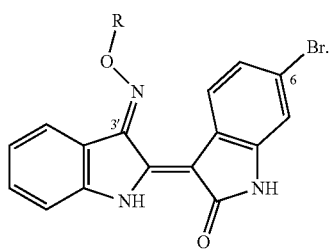

(XXIX)

PCT Patent Application Publication No. WO 1999/062503 by Eisenbrand et al. discloses indigoid bisindole derivatives of either Formula (XXX), Formula (XXXI), or Formula (XXXII) wherein: R$^1$ and R$^6$ are the same or different, and are hydrogen, halogen, hydroxy, methylenehydroxy, a straight-chain or branched-chain C$_1$-C$_{18}$ alkyl group, a straight-chain or branched-chain C$_1$-C$_{18}$ alkyloxy group, a straight-chain or branched-chain C$_1$-C$_{18}$ methylenealkyloxy group, a C$_3$-C$_7$ cycloalkyl group which can comprise one or more heteroatoms, a substituted or unsubstituted aryl group which can comprise one or more heteroatoms, a substituted or unsubstituted aralkyl group which can comprise one or more heteroatoms, a substituted or unsubstituted aryloxy group which can comprise one or more heteroatoms, a mono-, di-, or trialkylsilyl group having 1 to 6 carbon atoms independently of each other in each instance in the straight-chain or branched-chain alkyl group, a mono-, di-, or triarylsilyl group with substituted or unsubstituted aryl groups independently of each other in each instance, a trifluoromethyl group; a —COM group, a —COOM group, or a —CH$_2$COOM group, wherein M is hydrogen, a straight-chain or branched-chain C$_1$-C$_{18}$ alkyl group which can additionally carry one or more hydroxyl and/or amino groups, or an aryl group which can comprise one or more heteroatoms and can be substituted with one or more halogen atoms, one or more alkyl groups, or one or more alkoxy groups; a —NR$^{11}$R$^{12}$ group, wherein R$^{11}$ and R$^{12}$ are the same or different and are hydrogen, a straight-chain or branched-chain C$_1$-C$_{18}$ alkyl group which can additionally carry one or more hydroxyl and/or amino groups, a substituted or unsubstituted aryl group which can comprise one or more heteroatoms, or an acyl group; —CH$_2$NR$^{11}$R$^{12}$, wherein R$^{11}$ and R$^{12}$ are as defined above; a benzyl group, wherein the benzene nucleus can comprise one or more heteroatoms; a C$_3$-C$_7$ methylenecycloalkyl group which can comprise one or more heteroatoms; a physiological amino acid residue bound to the nitrogen as an amide; an O-glycoside or an N-glycoside, wherein the glycoside is selected from monosaccharides and disaccharides; or a methylenesulfonate group; R$^2$, R$^3$, R$^4$, R$^5$, R$^7$, R$^8$, R$^9$ and R$^{10}$ can be the same or different and are hydrogen, halogen, hydroxy, nitroso, nitro, alkoxy, a straight-chain or branched-chain C$_1$-C$_{18}$ alkyl group which can additionally carry one or more hydroxyl and/or amino groups, a substituted or unsubstituted aryl group which can comprise one or more heteroatoms; a substituted or unsubstituted aralkyl group which can comprise one or more heteroatoms; a substituted or unsubstituted aryloxy group which can comprise one or more heteroatoms; a substituted or unsubstituted methylenearyloxy group which can comprise one or more heteroatoms; a C$_3$-C$_7$ cycloalkyl group which can comprise one or more heteroatoms; a C$_3$-C$_7$ methylenecycloalkyl group which can comprise one or more heteroatoms; a trifluoromethyl group; a —COM group, a —COOM group, or a —CH$_2$COOM group, wherein M is hydrogen, a straight-chain or branched-chain C$_1$-C$_{18}$ alkyl group which can additionally carry one or more hydroxyl and/or amino groups, or an aryl group which can comprise one or more heteroatoms and which can be substituted with one or more halogen atoms, one or more alkyl groups, or one or more alkoxy groups; a —NR$^{11}$R$^{12}$ group, wherein R$^{11}$ and R$^{12}$ are the same or different and are hydrogen, a straight-chain or branched-chain C$_1$-C$_{18}$ alkyl group which can additionally carry one or more hydroxyl and/or amino groups, a substituted or unsubstituted aryl group which can comprise one or more heteroatoms, or an acyl group, or wherein the nitrogen atom is part of a C$_3$-C$_7$ cycloalkyl group which can comprise one or more heteroatoms; a —CONR$^{11}$R$^{12}$ group, wherein R$^{11}$ and R$^{12}$ are as defined above; a hydroxylamino group; a phosphate group; a phosphonate group; a sulfate group; a sulfonate group; a sulfonamide group; a —SO$_2$NR$^{11}$R$^{12}$ group, wherein R$^{11}$ and R$^{12}$ are as defined above; an azo group —N═NR$^{13}$, wherein R$^{13}$ is an aromatic system which can be substituted by one or more carboxyl groups, phosphoryl groups, or sulfonate groups; or an O-glycoside or an N-glycoside, wherein the glycoside is selected from the group consisting of monosaccharides and disaccharides; or R$^1$ and R$^5$, and R$^6$ and R$^{10}$ can, respectively, form independently from each other a ring having 1 to 4, optionally substituted, CH$_2$ groups; and X and Y can be the same or different and can be an oxygen atom, a sulfur atom, a selenium atom, a tellurium atom, a —NR$^{14}$ group in which R$^{14}$ represents a hydrogen atom, a C$_1$-C$_{18}$ straight-chain or branched-chain alkyl group which can be substituted by one or more carboxyl groups, phosphoryl groups, or sulfonate groups, a substituted or unsubstituted aryl group which can comprise one or more heteroatoms, an aralkyl group, or a sulfonate group; or an —NR$^{14}$ group in which R$^{14}$ is defined above. The compounds include: 5-iodoindirubin, 5-bromoindirubin, 5-chloroindirubin, 5-fluoroindirubin, 5-methylindirubin, 5-nitroindirubin, 5'-bromoindirubin, 5,5'-dibromoindirubin, indirubin-3'-oxime, indirubin-5-sulfonic acid, and isoindigo. The compounds can be covalently bound to a polyethylene glycol ester or a polyethylene glycol ether.

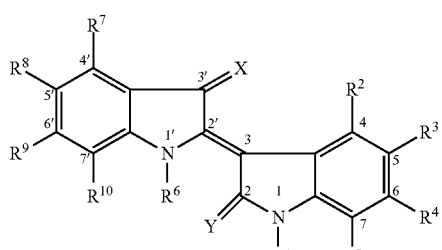
(XXX)

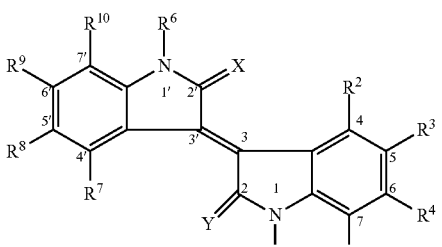
(XXXI)

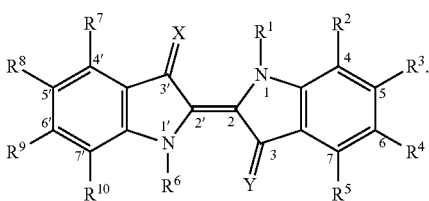
(XXXII)

U.S. Pat. No. 8,349,822 to Yu, incorporated herein by this reference, discloses several indirubin derivatives as GSK-3 antagonists and Wnt canonical pathway agonists, including 6-bromoindirubin-3'-oxime and 1-methyl-6-bromoindirubin-3'-oxime.

United States Patent Application Publication No. 2012/0295948 by Kim et al., incorporated herein by this reference, discloses 5-nitroindirubin-3'-oxime, 5'-bromo-5-nitroindirubin-3'-oxime, 5'-hydroxy-5-nitroindirubin-3'-oxime, 5'-hydroxy-5-chloroindirubin-3'-oxime, 5'-hydroxy-5-fluoroindirubin-3'-oxime, 5'-chloro-5-nitroindirubin-3'-oxime, and 5'-methyl-5-nitroindirubin-3'-oxime. Additional compounds of Formula (XXXIII) are disclosed:

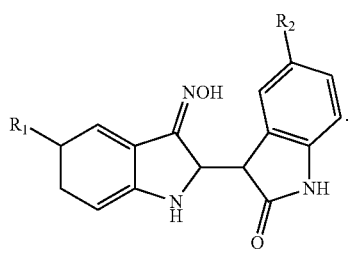
(XXXIII)

wherein: $R_1$ is selected from the group consisting of F, Cl, OH, and $CH_3$; and $R_2$ is selected from the group consisting of F, Cl, and $NO_2$.

United States Patent Application Publication No. 2012/0101042 by Duffield et al., incorporated herein by this reference, discloses indirubin-5-sulfonic acid (2-hydroxyethyl)-amide.

United States Patent Application Publication No. 2012/0053208 by Li et al., incorporated herein by this reference, discloses (3-[3-(3,4-dihydroxybutoxyamino)-1H-indol-2-yl]indol-2-one). This compound is compound E804 from a publication, S. Nam et al., "Indirubin Derivatives Inhibit Stat Signaling and Induce Apoptosis in Human Cancer Cells," *Proc. Natl. Acad. Sci.* 102: 5998-6003 (2005), incorporated herein by this reference, which discloses compounds of Formula (XXXIV):

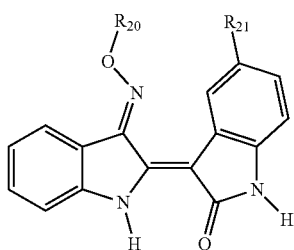
(XXXIV)

with the following alternatives for $R_{20}$ and $R_{21}$: (i) $R_{20}$ is

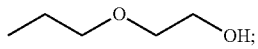

$R_{21}$ is H

(compound E564); (ii) $R_{20}$ is $R_{21}$ is H (compound E565); (iii) $R_{20}$ is

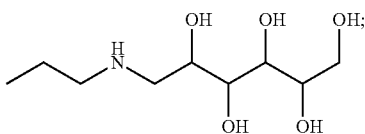

$R_{21}$ is H (compound E673); (iv) $R_{20}$ is $R_{21}$ is I (compound E692); (v) E721: $R_{20}$ is H; $R_{21}$ is COOH (compound E721); (vi) E728: $R_{20}$ is

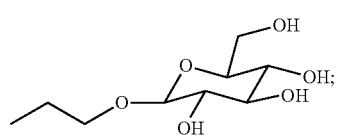

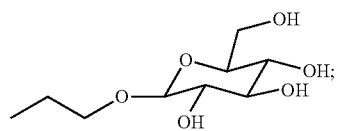

H; R$_{21}$ is OCH$_3$ (compound E728); (vii) R$_{20}$ is R$_{21}$ is OCH$_3$

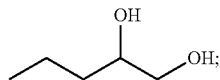

(compound E729); (viii) R$_{20}$ is R$_{21}$ is H (compound E804); (ix) R$_{20}$ is

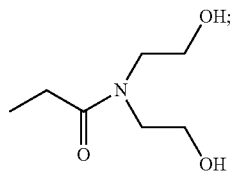

R$_{21}$ is H (compound E805); and R$_{20}$ is

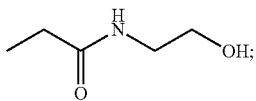

and R$_{21}$ is H (compound E806).

Additional indirubin derivatives and analogs are disclosed in: U.S. Pat. No. 6,989,362 to Bibb et al.; U.S. Pat. No. 7,196,090 to Connolly et al.; U.S. Pat. No. 7,572,923 to Kim et al.; United States Patent Application Publication No. 2006/0204980 by Altieri et al.; United States Patent Application Publication No. 2006/0217368 by Morishita et al.; United States Patent Application Publication No. 2007/0276025 by Meijer et al.; United States Patent Application Publication No. 2010/0016252 by Keana et al.; and United States Patent Application Publication No. 2010/068303 by Wu, all of which are incorporated herein by this reference.

Accordingly, the following indirubin analogs, indirubin derivatives, and derivatives of indirubin analogs are usable in compositions and methods according to the present invention: (1) indirubin 3'-monooxime; (2) indirubin 5-sulfonic acid; (3) 5-chloroindirubin; (4) 1H,1'H-[2,3]biindolylidene-3,2'-dione; (5) 5-fluoro-1H,1'H-[2,3]biindolylidene-3,2'-dione; (6) 1H,1'H-[2,3]biindolylidene-3,2'-dione-3-oxime; (7) 1-acetyl-1H,1'H-[2,3]biindolylidene-3,2'-dione; (8) 5'-nitro-1H,1'H-[2,3]biindolylidene-3,2'-dione; (9) 5'-nitro-1H,1'H-[2,3]biindolylidene-3,2'-dione-3-oxime; (10) 5-fluoro-1H,1'H-[2,3]biindolylidene-3,2'-dione-3-oxime; (11) 5'-methyl-1H,1'H-[2,3]biindolylidene-3,2'-dione-3-oxime; (12) 5'-chloro-1H,1'H-[2,3]biindolylidene-3,2'-dione-3-oxime; (13) 5'-iodo-1H,1'H-[2,3]biindolylidene-3,2'-dione-3-oxime; (14) 5',7'-dimethyl-1H,1'H-[2,3]biindolylidene-3,2'-dione-3-oxime; (15) 5'-chloro-7'-methyl-1H,1'H-[2,3]biindolylidene-3,2'-dione-3-oxime; (16) 5-bromo-1H,1'H-[2,3]biindolylidene-3,2'-dione-3-oxime; (17) 3,2'-dioxo-1,3,1',2'-tetrahydro-[2,3']biindolylidene-5'-sodium sulfonate; (18) 3-hydroxyimino-2'-oxo-,3,1',2'-tetrahydro-[2,3']biindolylidene-5'-sodium sulfonate; (19) 5-bromo-1H,1'H-[2,3]-biindolylidene-3,2'-dione; (20) 5-bromo-5'-nitro-1H,1'H-[2,3']-biindolylidene-3,2'-dione-3-oxime; (21) 5'-methyl-1H,1'H-[2,3]-biindolylidene-3,2'-dione; (22) 5'-chloro-1H,1'H-[2,3]-biindolylidene-3,2'-dione; (23) 5'-iodo-1H,1'H-[2,3']-biindolylidene-3,2'-dione; (24) 5',7'-dimethyl-1H,1'H-[2,3]-biindolylidene-3,2'-dione; (25) 5'-chloro, 7'-methyl-1H,1'H-[2,3]-biindolylidene-3,2'-dione; (26) 5'-amino-1H,1'H-[2,3']-biindolylidene-3,2'-dione; (27) 5-NH-trimethylacetyl-indirubin-3-oxime; (28) 5'-amino-1H,1'H-[2,3]-biindolylidene-3,2'-dione-3-oxime; (29) 6-hydroxy-5-methylindirubin; (30) 6,7'-dihydroxy-5-methylindirubin; (31) 3,4,5-trihydroxy-6-(5-methyl-1H,1'H-[2',3]bis-indolyliden-2,3'-dion-6-yl)-tetrahydropyran-2-carboxylic acid; (32) 3,4,5-trihydroxy-6-(7'-hydroxy-5-methyl-1H1'H-[2',3]bisindolyliden-2,3'-dion-6-yl)-tetrahydropyran-2-carboxylic acid; (33) 5-methylindirubin; (34) indirubin-5-sulfonamide; (35) indirubin-5-sulfonic acid (2-hydroxyethyl)-amide; (36) 5-iodoindirubin-3'-monooxime; (37) 5-fluoroindirubin; (38) 5,5'-dibromoindirubin; (39) 5-nitroindirubin; (40) 5-bromoindirubin; (41) (2'Z,3'E)-6-bromoindirubin-3'-oxime (B10); (42) 5-iodoindirubin; (43) indirubin-5-sulfonic acid-3'-monooxime; (44) 3,4-bis(1-methylindole-3-yl)-1H-pyrrole-2,5-dione; (45) 3-[1-methylindole-3-yl]-4-(1-propylindole-3-yl)-1H-pyrrole-2,5-dione; (46) 3-[1-(3-cyanopropyl)indole-3-yl]-4-(1-methyl-indole-3-yl)-1H-pyrrole-2,5-dione; (47) 3-[1-(3-aminopropyl)-indole-3-yl]-4-(1-methylindole-3-yl)-1H-pyrrole-2,5-dione; (48) 3-[1-(3-carboxypropyl)indole-3-yl]-4-(1-methyl-indole-3-yl)-1H-pyrrole-2,5-dione; (49) 3-[1-(3-carbamoyl-propyl)indole-3-yl]-4-(1-methylindole-3-yl)-1H-pyrrole-2,5-dione; (50) 3-[1-(3-aminopropyl)indole-3-yl]-4-(1-methyl-5-propyloxyindole-3-yl)-1H-pyrrole-2,5-dione; (51) 3-[1-(3-hydroxypropyl)indole-3-yl]-4-(1-methyl-5-phenylindole-3-yl)-1H-pyrrole-2,5-dione; (52) 3-[1-(3-aminopropyl)indole-3-yl]-4-(1-methyl-5-phenylindole-3-yl)-1H-pyrrole-2,5-dione; (53) 3-[1-(3-hydroxypropyl)indole-3-yl]-4-(1-methyl-5-methoxycarbonylindole-3-yl)-1H-pyrrole-2,5-dione; (54) 3-[1-(3-hydroxypropyl)indole-3-yl]-4-(1-methyl-5-nitroindole-3-yl)-1H-pyrrole-2,5-dione; (55) 3-(1-methylindole-3-yl)-4-[1-(3-hydroxypropyl)-5-nitroindole-3-yl]-1H-pyrrole-2,5-dione; (56) 3-(2-chlorophenyl)-4-(1-methylindole-3-yl)-1H-pyrrole-2,5-dione; (57) 3-(2,4-dichlorophenyl)-4-(1-methylindole-3-yl)-1H-pyrrole-2,5-dione; (58) 3-(2-chlorophenyl)-4-[1-(3-hydroxypropyl)indole-3-yl]-1H-pyrrole-2,5-dione; (59) 4-[1-(3-aminopropyl)indole-3-yl]-3-(2-chlorophenyl)-1H-pyrrole-2,5-dione; (60) 7,12-dihydro-indolo[3,2-d][1]benzazepin-6(5H)-one; (61) 2-bromo-7,12-dihydro-indolo[3,2-d][1]benzazepin-6(5H)-one; (62) 9-bromo-7,12-dihydro-indolo[3,2-d][1]benzazepin-6(5H)-one; (63) 9-chloro-7,12-dihydro-indolo[3,2-d][1]benzazepin-6(5H)-one; (64) 11-chloro-7,12-dihydro-indolo[3,2-d][1]benzazepin-6(5H)-one; (65) 10-bromo-7,12-dihydro-indolo[3,2-d][1]benzazepin-6(5H)-one; (66) 8-bromo-6,11-dihydro-thieno[3',2':2,3]azepino-[4,5-b]indol-5(4H)-one; (67) 9-bromo-7,12-dihydro-4-methoxy-indolo[3,2-d][1]benzazepin-6(5H)-one; (68) 9-bromo-7,12-dihydro-4-hydroxy-indolo[3,2-d][1]benzazepin-6(5H)-one; (69) 7,12-dihydro-4-methoxy-indolo[3,2-d][1]benzazepin-6(5H)-one; (70) 9-bromo-7,12-dihydro-2,3-dimethoxy-indolo[3,2-d][1]benzazepin-6(5H)-one; (71) 9-bromo-7,12-dihydro-2,3-di-hydroxy-indolo[3,2-d][1]benzazepin-6(5H)-one; (72) 7,12-dihydro-2,3-dimethoxy-indolo[3,2-d][1]benzazepin-6(5H)-one; (73) 7,12-dihydro-9-trifluormethyl-indolo[3,2-d][1]benzazepin-6(5H)-one; (74) 7,12-dihydro-2,3-dimethoxy-9-trifluoromethyl-indolo[3,2-d][1]benzazepin-6-(5H)-one; (75) 2-bromo-7,12-dihydro-9-trifluoromethyl-indolo[3,2-d][1]benzazepin-6(5H)-one; (76) 9-bromo-7,12-dihydro-indolo[3,2-d][1]benzazepin-6(5H)-thione; (77) 9-bromo-5,12-bis-(t-butyloxycarbonyl)-7,12-dihydro-indolo[3,2-d][1]benzazepin-6(5H)-one; (78) 9-bromo-12-(t-butyloxycarbonyl)-7,12-dihydro-indolo[3,2-d][1]benzazepin-6-(5H)-one; (79) 9-bromo-5,7-bis-(t-butyloxycarbonyl)-7,12-dihydro-indolo[3,2-d][1]benzazepin-6(5H)-one; (80) 9-bromo-5,7,12-tri-(t-butyloxycarbonyl)-7,12-dihydro-indolo[3,2-d][1]benzazepin-6(5H)-one; (81) 9-bromo-7,12-dihydro-5-methyloxycarbonylmethyl-indolo[3,2-d][1]benzazepin-6(5H)-one; (82) 9-bromo-7,12-dihydro-12-methyloxycarbonylmethyl-indolo[3,2-d][1]benzazepin-6(5H)-one; (83) 9-bromo-7,12-dihydro-12-(2-hydroxyethyl)-indolo[3,2-d][1]benzazepin-6-(5H)-one; (84) 2,9-dibromo-7,12-dihydro-indolo[3,2-d][1]benzazepin-6(5H)-one; (85) 8,10-dichloro-7,12-dihydro-indolo-[3,2-d][1]benzazepin-6(5H)-one; (86) 9-cyano-7,12-dihydro-indolo[3,2-d][1]benzazepin-6(5H)-one; (87) 9-bromo-7,12-dihydro-5-methyl-indolo[3,2-d][1]benzazepin-6(5H)-one; (88) 5-benzyl-9-bromo-7,12-dihydro-5-methyl-indolo[3,2-d][1]-benzazepin-6(5H)-one; (89) 9-bromo-7,12-dihydro-12-methyl-indolo-[3,2-d][1]benzazepin-6(5H)-one; (90) 9-bromo-12-ethyl-7,12-dihydro-indolo[3,2-d][1]benzazepin-6(5H)-one; (91) 9-bromo-7,12-dihydro-12-(2-propenyl)-indolo[3,2-d][1]benzazepin-6(5H)-one; (92) 7,12-dihydro-9-methyl-indolo[3,2-d][1]-benzazepin-6(5H)-one; (93) 7,12-dihydro-9-methoxy-indolo[3,2-d][1]benzazepin-6(5H)-one; (94) 9-fluoro-7,12-dihydro-12-(2-propenyl)-indolo[3,2-d][1]benzazepin-6(5H)-one; (95) 11-bromo-7,12-dihydro-indolo[3,2-d][1]benzazepin-6(5H)-one; (96) 9-bromo-7,12-dihydro-2-(methyliminoamine)-indolo[3,2-d][1]benzazepin-6(5H)-one; (97) 9-bromo-7,12-dihydro-2-(carboxylic acid)indolo[3,2-d][1]benzazepin-6(5H)-one; (98) 9-bromo-7,12-dihydro-10-hydroxy-indolo[3,2-d][1]benzazepin-6(5H)-one; (99) 9-bromo-7,12-dihydro-11-hydroxymethyl-indolo[3,2-d][1]-benzazepin-6(5H)-one; (100) 7,12-dihydro-4-hydroxy-indolo[3,2-d][1]benzazepin-6(5H)-one; (101) 7,12-dihydro-2,3-dihydroxy-indolo[3,2-d][1]benzazepin-6(5H)-one; (102) 2,3-dimethoxy-9-nitro-7,12-dihydro-indolo[3,2-d][1]benzazepin-6(5H)-one; (103) 9-cyano-7,12-dihydro-indolo[3,2-d][1]benzazepin-6(5H)-one; (104) 2,3-dimethoxy-9-cyano-7,12-dihydro-indolo[3,2-d][1]benzazepin-6(5H)-one; (105) 9-nitro-7,12-dihydro-indolo[3,2-d][1]benzazepin-6(5H)-one; (106) 3-(6-oxo-9-trifluoromethyl-5,6,7,12-tetrahydro-indolo[3,2-d][1]benzazepin-2-yl)-propionitrile; (107) 2-bromo-9-nitro-7,12-dihydro-indolo[3,2-d][1]benzazepin-6(5H)-one; (108) 3-(6-oxo-9-trifluoromethyl-5,6,7,12-tetrahydro-indolo[3,2-d][1]benzazepin-2-yl)acrylonitrile; (109) 2-(3-hydroxy-1-propinyl)-9-trifluoromethyl-7,12-dihydro-indolo[3,2-d][1]benzazepin-6(5H)-one; (110) 2-iodo-9-bromo-7,12-dihydro-indolo[3,2-d][1]benzazepin-6(5H)-one; (111) 2-(3-oxo-1-butenyl)-9-trifluoromethyl-7,12-tetrahydro-indolo[3,2-d][1]benzazepin-6(5H)-one; (112) 8-chloro-6,11-dihydro-thieno[3',2':2,3]azepino[4,5-b]indol-5(4H)-one; (113) 2-iodo-9-trifluoromethyl-7,12-dihydro-indolo[3,2-d][1]-benzazepin-6(5H)-one; (114) 7,12-dihydro-pyrido[3',2':4,5]-pyrrolo[3,2-d][1]benzazepin-6(5H)-one; (115) 11-methyl-7,12-dihydro-indolo[3,2-d][1]-benzazepin-6(5H)-one; (116) 2-[2-(1-hydroxycyclohexyl)-ethinyl]-9-trifluoromethyl-7,12-dihydro-indolo-[3,2-d][1]benzazepin-6(5H)-one; (117) 2-cyano-7,12-dihydro-indolo[3,2-d][1]benzazepin-6(5H)-one; (118) 2-iodo-7,12-dihydro-indolo[3,2-d][1]benzazepin-6(5H)-one; (119) 11-ethyl-7,12-dihydro-indolo[3,2-d][1]benzazepin-6(5H)-one; (120) 8-methyl-6,11-dihydro-thieno[3',2':2,3]azepino[4,5-b]indol-5(4H)-one; (121) 3-(6-oxo-9-trifluoromethyl-5,6,7,12-tetrahydro-indolo[3,2-d][1]benzazepin-2-yl)acrylic acid methyl ester; (122) 9-cyano-7,12-dihydro-indolo[3,2-d][1]benzazepin-6(5H)-one; (123) 9-bromo-7,12-dihydro-2,3-dimethoxy-indolo[3,2-d][1]benzazepin-6(5H)-one; (124) 2-bromo-7,12-dihydro-9-trifluoromethyl-indolo[3,2-d][1]benzazepin-6(5H)-one; (125) 7,12-dihydro-2,3-dimethoxy-9-trifluoromethyl-indolo[3,2-d][1]benzazepin-6(5H)-one; (126) 2,9-dibromo-7,12-dihydro-indolo[3,2-d][1]-benzazepin-6(5H)-one; (127) 7,12-dihydro-9-trifluoromethyl-indolo-[3,2-d][1]benzazepin-6(5H)-one; (128) 9-chloro-7,12-dihydro-indolo[3,2-d][1]benzazepin-6(5H)-one; (129) 8-bromo-6,11-dihydro-thieno[3',2':2,3]azepino[4,5-b]indole-5(4H)-one; (130) 7,12-dihydro-9-methoxy-indolo[3,2-d][1]benzazepin-6(5H)-one; (131) 10-bromo-7,12-dihydro-indolo[3,2-d][1]benzazepin-6(5H)-one; (132) 11-bromo-7,12-dihydro-indolo[3,2-d][1]-benzazepin-6(5H)-one; (133) 11-chloro-7,12-dihydro-indolo[3,2-d]-[1]benzazepin-6(5H)-one; (134) 9-fluoro-7,12-dihydro-indolo-[3,2-d][1]benzazepin-6(5H)-one; (135) 9-methyl-7,12-dihydro-indolo[3,2-d][1]benzazepin-6(5H)-one; (136) 9-bromo-7,12-dihydro-indolo[3,2-d][1]benzazepin-6(5H)-thione; (137) 8,10-dichloro-7,12-dihydro-indolo[3,2-d][1]benzazepin-6(5H)-one; (138) 9-bromo-7,12-dihydro-12-(2-hydroxyethyl)-indolo[3,2-d][1]-benzazepin-6(5H)-one; (139) 9-bromo-7,12-dihydro-2,3-dihydroxy-indolo[3,2-d][1]benzazepin-6(5H)-one; (140) 2-bromo-7,12-dihydro-indolo[3,2-d][1]benzazepin-6(5H)-one; (141) 7,12-dihydro-2,3-dimethoxy-indolo[3,2-d][1]benzazepin-6(5H)-one; (142) 9-bromo-7,12-dihydro-12-methyl-indolo[3,2-d][1]benzazepin-6(5H)-one; (143) 9-bromo-7,12-dihydro-5-methyloxycarbonylmethyl-indolo[3,2-d][1]benzazepin-6(5H)-one; (144) 7,12-dihydro-indolo[3,2-d][1]benzazepin-6(5H)-one; (145) 9-cyano-7,12-dihydro-indolo[3,2-d][1]benzazepin-6(5H)-one; (146) 9-bromo-7,12-dihydro-2,3-dimethoxy-indolo[3,2-d][1]benzazepin-6(5H)-one; (147) 2-bromo-7,12-dihydro-9-trifluoromethyl-indolo[3,2-d][1]benzazepin-6(5H)-one; (148) 7,12-dihydro-2,3-dimethoxy-9-trifluoromethyl-indolo[3,2-d][1]benzazepin-6(5H)-one; (149) 2,9-dibromo-7,12-dihydro-indolo[3,2-d][1]-benzazepin-6(5H)-one; (150) 7,12-dihydro-9-trifluoromethyl-indolo-[3,2-d][1]benzazepin-6(5H)-one; (151) 9-chloro-7,12-dihydro-indolo[3,2-d][1]benzazepin-6(5H)-one; (152) 8-bromo-6,11-dihydro-thieno[3',2':2,3]azepino[4,5-b]indol-5(4H)-one; (153) 7,12-dihydro-9-methoxy-indolo[3,2-d][1]benzazepin-6(5H)-one; (154) 9-bromo-7,12-dihydro-indolo[3,2-d][1]benzazepin-6(5H)-one; (155) 9-chloro-7,12-dihydro-indolo[3,2-d][1]benzazepin-6(5H)-one; (156) 11-chloro-7,12-dihydro-indolo[3,2-d][1]benzazepin-6(5H)-one; (157) 10-bromo-7,12-dihydro-indolo[3,2-d][1]benzazepin-6(5H)-one; (158) 8-bromo-6,11-dihydro-thieno[3',2':2,3]azepino-[4,5-b]indol-5(4H)-one; (159) 9-bromo-7,12-dihydro-4-methoxy-indolo[3,2-d][1]benzazepin-6(5H)-one; (160) 9-bromo-7,12-dihydro-4-hydroxy-indolo[3,2-d][1]benzazepin-6(5H)-one; (161) 7,12-dihydro-4-methoxy-indolo[3,2-d][1]benzazepin-6(5H)-one; (162) 9-bromo-7,12-dihydro-2,3-dimethoxy-indolo[3,2-d][1]benzazepin-6(5H)-one; (163) 9-bromo-7,12-dihydro-2,3-di-hydroxy-indolo[3,2-d][1]benzazepin-6(5H)-one; (164) 7,12-dihydro-2,3-dimethoxy-indolo[3,2-d][1]benzazepin-6(5H)-one; (165) 7,12-dihydro-9-trifluormethyl-indolo[3,2-d][1]benzazepin-6(5H)-one; (166) 7,12-dihydro-2,3-dimethoxy-9-trifluoromethyl-indolo[3,2-d][1]benzazepin-6-(5H)-one; (167) 2-bromo-7,12-dihydro-9-trifluoromethyl-indolo[3,2-d][1]benzazepin-6(5H)-one; (168) 9-bromo-7,12-dihydro-indolo[3,2-d][1]benzazepin-6(5H)-thione; (169) 9-bromo-5,12-bis-(t-butyloxycarbonyl)-7,12-dihydro-indolo[3,2-d][1]benzazepin-6(5H)-one; (170) 9-bromo-12-(t-butyloxycarbonyl)-7,12-dihydro-indolo[3,2-d][1]benzazepin-6-(5H)-one; (171) 9-bromo-5,7-bis-(t-butyloxycarbonyl)-7,12-dihydro-indolo[3,2-d][1]benzazepin-6(5H)-one; (172) 9-bromo-5,7,12-tri-(t-butyloxycarbonyl)-7,12-dihydro-indolo[3,2-d][1]benzazepin-6(5H)-one; (173) 9-bromo-7,12-dihydro-5- methyloxycarbonylmethyl-indolo[3,2-d][1]benzazepin-6(5H)-one; (174) 9-bromo-7,12-dihydro-12-methyloxycarbonylmethyl-indolo[3,2-d][1]benzazepin-6(5H)-one; (175) 9-bromo-7,12-dihydro-12-(2-hydroxyethyl)-indolo[3,2-d][1]benzazepin-6-(5H)-one: (176) 2,9-dibromo-7,12-dihydro-indolo[3,2-d][1]benzazepin-6(5H)-one; (177) 8,10-dichloro-7,12-dihydro-indolo-[3,2-d][1]benzazepin-6(5H)-one: (178) 9-cyano-7,12-dihydro-indolo[3,2-d][1]benzazepin-6(5H)-one: (179) 9-bromo-7,12-dihydro-5-methyl-indolo[3,2-d][1]benzazepin-6(5H)-one; (180) 5-benzyl-9-bromo-7,12-dihydro-5-methyl-indolo[3,2-d][1]-benzazepin-6(5H)-one; (181) 9-bromo-7,12-dihydro-12-methyl-indolo-[3,2-d][1]benzazepin-6(5H)-one; (182) 9-bromo-12-ethyl-7,12-dihydro-indolo[3,2-d][1]benzazepin-6(5H)-one; (183) 9-bromo-7,12-dihydro-12-(2-propenyl)-indolo[3,2-d][1]benzazepin-6(5H)-one; (184) 7,12-dihydro-9-methyl-indolo[3,2-d][1]-benzazepin-6(5H)-one; (185) 7,12-dihydro-9-methoxy-indolo[3,2-d][1]benzazepin-6(5H)-one; (186) 9-fluoro-7,12-dihydro-12-(2-propenyl)-indolo[3,2-d][1]benzazepin-6(5H)-one; (187) 11-bromo-7,12-dihydro-indolo[3,2-d][1]benzazepin-6(5H)-one; (188) 9-bromo-7,12-dihydro-2-(methyliminoamine)-indolo[3,2-d][1]benzazepin-6(5H)-one; (189) 9-bromo-7,12-dihydro-2-(carboxylic acid)-indolo[3,2-d][1]benzazepin-6(5H)-one; (190) 9-bromo-7,12-dihydro-10-hydroxy-indolo[3,2-d][1]benzazepin-6(5H)-one: (191) 9-bromo-7,12-dihydro-11-hydroxymethyl-indolo[3,2-d][1]-benzazepin-6(5H)-one: (192) 7,12-dihydro-4-hydroxy-indolo[3,2-d][1]benzazepin-6(5H)-one; (193) 7,12-dihydro-2,3-dihydroxy-indolo[3,2-d][1]benzazepin-6(5H)-one; (194) 2,3-dimethoxy-9-nitro-7,12-dihydro-indolo[3,2-d][1]benzazepin-6(5H)-one; (195) 9-cyano-7,12-dihydro-indolo[3,2-d][1]benzazepin-6(5H)-one; (196) 2,3-dimethoxy-9-cyano-7,12-dihydro-indolo[3,2-d][1]benzazepin-6(5H)-one; (197) 9-nitro-7,12-dihydro-indolo[3,2-d][1]benzazepin-6(5H)-one; (198) 3-(6-oxo-9-trifluoromethyl-5,6,7,12-tetrahydro-indolo[3,2-d][1]benzazepin-2-yl)-propionitrile; (199) 2-bromo-9-nitro-7,12-dihydro-indolo[3,2-d][1]benzazepin-6(5H)-one; (200) 3-(6-oxo-9-trifluoromethyl-5,6,7,12-tetrahydro-indolo[3,2-d][1]benzazepin-2-yl)acrylonitrile; (201) 2-(3-hydroxy-1-propinyl)-9-trifluoromethyl-7,12-dihydro-indolo[3,2-d][1]benzazepin-6(5H)-one; (202) 2-iodo-9-bromo-7,12-dihydro-indolo[3,2-d][1]benzazepin-6(5H)-one; (203) 2-(3-oxo-1-butenyl)-9-trifluoromethyl-7,12-tetrahydro-indolo[3,2-d][1]benzazepin-6(5H)-one; (204) 8-chloro-6,11-dihydro-thieno[3',2':2,3]azepino[4,5-b]indol-5(4H)-one; (205) 2-iodo-9-trifluoromethyl-7,12-dihydro-indolo[3,2-d][1]-benzazepin-6(5H)-one; (206) 7,12-dihydro-pyrido[3',2':4,5]-pyrrolo[3,2-d][1]benzazepin-6(5H)-one; (207) 11-methyl-7,12-dihydro-indolo[3,2-d][1]-benzazepin-6(5H)-one; (208) 2-[2-(1-hydroxycyclohexyl)-ethinyl]-9-trifluoromethyl-7,12-dihydro-indolo-[3,2-d][1]benzazepin-6(5H)-one; (209) 2-cyano-7,12-dihydro-indolo[3,2-d][1]benzazepin-6(5H)-one; (210) 2-iodo-7,12-dihydro-indolo[3,2-d][1]benzazepin-6(5H)-one; (211) 11-ethyl-7,12-dihydro-indolo[3,2-d][1]benzazepin-6(5H)-one; (212) 8-methyl-6,11-dihydro-thieno[3',2':2,3]azepino[4,5-b]indol-5(4H)-one; (213) 3-(6-oxo-9-trifluoromethyl-5,6,7,12-tetrahydro-indolo[3,2-d][1]benzazepin-2-yl)acrylic acid methyl ester; (214) 9-cyano-7,12-dihydro-indolo[3,2-d][1]benzazepin-6(5H)-one; (215) 9-bromo-7,12-dihydro-2,3-dimethoxy-indolo[3,2-d][1]benzazepin-6(5H)-one; (216) 2-bromo-7,12-dihydro-9-trifluoromethyl-indolo[3,2-d][1]benzazepin-6(5H)-one; (217) 7,12-dihydro-2,3-dimethoxy-9-trifluoromethyl-indolo[3,2-d][1]benzazepin-6(5H)-one; (218) 2,9-dibromo-7,12-dihydro-indolo[3,2-d][1]-benzazepin-6(5H)-one; (219) 7,12-dihydro-9-trifluoromethyl-indolo-[3,2-d][1]benzazepin-6(5H)-one; (220) 9-chloro-7,12-dihydro-indolo[3,2-d][1]benzazepin-6(5H)-one; (221) 8-bromo-6,11-dihydro-thieno[3',2':2,3]azepino[4,5-b]indole-5(4H)-one: (222) 7,12-dihydro-9-methoxy-indolo[3,2-d][1]benzazepin-6(5H)-one; (223) 10-bromo-7,12-dihydro-indolo[3,2-d][1]benzazepin-6(5H)-one; (224) 11-bromo-7,12-dihydro-indolo[3,2-d][1]-benzazepin-6(5H)-one; (225) 11-chloro-7,12-dihydro-indolo[3,2-d][1]benzazepin-6(5H)-one: (226) 9-fluoro-7,12-dihydro-indolo-[3,2-d][1]benzazepin-6(5H)-one; (227) 9-methyl-7,12-dihydro-indolo[3,2-d][1]benzazepin-6(5H)-one; (228) 9-bromo-7,12-dihydro-indolo[3,2-d][1]benzazepin-6(5H)-thione; (229) 8,10-dichloro-7,12-dihydro-indolo[3,2-d][1]benzazepin-6(5H)-one: (230) 9-bromo-7,12-dihydro-12-(2-hydroxyethyl)-indolo[3,2-d][1]-benzazepin-6(5H)-one; (231) 9-bromo-7,12-dihydro-2,3-dihydroxy-indolo[3,2-d][1]benzazepin-6(5H)-one; (232) 2-bromo-7,12-dihydro-indolo[3,2-d][1]benzazepin-6(5H)-one; (233) 7,12-dihydro-2,3-dimethoxy-indolo[3,2-d][1]benzazepin-6(5H)-one; (234) 9-bromo-7,12-dihydro-12-methyl-indolo[3,2-d][1]benzazepin-6(5H)-one; (235) 9-bromo-7,12-dihydro-5-methyloxycarbonylmethyl-indolo[3,2-d][1]benzazepin-6(5H)-one; (236) 7,12-dihydro-indolo[3,2-d][1]benzazepin-6(5H)-one; (237) 9-cyano-7,12-dihydro-indolo[3,2-d][1]benzazepin-6(5H)-one; (238) 9-bromo-7,12-dihydro-2,3-dimethoxy-indolo[3,2-d][1]benzazepin-6(5H)-one; (239) 2-bromo-7,12-dihydro-9-trifluoromethyl-indolo[3,2-d][1]benzazepin-6(5H)-one; (240) 7,12-dihydro-2,3-dimethoxy-9-trifluoromethyl-indolo[3,2-d][1]benzazepin-6(5H)-one; (241) 2,9-dibromo-7,12-dihydro-indolo[3,2-d][1]-benzazepin-6(5H)-one; (242) 7,12-dihydro-9-trifluormethyl-indolo-[3,2-d][1]benzazepin-6(5H)-one; (243) 9-chloro-7,12-dihydro-indolo[3,2-d][1]benzazepin-6(5H)-one: (244) 8-bromo-6,11-dihydro-thieno[3',2':2,3]azepino[4,5-b]indol-5(4H)-one; (245) 7,12-dihydro-9-methoxy-indolo[3,2-d][1]benzazepin-6(5H)-one; (246) 9-bromo-7,12-dihydro-indolo[3,2-d][1]benzazepin-6(5H)-one (247) 6-bromoindirubin; (248) 6,6'-dibromoindirubin-3-oxime; (249) 6-bromoindirubin-3'-methoxime; (250) 6-bromo-5-methyl-indirubin; (251) 6-bromo-5-aminoindirubin; (252) 6-bromo-5-methyl-indirubin-3'-oxime; (253) 6-bromo-indirubin-3'-acetoxime; (254) 5-amino-indirubin; (255) 5-amino-indirubin-3'-oxime; (256) 1-methylindirubin; (257)N-1-methylisoindigo; (258) indirubin-5-sulfone-(2-hydroxyethyl)amide; (259) 5-ethyl-indirubin; (260) 5-isopropylindirubin; (261) 5-n-propylindirubin; (262) 5-carboxymethylindirubin; (263) 5-[2-(piperazin-1-yl)-ethan-2-on-1-yl]indirubin; (264) 5-[2-(morpholin-1-yl)-ethan-2-on-1-yl]indirubin; (265)N-(2-aminoethyl)-2-[3-(3'-oxo-(2'H,3'H)indol-2'-ylidene)-(2H,3H)indol-2-one-5-yl]acetamide; (266)N-methyl-2-[3-(3'-oxo-(2'H,3'H)indol-2'-ylidene)-(2H,3H)indol-2-one-5-yl]acetamide; (267) N,N-dimethyl-2-[3-(3'-oxo-(2'H,3'H)indol-2'-ylidene)-(2H,3H)indol-2-one-5-yl]acetamide; (268) 2-{2-[3'-oxo-(2'H,3'H)indol-2'-ylidene)-(2H,3H)indol-2-one-5-yl]-acetylamino}-acetic acid; (269) methyl-2-{2-[3'-oxo-(2'H,3'H)indol-2'-ylidene)-(2H,3H)indol-2-one-5-yl]-acetylamino}-acetate; (270) [3'-oxo-(2'H,3'H)indol-2'-ylidene)-(2H,3H)indol-2-one-5-yl]-methylphosphonic acid; (271) diethyl-[3'-oxo-(2'H,3'H)indol-2'-ylidene)-(2H,3H)indol-2-one-5-yl]-methylphosphonate; (272) 5-acetylaminoindirubin; (273) [3'-oxo-(2'H,3'H)indol-2'-ylidene)-(2H,3H)indol-2-one-5-yl]-succinamic acid; (274) 2-amino-N-[3'-oxo-(2'H,3'H)indol-2'-ylidene)-(2H,3H)indol-2-one-5-yl]-acetamide; (275) 2-amino-N-[3'-oxo-(2'H,3'H)indol-2'-ylidene)-(2H,3H)indol-2-one-5-yl]-propionamide; (276) 5-(2-aminoethyl)-aminoindirubin; (277) 5-(2-hydroxyethyl)-aminoindirubin; (278) indirubin-5-sulfonic acid-(piperazin-1-yl-amide); (279) indirubin-5-sulfonic acid-(morpholin-1-yl-amide); (280) methyl-2-{[3'-oxo-(2'H,3'H)indol-2'-ylidene)-(2H,3H)indol-2-one-5-yl]-sulfonamidyl}-acetate; (281) 5-methylindirubin-3'-monooxime; (282) 5-ethylindirubin-3'-monooxime; (283) 5-isopropylindirubin-3'-monooxime; (284) 5-aminoindirubin-3'-monooxime; (285) 5-acetylaminoindirubin-3'-monooxime; (286) 2-amino-N-[3-(3'-hydroxyimino)(2'H,3'H)indol-2'-ylidene)-(2H,3H)indol-2-one-5-yl]-acetamide; (287) 3-[3'-(iminooxy-O-(2-hydroxyethyl)-(2'H,3'H)indol-2'-ylidene]-(2H,3H)indol-2-one; (288) 3-[3'-(iminooxy-O-(3-hydroxypropyl)-(2'H,3'H)indol-2'-ylidene]-(2H,3H)indol-2-one; (289) 3-[3'-(iminooxy-O-(2-(2-hydroxyethoxy)ethyl)-(2'H,3'H)indol-2'-ylidene]-(2H,3H)indol-2-one; (290) 3-[3'-(iminooxy-O-(2-(2-hydroxy-2-methyl)propyl)-(2'H,3'H)indol-2'-ylidene]-(2H,3H)indol-2-one; (291) 2-{O-[2'-(2-oxo-(2H,3H)indol-3-ylidene)-2'H,3'H-indol-3'-ylidene]aminoxy}acetic acid sodium salt; (292) 3-{O-[2'-(2-oxo-(2H,3H)indol-3-ylidene)-2'H,3'H-indol-3'-ylidene]aminoxy}propionic acid sodium salt; (293) 4-{O-[2'-(2-oxo-(2H,3H)indol-3-ylidene)-2'H,3'H-indol-3'-ylidene]aminoxy}butyric acid sodium salt; (294) 5-{O-[2'-(2-oxo-(2H,3H)indol-3-ylidene)-2'H,3'H-indol-3'-ylidene]aminoxy}pentanoic acid sodium salt; (295) 3-[3'-iminooxy-O-carbethoxy)-(2'H,3'H)-indol-2'-ylidene]-(2H,3H)indol-2-one; (296) ethyl-2-{O-2'-(2-oxo-(2H,3H)indol-3-ylidene-(2'H,3'H)-indol-3'-ylidene]-aminooxy}-acetate; (297) 3-[3'-iminooxy-O—(N,N)-dimethylcarbamoyl)]-(2'H,3'H)-indol-2'-ylidene]-(2H,3H)indol-2-one); (298) 3'-oximido-7-azaindirubin; (299) 7-azaindirubin-3'-oxime ether; (300) 1-methyl-5-azaindirubin; (301) 1-benzyl-5'-chloro-5-azaindirubin; (302) 1-butyl-5-azaindirubin-3'-oxime; (303) 1-butyl-5-azaindirubin-3'-oxime O-methyl ether; (304) 1-isopropyl-5-azaisoindigo; (305) 1-methyl-7-azaindirubin; (306) 1-benzyl-5'-bromo-7-azaindirubin; (307) 1-butyl-7-azaindirubin-3'-oxime; (308) 1-butyl-7-azaindirubin-3'-oxime O-methyl ether; (309) 1-isopropyl-7-azaisoindigo; (310) 2-methyl-7-[1,2-dihydro-2-oxo-3H-indol-(Z)-3-ylidene]-4,5,6,7-tetrahydro-1H-indole-3-carboxylic acid; (311) 2-methyl-7-[1,2-dihydro-5-fluoro-2-oxo-3H-indol-(Z)-3-ylidene]-4,5,6,7-tetrahydro-1H-indole-3-carboxylic acid; (312) 2-methyl-7-[1,2-dihydro-5-chloro-2-oxo-3H-indol-(Z)-3-ylidene]-4,5,6,7-tetrahydro-1H-indole-3-carboxylic acid; (313) 2-methyl-7-[1,2-dihydro-5-methyl-2-oxo-3H-indol-(Z)-3-ylidene]-4,5,6,7-tetrahydro-1H-indole-3-carboxylic acid; (314) ethyl 2-methyl-7-[1,2-dihydro-5-fluoro-2-oxo-3H-indol-(Z)-3-ylidene]-4,5,6,7-tetrahydro-1H-indole-3-carboxylate; (315)N-(2-(diethylamino)ethyl)-2-methyl-7-[1,2-dihydro-5-fluoro-2-oxo-3H-indol-(Z)-3-ylidene]-4,5,6,7-tetrahydro-1H-indole-3-carboxamide; (316)N-(2-(diethylamino)ethyl)-2-methyl-7-[1,2-dihydro-5-chloro-2-oxo-3H-indol-(Z)-3-ylidene]-4,5,6,7-tetrahydro-1H-indole-3-carboxamide; (317)N-(2-(diethylamino)ethyl)-2-methyl-7-[1,2-dihydro-5-methyl-2-oxo-3H-indol-(Z)-3-ylidene]-4,5,6,7-tetrahydro-1H-indole-3-carboxamide; (318)N-(2-(diethylamino)ethyl)-2-methyl-7-[1,2-dihydro-2-oxo-3H-indol-(Z)-3-ylidene]-4,5,6,7-tetrahydro-1H-indole-3-carboxamide; (319)N-(2-(dimethylamino)ethyl)-2-methyl-7-[1,2-dihydro-5-fluoro-2-oxo-3H-indo-I—(Z)-3-ylidene]-4,5,6,7-tetrahydro-1H-indole-3-carboxamide; (320)N-(3-(dimethylamino)propyl)-2-methyl-7-[1,2-dihydro-5-chloro-2-oxo-3H-indol-(Z)-3-ylidene]-4,5,6,7-tetrahydro-1H-indole-3-carboxamide; (321)N-(2-hydroxyethyl)-2-methyl-7-[1,2-dihydro-2-oxo-3H-indol-(Z)-3-ylidene]-4,5,6,7-tetrahydro-1H-indole-3-carboxamide; (322)N-(2-hydroxyethyl)-2-methyl-7-[1,2-dihydro-5-fluoro-2-oxo-3H-indol-(Z)-3-ylidene]-4,5,6,7-tetrahydro-1H-indole-3-carboxamide; (323) 2-methyl-3-(morpholine-4-carbonyl)-7-[1,2-dihydro-5-fluoro-2-oxo-3H-indol-(Z)-3-ylidene]-4,5,6,7-tetrahydro-1H-indole; (324) 2-methyl-3-(morpholine-4-carbonyl)-7-[1,2-dihydro-5-chloro-2-oxo-3H-indol-(Z)-3-ylidene]-4,5,6,7-tetrahydro-1H-indole; (325) 2-methyl-3-(morpholine-4-carbonyl)-7-[1,2-dihydro-2-oxo-3H-indol-(Z)-3-ylidene]-4,5,6,7-tetrahydro-1H-indole; (326) 2-methyl-3-(4-methylpiperazine-1-carbonyl)-7-[1,2-dihydro-2-oxo-3H-indol-(Z)-3-ylidene]-4,5,6,7-tetrahydro-1H-indole; (327) 2-methyl-3-(4-methylpiperazine-1-carbonyl)-7-[1,2-dihydro-5-fluoro-2-oxo-3H-indol-(Z)-3-ylidene]-4,5,6,7-tetrahydro-1H-indole; (328) N,N,2-trimethyl-7-[1,2-dihydro-2-oxo-3H-indol-(Z)-3-ylidene]-4,5,6,7-tetrahydro-1H-indole-3-carboxamide; (329)N-(2-morpholinoethyl)-2-methyl-7-[1,2-dihydro-5-methyl-2-oxo-3H-indol-(Z)-3-ylidene]-4,5,6,7-tetrahydro-1H-indole-3-carboxamide; (330)N-(2-morpholinoethyl)-2-methyl-7-[1,2-dihydro-5-methyl-2-oxo-3H-indol-(Z)-3-ylidene]-4,5,6,7-tetrahydro-1H-indole-3-carboxamide; (331)N-(2-morpholinoethyl)-2-methyl-7-[1,2-dihydro-2-oxo-3H-indol-(Z)-3-ylidene]-4,5,6,7-tetrahydro-1H-indole-3-carboxamide; (332)N-(2-morpholinoethyl)-2-methyl-7-[1,2-dihydro-5-chloro-2-oxo-3H-indol-(Z)-3-ylidene]-4,5,6,7-tetrahydro-1H-indole-3-carboxamide; (333)N-(2-morpholinoethyl)-2-methyl-7-[1,2-dihydro-5-fluoro-2-oxo-3H-indol-(Z)-3-ylidene]-4,5,6,7-tetrahydro-1H-indole-3-carboxamide; (334)N-(3-morpholinopropyl)-2-methyl-7-[1,2-dihydro-5-fluoro-2-oxo-3H-indol-(Z)-3-ylidene]-4,5,6,7-tetrahydro-1H-indole-3-carboxamide; (335)N-(3-morpholinopropyl)-2-methyl-7-[1,2-dihydro-5-bromo-2-oxo-3H-indol-(Z)-3-ylidene]-4,5,6,7-tetrahydro-1H-indole-3-carboxamide; (336)N-(2-morpholinoethyl)-2-methyl-7-[1,2-dihydro-7-fluoro-2-oxo-3H-indol-(Z)-3-ylidene]-4,5,6,7-tetrahydro-1H-indole-3-carboxamide; (337)N-(2-(pyrrolidin-1-yl)ethyl)-2-methyl-7-[1,2-dihydro-2-oxo-3H-indol-(Z)-3-ylidene]-4,5,6,7-tetrahydro-1H-indole-3-carboxamide; (338)N-(2-(piperidin-1-yl)ethyl)-2-methyl-7-[1,2-dihydro-2-oxo-3H-indol-(Z)-3-ylidene]-4,5,6,7-tetrahydro-1H-indole-3-carboxamide; (339)N-(2-(piperidin-1-yl)ethyl)-2-methyl-7-[1,2-dihydro-5-fluoro-2-oxo-3H-indol-(Z)-3-ylidene]-4,5,6,7-tetrahydro-1H-indole-3-carboxamide; (340)N-(2-(pyrrolidin-1-yl)ethyl)-2-methyl-7-[1,2-dihydro-5-fluoro-2-oxo-3H-indol-(Z)-3-ylidene]-4,5,6,7-tetrahydro-1H-indole-3-carboxamide; (341)N-(3-(pyrrolidin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide; (342)N-(3-(4-methylpiperazin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide; (343)N-(3-(pyrrolidin-1-yl)propyl)-2-methyl-7-[1,2-dihydro-5-bromo-2-oxo-3H-indol-(Z)-3-ylidene]-4,5,6,7-tetrahydro-1H-indole-3-carboxamide; (344)N-(2-(piperidin-1-yl)ethyl)-2-methyl-7-[1,2-dihydro-6-chloro-2-oxo-3H-indol-(Z)-3-ylidene]-4,5,6,7-tetrahydro-1H-indole-3-carboxamide; (345)N-(3-(pyrrolidin-1-yl)propyl)-2-methyl-7-[1,2-dihydro-4-fluoro-2-oxo-3H-indol-(Z)-3-ylidene]-4,5,6,7-tetrahydro-1H-indole-3-carboxamide; (346)N-(3-(pyrrolidin-1-yl)propyl)-2-methyl-7-[1,2-dihydro-7-fluoro-2-oxo-3H-indol-(Z)-3-ylidene]-4,5,6,7-tetrahydro-1H-indole-3-carboxamide; (347) N-(2-(diethylamino)ethyl)-2-methyl-7-[1,2-dihydro-5,7-dimethyl-2-oxo-3H-indol-(Z)-3-ylidene]-4,5,6,7-tetrahydro-1H-indole-3-carboxamide; (348)N-(2-(diethylamino)ethyl)-2-methyl-7-[N-isopropyl-1,2-dihydro-2-oxo-3H-indol-5-sulfonamide-(Z)-3-ylidene]-4,5,6,7-tetrahydro-1H-indole-3-carboxamide; (349) N-(2-(diethylamino)ethyl)-2-methyl-7-[1,2-dihydro-5-bromo-2-oxo-3H-indol-(Z)-3-ylidene]-4,5, 6,7-tetrahydro-1H-indole-3-carboxamide; (350)N-(2-(diethylamino)ethyl)-2-methyl-7-[1,2-dihydro-5-nitro-2-oxo-3H-indol-(Z)-3-ylidene]-4,5,6,7-tetrahydro-1H-indole-3-carboxamide; (351)N-(3-(dimethylamino)propyl)-2-methyl-7-[1,2-dihydro-5-fluoro-2-oxo-3H-indol-(Z)-3-ylidene]-4,5,6,7-tetrahydro-1H-indole-3-carboxamide; (352)N-(2-(diethylamino)ethyl)-2-methyl-7-[1,2-dihydro-5-methoxycarbonyl-2-oxo-3H-indol-(Z)-3-ylidene]-4,5,6,7-tetrahydro-1H-indole-3-carboxamide; (353)N-(2-(diethylamino)ethyl)-2-methyl-7-[1,2-dihydro-7-fluoro-2-oxo-3H-indol-(Z)-3-ylidene]-4,5,6,7-tetrahydro-1H-indole-3-carboxamide; (354)N-(2-(diethylamino)ethyl)-2-methyl-7-[N-(4-fluorophenyl)-1,2-dihydro-2-oxo-3H-indol-5-sulfonamide-(Z)-3-ylidene]-4,5,6,7-tetrahydro-1H-indole-3-carboxamide); (355)N-(2-(diethylamino)ethyl)-2-methyl-7-[5-(piperidin-1-ylsulfonyl)-1,2-dihydro-2-oxo-3H-indol-5-sulfonamide-(Z)-3-ylidene]-4,5,6,7-tetrahydro-1H-indole-3-carboxamide; (356)N-(3-(diethylamino)propyl)-2-methyl-7-[1,2-dihydro-5-fluoro-2-oxo-3H-indo-1-(Z)-3-ylidene]-4,5,6,7-tetrahydro-1H-indole-3-carboxamide; (357)N-(2-(diethylamino)ethyl)-2-methyl-7-[1,2-dihydro-5-carboxyl-2-oxo-3H-indol-(Z)-3-ylidene]-4,5,6,7-tetrahydro-1H-indole-3-carboxamide; (358)N-(2-(diethylamino)ethyl)-2-methyl-7-[1,2-dihydro-5-carboxyl-2-oxo-3H-indol-(Z)-3-ylidene]-4,5,6,7-tetrahydro-1H-indole-3-carboxamide; (359)N-(2-(diethylamino)ethyl)-2-methyl-7-[1,2-dihydro-6-chloro-2-oxo-3H-indol-(Z)-3-ylidene]-4,5,6,7-tetrahydro-1H-indole-3-carboxamide; (360)N-(3-(diethylamino)propyl)-2-methyl-7-[1,2-dihydro-6-chloro-2-oxo-3H-indol-(Z)-3-ylidene]-4,5,6,7-tetrahydro-1H-indole-3-carboxamide; (361)N-(3-(diethylamino)propyl)-2-methyl-7-[1,2-dihydro-5-bromo-2-oxo-3H-indol-(Z)-3-ylidene]-4,5,6,7-tetrahydro-1H-indole-3-carboxamide; (362)N-(2-(diethylamino)ethyl)-2-methyl-7-[1,2-dihydro-4-fluoro-2-oxo-3H-indol-(Z)-3-ylidene]-4,5,6,7-tetrahydro-1H-indole-3-carboxamide; (363)N-(2-(diethylamino)ethyl)-2-methyl-7-[5-(pyrrolidine-1-carbonyl)-1,2-dihydro-2-oxo-3H-indol-(Z)-3-ylidene]-4,5,6,7-tetrahydro-1H-indole-3-carboxamide; (364)N-(2-(diethylamino)ethyl)-2-methyl-7-[N-(4-fluorophenyl)-5-carboxamide-1,2-dihydro-2-oxo-3H-indol-(Z)-3-ylidene]-4,5,6,7-tetrahydro-1H-indole-3-carboxamide; (365)N-(3-(diethylamino)propyl)-2-methyl-7-[1,2-dihydro-7-fluoro-2-oxo-3H-indol-(Z)-3-ylidene]-4,5,6,7-tetrahydro-1H-indole-3-carboxamide; (366)N-(2-(diethylamino)ethyl)-2-methyl-7-[1,2-dihydro-5-methoxy-2-oxo-3H-indol-(Z)-3-ylidene]-4,5,6,7-tetrahydro-1H-indole-3-carboxamide; (367)N-(2-(diethylamino)ethyl)-2-methyl-7-[1,2-dihydro-5-trifluoromethoxy-2-oxo-3H-indol-(Z)-3-ylidene]-4,5,6,7-tetrahydro-1H-indole-3-carboxamide; (368)N-(2-(diethylamino)ethyl)-2-methyl-7-[N-methyl-1,2-dihydro-2-oxo-3H-indol-5-sulfonamide-(Z)-3-ylidene]-4,5,6,7-tetrahydro-1H-indole-3-carboxamide; (369)N-(2-(pyridin-2-yl)ethyl)-2-methyl-7-[1,2-dihydro-5-fluoro-2-oxo-3H-indol-(Z)-3-ylidene]-4,5,6,7-tetrahydro-1H-indole-3-carboxamide; (370)N-(2-(dimethylamino)ethyl)-N,2-dimethyl-7-[1,2-dihydro-5-fluoro-2-oxo-3H-indol-(Z)-3-ylidene]-4,5,6,7-tetrahydro-1H-indole-3-carboxamide; (371)N-(2-(dimethylamino)ethyl)-N,2-dimethyl-7-[1,2-dihydro-6-chloro-2-oxo-3H-indol-(Z)-3-ylidene]-4,5,6,7-tetrahydro-1H-indole-3-carboxamide; (372)N-benzyl-N,2-dimethyl-7-[1,2-dihydro-5-fluoro-2-oxo-3H-indol-(Z)-3-ylidene]-4,5,6,7-tetrahydro-1H-indole-3-carboxamide; (373) 2-methyl-3-[(S)-2-(pyrrolidin-1-ylmethyl)pyrrolidin-1-carbonyl)]-7-[1,2-dihydro-5-fluoro-2-oxo-3H-indol-(Z)-3-ylidene]-4,5,6,7-tetrahydro-1H-indole; (374) 2-methyl-3-[4-(2-hydroxyethyl)-piperazin-1-carbonyl]-7-[1,2-dihydro-5-fluoro-2-oxo-3H-indol-(Z)-3-ylidene]-4,5,6,7-tetrahydro-1H-indole; (375) 2-methyl-3-(1,4'-bipiperidin-1'-carbonyl)-7-[1,2-dihydro-5-fluoro-2-oxo-3-H-indol-(Z)-3-ylidene]-4,5,6,7-tetrahydro-1H-indole; (376)N-(3-(diethylamino)-2-hydroxypropyl)-2-methyl-7-[1,2-dihydro-2-oxo-3H-indol-(Z)-3-ylidene]-4,5,6,7-tetrahydro-1H-indole-3-carboxamide; (377)N-(3-(diethylamino)-2-hydroxypropyl)-2-methyl-7-[1,2-dihydro-2-oxo-3H-indol-(Z)-3-ylidene]-4,5,6,7-tetrahydro-1H-indole-3-carboxamide; (378)N-(3-(diethylamino)-2-hydroxypropyl)-2-methyl-7-[1,2-dihydro-5-chloro-2-oxo-3H-indol-(Z)-3-ylidene]-4,5,6,7-tetrahydro-1H-indole-3-carboxamide; (379)N-(3-(dimethylamino)-2-hydroxypropyl)-2-methyl-7-[1,2-dihydro-5-fluoro-2-oxo-3H-indol-(Z)-3-ylidene]-4,5,6,7-tetrahydro-1H-indole-3-carboxamide; (380)N-(2-hydroxy-3-morpholinopropyl)-2-methyl-7-[1,2-dihydro-2-oxo-3H-indol-(Z)-3-ylidene]-4,5,6,7-tetrahydro-1H-indole-3-carboxamide; (381)N-(2-hydroxy-3-morpholinopropyl)-2-methyl-7-[1,2-dihydro-5-fluoro-2-oxo-3-H-indol-(Z)-3-ylidene]-4,5,6,7-tetrahydro-1H-indole-3-carboxamide; (382)N-(2-hydroxy-3-morpholinopropyl)-2-methyl-7-[1,2-dihydro-5-chloro-2-oxo-3-H-indol-(Z)-3-ylidene]-4,5,6,7-tetrahydro-1H-indole-3-carboxamide; (383)N-(2-hydroxy-3-(pyrrolidin-1-yl)propyl)-2-methyl-7-[1,2-dihydro-2-oxo-3H-indol-(Z)-3-ylidene]-4,5,6,7-tetrahydro-1H-indole-3-carboxamide; (384)N-(2-hydroxy-3-(pyrrolidin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide; (385)N-(2-hydroxy-3-(pyrrolidin-1-yl)propyl)-2-methyl-7-[1,2-dihydro-5-chloro-2-oxo-3H-indol-(Z)-3-ylidene]-4,5,6,7-tetrahydro-1H-indole-3-carboxamide; (386) N-(2-hydroxy-3-(piperidin-1-yl)propyl)-2-methyl-7-[1,2-dihydro-2-oxo-3H-indol-(Z)-3-ylidene]-4,5,6,7-tetrahydro-1H-indole-3-carboxamide; (387)N-(2-hydroxy-3-(piperidin-1-yl)propyl)-2-methyl-7-[1,2-dihydro-5-fluoro-2-oxo-3H-indol-(Z)-3-ylidene]-4,5,6,7-tetrahydro-1H-indole-3-carboxamide; (388)N-(2-hydroxy-3-(piperidin-1-yl)propyl)-2-methyl-7-[1,2-dihydro-5-chloro-2-oxo-3H-indol-(Z)-3-ylidene]-4,5,6,7-tetrahydro-1H-indole-3-carboxamide; (389)N-[2-hydroxy-3-(4-methylpiperazin-1-yl)propyl]-2-methyl-7-[1,2-dihydro-2-oxo-3H-indol-(Z)-3-ylidene]-4,5,6,7-tetrahydro-1H-indole-3-carboxamide; (390) N-[2-hydroxy-3-(4-methylpiperazin-1-yl)propyl]-2-methyl-7-[1,2-dihydro-5-fluoro-3H-indol-(Z)-3-ylidene]-4,5,6,7-tetrahydro-1H-indole-3-carboxamide; (391)N-[2-hydroxy-3-(4-methylpiperazin-1-yl)propyl]-2-methyl-7-[1,2-dihydro-5 chloro-2-oxo-3H-indol-(Z)-3-ylidene]-4,5,6,7-tetrahydro-1H-indole-3-carboxamide; (392) N-[3-(cyclohexyl(methyl)amino)-2-hydroxypropyl]-2-methyl-7-[1,2-dihydro-5-methyl-2-oxo-3H-indol-(Z)-3-ylidene]-4,5,6,7-tetrahydro-1H-indole-3-carboxamide; (393)N-(3-(diethylamino)-2-hydroxypropyl)-2-methyl-7-[1,2-dihydro-5-bromo-2-oxo-3H-indol-(Z)-3-ylidene]-4,5,6,7-tetrahydro-1H-indole-3-carboxamide; (394)N-(2-hydroxy-3-morpholinopropyl)-2-methyl-7-[1,2-dihydro-6-chloro-2-oxo-3-H-indol-(Z)-3-ylidene]-4,5,6,7-tetrahydro-1H-indole-3-carboxamide; (395)N-[3-(cyclohexyl(methyl)amino)-2-hydroxypropyl]-2-methyl-7-[1,2-dihydro-5-fluoro-2-oxo-3H-indol-(Z)-3-ylidene]-4,5,6,7-tetrahydro-1H-indole-3-carboxamide; (396) 5-bromoindirubin-3'-oxime; (397) 7-bromoindirubin-3'-oxime; (398) 7-chloroindirubin-3'-oxime; (399) 7-iodoindirubin-3'-oxime; (400) 7-fluoroindirubin-3'-oxime; (401) 1-methyl-7-bromoindirubin-3'-oxime; (402) (2'Z)-7-fluoroindirubin; (403) (2'Z)-7-chloroindirubin; (404) (2'Z)-7-bromoindirubin; (405) (2'Z)-7-iodoindirubin; (406) (2'Z)-7-fluoro-1-methylindirubin; (407) (2'Z)-7-chloro-1-methylindirubin; (408) (2'Z)-7-bromo-1-methylindirubin;

(409) (2'Z)-7-iodo-1-methylindirubin; (410) (2'Z,3'E)-7-fluoroindirubin-3'-oxime; (411) (2'Z,3'E)-7-chloroindirubin-3'-oxime; (412) (2'Z,3'E)-7-bromoindirubin-3'-oxime; (413) (2'Z,3'E)-7-iodoindirubin-3'-oxime; (414) (2'Z,3'E)-7-fluoro-1-methylindirubin-3'-oxime; (415) (2'Z,3'E)-7-chloro-1-methylindirubin-3'-oxime; (416) (2'Z,3'E)-7-bromo-1-methylindirubin-3'-oxime; (417) (2'Z,3'E)-7-iodo-1-methylindirubin-3'-oxime; (418) (2'Z,3'E)-7-fluoroindirubin-3'-acetoxime; (419) (2'Z,3'E)-7-chloroindirubin-3'-acetoxime; (420) (2'Z,3'E)-7-bromoindirubin-3'-acetoxime; (421) (2'Z,3'E)-7-iodoindirubin-3'-acetoxime; (422) (2'Z,3'E)-7-fluoro-1-methylindirubin-3'-acetoxime; (423) (2'Z,3'E)-7-chloro-1-methylindirubin-3'-acetoxime; (424) (2'Z,3'E)-7-bromo-1-methylindirubin-3'-acetoxime; (425) (2'Z,3'E)-7-iodo-1-methylindirubin-3'-acetoxime; (426) (2'Z,3'E)-7-fluoroindirubin-3'-methoxime; (427) (2'Z,3'E)-7-chloroindirubin-3'-methoxime; (428) (2'Z,3'E)-7-bromoindirubin-3'-methoxime: (429) (2'Z,3'E)-7-iodoindirubin-3'-methoxime; (430) (2'Z,3'E)-7-fluoro-1-methylindirubin-3'-methoxime; (431) (2'Z,3'E)-7-chloro-1-methylindirubin-3'-methoxime; (432) (2'Z,3'E)-7-bromo-1-methylindirubin-3'-methoxime, (2'Z,3'E)-7-iodo-1-methylindirubin-3'-methoxime; (433) (2'Z,3'E)-7-bromoindirubin-3'-[O-(2-bromoethyl)-oxime]; (434) (2'Z, 3'E)-1-methyl-7-bromoindirubin-3'-[O-(2-bromoethyl)-oxime]; (435) (2'Z,3'E)-7-bromoindirubin-3'-[O—(N,N-diethylcarbamyl)-oxime]; (436) 2'Z,3'E)-1-methyl-7-bromoindirubin-3'-[O—(N,N-diethylcarbamyl)-oxime]; (437) (2'Z,3'E)-7-bromoindirubin-3'-[O-(2-pyrrolidin-1-yl-ethyl)-oxime]; (438) (2'Z,3'E)-1-methyl-7-bromoindirubin-3'-[O-(2-pyrrolidin-1-yl-ethyl)-oxime], (439) (2'Z,3'E)-7-bromoindirubin-3'-[O-(2-morpholin-1-yl-ethyl)-oxime], (440) (2'Z,3'E)-1-methyl-7-bromoindirubin-3'-[O-(2-morpholin-1-yl-ethyl)-oxime]; (441) (2'Z,3'E)-7-bromoindirubin-3'-[O-(2-imidazol-1-yl-ethyl)-oxime]; (442) (2'Z,3'E)-1-methyl-7-bromoindirubin-3'-[O-(2-imidazol-1-yl-ethyl)-oxime]; (443) (2'Z,3'E)-7-bromoindirubin-3'-[O-(2-piperazin-1-yl-ethyl)-oxime]; (444) (2'Z,3'E)-7-bromoindirubin-3'-[O-(2-dimethylaminoethyl)-oxime]; (445) (2'Z,3'E)-1-methyl-7-bromoindirubin-3'-[O-(2-dimethylaminoethyl)-oxime]; (446) (2'Z,3'E)-7-bromoindirubin-3'-[O-(2-diethylaminoethyl)-oxime](447) (2'Z,3'E)-1-methyl-7-bromoindirubin-3'-[O-(2-diethylaminoethyl)-oxime]; (448)N-(2-hydroxy-3-morpholinopropyl)-2-methyl-7-[1,2-dihydro-5-bromo-2-oxo-3H-indol-(Z)-3-ylidene]-4,5,6,7-tetrahydro-1H-indole-3-carboxamide;
(449) 6-bromoindirubin-3'-oxime; (450) (2'Z,3'E)-6-bromoindirubin-3'-[O-(2-bromoethyl)-oxime]; (451) (2'Z,3'E)-6-bromoindirubin-3'-[O-(2-hydroxyethyl)-oxime]; (452) (2'Z,3'E)-6-bromoindirubin-3'-[O-(2,3-dihydroxypropyl)-oxime]; (453) (2'Z,3'E)-6-bromoindirubin-3-[O—(N,N-diethylcarbamyl)-oxime]; (454) (2'Z,3'E)-6-bromoindirubin-3'-[O-(2-dimethylaminoethyl)-oxime]; (455) (2'Z,3'E)-6-bromoindirubin-3-[O-(2-diethylaminoethyl)-oxime]; (456) (2'Z,3'E)-6-bromoindirubin-3'-[O-(2-pyrrolidin-1-ylethyl)-oxime]; (457) (2'Z,3'E)-6-bromoindirubin-3'-[O-(2-morpholin-1-ylethyl)-oxime]; (458) (2'Z,3'E)-6-bromoindirubin-3'-[O-(2-N,N-(2-hydroxyethyl)aminoethyl)-oxime]; (459) (2'Z,3'E)-6-bromoindirubin-3'-(O-{2-N,N-dimethyl, N-(2,3-dihydroxypropyl)amino]ethyl}oxime; (460) (2'Z,3'E)-6-bromoindirubin-3'-[O-(2-piperazin-1-ylethyl)-oxime]; (461) (2'Z,3'E)-6-bromoindirubin-3'-{O-[2-(4-methyl-piperazin-1-yl)ethyl]oxime; (462) (2'Z,3'E)-6-bromoindirubin-3'-O-{2-[4-(2-hydroxyethyl)piperazin-1-yl]ethyl}oxime; (463) (2'Z,3'E)-6-bromoindirubin-3'-O-{2-[4-(2-methoxyethyl) piperazin-1-yl]ethyl}oxime; (464) (2'Z,3'E)-6-bromoindirubin-3'-O—[O-2-{4-[2-(2-hydroxyethoxy)-ethyl]piperazin-1-yl}ethyl)oxime; (465) isoindigo; (466) 5-nitroindirubin-3'-oxime; (467) 5'-bromo-5-nitroindirubin-3'-oxime; (468) 5'-hydroxy-5-nitroindirubin-3'-oxime; (469) 5'-hydroxy-5-chloroindirubin-3'-oxime; (470) 5'-hydroxy-5-fluoroindirubin-3'-oxime; (471) 5'-chloro-5-nitroindirubin-3'-oxime; (472) 5'-methyl-5-nitroindirubin-3'-oxime; (473) indirubin-5-sulfonic acid (2-hydroxyethyl)-amide; (474) (3-[3-(3,4-dihydroxybutoxyamino)-1H-indol-2-yl]indol-2-one); and the salts, solvates, analogues, congeners, bioisosteres, hydrolysis products, metabolites, precursors, and prodrugs thereof (referred to herein as "Alternatives (1)-(486)").

As described above, and as detailed more generally below, derivatives and analogs of meisoindigo can be optionally substituted with one or more groups that do not substantially affect the pharmacological activity of the derivative or analog. These groups are generally known in the art. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl and naphthyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicylic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxyheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. When a range of values is listed, such as for the number of carbon atoms in an alkyl group, it is intended to encompass each value and subrange within the range. For example, "$C_1$-$C_6$ alkyl" includes alkyl groups with 1, 2, 3, 4, 5, or 6 carbon atoms and all possible subranges.

As used herein, the term "heterocycle," "heterocyclyl," "heterocyclic ring" or "heterocyclic group" is intended to mean a stable 4-, 5-, 6-, or 7-membered monocyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O, and S; and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another.

When the term "heterocycle," "heterocyclyl," "heterocyclic ring" or "heterocyclic group" is used, it is intended to include heteroaryl unless heteroaryl is excluded. Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule and such that a stable compound is formed thereby, i.e., a compound that does not spontaneously undergo transformation such as by rearrangement, cyclization, elimination, hydrolysis, or other reaction. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, =O, —$OZ^b$, —$SZ^b$, =$S^-$, —$NZ^cZ^c$, =$NZ^b$, =N—$OZ^b$, trihalomethyl, —$CF_3$, —CN, —OCN, —SCN, —NO, —$NO_2$, =$N_2$, —$N_3$, —$S(O)_2Z^b$, —$S(O)_2NZ^b$, —$S(O_2)O^-$, —$S(O_2)OZ^b$, —$OS(O_2)OZ^b$, —$OS(O_2)O^-$, —$OS(O_2)OZ^b$, —$P(O)(O^-)_2$, —$P(O)(OZ^b)$ (O$^-$), —P(O)(OZ$^b$)(OZ$^b$), —C(O)Z$^b$, —C(S)Z$^b$, —C(NZ$^b$)Z$^b$, —C(O)O$^-$, —C(O)OZ$^b$, —C(S)OZ$^b$, —C(O)NZ$^c$Z$^c$, —C(NZ$^b$)NZ$^c$Z$^c$, —OC(O)Z$^b$, —OC(S)Z$^b$, —OC(O)O$^-$, —OC(O)OZ$^b$, —OC(S)OZ$^b$, —NZ$^b$C(O)Z$^b$, —NZ$^b$C(S)Z$^b$, —NZ$^b$C(O)O$^-$, —NZ$^b$C(O)OZ$^b$, —NZ$^b$C(S)OZ$^b$, —NZ$^b$C(O)NZ$^c$Z$^c$, —NZ$^b$C(NZ$^b$)Z$^b$, —NZ$^b$C(NZ$^b$)NZ$^c$Z$^c$, wherein Z$^a$ is selected from the group consisting of alkyl, cycloalkyl, heteroalkyl, cycloheteroalkyl, aryl, arylalkyl, heteroaryl and heteroarylalkyl; each Z$^b$ is independently hydrogen or Z$^a$; and each Z$^c$ is independently Z$^b$ or, alternatively, the two Z$^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —NZ$^c$Z$^c$ is meant to include —NH$_2$, —NH-alkyl, —N-pyrrolidinyl, and —N-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-C(O)OZ$^b$, -alkylene-C(O)NZ$^b$Z$^b$, and —CH$_2$—CH$_2$—C(O)—CH$_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —Z$^a$, halo, —O$^-$, —OZ$^b$, —SZ$^b$, —S$^-$, —NZ$^c$Z$^c$, trihalomethyl, —CF$_3$, —CN, —OCN, —SCN, —NO, —NO$_2$, —N$_3$, —S(O)$_2$Z$^b$, —S(O$_2$)O$^-$, —S(O$_2$)OZ$^b$, —OS(O$_2$)OZ$^b$, —OS(O$_2$)O$^-$, —P(O)(O$^-$)$_2$, —P(O)(OZ$^b$)(O$^-$), —P(O)(OZ$^b$)(OZ$^b$), —C(O)Z$^b$, —C(S)Z$^b$, —C(NZ$^b$)Z$^b$, —C(O)O$^-$, —C(O)OZ$^b$, —C(S)OZ$^b$, —C(O)NZ$^c$Z$^c$, —C(NZ$^b$)NZ$^c$Z$^c$, —OC(O)Z$^b$, —OC(S)Z$^b$, —OC(O)O$^-$, —OC(O)OZ$^b$, —OC(S)OZ$^b$, —NZ$^b$C(O)OZ$^b$, —NZ$^b$C(S)OZ$^b$, —NZ$^b$C(O)NZ$^c$Z$^c$, —NZ$^b$C(NZ$^b$)Z$^b$, and —NZ$^b$C(NZ$^b$)NZ$^c$Z$^c$, wherein Z$^a$, Z$^b$, and Z$^c$ are as defined above.

Similarly, substituent groups useful for substituting nitrogen atoms in heteroalkyl and cycloheteroalkyl groups include, but are not limited to, —Z$^a$, halo, —O$^-$, —OZ$^b$, —SZ$^b$, —S$^-$, —NZ$^c$Z$^c$, trihalomethyl, —CF$_3$, —CN, —OCN, —SCN, —NO, —NO$_2$, —S(O)$_2$Z$^b$, —S(O$_2$)O$^-$, —S(O$_2$)OZ$^b$, —OS(O$_2$)OZ$^b$, —OS(O$_2$)O$^-$, —P(O)(O$^-$)$_2$, —P(O)(OZ$^b$)(O$^-$), —P(O)(OZ$^b$)(OZ$^b$), —C(O)Z$^b$, —C(S)Z$^b$, —C(NZ$^b$)Z$^b$, —C(O)OZ$^b$, —C(S)OZ$^b$, —C(O)NZ$^c$Z$^c$, —C(NZ$^b$)NZ$^c$Z$^c$, —OC(O)Z$^b$, —OC(S)Z$^b$, —OC(O)OZ$^b$, —OC(S)OZ$^b$, —NZ$^b$C(O)Z$^b$, —NZ$^b$C(S)Z$^b$, —NZ$^b$C(O)OZ$^b$, —NZ$^b$C(S)OZ$^b$, —NZ$^b$C(O)NZ$^c$Z$^c$, —NZ$^b$C(NZ$^b$)Z$^b$, and —NZ$^b$C(NZ$^b$)NZ$^c$Z$^c$, wherein Z$^a$, Z$^b$, and Z$^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other stereoisomeric forms) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Such separation techniques include, but are not limited to, chiral high pressure liquid chromatography (HPLC) and formation and crystallization of chiral salts. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted olefin isomer. When the chemical name does not specify the isomeric form of the compound, it denotes any one of the possible isomeric forms or mixtures of those isomeric forms of the compound.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein includes two or more interconvertible compounds resulting from at least one formal migration of a hydrogen atom and at least one change in valency (e.g., a single bond to a double bond, a triple bond to a double bond, a triple bond to a single bond, or vice versa). The exact ratio of the tautomers present can depend on several factors, including pH, solvent, and temperature. Tautomerization reactions can be catalyzed by acid or base. Examples of tautomerization include keto/enol, amide/imide, lactam/lactim, and enamine/imine.

As used herein, the terms "nucleic acid," "oligonucleotide," "polynucleotide," and similar terms typically refer to polymers of deoxyribonucleotides (DNA) or ribonucleotides (RNA) in either single- or double-stranded form, and complements thereof according to the conventional Watson-Crick base-pairing scheme unless the complementary sequence is excluded. Unless specifically excluded, the terms also refer to nucleic acids containing known nucleotide analogs or modified backbone residues or linkages, which are synthetic, naturally-occurring, or non-naturally-occurring, which have similar binding properties to a corresponding nucleic acid comprising naturally-occurring conventional bases (adenine, guanine, cytosine, and thymine (for DNA) or uracil (for RNA), and which typically are metabolized in a manner similar to a corresponding nucleic acid comprising naturally-occurring conventional bases; however, in some contexts, the requirement for metabolism in a manner similar to a corresponding nucleic acid comprising naturally-occurring conventional bases can be dispensed with. Examples of such analogs include, but are not necessarily limited to, phosphorothioates, phosphoramidates, methyl phosphonates, chiral methyl phosphonates, 2-O-methyl ribonucleotides, and peptide nucleic acids (PNAs).

As used herein, the term "solvate" means a compound formed by solvation (the combination of solvent molecules with molecules or ions of the solute), or an aggregate that consists of a solute ion or molecule, i.e., a compound of the invention, with one or more solvent molecules. The term "solvate" typically means a physical association of a compound involving varying degrees of ionic and/or covalent bonding, including hydrogen bonding. In certain instances the solvate will be capable of isolation, for example when one or more solvent atoms are incorporated into the crystal lattice of the crystalline solid. The term "solvate" encompasses both solution-phase and isolatable solvates. Suitable solvates in which the solvent is other than water include, but are not limited to, ethanolates or methanolates. When water is the solvent, the corresponding solvate is a "hydrate." Examples of hydrates include, but are not limited to, hemihydrate, monohydrate, dihydrate, trihydrate, hexahydrate, and other hydrated forms. It should be understood by one of ordinary skill in the art that the pharmaceutically acceptable salt and/or prodrug of the present compound may also exist in a solvate form. When the solvate is a hydrate, the hydrate is typically formed via hydration which is either part of the preparation of the present compound or through natural absorption of moisture by the anhydrous compound of the present invention. Additionally, compounds may exist as clathrates or other complexes, which are therapeutic agent-host inclusion complexes wherein the therapeutic agent and the host are present in stoichiometric or non-stoichiometric amounts.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolyzable esters of the present compounds are the compounds whose carboxyls are present in the form of hydrolyzable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a $C_7$-arylalkyl group, and phenylethyl is a $C_8$-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. The general term "alkylene" encompasses more specific examples such as "ethylene," wherein n is 2, "propylene," wherein n is 3, and "butylene," wherein n is 4. The hydrocarbyl groups of the alkylene can be optionally substituted as described above.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —$NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the general term "carbocyclyl" encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S, more typically from.

As used herein, the term "alkanoyl" refers to an alkyl group covalently linked to a carbonyl (C═O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Alk_2$ and -$Alk_1$-N($Alk_2$)(Alk3), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —$S(O)_2$—Ar wherein Ar refers to an aryl group as described above. The term "aryloxyalkylsulfonyl" refers to a group of the structure —$S(O)_2$-Alk-O—Ar, where Alk is an alkyl group as described above and Ar is an aryl group as described above. The term "arylalkylsulfonyl" refers to a group of the structure —$S(O)_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is $CH_3CH_2OC(O)$—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al., incorporated herein by this reference. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

Accordingly, methods and compositions according to the present invention encompass meisoindigo derivatives and analogs including one or more optional substituents as defined above, provided that the optionally substituted meisoindigo derivative or analog possesses substantially equivalent pharmacological activity to the meisoindigo derivative or analog as defined in terms of cell cycle arrest or apoptosis enhancement. Methods for determining cell cycle arrest are known in the art and are described in K. Polyak et al., "p27Kip1, a Cyclin-Cdk Inhibitor, Links Transforming Growth Factor-Beta and Contact Inhibition to Cell Cycle Arrest," *Genes & Develop.* 8: 9-22 (1994), incorporated herein by this reference. Methods for determining enhancement of apoptosis are known in the art and are described in M. Faber et al., "Overexpression of the Rabies Virus Glycoprotein Results in Enhancement of Apoptosis and Antiviral Immune Response," *J. Virol.* 76: 3374-3381 (2002), incorporated herein by this reference.

A number of indirubin derivatives have the activity of glycogen synthase kinase-3 antagonists or Wnt agonists, as described in U.S. Pat. No. 8,349,822 to Yu, incorporated herein by this reference. The Wnt signaling pathway is described in C. Y. Logan & R. Nusse, "The Wnt Signaling Pathway in Development and Disease," *Annu. Rev. Cell. Dev. Biol.* 20: 781-810 (2004), incorporated herein by this reference. The Wnt pathway involves a diverse family of Wnt glycoproteins that act as ligands to regulate the production of intracellular signaling molecules to produce a cellular response. These Wnt glycoprotein ligands include several different proteins such as WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16. There are several variations of the Wnt pathway, namely the canonical Wnt pathway, the noncanonical Planar Cell Polarity pathway, and the noncanonical Wnt/calcium pathway. The canonical pathway, the best known, causes an accumulation of β-catenin in the cytoplasm and the eventual translocation of the β-catenin to the nucleus to act as a transcriptional coactivator of transcription factors that belong to the TCF/LEF family. GSK-3 is a kinase that phosphorylates serine and threonine amino acid residues in glycogen synthase and other proteins. GSK-3 phosphorylates β-catenin, thus tying GSK-3 to the Wnt pathway; phosphorylated β-catenin is targeted for degradation. The activity of GSK-3 is described in R. S. Jope, "The Glamour and Gloom of Glycogen Synthase Kinase-3," *Trends Biochem. Sci.* 29: 95-102 (2004), incorporated herein by this reference. Indirubin and some indirubin derivatives also have the activity of inhibiting cyclin-dependent protein kinase-2 (CDK2). CDK2 is a member of the cyclin-dependent family of serine/threonine protein kinase and regulates the cell cycle. The activity of CDK2 is described in J. Du et al., "Critical Role of CDK2 for Melanoma Growth Linked to Its Melanocyte-Specific Transcriptional Regulation by MITF," *Cancer Cell:* 6: 565-576 (2004), incorporated herein by this reference. Accordingly, within the scope of the present invention are indirubin derivatives and analogs that are GSK-3 antagonists. Also within the scope of the present invention are indirubin derivatives and analogs that are Wnt agonists. Additionally, within the scope of the present invention are indirubin derivatives and analogs that are CDK2 inhibitors.

Also within the scope of the present invention are pharmaceutically acceptable salts of indirubin analogs and derivatives as described above, including pharmaceutically acceptable salts of meisoindigo. "Pharmaceutically acceptable salt" refers to conventional acid-addition or base-addition salts that retain the biological effectiveness and properties of the indirubin analogs and derivatives described above and are formed from suitable non-toxic organic or inorganic acids or organic or inorganic bases. All of these salts may be prepared by conventional means from the corresponding compound of the invention by reacting, for example, the appropriate acid or base with the compound of the invention. When a basic group and an acid group are present in the same molecule, a compound of the invention may also form internal salts. Accordingly, when the indirubin analog or derivative is negatively charged, pharmaceutically acceptable salts can be formed with the following positively-charged ions: sodium, potassium, aluminum, lithium, calcium, magnesium, zinc, ammonium, caffeine, arginine, diethylamine, N-ethylpiperidine, histidine, glucamine, isopropylamine, lysine, morpholine, N-ethylmorpholine, piperazine, piperidine, triethylamine, trimethylamine, ethanolamine, diethanolamine, N-methylglucamine, and tris(hydroxymethyl)aminomethane. When the indirubin analog or derivative is positively charged, pharmaceutically acceptable salts can be formed with the following negatively charged ions: chloride, bromide, iodide, carbonate, nitrate, sulfate, bisulfate, phosphate, monohydrogen phosphate, dihydrogen phosphate, metaphosphate, pyrophosphate, formate, acetate, adipate, butyrate, propionate, succinate, glycolate, gluconate, lactate, malate, tartrate, citrate, ascorbate, glucuronate, maleate, fumarate, pyruvate, aspartate, glutamate, benzoate, anthranilate, mesylate, 4'-hydroxybenzoate, phenylacetate, mandelate, embonate (pamoate), methanesulfonate, ethanesulfonate, ethanedisulfonate, benzenesulfonate, pantothenate, 2-hydroxyethanesulfonate, p-toluenesulfonate, sulfanilate, cyclohexylaminosulfonate, camphorate, camphorsulfonate, digluconate, cyclopentanepropionate, dodecylsulfonate, glucoheptanoate, glycerophosphonate, heptanoate, hexanoate, 2-hydroxyethanesulfonate, nicotinate, isonicotinate, 1-naphthalenesulfonate, 2-naphthalenesulfonate, oxalate, palmoate, pectinate, persulfurate, 2-phenylpropionate, picrate, pivalate, thiocyanate, mesylate, undecanoate, stearate, algenate, β-hydroxybutyrate, salicylate, galactarate, galacturonate, caprylate, isobutyrate, malonate, suberate, sebacate, chlorobenzoate, methylbenzoate, dinitrobenzoate, phthalate, phenylacetate, isethionate, lactobionate, p-aminobenzoate, sulfamate, diethylacetate, pimelate, aminosulfonate, acrylate, γ-hydroxybutyrate, and methoxybenzoate.

Prodrugs of indirubin and analogs and derivatives thereof, including prodrugs of meisoindigo, are described below.

(II) Dose Modification

Improvements for suboptimal chemotherapeutics including indirubin or analogs and derivatives thereof, including meisoindigo, are made by alterations to the time that the compound is administered, the use of dose-modifying agents that control the rate of metabolism of the compound, normal tissue protective agents, and other alterations. General examples include: variations of infusion schedules (e.g., bolus i.v. versus continuous infusion), the use of lymphokines (e.g., G-CSF, GM-CSF, EPO) to increase leukocyte count for improved immune response or for preventing anemia caused by myelosuppressive agents, or the use of rescue agents. Specific inventive examples for indirubin or analogs and derivatives thereof, including meisoindigo, include: continuous i.v. infusion for hours to days; biweekly administration; doses greater than 5 mg/m$^2$/day; progressive escalation of dosing from 1 mg/m$^2$/day based on patient tolerance; doses less than 1 mg/m$^2$ for greater than 14 days; use of caffeine to modulate metabolism; use of isoniazid to modulate metabolism; selected and intermittent boost dose administrations; bolus single and multiple doses escalating from 5 mg/m$^2$, oral doses below 30 or above 130 mg/m$^2$; chronic low dose administration of from about 10 mg/day to about 25 mg/day; intermittent administration of from about 50 mg to about 150 mg twice weekly or three times weekly; administration of from about 50 mg/day to about 150 mg/day for 10-14 days per month; or chronic daily dosing at a dose of equal to or greater than 100 mg/day.

(III) Route of Administration

Improvements for suboptimal chemotherapeutics including indirubin or analogs and derivatives thereof, including meisoindigo, are made by alterations in the route by which the compound is administered. General examples include: changing route from oral to intravenous administration and vice versa; or the use of specialized routes such as subcutaneous, intramuscular, intraarterial, intraperitoneal, intralesional, intralymphatic, intratumoral, intrathecal, intravesicular, intracranial. Specific inventive examples for indirubin or analogs and derivatives thereof, including meisoindigo, include: topical; intravesicular for bladder cancer; oral administration; slow release oral delivery; intrathecal; intraarterial; continuous infusion; or intermittent infusion.

(IV) Schedule of Administration

Improvements for suboptimal chemotherapeutics including indirubin or analogs and derivatives thereof, including meisoindigo, are made by alterations to the time that the compound is administered. General examples include: changing from a monthly administration to a weekly or daily dosing or variations of the schedule. Specific inventive examples for indirubin or analogs and derivatives thereof, including meisoindigo, include: daily; weekly for three weeks, weekly for two weeks, biweekly; biweekly for three weeks with a 1-2 week rest period; intermittent boost dose administration; daily for one week then once per week for multiple weeks.

(V) Indications for Use

Improvements for suboptimal chemotherapeutics including indirubin or analogs and derivatives thereof, including meisoindigo, are made by alterations in the types of disease or the clinical stage of disease that the compound is administered. General examples include: the use of solid tumor agents for leukemias and vice versa, the use of antitumor agents for the treatment of benign hyperproliferative disease such as psoriasis or benign prostate hypertrophy. Specific inventive examples for indirubin or analogs and derivatives thereof, including meisoindigo, include: use for the treatment of leukemias (acute and chronic, ALL, CLL, CML, CLL); use for the treatment of acute promyelocytic leukemia (APL); use for the treatment of myelodysplastic syndrome (MDS); use for the treatment of T-cell lymphomas; use for the treatment of B-cell lymphomas; use for the treatment of mantle cell lymphomas; use for the suppression of proliferation of cancer stem cells; use for the treatment of malignant pericardial effusions; use for the treatment of ovarian carcinoma; use for the treatment of carcinoma of the lung; use for the treatment of angiogenic diseases; use for the treatment of benign prostate hypertrophy; use for the treatment of psoriasis; use for the treatment of gout; use for the treatment of autoimmune conditions; use for the treatment of rheumatoid arthritis; use for treatment of insulin-resistant diabetes; use for prevention of transplantation rejection; use for restenosis prevention in cardiovascular disease; use for the treatment of mycosis fungoides; use in bone marrow transplantation; use as an antiinfective; use for the treatment of AIDS; or use for the treatment of Alzheimer's disease, including disease prevention, slowing of disease progression, and amelioration or reversal of disease symptoms, due to the effect of meisoindigo on the phosphorylation of τ (tau) protein.

(VI) Disease Stages

Improvements for suboptimal chemotherapeutics including indirubin or analogs and derivatives thereof, including meisoindigo, are made by alterations in the stage of disease at diagnosis/progression that the compound is administered. General examples include: the use of chemotherapy for non-resectable local disease, prophylactic use to prevent metastatic spread or inhibit disease progression or conversion to more malignant stages. Specific inventive examples for indirubin or analogs and derivatives thereof, including meisoindigo, include: use for the treatment of localized polyp stage colon cancer; leukoplakia in the oral cavity; angiogenesis inhibition to prevent or limit metastatic spread; against HIV with AZT, DDI, reverse transcriptase inhibitors.

(VII) Other Indications

Improvements for suboptimal chemotherapeutics including indirubin or analogs and derivatives thereof, including meisoindigo, are made by using the compound for non-malignant diseases and conditions. General examples include: premalignant conditions, benign hyperproliferative conditions, treatment of infections, parasites, usage to relieve pain, control of pleural effusions. Specific inventive examples for indirubin or analogs and derivatives thereof, including meisoindigo, include: use as antiinfectives, anti-virals; antibacterials; for pleural effusions; antifungals; anti-parasitics; eczema; shingles; condylomata; anti HPV; or anti HSV.

(VIII) Patient Selection

Improvements for suboptimal chemotherapeutics including indirubin or analogs and derivatives thereof, including meisoindigo, are made by alterations to the type of patient that would best tolerate or benefit from the use of the compound. General examples include: use of pediatric doses for elderly patients, altered doses for obese patients; exploitation of co-morbid disease conditions such as diabetes, cirrhosis, or other conditions that may uniquely exploit a feature of the compound. Specific inventive examples for indirubin or analogs and derivatives thereof, including meisoindigo, include: patients with disease conditions with high levels of metabolic enzymes, histone deacetylase, protein kinases, ornithine decarboxylase; patients with disease conditions with low levels of metabolic enzymes, histone deacetylase, protein kinases, ornithine decarboxylase; patients with low or high susceptibility to thrombocytopenia, neutropenia; patients intolerant of GI toxicities; over- or under-expression of jun, GPCR's and signal transduction proteins, VEGF, prostate specific genes, protein kinases, or telomerase.

(IX) Patient/Disease Phenotype

Improvements for suboptimal chemotherapeutics including indirubin or analogs and derivatives thereof, including meisoindigo, are made by more precise identification of a patient's ability to tolerate, metabolize and exploit the use of the compound. General examples include: use of diagnostic tools and kits to better characterize a patient's ability to process/metabolize a chemotherapeutic agent or their susceptibility to toxicity caused by potential specialized cellular, metabolic, or organ system phenotypes. Specific inventive examples for indirubin or analogs and derivatives thereof, including meisoindigo, include: diagnostic tools, techniques, kits and assays to confirm a patient's particular phenotype and for the measurement of metabolism enzymes and metabolites, histone deacetylase, protein kinases, ornithine decarboxylase, VEGF, prostate specific genes, protein kinases, telomerase, jun GPCR's; or surrogate compound dosing or low dose drug pre-testing for enzymatic status.

(X) Patient/Disease Genotype

Improvements for suboptimal chemotherapeutics including indirubin or analogs and derivatives thereof, including meisoindigo, are made by testing and analyzing a patient's genotype for unique features that may be of value to predict efficacy, toxicity, metabolism, or other factors affecting the therapeutic efficacy of the drug. General examples include: biopsy samples of tumors or normal tissues (e.g., white blood cells) that may also be taken and analyzed to specifically tailor or monitor the use of a particular drug against a gene target; studies of unique tumor gene expression patterns; or analysis of SNP's (single nucleotide polymorphisms), to enhance efficacy or to avoid particular drug-sensitive normal tissue toxicities. Specific inventive examples for indirubin or analogs and derivatives thereof, including meisoindigo, include: diagnostic tools, techniques, kits and assays to confirm a patient's particular genotype; gene/protein expression chips and analysis; Single Nucleotide Polymorphisms (SNP's) assessment; SNP's for histone deacetylase, ornithine decarboxylase, GPCR's, protein kinases, telomerase, jun; or identification and measurement of metabolism enzymes and metabolites.

(XI) Pre/Post-Treatment Preparation

Improvements for suboptimal chemotherapeutics including indirubin or analogs thereof, including meisoindigo, are made by specialized preparation of a patient prior to or after the use of a chemotherapeutic agent. General examples include: induction or inhibition of metabolizing enzymes, specific protection of sensitive normal tissues or organ systems. Specific inventive examples for indirubin or analogs and derivatives thereof, including meisoindigo, include: the use of colchicine or analogs; use of diuretics such as probenecid; use of uricase; non-oral use of nicotinamide; sustained release forms of nicotinamide; use of inhibitors of polyADP ribose polymerase; use of caffeine; leucovorin rescue; infection control; or antihypertensives.

(XII) Toxicity Management

Improvements for suboptimal chemotherapeutics including indirubin or analogs and derivatives thereof, including meisoindigo, are made by use of additional drugs or procedures to prevent or reduce potential side-effects or toxicities. General examples include: the use of anti-emetics, anti-nausea, hematological support agents to limit or prevent neutropenia, anemia, thrombocytopenia, vitamins, antidepressants, treatments for sexual dysfunction, and other supportive techniques. Specific inventive examples for indirubin or analogs and derivatives thereof, including meisoindigo, include: the use of colchicine or analogs; use of diuretics such as probenecid; use of uricase; non-oral use of nicotinamide; sustained release forms of nicotinamide; use of inhibitors of poly ADP-ribose polymerase; use of caffeine; leucovorin rescue; use of sustained release allopurinol; non-oral use of allopurinol; bone marrow transplant stimulants; blood, platelet infusions, Neupogen, G-CSF; GM-CSF; pain management; anti-inflammatories; fluids; corticosteroids; insulin control medications; antipyretics; anti-nausea treatments; anti-diarrhea treatment; N-acetyl cysteine; or antihistamines.

(XIII) Pharmacokinetic/Pharmacodynamic Monitoring

Improvements for suboptimal chemotherapeutics including indirubin or analogs and derivatives thereof are made by the use of monitoring drug levels after dosing in an effort to maximize a patient's drug plasma level, to monitor the generation of toxic metabolites, monitoring of ancillary medicines that could be beneficial or harmful in terms of drug-drug interactions. General examples include: the monitoring of drug plasma protein binding, and monitoring of other pharmacokinetic or pharmacodynamic variables. Specific inventive examples for indirubin or analogs and derivatives thereof include: multiple determinations of drug plasma levels; or multiple determinations of metabolites in the blood or urine.

(XIV) Drug Combinations

Improvements for suboptimal chemotherapeutics including indirubin or analogs and derivatives thereof, including meisoindigo, are made by exploiting unique drug combinations that may provide a more than additive or synergistic improvement in efficacy or side-effect management. General examples include: alkylating agents with anti-metabolites, topoisomerase inhibitors with antitubulin agents. Specific inventive examples for indirubin or analogs and derivatives thereof, including meisoindigo, include: use with topoisomerase inhibitors; use with fraudulent nucleosides; use with fraudulent nucleotides; use with thymidylate synthetase inhibitors; use with signal transduction inhibitors; use with cisplatin or platinum analogs such as oxaliplatin, satraplatin, or carboplatin; use with alkylating agents such as the nitrosoureas (BCNU, Gliadel wafers, CCNU) bendamustine (Treanda); use with anti-tubulin agents; use with antimetabolites; use with berberine; use with apigenin; use with amonafide; use with colchicine and analogs; use with genistein; use with etoposide; use with cytarabine; use with camptothecins; use with vinca alkaloids; use with 5-fluorouracil; use with curcumin; use with NF-κB inhibitors; use with rosmarinic acid; use with mitoguazone; use with tetrandrine; use with antineoplastic agents not metabolized by cytochrome P450 CYP 1A2 or CYP 2C19; use in combination with biological therapies such as antibodies such as Avastin, Rituxan, Herceptin, or Erbitux; use with tyrosine kinase inhibitors; use with all-trans-retinoic acid; use with arsenicals such as arsenic trioxide; use with hydroxyurea; use with thioguanine; use with mercaptopurine; use with homoharringtonine; use with oridonin; use with uracil mustard; use with nilotinib; use with dasatinib; use with lonidamine; use with 5-azacytidine; use with thalidomide or analogs thereof; use with EGFR inhibitors such as erlotinib, afatinib, lapatinib, or dacomitinib; use with gold salts such as aurothiomalate or aurothioglucose; use with dibromodulcitol; use with dianhydrogalactitol; use with decitabine; or use with bortezomib or other proteasome inhibitors. One particularly significant use is use with Nek9 inhibitors or agents that inhibit the expression of Nek9, addressed below.

(XV) Chemosensitization

Improvements for suboptimal chemotherapeutics including indirubin or analogs and derivatives thereof, including meisoindigo, are made by exploiting them as chemosensitizers where no measureable activity is observed when used alone but in combination with other therapeutics a more than additive or synergistic improvement in efficacy is observed. General examples include: misonidazole with alkylating agents, or tirapazamine with cisplatin. Specific inventive examples for indirubin or analogs and derivatives thereof, including meisoindigo, include: as a chemosensitizer in combination with topoisomerase inhibitors; use with fraudulent nucleosides; use with fraudulent nucleotides; use with thymidylate synthetase inhibitors; use with signal transduction inhibitors; use with cisplatin or platinum analogs; use with alkylating agents such as BCNU Gliadel wafers, CCNU, bendamustine (Treanda) Temozoloimide (Temodar); use with anti-tubulin agents; use with antimetabolites; use with berberine; use with apigenin; use with amonafide; use with colchicine or analogs thereof; use with genistein; use with etoposide; use with cytarabine; use with camptothecins; use with vinca alkaloids; use with topoisomerase inhibitors; use with 5-fluorouracil; use with curcumin; use with NF-κB inhibitors; use with rosmarinic acid; use with mitoguazone; or use with tetrandrine.

(XVI) Chemopotentiation

Improvements for suboptimal chemotherapeutics including indirubin or analogs and derivatives thereof, including meisoindigo, are made by exploiting them as chemopotentiators where minimal therapeutic activity is observed alone but in combination with other therapeutics unique drug a more than additive or synergistic improvement in efficacy is observed. General examples include: amonafide with cisplatin or 5-FU. Specific inventive examples for indirubin or analogs and derivatives thereof, including meisoindigo, include: as a chemopotentiator in combination with topoisomerase inhibitors; use with fraudulent nucleosides; use with thymidylate synthetase inhibitors; use with signal transduction inhibitors; use with cisplatin or platinum analogs; use with alkylating agents such as BCNU, BCNU wafers, Gliadel, bendamustine (Treanda); use with anti-tubulin agents; use with antimetabolites; use with berberine; use with apigenin; use with amonafide; use with colchicine or analogs thereof; use with genistein; use with etoposide; use with cytarabine; use with camptothecins; use with vinca alkaloids; use with topoisomerase inhibitors; use with 5-fluorouracil; use with curcumin; use with NF-κB inhibitors; use with rosmarinic acid; use with mitoguazone; or use with tetrandrine.

(XVII) Post-Treatment Patient Management

Improvements for suboptimal chemotherapeutics including indirubin or analogs and derivatives thereof, including meisoindigo, are made by drugs, treatments and diagnostics to allow for the maximum benefit to patients treated with a compound. General examples include: pain management, nutritional support, anti-emetics, anti-nausea therapies, anti-anemia therapy, anti-inflammatories. Specific inventive examples for indirubin or analogs and derivatives thereof, including meisoindigo, include: use with therapies associated with pain management; nutritional support; anti-emetics; anti-nausea therapies; anti-anemia therapy; anti-inflammatories: antipyretics; or immune stimulants.

(XVIII) Alternative Medicine/Therapeutic Support

Improvements for suboptimal chemotherapeutics including indirubin or analogs and derivatives thereof, including meisoindigo, are made by the use of unapproved/non-conventional therapeutics or methods to enhance effectiveness or reduce side effects. General examples include: hypnosis, acupuncture, meditation, herbal medications and extracts, applied kinesiology, prayer. Specific inventive examples for indirubin or analogs and derivatives thereof, including meisoindigo, include: hypnosis; acupuncture; meditation; herbal medications created either synthetically or through extraction including NF-κB inhibitors (such as parthenolide, curcumin, rosmarinic acid); natural anti-inflammatories (including rhein, parthenolide); immunostimulants (such as those found in *Echinacea*); antimicrobials (such as berberine); flavonoids, isoflavones, and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); or applied kinesiology.

(XIX) Bulk Drug Product Improvements

Improvements for suboptimal chemotherapeutics including indirubin or analogs and derivatives thereof, including meisoindigo, are made by alterations in the pharmaceutical bulk substance. General examples include: salt formation, homogeneous crystalline structure, pure isomers. Specific inventive examples for indirubin or analogs and derivatives thereof, including meisoindigo, include: salt formation; homogeneous crystalline structure; pure isomers; increased purity; or lower residual solvents and heavy metals.

(XX) Diluent Systems

Improvements for suboptimal chemotherapeutics including indirubin or analogs and derivatives thereof, including meisoindigo, are made by alterations in the diluents used to solubilize and deliver/present the compound for administration. General examples include: Cremophor-EL, cyclodextrins for poorly water soluble compounds. Specific inventive examples for indirubin or analogs and derivatives thereof, including meisoindigo, include: use of emulsions; dimethyl sulfoxide (DMSO); N-methylformamide (NMF); dimethylformamide (DMF); dimethylacetamide (DMA); ethanol; benzyl alcohol; dextrose containing water for injection; Cremophor; cyclodextrins; or polyethylene glycol (PEG).

(XXI) Solvent Systems

Improvements for suboptimal chemotherapeutics including indirubin or analogs and derivatives thereof, including meisoindigo, are made by alterations in the solvents used or required to solubilize a compound for administration or for further dilution. General examples include: ethanol, dimethylacetamide (DMA). Specific inventive examples for indirubin or analogs and derivatives thereof, including meisoindigo, include: the use of emulsions; DMSO; NMF; DMF; DMA; ethanol; benzyl alcohol; dextrose containing water for injection; Cremophor; or PEG.

(XXII) Excipients

Improvements for suboptimal chemotherapeutics including indirubin or analogs and derivatives thereof, including meisoindigo, are made by alterations in the materials/excipients, buffering agents, or preservatives required to stabilize and present a chemical compound for proper administration. General examples include: mannitol, albumin, EDTA, sodium bisulfite, benzyl alcohol. Specific inventive examples for indirubin or analogs and derivatives thereof, including meisoindigo, include: the use of mannitol; albumin; EDTA; sodium bisulfite; benzyl alcohol; carbonate buffers; or phosphate buffers.

(XXII) Dosage Forms

Improvements for suboptimal chemotherapeutics including indirubin or analogs and derivatives thereof, including meisoindigo, are made by alterations in the potential dosage forms of the compound dependent on the route of administration, duration of effect, plasma levels required, exposure to side-effect normal tissues and metabolizing enzymes. General examples include: tablets, capsules, topical gels, creams, patches, suppositories. Specific inventive examples for indirubin or analogs and derivatives thereof, including meisoindigo, include: the use of tablets; capsules; topical gels; topical creams; patches; suppositories; or lyophilized dosage fills.

(XXIV) Dosage Kits and Packaging

Improvements for suboptimal chemotherapeutics including indirubin or analogs and derivatives thereof, including meisoindigo, are made by alterations in the dosage forms, container/closure systems, accuracy of mixing and dosage preparation and presentation. General examples include:

amber vials to protect from light, stoppers with specialized coatings. Specific inventive examples for indirubin or analogs and derivatives thereof, including meisoindigo, include: the use of amber vials to protect from light; or stoppers with specialized coatings to improve shelf-life stability.

(XXV) Drug Delivery Systems

Improvements for suboptimal chemotherapeutics including indirubin or analogs and derivatives thereof, including meisoindigo, are made by the use of delivery systems to improve the potential attributes of a pharmaceutical product such as convenience, duration of effect, reduction of toxicities. General examples include: nanocrystals, bioerodible polymers, liposomes, slow release injectable gels, microspheres. Specific inventive examples for indirubin or analogs and derivatives thereof, including meisoindigo, include: the use of nanocrystals; bioerodible polymers; liposomes; slow release injectable gels; or microspheres.

(XXVI) Drug Conjugate Forms

Improvements for suboptimal chemotherapeutics including indirubin or analogs and derivatives thereof, including meisoindigo, are made by alterations to the parent molecule with covalent, ionic, or hydrogen bonded moieties to alter the efficacy, toxicity, pharmacokinetics, metabolism, or route of administration. General examples include: polymer systems such as polyethylene glycols, polylactides, polyglycolides, amino acids, peptides, or multivalent linkers. Specific inventive examples for indirubin or analogs and derivatives thereof, including meisoindigo, include: the use of polymer systems such as polyethylene glycols; polylactides; polyglycolides; amino acids; peptides; or multivalent linkers.

(XXVII) Compound Analogs

Improvements for suboptimal chemotherapeutics including indirubin or analogs and derivatives thereof, including meisoindigo, are made by alterations to the parent structure of a molecule with additional chemical functionalities that may alter efficacy, or reduce toxicity, pharmacological performance, route of administration, or another relevant factor for therapeutic efficacy. General examples include: alteration of side chains to increase or decrease lipophilicity, additional chemical functionalities to alter reactivity, electron affinity, binding capacity, salt forms. Specific inventive examples for indirubin or analogs and derivatives thereof, including meisoindigo, include: alteration of side chains to increase or decrease lipophilicity; additional chemical functionalities to alter reactivity; electron affinity; binding capacity; or salt forms. The additional chemical functionalities to alter reactivity can include, but are not necessarily limited to, alkylating functionalities or binding sites for colchicine.

(XXVIII) Prodrugs

Improvements for suboptimal chemotherapeutics including indirubin or analogs and derivatives thereof, including meisoindigo, are made by alterations to the molecule such that improved pharmaceutical performance is gained with a variant of the active molecule in that after introduction into the body a portion of the molecule is cleaved to reveal the preferred active molecule. General examples include: enzyme sensitive esters, dimers, Schiff bases. Specific inventive examples for indirubin or analogs and derivatives thereof, including meisoindigo, include: the use of enzyme sensitive esters; the use of dimers; the use of Schiff bases; the use of pyridoxal complexes; the use of caffeine complexes; the use of N-substituted carbohydrate derivatives; the use of Mannich N-oxides; the use of products of reaction with an acylating or carbamylating agent; the use of hexanoate conjugates; the use of polymer-agent conjugates; or the use of prodrugs that are subject to redox activation.

(XXIX) Multiple Drug Systems

Improvements for suboptimal chemotherapeutics including indirubin or analogs and derivatives thereof, including meisoindigo, are made by the use of additional compounds, biological agents that when administered in the proper fashion, a unique and beneficial effect can be realized. General examples include: inhibitors of multi-drug resistance, specific drug resistance inhibitors, specific inhibitors of selective enzymes, signal transduction inhibitors, repair inhibition. Specific inventive examples for indirubin or analogs and derivatives thereof, including meisoindigo, include: the use of inhibitors of multi-drug resistance; specific drug resistance inhibitors; specific inhibitors of selective enzymes; signal transduction inhibitors; repair inhibition; or topoisomerase inhibitors with non-overlapping side effects.

(XXX) Biotherapeutic Enhancement

Improvements for suboptimal chemotherapeutics including indirubin or analogs and derivatives thereof, including meisoindigo, are made by their use in combination as sensitizers/potentiators with biological response modifiers. General examples include: use in combination as sensitizers/potentiators with biological response modifiers, cytokines, lymphokines, therapeutic antibodies, antisense therapies, gene therapies. Specific inventive examples for indirubin or analogs and derivatives thereof, including meisoindigo, include: use in combination as sensitizers/potentiators with biological response modifiers; cytokines; lymphokines; therapeutic antibodies; antisense therapies such as Avastin, Herceptin, Rituxan, and Erbitux; gene therapies; ribozymes; or RNA interference.

(XXXI) Biotherapeutic Resistance Modulation

Improvements for suboptimal chemotherapeutics including indirubin or analogs and derivatives thereof, including meisoindigo, are made by exploiting their selective use to overcome developing or complete resistance to the efficient use of biotherapeutics. General examples include: tumors resistant to the effects of biological response modifiers, cytokines, lymphokines, therapeutic antibodies, antisense therapies, gene therapies. Specific inventive examples for indirubin or analogs and derivatives thereof, including meisoindigo, include: the use against tumors resistant to the effects of biological response modifiers; cytokines; lymphokines; therapeutic antibodies; antisense therapies; therapies such as Avastin, Rituxan, Herceptin, Erbitux; gene therapies; ribozymes; or RNA interference.

(XXXII) Radiation Therapy Enhancement

Improvements for suboptimal chemotherapeutics including indirubin or analogs and derivatives thereof, including meisoindigo, are made by exploiting their use in combination with ionizing radiation, phototherapies, heat therapies, or radio-frequency generated therapies. General examples include: hypoxic cell sensitizers, radiation sensitizers/protectors, photosensitizers, radiation repair inhibitors. Specific inventive examples for indirubin or analogs and derivatives thereof, including meisoindigo, include: the use with hypoxic cell sensitizers; radiation sensitizers/protectors; photosensitizers; radiation repair inhibitors; thiol depletion; vaso-targeted agents; use with radioactive seeds; use with radionuclides; use with radiolabeled antibodies; or use with brachytherapy.

(XXXIII) Novel Mechanisms of Action

Improvements for suboptimal chemotherapeutics including indirubin or analogs and derivatives thereof, including meisoindigo, are made by optimizing their utility by determining the various mechanisms of action, biological targets of a compound for greater understanding and precision to better exploit the utility of the molecule. General examples include: Gleevec for chronic myelocytic leukemia (CML), arsenic trioxide for acute promyelocytic leukemia (APL), retinoic acid for APL. Specific inventive examples for indirubin or analogs and derivatives thereof, including meisoindigo, include: the use with inhibitors of poly-ADP ribose polymerase; agents that effect vasculature; vasodilation; oncogenic targeted agents; signal transduction inhibitors; EGFR inhibition; Protein Kinase C inhibition; Phospholipase C down-regulation; jun down-regulation; histone genes; VEGF; ornithine decarboxylase; jun D; v-jun; GPCRs; protein kinase A; telomerase, prostate specific genes; protein kinases; or histone deacetylase.

(XXXIV) Selective Target Cell Population Therapeutics

Improvements for suboptimal chemotherapeutics including indirubin or analogs and derivatives thereof, including meisoindigo, are made by more precise identification and exposure of the compound to those select cell populations where the compound's effect can be maximally exploited. General examples include: tirapazamine and mitomycin C for hypoxic cells, vinca alkaloids for cells entering mitosis. Specific inventive examples for indirubin or analogs and derivatives thereof, including meisoindigo, include: use against radiation sensitive cells; radiation resistant cells; energy depleted cells; or endothelial cells.

Additional alternatives specifically applicable to indirubin derivatives and analogs, including meisoindigo, are further described below in the description of detailed alternatives for these categories.

Accordingly, one aspect of the present invention is a method to improve the efficacy and/or reduce the side effects of suboptimally administered drug therapy employing a therapeutic agent selected from the group consisting of indirubin and an analog or derivative thereof comprising the steps of:

(1) identifying at least one factor or parameter associated with the efficacy and/or occurrence of side effects of the drug therapy employing a therapeutic agent selected from the group consisting of indirubin and an analog or derivative thereof; and (2) modifying the factor or parameter to improve the efficacy and/or reduce the side effects of the drug therapy.

Typically, the factor or parameter is selected from the group consisting of:

(1) dose modification;
(2) route of administration;
(3) schedule of administration;
(4) indications for use;
(5) selection of disease stage;
(6) other indications;
(7) patient selection;
(8) patient/disease phenotype;
(9) patient/disease genotype;
(10) pre/post-treatment preparation
(11) toxicity management;
(12) pharmacokinetic/pharmacodynamic monitoring;
(13) drug combinations;
(14) chemosensitization;
(15) chemopotentiation;
(16) post-treatment patient management;
(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action; and
(33) selective target cell population therapeutics.

Typically, the hyperproliferative disease is cancer. Methods according to the present invention are applicable to many forms of cancer, including, but not limited to: (A) breast cancer, including: (1) ductal carcinoma, including ductal carcinoma in situ (DCIS) (comedocarcinoma, cribriform, papillary, micropapillary), infiltrating ductal carcinoma (IDC), tubular carcinoma, mucinous (colloid) carcinoma, papillary carcinoma, metaplastic carcinoma, and inflammatory carcinoma; (2) lobular carcinoma, including lobular carcinoma in situ (LCIS) and invasive lobular carcinoma; and (3) Paget's disease of the nipple; (B) cancers of the female reproductive system, including: (1) cancers of the cervix uteri, including cervical intraepithelial neoplasia (Grade I), cervical intraepithelial neoplasia (Grade II), cervical intraepithelial neoplasia (Grade III) (squamous cell carcinoma in situ), keratinizing squamous cell carcinoma, nonkeratinizing squamous cell carcinoma, verrucous carcinoma, adenocarcinoma in situ, adenocarcinoma in situ, endocervical type, endometrioid adenocarcinoma, clear cell adenocarcinoma, adenosquamous carcinoma, adenoid cystic carcinoma, small cell carcinoma, and undifferentiated carcinoma; (2) cancers of the corpus uteri, including endometrioid carcinoma, adenocarcinoma, adenocanthoma (adenocarcinoma with squamous metaplasia), adenosquamous carcinoma (mixed adenocarcinoma and squamous cell carcinoma, mucinous adenocarcinoma, serous adenocarcinoma, clear cell adenocarcinoma, squamous cell adenocarcinoma, and undifferentiated adenocarcinoma; (3) cancers of the ovary, including serous cystadenoma. serous cystadenocarcinoma, mucinous cystadenoma, mucinous cystadenocarcinoma, endometrioid tumor, endometrioid adenocarcinoma, clear cell tumor, clear cell cystadenocarcinoma, and unclassified tumor; (4) cancers of the vagina, including squamous cell carcinoma and adenocarcinoma; and (5) cancers of the vulva, including vulvar intraepithelial neoplasia (Grade I), vulvar intraepithelial neoplasia (Grade II), vulvar intraepithelial neoplasia (Grade III) (squamous cell carcinoma in situ); squamous cell carcinoma, verrucous carcinoma, Paget's disease of the vulva, adenocarcinoma (NOS), basal cell carcinoma (NOS), and Bartholin's gland carcinoma; (C) cancers of the male reproductive system, including: (1) cancers of the penis, including squamous cell carcinoma; (2) cancers of the prostate, including adenocarcinoma, sarcoma, and transitional cell carcinoma of the prostate; (3) cancers of the testis, including seminomatous tumor, nonseminomatous tumor, teratoma, embryonal carcinoma, yolk sac tumor, and Choriocarcinoma; (D) cancers of the cardiac system, including sarcoma (angiosarcoma, fibrosarcoma, rhabdomyosarcoma, liposarcoma), myxoma, rhabdomyoma, fibroma, lipoma and teratoma; (E) cancers of the respiratory system, including squamous cell carcinoma of the larynx, primary pleural mesothelioma, and squamous cell carcinoma of the pharynx; (F) cancers of the lung, including squamous cell carcinoma (epidermoid carcinoma), variants of squamous cell carcinoma, spindle cell carcinoma, small cell carcinoma, carcinoma of other cells, carcinoma of intermediate cell type, combined oat cell carcinoma, adenocarcinoma, acinar adenocarcinoma, papillary adenocarcinoma, bronchiolo-alveolar carcinoma, solid carcinoma with mucus formation, large cell carcinoma, giant cell carcinoma, clear cell carcinoma, and sarcoma; (G) cancers of the gastrointestinal tract, including: (1) cancers of the ampulla of Vater, including primary adenocarcinoma, carcinoid tumor, and lymphoma; (2) cancers of the anal canal, including adenocarcinoma, squamous cell carcinoma, and melanoma; (3) cancers of the extrahepatic bile ducts, including carcinoma in situ, adenocarcinoma, papillary adenocarcinoma, adenocarcinoma, intestinal type, mucinous adenocarcinoma, clear cell adenocarcinom, segnet-ring cell carcinoma, adenosquamous carcinoma, squamous cell carcinoma, small cell (oat) carcinoma, undifferentiated carcinoma, carcinoma (NOS), sarcoma, and carcinoid tumor; (4) cancers of the colon and rectum, including adenocarcinoma in situ, adenocarcinoma, mucinous adenocarcinoma (colloid type; greater than 50% mucinous carcinoma), signet ring cell carcinoma (greater than 50% signet ring cell), squamous cell (epidermoid) carcinoma, adenosquamous carcinoma, small cell (oat cell) carcinoma, undifferentiated carcinoma, carcinoma (NOS), sarcoma, lymphoma, and carcinoid tumor; (5) cancers of the esophagus, including squamous cell carcinoma, adenocarcinoma, leiomyosarcoma, and lymphoma; (6) cancers of the gallbladder, including adenocarcinoma, adenocarcinoma, intestinal type, adenosquamous carcinoma, carcinoma in situ, carcinoma (NOS), clear cell adenocarcinoma, mucinous adenocarcinoma, papillary adenocarcinoma, signet-ring cell carcinoma, small cell (oat cell) carcinoma, squamous cell carcinoma, and undifferentiated carcinoma; (7) cancers of the lip and oral cavity, including squamous cell carcinoma; (8) cancers of the liver, including hepatoma (hepatocellular carcinoma), cholangiocarcinoma, hepatoblastoma, angiosarcoma, hepatocellular adenoma, and hemangioma; (9) cancers of the exocrine pancreas, including duct cell carcinoma, pleomorphic giant cell carcinoma, giant cell carcinoma, osteoclastoid type, adenocarcinoma, adenosquamous carcinoma, mucinous (colloid) carcinoma, cystadenocarcinoma, acinar cell carcinoma, papillary carcinoma, small cell (oat cell) carcinoma, mixed cell typed, carcinoma (NOS), undifferentiated carcinoma, endocrine cell tumors arising in the islets of langerhans, and carcinoid; (10) cancers of the salivary glands, including acinic (acinar) cell carcinoma, adenoid cystic carcinoma (cylindroma), adenocarcinoma, squamous cell carcinoma, carcinoma in pleomorphic adenoma (malignant mixed tumor), mucoepidermoid carcinoma (well differentiated or low grade), and mucoepidermoid carcinoma (poorly differentiated or high grade); (11) cancers of the stomach, including adenocarcinoma, papillary adenocarcinoma, tubular adenocarcinoma, mucinous adenocarcinoma, signet ring cell carcinoma, adenosquamous carcinoma, squamous cell carcinoma, small cell carcinoma, undifferentiated carcinoma, lymphoma, sarcoma, and carcinoid tumor; and (12) cancers of the small intestine, including adenocarcinoma, lymphoma, carcinoid tumors, Kaposi's sarcoma, leiomyoma, hemangioma, lipoma, neurofibroma, and fibroma; (H) cancers of the urinary system, including: (1) cancers of the kidney, including renal cell carcinoma, carcinoma of Bellini's collecting ducts, adenocarcinoma, papillary carcinoma, tubular carcinoma, granular cell carcinoma, clear cell carcinoma (hypernephroma), sarcoma of the kidney, and nephroblastoma; (2) cancers of the renal pelvis and ureter, including transitional cell carcinoma, papillary transitional cell carcinoma, squamous cell carcinoma, and adenocarcinoma; (3) cancers of the urethra, including transitional cell carcinoma, squamous cell carcinoma, and adenocarcinoma; and (4) cancers of the urinary bladder, including carcinoma in situ, transitional urothelial cell carcinoma, papillary transitional cell carcinoma, squamous cell carcinoma, adenocarcinoma, undifferentiated; (l) cancers of muscle, bone, and soft tissue, including: (1) cancers of bone, including: (a) bone-forming: osteosarcoma; (b) cartilage-forming: chondrosarcoma and mesenchymal chondrosarcoma; (c) diant cell tumor, malignant; (d) Ewing's sarcoma; (e) vascular tumors: hemangioendothelioma, hemangiopericytoma, and angiosarcoma; (f) connective tissue tumors: fibrosarcoma, liposarcoma, malignant mesenchymoma, and undifferentiated sarcoma; and (g) other tumors: chordoma and adamantinoma of long bones; (2) cancers of soft tissues, including: alveolar soft-part sarcoma, angiosarcoma, epithelioid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, rhabdomyosarcoma, synovial sarcoma, and sarcoma (NOS); (3) cancers of the nervous system, including cancers of the skull (osteoma, hemangioma, granuloma, xanthoma, osteitis deformans), cancers of the meninges (meningioma, meningiosarcoma, gliomatosis), cancers of the brain (astrocytoma, medulloblastoma, glioma, ependymoma, germinoma (pilealoma), glioblastoma multiform, oligodendroglioma, schwannoma, retinoblastoma, congenital tumors), and cancers of the spinal cord neurofibroma, meningioma, glioma, sarcoma); (4) hematologic cancers, including myeloid leukemia (acute and chronic), acute lymphloblastic leukemia, chronic lymphocytic leukemia, myeloproliferative diseases, multiple myeloma; myelodysplastic syndrome), Hodgkin's disease, and non-Hodgkin's lymphoma (malignant lymphoma); (5) cancers of the endocrine system, including: (a) cancers of the thyroid gland, including papillary carcinoma (including those with follicular foci), follicular carcinoma, medullary carcinoma, and undifferentiated (anaplastic) carcinoma; and (b) neuroblastomas, including sympathicoblastoma, sympathicogonioma, malignant ganglioneuroma, gangliosympathicoblastoma, and ganglioneuroma; (6) cancers of the skin, including squamous cell carcinoma, spindle cell variant of squamous cell carcinoma, basal cell carcinoma, adenocarcinoma developing from sweat or sebaceous gland, and malignant melanoma; (7) cancers of the eye, including: (a) cancers of the conjunctiva, including carcinoma of the conjunctiva; (b) cancers of the eyelid, including basal cell carcinoma, squamous cell carcinoma, melanoma of the eyelid, and sebaceous cell carcinoma; (c) cancers of the lacrimal gland, including adenocarcinoma, adenoid cystic carcinoma, carcinoma in pleomorphic adenoma, mucoepidermoid carcinoma, and squamous cell carcinoma; (d) cancers of the uvea, including spindle cell melanoma, mixed cell melanoma, and epithelioid cell melanoma; (e) cancers of the orbit, including sarcoma of the orbit, soft tissue tumor, and sarcoma of bone; and (f) retinoblastoma; and (l) cancers of unknown primary origin. In particular, methods according to the present invention and compositions suitable for use according to those methods are applicable to lower grade astrocytomas and other primary central nervous system tumors besides glioblastoma multiforme (GBM), as well as to central nervous system metastases of other tumors including solid tumors and hematologic tumors (e.g., breast, lung, bladder, and bowel tumors, leukemias, and lymphomas), in addition to squamous cell non-small cell lung cancer. In addition, methods according to the present invention and compositions suitable for use according to those methods are applicable to melanoma, breast lymphoma (both Hodgkins and non-Hodgkins), colorectal cancer, acute lymphoblastic leukemia, and for lowering the incidence of central nervous system leukemia, non-small cell lung cancer, cervical carcinoma, bladder carcinoma, and metastatic hemangiopericytoma. In particular, when the therapeutically active compound is meisoindigo, methods according to the present invention and compositions suitable for use according to those methods are applicable to acute myelogenous leukemia, chronic myelogenous leukemia, and colon cancer.

In one alternative, the therapeutic agent is indirubin, an analog thereof, or a derivative of indirubin or an analog thereof. Analogs of indirubin and derivatives of indirubin and analogs of indirubin are described above as Alternatives (1)-(486). In particular, methods and compositions according to the present invention are applicable to meisoindigo.

The following improvements all apply either to indirubin, analogs of indirubin, or derivatives of indirubin or analogs of indirubin, including, but not limited to, Alternatives (1)-(486), as indicated with respect to the specific improvement described below. Methods according to the present invention are particularly applicable to meisoindigo, and all methods encompass the use of meisoindigo or a derivative thereof as specifically described.

When the improvement is dose modification, the dose modification can be, but is not limited to, at least one dose modification selected from the group consisting of:
(a) continuous i.v. infusion for hours to days;
(b) biweekly administration;
(c) doses greater than 5 mg/m$^2$/day;
(d) progressive escalation of dosing from 1 mg/m$^2$/day based on patient tolerance;
(e) use of caffeine to modulate metabolism;
(f) use of isonazid to modulate metabolism;
(g) selected and intermittent boosting of dosage administration;
(h) administration of single and multiple doses escalating from 5 mg/m$^2$/day via bolus;
(i) oral dosages of below 30 mg/m$^2$;
(j) oral dosages of above 130 mg/m$^2$;
(k) chronic low dose administration of from about 10 mg/day to about 25 mg/day;
(l) intermittent administration of from about 50 mg to about 150 mg twice weekly or three times weekly;
(m) administration of from about 50 mg/day to about 150 mg/day for 10-14 days per month; and
(n) chronic daily dosing at a dose of equal to or greater than 100 mg/day.

When the improvement is made by route of administration, the route of administration can be, but is not limited to, at least one route of administration selected from the group consisting of:
(a) topical administration;
(b) intravesicular administration for bladder cancer;
(c) oral administration;
(d) slow release oral delivery;
(e) intrathecal administration;
(f) intraarterial administration;
(g) continuous infusion; and
(h) intermittent infusion.

When the improvement is made by schedule of administration, the schedule of administration can be, but is not limited to, at least one schedule of administration selected from the group consisting of:
(a) daily administration;
(b) weekly administration;
(c) weekly administration for three weeks;
(d) biweekly administration;
(e) biweekly administration for three weeks with a 1-2 week rest period;
(f) intermittent boost dose administration; and
(g) daily administration for one week for multiple weeks.

When the improvement is made by indication for use, the indication for use can be, but is not limited to, at least one indication for use selected from the group consisting of:
(a) use for treatment of leukemias;
(b) use for treatment of myelodysplastic syndrome;
(c) use for treatment of T-cell lymphomas;
(d) use for treatment of B-cell lymphomas;
(e) use for treatment of mantle cell lymphoma;
(f) use for suppression of proliferation of cancer stem cells;
(g) use for treatment of ovarian carcinoma;
(h) use for treatment of carcinoma of the lung;
(i) use for treatment of angiogenic diseases;
(j) use for treatment of benign prostatic hyperplasia;
(k) use for treatment of psoriasis;
(l) use for treatment of gout;
(m) use for treatment of autoimmune conditions;
(n) use for treatment of treatment of insulin-resistant diabetes;
(o) use for treatment of transplantation rejection;
(p) use for prevention of restenosis in cardiovascular disease;
(q) use for treatment of mycosis fungoides;
(r) use in bone marrow transplantation;
(s) use as an anti-infective agent;
(t) use for treatment of AIDS; and
(u) use for treatment of Alzheimer's disease, including disease prevention, slowing of disease progression and amelioration or reversal or disease symptoms, based on the effect of meisoindigo on phosphorylation of $\tau$ (tau) protein.

The leukemia to be treated can be, but is not limited to, acute myelocytic leukemia (AML), chronic myelocytic leukemia (CML), acute lymphocytic leukemia (ALL), chronic lymphocytic leukemia (CLL), or acute promyelocytic leukemia (APL).

In one alternative, the indication for use is for treatment of AML with or without administration of a therapeutically effective quantity of an antifungal agent, wherein the antifungal agent is metabolized by a different cytochrome P450 enzyme than the cytochrome P450 enzyme metabolizing the indirubin derivative or analog. Antifungal agents include, but are not limited to, amphotericin B, voriconazole, itraconazole, fluconazole, caspofungin, flucytosine, ketoconazole, posaconazole, clotrimazole, miconazole, econazole, butozonazole, oxiconazole, sertaconazole, sulconazole, and terconazole.

In another alternative, the indication for use is for treatment of APL with or without the administration of a therapeutically effective quantity of retinoic acids such as all-trans-retinoic acid (tretinoin) and arsenicals such as arsenic trioxide.

In still another alternative, the indication for use is for treatment of CML. In one aspect of this alternative, the treatment of CML is of CML subsequent to or simultaneously with failure of treatment by tyrosine kinase inhibitors (TKIs). In another aspect of this alternative, the treatment of CML is of CML that is transitioning or has transitioned to blast crisis. In still another aspect of this alternative, the treatment of CML is in combination with administration of a therapeutically effective quantity of a tyrosine kinase inhibitor (TKI). Tyrosine kinase inhibitors used for treatment of chronic myelocytic leukemia (CML) include, but are not limited to, imatinib, bosutinib, nilotinib, dasatinib, erlotinib, afatinib, and dacomitinib. Additional tyrosine kinase inhibitors are known in the art. For example, the use of tyrosine kinase inhibitors is described in United States Patent Application Publication No. 2011/0206661 by Zhang et al., which is directed to trimethoxyphenyl inhibitors of tyrosine kinase, and in United States Patent Application Publication No. 2011/0195066, which is directed to quinoline inhibitors of tyrosine kinase, both of which are incorporated herein by this reference. The use of tyrosine kinase inhibitors is also described in United States Patent Application Publication No. 2011/053968 by Zhang et al., incorporated herein by this reference, which is directed to aminopyridine inhibitors of tyrosine kinase. The use of tyrosine kinase inhibitors is also described in United States Patent Application Publication No. 2010/0291025, incorporated herein by this reference, which is directed to indazole inhibitors of tyrosine kinase. The use of tyrosine kinase inhibitors is also described in United States Patent Application Publication No. 2010/0190749 by Ren et al., incorporated herein by this reference; these tyrosine kinase inhibitors are benzoxazole compounds; compounds of this class can also inhibit mTOR and lipid kinases such as phosphoinositide 3-kinases. The use of tyrosine kinase inhibitors is also described in U.S. Pat. No. 8,242,270 by Lajeunesse et al., incorporated herein by this reference; these tyrosine kinase inhibitors are 2-aminothiazole-5-aromatic carboxamides. Still other tyrosine kinase inhibitors are known in the art or are under development, and are described in B. J. Druker & N. B. Lydon, "Lessons Learned from the Development of an Abl Tyrosine Kinase Inhibitor for Chronic Myelogenous Leukemia," *J. Clin. Invest.* 105: 3-7 (2000), incorporated herein by this reference. In still another aspect of this alternative, the treatment of CML is in combination with administration of a therapeutically effective quantity of homoharringtonine. Homoharringtonine (omacetaxine mepesuccinate) has the structure shown below:

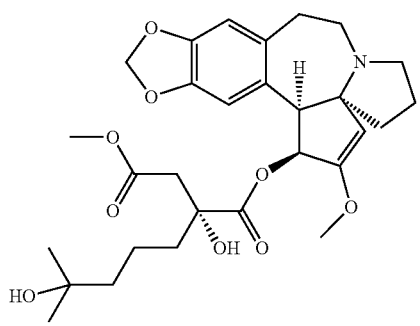

and is a protein translation inhibitor. Homoharringtonine inhibits protein translation by preventing the initial elongation step of protein synthesis. It interacts with the ribosomal A-site and prevents the correct positioning of amino acid side chains of incoming aminoacyl-tRNAs. In still another aspect of this alternative, the treatment of CML is in combination with administration of a therapeutically effective quantity of an alkylating agent. Alkylating agents include, but are not limited to, Shionogi 254-S, aldo-phosphamide analogues, altretamine, anaxirone, Boehringer Mannheim BBR-2207, bendamustine, bestrabucil, budotitane, busulfan, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)$_2$, dianhydrogalactitol, dibromodulcitol, other substituted hexitols, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, trimelamol, and uramustine, as described in U.S. Pat. No. 7,446,122 by Chao et al., incorporated herein by this reference. In still another aspect of this alternative, the treatment of CML is in combination with administration of a therapeutically effective quantity of hydroxyurea.

When the improvement is made by selection of disease stage, the selection of disease stage can be, but is not limited to, at least one selection of disease stage selected from the group consisting of:
(a) use for the treatment of localized polyp stage colon cancer;
(b) use for leukoplakia in the oral cavity;
(c) use for angiogenesis inhibition to prevent or limit metastatic spread of a malignancy; and
(d) use for treatment of HIV with a therapy selected from the group consisting of azidothymidine (AZT), dideoxyadenosine (DDI), and reverse transcriptase inhibitors.

When the improvement is made by other indications, the other indications can be, but are not limited, to at least one other indication selected from the group consisting of:
(a) use as an anti-infective agent;
(b) use as an antiviral agent;
(c) use as an antibacterial agent;
(d) use as an agent to treat pleural effusion;
(e) use as an antifungal agent;
(f) use as an anti-parasitic agent;
(g) use as an agent to treat eczema;
(h) use as an agent to treat herpes zoster (shingles);
(i) use as an agent to treat condylomata;
(j) use as an agent to treat human papilloma virus (HPV); and
(k) use as an agent to treat herpes simplex virus (HSV).

When the improvement is made by patient selection, the patient selection can be, but is not limited to, a patient selection carried out by a criterion selected from the group consisting of:
(a) selecting patients with a disease condition characterized by a high level of a metabolic enzyme selected from the group consisting of histone deacetylase and ornithine decarboxylase;
(b) selecting patients with a low or high susceptibility to a condition selected from the group consisting of thrombocytopenia and neutropenia;
(c) selecting patients intolerant of GI toxicities; and
(d) selecting patients characterized by over- or under-expression of a gene selected from the group consisting of c-Jun, a GPCR, a signal transduction protein, VEGF, a prostate-specific gene, and a protein kinase.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, $β_3$-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

When the improvement is made by analysis of patient or disease phenotype, the analysis of patient or disease phenotype can be, but is not limited to, a method of analysis of patient or disease phenotype carried out by a method selected from the group consisting of:
(a) use of a diagnostic tool, a diagnostic technique, a diagnostic kit, or a diagnostic assay to confirm a patient's particular phenotype;
(b) use of a method for measurement of a marker selected from the group consisting of histone deacetylase, ornithine decarboxylase, VEGF, a protein that is a gene product of a prostate specific gene, a protein that is a gene product of jun, and a protein kinase;
(c) surrogate compound dosing; and
(d) low dose pre-testing for enzymatic status.

When the improvement is made by analysis of patient or disease genotype, the analysis of patient or disease genotype can be, but is not limited to, a method of analysis of patient or disease genotype carried out by a method selected from the group consisting of:
(a) use of a diagnostic tool, a diagnostic technique, a diagnostic kit, or a diagnostic assay to confirm a patient's particular genotype;
(b) use of a gene chip;
(c) use of gene expression analysis;
(d) use of single nucleotide polymorphism (SNP) analysis; and
(e) measurement of the level of a metabolite or a metabolic enzyme.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference.

When the improvement is made by pre/post-treatment preparation, the pre/post-treatment preparation can be, but is not limited to, a method of pre/post treatment preparation selected from the group consisting of:
(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) infection control; and
(j) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity.

Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

When the improvement is made by toxicity management, the toxicity management can be, but is not limited to, a method of toxicity management selected from the group consisting of:

(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) the use of sustained-release allopurinol;
(j) the non-oral use of allopurinol;
(k) the use of bone marrow transplants;
(l) the use of a blood cell stimulant;
(m) the use of blood or platelet infusions;
(n) the administration of an agent selected from the group consisting of filgrastim (Neupogen®), G-CSF, and GM-CSF;
(o) the application of a pain management technique;
(p) the administration of an anti-inflammatory agent;
(q) the administration of fluids;
(r) the administration of a corticosteroid;
(s) the administration of an insulin control medication;
(t) the administration of an antipyretic;
(u) the administration of an anti-nausea treatment;
(v) the administration of an anti-diarrheal treatment;
(w) the administration of N-acetylcysteine; and
(x) the administration of an antihistamine.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" in *Goodman & Gilman's The Pharmacological Basis of Therapeutics* (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

When the improvement is made by pharmacokinetic/pharmacodynamic monitoring, the pharmacokinetic/pharmacodynamic monitoring can be, but is not limited to a method selected from the group consisting of:
  (a) multiple determinations of blood plasma levels; and
  (b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods. Immunoassays can be sandwich or competitive immunoassays. In another alternative, the determination of plasma levels of meisoindigo can be determined by liquid chromatograpy-mass spectrometry (LC-MS). The use of LC-MS is well known in the art and is described in M. S. Lee & E. H. Kerns, "LC/MS Applications in Drug Development," *Mass Spectrometry Rev.* 18: 187-279 (1999), incorporated herein by this reference.

When the improvement is made by drug combination, the drug combination can be, but is not limited to, a drug combination selected from the group consisting of:
  (a) use with topoisomerase inhibitors;
  (b) use with fraudulent nucleosides;
  (c) use with fraudulent nucleotides;
  (d) use with thymidylate synthetase inhibitors;
  (e) use with signal transduction inhibitors;
  (f) use with cisplatin or platinum analogs;
  (g) use with alkylating agents;
  (h) use with anti-tubulin agents;
  (i) use with antimetabolites;
  (j) use with berberine;
  (k) use with apigenin;

(l) use with amonafide;
(m) use with colchicine or an analog thereof;
(n) use with genistein;
(o) use with etoposide;
(p) use with cytarabine;
(q) use with a camptothecin;
(r) use with a vinca alkaloid;
(s) use with 5-fluorouracil;
(t) use with curcumin;
(u) use with an NF-κB inhibitor;
(v) use with rosmarinic acid;
(w) use with mitoguazone;
(x) use with tetandrine;
(y) use with an antineoplastic agent not metabolized by cytochrome P450 CYP 1A2 or CYP 2C19;
(z) use with a biological therapy;
(aa) use with a tyrosine kinase inhibitor;
(ab) use with all-trans-retinoic acid;
(ac) use with an arsenical;
(ad) use with hydroxyurea;
(ae) use with thioguanine;
(af) use with mercaptopurine;
(ag) use with homoharringtonine;
(ah) use with oridonin;
(ai) use with uracil mustard;
(ak) use with nilotinib;
(al) use with dasatinib;
(am) use with lonidamine;
(an) use with 5-azacytidine;
(ao) use with thalidomide or an analog thereof;
(ap) use with an EGFR inhibitor such as erlotinib, afatinib, lapatinib, or dacomitinib;
(aq) use with a gold salt such as aurothiomalate or aurothioglucose;
(ar) use with dibromodulcitol;
(as) use with dianhydrogalactitol;
(at) use with decitabine;
(au) use with a proteasome inhibitor; and
(av) use with a Nek9 inhibitor or an agent inhibiting the expression of the NEK9 gene.

Topoisomerase inhibitors include, but are not limited to, irinotecan, topotecan, camptothecin, lamellarin D, amsacrine, etoposide, etoposide phosphate, teniposide, doxorubicin, and ICRF-193.

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference.

Cisplatin or platinum analogs include, but are not limited to, cisplatin, oxaliplatin, satraplatin, and carboplatin.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al., incorporated herein by this reference.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Amonafide is a topoisomerase inhibitor and DNA intercalator that has anti-neoplastic activity.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to, bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Tetrandrine has the chemical structure 6,6',7,12-tetramethoxy-2,2'-dimethyl-1 β-berbaman and is a calcium channel blocker that has anti-inflammatory, immunologic, and antiallergenic effects, as well as an anti-arrhythmic effect similar to that of quinidine. It has been isolated from *Stephania tetranda* and other Asian herbs.

Etoposide is an antineoplastic agent that forms a ternary complex with DNA and the enzyme topoisomerase II and thereby prevents religation of the DNA strands and causes DNA strand breakage. This causes errors in DNA synthesis and promotes apoptosis of the cancer cells.

Cytarabine (cytosine arabinoside) is an antimetabolite that interferes with DNA synthesis in cancer cells when converted to its triphosphate, cytosine arabinoside triphosphate.

Camptothecins include, but are not limited to, camptothecin, topotecan, and irinotecan. Other camptothecins include DB 67, BNP 1350, exatecan, lurtotecan, ST 1481, and CKD 602. The activity of camptothecins is described in H. Ulukan & P. W. Swaan, "Camptothecins, a Review of Their Chemotherapeutical Potential," *Drugs* 62: 2039-2057 (2002), incorporated herein by this reference.

*Vinca* alkaloids include, but are not limited to, vinblastine, vincristine, vinorelbine, and vindesine.

5-Fluorouracil is a pyrimidine analog that acts by inhibiting the enzyme thymidylate synthase and thus prevents the synthesis of thymidine.

Oridonin is a diterpenoid purified from *Rabdosia rubescens* and inhibits proliferation of cells from lymphoid malignancies; its primary action appears to be blockage of the NF-κB signal pathway; its activity is described in T. Ikezoe et al., "Oridonin, a Diterpenoid Purified from *Rabdosia rubescens*, Inhibits the Proliferation of Cells from Lymphoid Malignancies in Association with Blockade of the NF-κB Signal Pathways," *Mol. Cancer Ther.* 4: 578-586 (2005), incorporated herein by this reference.

Nilotinib and dasatinib are tyrosine kinase inhibitors.

Lonidamine (1-(2,4-dichlorobenzyl)-1H-indazole-3-carboxylic acid) is an aerobic glycolysis inhibitor in cancer cells; its activity is described in H. Pelicano et al., "Glycolysis Inhibition for Anticancer Treatment," *Oncogene* 25: 4633-4646 (2006), incorporated herein by this reference.

5-Azacytidine inhibits DNA methyltransferase and can be incorporated directly into RNA and DNA, causing cell death.

Thalidomide, and its analogs lenalidomide and pomalidomide, inhibit myeloma cells by a number of mechanisms, including inhibition of angiogenesis, inhibition of production of interleukin-6, activation of apoptotic pathways through caspase-8-mediated cell death, and other mechanisms. The antineoplastic activity of thalidomide is described in W. D. Figg et al., "A Randomized Phase II Trial of Thalidomide, an Angiogenesis Inhibitor, in Patients with Androgen-Independent Prostate Cancer," *Clin. Cancer Res.* 7: 1888-1893 (2001), incorporated herein by this reference.

Epidermal growth factor receptor (EGFR) inhibitors include, but are not limited to, erlotinib, afatinib, lapatinib, and dacomitinib. Other EGFR inhibitors are known in the art.

Hydroxyurea is an antineoplastic agent that may act by inhibiting the enzyme ribonucleotide reductase and also may induce double-stranded DNA breaks.

Thioguanine is a purine analog of guanine and is incorporated into DNA, as well as inhibition of the GTP-binding protein Rac1.

Mercaptopurine inhibits purine nucleotide synthesis and metabolism by inhibiting the enzyme phosphoribosyl pyrophosphate amidotransferase.

Gold salts, including, but not limited to, aurothiomalate or aurothioglucose, act as inhibitors of lymphocyte proliferation.

Decitabine (5-aza-2'-deoxycytidine) is an agent that inhibits DNA methyltransferase and acts in a similar manner to 5-azacytidine.

Proteasome inhibitors include, but are not limited to, bortezomib. Other proteasome inhibitors are known in the art, including disulfiram, epigallocatechin-3-gallate, salinosporamide A, carfilzomib, oprozomib, delanzomib, MLN9708 (4-(carboxymethyl)-2-((R)-1-(2-(2,5-dichlorobenzamido)acetamido)-3-methylbutyl)-6-oxo-1,3,2-dioxaborinane-4-carboxylic acid), epoxomicin, and MG132 (N-(benzyloxycarbonyl)leucinylleucinylleucinal-Z-Leu-Leu-Leu-al).

As detailed below, a significant application of indirubin analogs and derivatives, particularly meisoindigo, is for inhibiting Nek9 kinase. Therefore, indirubin analogs and derivatives, particularly meisoindigo, can be used in a drug combination with Nek9 inhibitors or agents for inhibiting the expression of the Nek9 gene. Other Nek9 inhibitors and agents for inhibiting the expression of the NEK9 gene are detailed below.

United States Patent Application Publication No. 2010/0069458 by Atadja et al., incorporated herein by this reference discloses the use of the following additional therapeutic agents, which can be used together with indirubin analogs and derivatives:

(1) ACE inhibitors, including, but not limited to, benazepril, enazepril, captopril, enalapril, fosinopril, lisinopril, moexipril, quinapril, ramipril, perindopril and trandolapril;

(2) adenosine kinase inhibitors, including, but not limited to, 5-iodotubericidin;

(3) adrenal cortex antagonists, including, but not limited to, mitotane;

(4) AKT pathway inhibitors (protein kinase B inhibitors) including, but not limited to, deguelin and 1,5-dihydro-5-methyl-1-β-D-ribofuranosyl-1,4,5,6,8-pentaazaacenaphthylen-3-amine;

(5) angiogenesis inhibitors, including, but not limited to, fumagillin, Shikonin, Tranilast, ursolic acid; suramin; thalidomide, lenalidomide; phthalazines, including, but not limited to, 1-(4-chloroanilino)-4-(4-pyridylmethyl)phthalazine, 1-(4-methylanilino)-4-(4-pyridylmethyl)phthalazine, 1-(3-chloroanilino)-4-(4-pyridylmethyl)phthalazine, 1-anilino-4-(4-pyridylmethyl)phthalazine, 1-benzylamino-4-(4-pyridylmethyl)phthalazine, 1-(4-methoxyanilino)-4-(4-pyridylmethyl)phthalazine, 1-(3-benzyloxyanilino)-4-(4-pyridylmethyl)phthalazine, 1-(3-methoxyanilino)-4-(4-pyridylmethyl)phthalazine, 1-(2-methoxyanilino}-4-(4-pyridylmethyl)phthalazine, 1-(4-trifluoromethylanilino)-4-(4-pyridylmethyl)phthalazine, 1-(4-fluoroanilino)-4-(4-pyridylmethyl)phthalazine, 1-(3-hydroxyanilino)-4-(4-pyridylmethyl)phthalazine, 1-(4-hydroxyanilino)-4-(4-pyridylmethyl)phthalazine, 1-(3-aminoanilino)-4-(4-pyridylmethyl)phthalazine, 1-(3,4-dichloroanilino)-4-(4-pyridylmethyl)phthalazine, 1-(4-bromoanilino)-4-(4-pyridylmethyl)phthalazine, 1-(3-chloro-4-methoxyanilino)-4-(4-pyridylmethyl)phthalazine, 1-(4-cyanoanilino)-4-(4-pyridylmethyl)phthalazine, 1-(3-chloro-4-fluoroanilino)-4-(4-pyridylmethyl)phthalazine, 1-(3-methylanilino)-4-(4-pyridylmethyl)phthalazine, and other phthalazines disclosed in PCT Patent Application Publication No. WO 98/035958 by Bold et al., incorporated herein in its entirety by this reference, isoquinolines disclosed in PCT Patent Application Publication No. WO 00/09495 by Altmann et al., incorporated herein in its entirety by this reference, including 1-(3,5-dimethylanilino)-4-(pyridin-4-ylmethyl)-isoquinoline; phthalazines disclosed in PCT Patent Application Publication No. WO 00/59509 by Bold et al., incorporated herein in its entirety by this reference, including E-1-(3-methylanilino)-4-[(2-(pyridin-3-yl)vinyl]phthalazine, Z-1-(3-methylanilino)-4-[(2-(pyridin-3-yl)vinyl]phthalazine, 1-(3-methylanilino)-4-[(2-(pyridin-3-yl)ethyl]phthalazine, 1-(3-methylanilino)-4-[{2-(pyridin-4-yl)vinyl]phthalazine, 1-(4-chloro-3-trifluoromethylanilino)-4-[(2-(pyridin-3-yl)

ethyl]phthalazine, 1-(4-chloroanilino)-4-[(2-(pyridin-3-yl) ethyl]phthalazine, 1-(3-chlorobenzylamino)-4-[(2-(pyridin-3-yl)ethyl]phthalazine, 1-(4-chloro-3-trifluoromethylanilino)-4-[3-(pyridin-3-yl)propyl] phthalazine, 1-(4-chloroanilino)-4-[3-(pyridin-3-yl)propyl] phthalazine, 1-(3-chloro-5-trifluoromethylanilino)-4-[3-(pyridin-3-yl)propyl]phthalazine, and 1-(4-tert-butylanilino)-4-[3-(pyridin-3-yl)propyl]phthalazine; and monoclonal antibodies;

(6) angiostatic steroids, including, but not limited to, anecortave, triamcinolone, hydrocortisone, 11α-epihydrocotisol, cortexolone, 17α-hydroxyprogesterone, corticosterone, desoxycorticosterone, testosterone, estrone, and dexamethasone;

(7) anti-androgens, including, but not limited to, nilutamide and bicalutamide;

(8) anti-estrogens, including, but not limited to, toremifene, letrozole, testolactone, anastrozole, bicalutamide, flutamide, exemestane, tamoxifen, fulvestrant, and raloxifene;

(9) anti-hypercalcemia agents, including, but not limited to, gallium (III) nitrate hydrate and pamidronate disodium;

(10) apoptosis inducers, including, but not limited to, 2-[[3-(2,3-dichlorophenoxy)propyl]amino]-ethanol, gambogic acid, embellin, and arsenic trioxide;

(11) ATI receptor antagonists, including, but not limited to, valsartan;

(12) aurora kinase inhibitors, including, but not limited to, binucleine 2;

(13) aromatase inhibitors, including, but not limited to: (a) steroids, including, but not limited to, atamestane, exemestane, and formestane; and (b) non-steroids, including, but not limited to, aminoglutethimide, roglethimide, pyridoglutethimide, trilostane, testolactone, ketokonazole, vorozole, fadrozole, anastrozole, and letrozole;

(14) bisphosphonates, including, but not limited to, etidronic acid, clodronic acid, tiludronic acid, alendronic acid, ibandronic acid, risedronic acid, and zoledronic acid;

(15) Bruton's tyrosine kinase inhibitors, including, but not limited to, terreic acid;

(16) calcineurin inhibitors, including, but not limited to, cypermethrin, deltamethrin, fenvalerate, and tyrphostin 8;

(17) CaM kinase II inhibitors, including, but not limited to, the 5-isoquinolinesulfonic acid 4-[(2S)-2-[(5-isoquinolinylsulfonyl)methylamino]-3-oxo-3-(4-phenyl-1-piperazinyl)propyl]phenyl ester, and N-[2-[[[3-(4-chlorophenyl)-2-propenyl]methyl]amino]methyl]phenyl]-N-(2-hydroxyethyl)-4-methoxy-benzenesulfonamide;

(18) CD45 tyrosine phosphatase inhibitors, including, but not limited to, [[2-(4-bromophenoxy)-5-nitrophenyl]hydroxymethyl]-phosphonic acid;

(19) CDC25 phosphatase inhibitors, including, but not limited to, 2,3-bis[(2-hydroyethyl)thio]-1,4-naphthalenedione;

(20) CHK kinase inhibitors, including, but not limited to, debromohymenialdisine;

(21) compounds targeting/decreasing a protein or lipid kinase activity; or a protein or lipid phosphatase activity; or further anti-angiogenic compounds, including, but not limited to, protein tyrosine kinase and/or serine and/or threonine kinase inhibitors or lipid kinase inhibitors, including, but not limited to:

(a) compounds targeting, decreasing or inhibiting the activity of the vascular endothelial growth factor receptors (VEGFR) or of vascular endothelial growth factor (VEGF), including, but not limited to, 7H-pyrrolo[2,3-d]pyrimidine derivatives, including: [6-[4-(4-ethyl-piperazine-1-ylmethyl)-phenyl]-7H-pyrrolo[2,3-d]pyrimidinpyrimidin-4-yl]-(R)-1-phenyl-ethyl)-amine (known as AEE788), BAY 43-9006; and isoquinoline compounds disclosed in PCT Patent Application Publication No. WO 00/09495, such as (4-tert-butyl-phenyl)-94-pyridin-4-ylmethyl-isoquinolin-1-yl)-amine;

(b) compounds targeting, decreasing or inhibiting the activity of the platelet-derived growth factor-receptor (PDGFR), including, but not limited to: N-phenyl-2-pyrimidine-amine derivatives, e.g., imatinib, SU101, SU6668 and GFB-111;

(c) compounds targeting, decreasing or inhibiting the activity of the fibroblast growth factor-receptor (FGFR);

(d) compounds targeting, decreasing or inhibiting the activity of the insulin-like growth factor receptor 1 (IGF-1R), including, but not limited to: the compounds disclosed in WO 02/092599 and derivatives thereof of 4-amino-5-phenyl-7-cyclobutyl-pyrrolo[2,3-d]pyrimidine derivatives;

(e) compounds targeting, decreasing or inhibiting the activity of the Trk receptor tyrosine kinase family;

(f) compounds targeting, decreasing or inhibiting the activity of the Axl receptor tyrosine kinase family;

(g) compounds targeting, decreasing or inhibiting the activity of the c-Met receptor;

(h) compounds targeting, decreasing or inhibiting the activity of the Ret receptor tyrosine kinase;

(i) compounds targeting, decreasing or inhibiting the activity of the Kit/SCFR receptor tyrosine kinase;

(j) compounds targeting, decreasing or inhibiting the activity of the C-kit receptor tyrosine kinases, including, but not limited to, imatinib;

(k) compounds targeting, decreasing or inhibiting the activity of members of the c-Abl family and their gene-fusion products, e.g., BCR-Abl kinase, such as N-phenyl-2-pyrimidine-amine derivatives, including, but not limited to: imatinib, 6-(2,6-dichlorophenyl)-2-[(4-fluoro-3-methylphenyl)amino]-8-methyl-pyrido[2,3-d]pyrimidin-7(8H)-one (PD180970), methyl-4-[N-(2',5'-dihydroxybenzyl)amino]benzoate (Tyrphostin AG957), 4-[[(2,5-dihydroxyphenyl)methyl]amino] benzoic acid tricyclo[3.3.1.13,7]dec-1-yl ester (adaphostin or NSC 680410), 6-(2,6-dichlorophenyl)-8-methyl-2-(3-methylsulfanylanilino)pyrido[2,3-d] pyrimidin-7-one (PD173955), and desatinib;

(l) compounds targeting, decreasing or inhibiting the activity of members of the protein kinase C (PKC) and Raf family of serine/threonine kinases, members of the MEK, SRC, JAK, FAK, PDK and Ras/MAPK family members, or P1(3) kinase family, or of the PI(3)-kinase-related kinase family, and/or members of the cyclin-dependent kinase family (CDK) and are especially those staurosporine derivatives disclosed in U.S. Pat. No. 5,093,330, such as, but not limited to, midostaurin; examples of further compounds include, e.g., UCN-01; safingol, sorafenib, Bryostatin 1; Perifosine; Ilmofosine; 3-[3-[2,5-Dihydro-4-(1-methyl-1H-indol-3-yl)-2,5-dioxo-1H-pyrrol-3-yl]-1H-indol-1-yl] propyl carbamimidothioic acid ester (RO 318220), 3-[(8S)-8-[(dimethylamino)methyl]-6,7,8,9-tetrahydropyrido[1,2-a]indol-10-yl]-4-(1-methyl-1H-indol-3-yl)-1H-pyrrole-2,5-dione (RO 320432), 12-(2-cyanoethyl)-6,7,12,13-tetrahydro-13-methyl-5-oxo-5H-indolo[2,3-a]pyrrolo[3,4-c]carbazole (GO 6976); Isis 3521; (S)-13-[(dimethylamino)methyl]-10,11,14,15-tetrahydro-4,9:16, 21-dimetheno H, 13H-dibenzo[e,k]

pyrrolo[3,4-h][1,4,13]oxadiazacy clohexadecene-1,3 (2H)-dione (LY333531), LY379196; isoquinoline compounds, such as those disclosed in PCT Patent Application Publication No. WO 00/09495; farnesyltransferase inhibitors, including, but not limited to, tipifarnib and lonafarnib; 2-(2-chloro-4-iodo-phenylamino)-N-cyclopropylmethoxy-3,4-difluoro-benzamide (PD184352); and QAN697, a PI3K inhibitor;

(m) compounds targeting, decreasing or inhibiting the activity of protein-tyrosine kinase, such as, but not limited to, imatinib mesylate, a tyrphostin, pyrymidylaminobenzamide and derivatives thereof; a tyrphostin is preferably a low molecular weight ($M_r$<1500) compound, or a pharmaceutically acceptable salt thereof, especially a compound selected from the benzylidenemalonitrile class or the 5-arylbenzenemalonirile or bisubstrate quinoline class of compounds, more especially any compound selected from the group consisting of Tyrphostin A23/RG-50810, Tyrphostin AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556; Tyrphostin AG957, and adaphostin (4-{[(2,5-dihydroxyphenyl)methyl]amino}-benzoic acid adamantyl ester or NSC 680410);

(n) compounds targeting, decreasing or inhibiting the activity of the epidermal growth factor family of receptor tyrosine kinases (EGFR, ErbB2, ErbB3, ErbB4 as homodimers or heterodimers), such as, but not limited to, those compounds, proteins or monoclonal antibodies generically and specifically disclosed in PCT Patent Application Publication No. WO 97/02266 by Traxler et al. such as (R)-6-(4-hydroxyphenyl)-4-[(1-phenylethyl)-amino]-7H-pyrrolo-[2,3-d]pyrimidine, or in European Patent Application Publication No. EP 0564409 by Zimmermann, PCT Patent Application Publication No. WO 99/03854 by Zimmermann et al., European Patent Application Publication No. EP 0520722 by Barker et al., European Patent Application Publication No. EP 0566226 by Barker et al., European Patent Application Publication EP 0787722 by Wissner et al., European Patent Application Publication EP 0837063 by Arnold et al., U.S. Pat. No. 5,747,498 by Schnur et al., PCT Patent Application Publication WO 98/10767 by McMahon et al., PCT Patent Application Publication WO 97/30034 by Barker, PCT Patent Application Publication WO 97/49688 by Schnur, PCT Patent Application Publication WO 97/38983 by Bridges et al., PCT Patent Application Publication WO 96/30347 by Schnur et al., including, but not limited to, N-(3-ethylnylphenyl)-6,7-bis(2-methoxyethoxy)-4-quinazolinamine (CP 358774 or erlotinib), PCT Patent Application Publication WO 96/33980 by Gibson et al., including, but not limited to, N-(3-chloro-4-fluorophenyl)-7-methoxy-6-(3-morpholin-4-ylpropoxy)quinazolin-4-amine (gefitinib); and PCT Patent Application Publication WO 95/03283 by Barker et al., including, but not limited to, compound 6-amino-4-(3-methylphenyl-amino)-quinazoline (ZM105180); monoclonal antibodies, including, but not limited to trastuzumab and cetuximab; and other small molecule inhibitors, including, but not limited to: canertinib, pelitinib, lapatinib, and 7H-pyrrolo-[2,3-d]pyrimidine derivatives which are disclosed in PCT Patent Application Publication WO 03/013541 by Bold et al.;

(22) compounds which target, decrease or inhibit the activity of a protein or lipid phosphatase, including, but not limited to, inhibitors of phosphatase 1, phosphatase 2A, PTEN or CDC25, such as, but not limited to okadaic acid or a derivative thereof;

(23) compounds which induce cell differentiation processes, including, but not limited to, retinoic acid, α-tocopherol, γ-tocopherol, δ-tocopherol, α-tocotrienol, γ-tocotrienol, and δ-tocotrienol;

(24) cRAF kinase inhibitors, including, but not limited to, 3-(3,5-dibromo-4-hydroxybenzylidene)-5-iodo-1,3-dihydroindol-2-one and 3-(dimethylamino)-N-[3-[(4-hydroxybenzoyl)amino]-4-methylphenyl]-benzamide;

(25) cyclin dependent kinase inhibitors, including, but not limited to, N9-isopropyl-olomoucine; olomoucine; purvalanol B, roascovitine, kenpaullone, and purvalanol A;

(26) cysteine protease inhibitors, including, but not limited to, N-[(1S)-3-fluoro-2-oxo-1-(2-phenyl)ethyl)propyl]amino]-2-oxo-1-(phenylmethyl)ethyl]-4-morpholinecarboxamide;

(27) DNA intercalators, including, but not limited to, plicamycin and dactinomycin;

(28) DNA strand breakers, including, but not limited to, bleomycin;

(29) E3 ligase inhibitors, including, but not limited to, N-((3,3,3-trifluoro-2-trifluoromethyl)propionyl)sulfanilamide;

(30) EDG binders, including, but not limited to, FTY720;

(31) endocrine hormones, including, but not limited to, leuprolide and megestrol acetate;

(32) farnesyltransferase inhibitors, including, but not limited to, α-hydroxyfarnesylphosphonic acid, 2-[[(2S)-2-[[(2S,3S)-2-[[(2R)-2-amino-3-mercaptopropyl]amino]-3-methylpentyl]oxy]-1-oxo-3-phenylpropyl]amino]-4-(methylsulfonyl)-, 1-methylethyl butanoic acid ester (2S), and manumycin A;

(33) Flk-1 kinase inhibitors, including, but not limited to, 2-cyano-3-[4-hydroxy-3,5-bis(1-methylethyl)phenyl]-N-(3-phenylpropyl)-, (2-E)-2-propenamide;

(34) Flt-3 inhibitors, including, but not limited to, N-benzoyl-staurosporine, midostaurin, and N-(2-diethylaminoethyl)-5-[(Z)-(5-fluoro-2-oxo-1H-indol-3-ylidene)methyl]-2,4-dimethyl-1H-pyrrole-3-carboxamide (sunitinib);

(35) gonadorelin agonists, including, but not limited to, abarelix, goserelin, and goserelin acetate;

(36) heparanase inhibitors, including, but not limited to, phosphomannopentaose sulfate (PI-88);

(37) histone deacetylase (HDAC) inhibitors, including, but not limited to, compounds disclosed in PCT Patent Application Publication No. WO 02/22577 by Bair et al., including, but not limited to, N-hydroxy-3-[4-[[(2-hydroxyethyl)[2-(1H-indol-3-yl)ethyl]-amino]methyl]phenyl]-2E-2-propenamide, suberoylanilide hydroxamic acid, 4-(2-aminophenylcarbamoyl)-benzyl]-carbamic acid pyridine-3-ylmethyl ester and derivatives thereof, butyric acid, pyroxamide, trichostatin A, oxamflatin, apicidin, depsipeptide, depudecin, trapoxin, HC toxin, and sodium phenylbutyrate;

(38) HSP90 inhibitors, including, but not limited to: 17-allylamino,17-demethoxygeldanamycin (17AAG); a geldanamycin derivative; other geldanamycin-related compounds; radicicol; and 5-(2,4-dihydroxy-5-isopropyl-phenyl)-4-(4-morpholin-4-ylmethyl-phenyl)-isoxazole-3-carboxylic acid ethylamide;

(39) IκBα inhibitors (IKKs), including, but not limited to, 3-[(4-methylphenyl)sulfonyl]-(2E)-2-propenenitrile;

(40) insulin receptor tyrosine kinase inhibitors, including, but not limited to, hydroxy-2-naphthalenylmethylphosphonic acid;

(41) c-Jun N-terminal kinase inhibitors, including, but not limited to, pyrazoleanthrone and epigallocatechin gallate;

(42) microtubule binding agents, including, but not limited to: vinblastine sulfate; vincristine sulfate; vindesine; vinorelbine; docetaxel; paclitaxel; discodermolides; colchicines; and epothilones and derivatives thereof, such as epothilone B or a derivative thereof;

(43) mitogen-activated protein (MAP) kinase inhibitors, including, but not limited to, N-[2-[[[3-(4-chlorophenyl)-2-propenyl]methyl]amino]methyl]phenyl]-N-(2-hydroxyethyl)-4-methoxy-benzenesulfonamide;

(44) MDM2 inhibitors, including, but not limited to, trans-4-iodo,4'-boranyl-chalcone;

(45) MEK inhibitors, including, but not limited to, bis[amino[2-aminophenyl)thio]methylene]-butanedinitrile;

(46) methionine aminopeptidase inhibitors, including, but not limited to, bengamide and derivatives thereof;

(47) MMP inhibitors, including, but not limited to: actinonin; epigallocatechin gallate; collagen peptidomimetic and non-peptidomimetic inhibitors; tetracycline derivatives such as hydroxamate, batimastat, marimastat, primomastat, TAA211, N-hydroxy-2(R)-[[(4-methoxyphenyl)sulfonyl](3-picolyl)amino]-3-methylbutanamide hydrochloride (MMI270B), and AAJ996;

(48) NGFR tyrosine kinase inhibitors, including, but not limited to, Tyrphostin AG 879;

(49) p38 MAP kinase inhibitors, including, but not limited to, 3-(dimethylamino)-N-[3-[(4-hydroxybenzoyl)amino]-4-methylphenyl]-benzamide;

(50) p56 tyrosine kinase inhibitors, including, but not limited to, 9,10-dihydro-3-hydroxy-1-methoxy-9,10-dioxo-2-anthracenecarboxaldehyde and Tyrphostin 46;

(51) PDGFR tyrosine kinase inhibitors, including, but not limited to, Tyrphostin AG 1296; Tyrphostin 9, 2-amino-4-(1H-indol-5-yl)-1,3-butadiene-1,1,3-tricarbonitrile, and imatinib;

(52) phosphatidylinositol 3-kinase inhibitors, including, but not limited to, wortmannin and quercetin dihydrate;

(53) phosphatase inhibitors, including, but not limited to, cantharidic acid, cantharidin, and (E)-N-[4-(2-carboxyethenyl)benzoyl]glycyl-L-α-glutamyl-L-leucinamide;

(54) platinum agents, including, but not limited to, carboplatin, cisplatin, oxaliplatin, satraplatin, and ZD0473;

(55) protein phosphatase inhibitors, including, but not limited to:
  (a) PP1 and PP2A inhibitors, including, but not limited to, cantharidic acid and cantharidin; and
  (b) tyrosine phosphatase inhibitors, including, but not limited to, L-P-bromotetramisole oxalate, benzylphosphonic acid, and (5R)-4-hydroxy-5-(hydroxymethyl)-3-(1-oxohexadecyl)-2(5H)-furanone;

(56) PKC inhibitors, including, but not limited to, —[1-[3-(dimethylamino)propyl]-1H-indol-3-yl]-4-(1H-indol-3-yl)-1H-pyrrolo-2,5-dione, sphingosine, staurosporine, Tyrphostin 51, and hypericin;

(57) PKC delta kinase inhibitors, including, but not limited to, rottlerin;

(58) polyamine synthesis inhibitors, including, but not limited to, (RS)-2,5-diamino-2-(difluoromethyl)pentanoic acid (DMFO);

(59) proteasome inhibitors, including, but not limited to, aclacinomycin A, gliotoxin, and bortezomib;

(60) PTP1B inhibitors, including, but not limited to, (E)-N-[4-(2-carboxyethenyl)benzoyl]glycyl-L-α-glutamyl-L-leucinamide;

(61) protein tyrosine kinase inhibitors, including, but not limited to: Tyrphostin AG 126; Tyrphostin AG 1288; Tyrphostin AG 1295; geldanamycin; and genistein;

(62) SRC family tyrosine kinase inhibitors, including, but not limited to, 1-(1,1-dimethylethyl)-3-(1-naphthalenyl)-1H-pyrazolo[3,4-d]pyrimidin-4-amine, and 3-(4-chlorophenyl)-1-(1,1-dimethylethyl)-1H-pyrazolo[3,4-d]pyrimidin-4-amine;

(63) Syk tyrosine kinase inhibitors including, but not limited to, piceatannol;

(64) Janus (JAK-2 and/or JAK-3) tyrosine kinase inhibitors, including, but not limited to, Tyrphostin AG 490, and 2-naphthyl vinyl ketone;

(65) inhibitors of Ras oncogenic isoforms, including, but not limited to, (2S)-2-[[(2S)-2-[(2S,3S)-2-[(2R)-2-amino-3-mercaptopropyl]amino]-3-methylpentyl]oxy]-1-oxo-3-phenylpropyl]amino]-4-(methylsulfonyl)-butanoic acid 1-methylethyl ester (L-744832), DK8G557, and tipifarnib;

(66) retinoids, including, but not limited to, isotretinoin and tretinoin;

(67) ribonucleotide reductase inhibitors, including, but not limited to, hydroxyurea and 2-hydroxy-1H-isoindole-1,3-dione;

(68) RNA polymerase II elongation inhibitors, including, but not limited to, 5,6-dichloro-1-beta-D-ribofuranosylbenzimidazole;

(69) S-adenosylmethionine decarboxylase inhibitors, including, but not limited to, 5-amidino-1-tetralone-2'-amidinohydrazone and other compounds disclosed in U.S. Pat. No. 5,461,076 to Stanek et al., incorporated herein by this reference;

(70) serine/threonine kinase inhibitors, including, but not limited to, sorafenib and 2-aminopurine;

(71) compounds which target, decrease, or inhibit the activity or function of serine/threonine mTOR kinase, including, but not limited to, everolimus, temsirolimus, zotarolimus, rapamycin, derivatives and analogs of rapamycin, deforolimus, AP23841, sirolimus, and everolimus;

(72) somatostatin receptor antagonists, including, but not limited to, octreotide and pasireotide (SOM230);

(73) sterol biosynthesis inhibitors, including, but not limited to, terbinadine;

(74) telomerase inhibitors, including, but not limited to, telomestatin; and

(75) topoisomerase inhibitors, including, but not limited to:
  (a) topoisomerase I inhibitors, including, but not limited to, topotecan, gimatecan, irinotecan, camptothecin and its analogues, 9-nitrocamptothecin and the macromolecular camptothecin conjugate PNU-16614, macromolecular camptothecin conjugates described in PCT Patent Application Publication No. WO 99/17804 by Angelucci et al., 10-hydroxycamptothecin acetate salt, etoposide idarubicin hydrochloride, teniposide, doxorubicin; epirubicin hydrochloride, mitoxantrone hydrochloride, and daunorubicin hydrochloride; and
  (b) topoisomerase II inhibitors, including, but not limited to, anthracyclines, such as doxorubicin, including liposomal formulations thereof, daunorubicin, including liposomal formulations thereof, epirubicin, idarubicin, nemorubicin, mitoxantrone, losoxantrone, etoposide, and eniposide;

(76) VEGFR tyrosine kinase inhibitors, including, but not limited to, 3-(4-dimethylaminobenzylidenyl)-2-indolinone; and (77) RANKL inhibitors, including, but not limited to, denosumab.

In one alternative, when the drug combination is use with an alkylating agent, the alkylating agent can be selected from the group consisting of BCNU, BCNU wafers (Gliadel), and CCNU.

When the improvement is made by chemosensitization, the chemosensitization can comprise, but is not limited to, the use of indirubin, an analog of indirubin, or a derivative of indirubin or of an analog of indirubin as a chemosensitizer in combination with an agent selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone;
  (s) tetrandrine; and
  (t) proteasome inhibitors.

When the improvement is made by chemopotentiation, the chemopotentiation can comprise, but is not limited to, the use of indirubin, an analog of indirubin, or a derivative of indirubin or of an analog of indirubin as a chemopotentiator in combination with an agent selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone;
  (s) tetrandrine; and
  (t) proteasome inhibitors.

In one alternative, when the chemopotentiation involves chemopotentiation of an alkylating agent by the activity of indirubin, an analog of indirubin, or a derivative of indirubin or of an analog of indirubin. the alkylating agent can be selected from the group consisting of BCNU, BCNU wafers (Gliadel), CCNU, bendamustine (Treanda), and temozolimide (Temodar).

When the improvement is made by post-treatment management, the post-treatment management can be, but is not limited to, a method selected from the group consisting of:
  (a) a therapy associated with pain management;
  (b) administration of an anti-emetic;
  (c) an anti-nausea therapy;
  (d) administration of an anti-inflammatory agent;
  (e) administration of an anti-pyretic agent; and
  (f) administration of an immune stimulant.

When the improvement is made by alternative medicine/post-treatment support, the alternative medicine/post-treatment support can be, but is not limited to, a method selected from the group consisting of:
  (a) hypnosis;
  (b) acupuncture;
  (c) meditation;
  (d) a herbal medication created either synthetically or through extraction; and
  (e) applied kinesiology.

In one alternative, when the method is a herbal medication created either synthetically or through extraction, the herbal medication created either synthetically or through extraction can be selected from the group consisting of:
  (a) a NF-κB inhibitor;
  (b) a natural anti-inflammatory;
  (c) an immunostimulant;
  (d) an antimicrobial; and
  (v) a flavonoid, isoflavone, or flavone.

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an antimicrobial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

When the improvement is made by a bulk drug product improvement, the bulk drug product improvement can be, but is not limited to, a bulk drug product improvement selected from the group consisting of:
  (a) salt formation;
  (b) preparation as a homogeneous crystal structure;
  (c) preparation as a pure isomer;
  (d) increased purity;
  (e) preparation with lower residual solvent content; and
  (f) preparation with lower residual heavy metal content.

When the improvement is made by use of a diluent, the diluent can be, but is not limited to, a diluent selected from the group consisting of:
  (a) an emulsion;
  (b) dimethylsulfoxide (DMSO);
  (c) N-methylformamide (NMF)
  (d) DMF;
  (e) ethanol;
  (f) benzyl alcohol;
  (g) dextrose-containing water for injection;
  (h) Cremophor;
  (i) cyclodextrin; and
  (j) PEG.

When the improvement is made by use of a solvent system, the solvent system can be, but is not limited to, a solvent system selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

When the improvement is made by use of an excipient, the excipient can be, but is not limited to, an excipient selected from the group consisting of:
group consisting of:
(a) mannitol;
(b) albumin;
(c) EDTA;
(d) sodium bisulfite;
(e) benzyl alcohol;
(f) a carbonate buffer;
(g) a phosphate buffer; and
(h) methylcellulose.

When the improvement is made by use of a dosage form, the dosage form can be, but is not limited to, a dosage form selected from the group consisting of:
(a) tablets;
(b) capsules;
(c) topical gels;
(d) topical creams;
(e) patches;
(f) suppositories; and
(g) lyophilized dosage fills.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to indirubin, an analog of indirubin, or a derivative of indirubin or of an analog of indirubin, comprises the following steps:

(1) Dissolve the drug in water for injection precooled to below 10° C. Dilute to final volume with cold water for injection to yield a 40 mg/mL solution.

(2) Filter the bulk solution through an 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability.

When the improvement is made by use of a drug delivery system, the drug delivery system can be, but is not limited to, a drug delivery system selected from the group consisting of:
(a) nanocrystals;
(b) bioerodible polymers;
(c) liposomes;
(d) slow release injectable gels;
(e) microspheres;
(f) vascular disrupting agents; and
(g) polymer-coated stents.

Nanocrystals are described in U.S. Pat. No. 7,101,576 to Hovey et al., incorporated herein by this reference.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutryate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000), incorporated herein by this reference.

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

The use of vascular disrupting agents for delivery is disclosed in United States Patent Application Publication No. 2010/0272717 by Evans et al., incorporated herein by this reference. Such vascular disrupting agents include, but are not limited to, 5,6-dimethylxanthenone-4-acetic acid.

The use of polymer-coated stents for drug delivery is disclosed in U.S. Pat. No. 7,906,134 to Hauenstein, incorporated by this reference.

When the improvement is made by use of a drug conjugate form, the drug conjugate form can be, but is not limited to, a drug conjugate form selected from the group consisting of:
(a) a polymer system;
(b) polylactides;
(c) polyglycolides;
(d) amino acids;
(e) peptides; and
(f) multivalent linkers.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated herein by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonyldimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques," (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

When the improvement is made by use of a compound analog, the compound analog can be, but is not limited to, a compound analog selected from the group consisting of:
(a) alteration of side chains to increase or decrease lipophilicity;
(b) addition of an additional chemical functionality to alter a property selected from the group consisting of reactivity, electron affinity, and binding capacity; and
(c) alteration of salt form.

The addition of an additional chemical functionality to alter reactivity, can be, but is not limited to, an moiety that acts as an alkylating agent and a colchicine binding site.

Moieties that act as alkylating agents can include, for example, nitrogen atoms substituted with two chloroalkyl moieties, as occur in nitrogen mustards, nitrosourea moieties, and alkylsulfonate moieties. Moieties that act as colchicine binding sites are described in A. Jordan et al., "Tubulin as a Target for Anticancer Drugs: Agents Which Interact With the Mitotic Spindle," *Med. Res. Rev.* 18: 259-296 (1998), incorporated herein by this reference. The compound analog is typically a compound analog of meisoindigo; alternatively, the compound analog can be a compound analog of one of Alternatives (1)-(486) as described above.

When the improvement is made by use of a prodrug system, the prodrug system can be, but is not limited to, a prodrug system selected from the group consisting of:
(a) the use of enzyme sensitive esters;
(b) the use of dimers;
(c) the use of Schiff bases;
(d) the use of pyridoxal complexes;
(e) the use of caffeine complexes;
(f) the use of N-substituted carbohydrate derivatives;
(g) the use of Mannich N-oxides;
(h) the use of products of reaction with an acylating or carbamylating agent;
(i) the use of hexanoate conjugates;
(j) the use of polymer-agent conjugates; and
(k) the use of prodrugs that are subject to redox activation.

The use of prodrug systems is described in T. Jarvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference.

Still other prodrug systems applicable to indirubin derivatives or analogs are carbohydrate derivatives such as those described in U.S. Pat. No. 6,566,341 to Wang et al., incorporated by this reference. Typically, these prodrugs are N-substituted carbohydrate derivatives. The carbohydrate can be, for example, a monosaccharide or a disaccharide. The monosaccharide or disaccharide can be, for example, glucose, fructose, ribulose, galactose, mannose, cellobiose, allose, altrose, ribose, xylose, arabinose, sucrose, or lactose. A particularly suitable prodrug is an N-triacetylxylopyranosyl derivative of indirubin or an analog or derivative of indirubin, including an N-triacetylxylopyranosyl derivative or meisoindigo.

Still other prodrug systems applicable to indirubin derivatives or analogs include Mannich N-oxides of indirubin derivatives or analogs, including meisoindigo, as described in United States Patent Application Publication No. 2010/0016252 by Keana et al., incorporated herein by this reference.

Yet other prodrug systems applicable to indirubin derivatives or analogs include prodrugs that are prepared by reacting a compound with an acylating or carbamylating agent, such as 1,1-acyloxyalkylcarbonochloridate, p-nitrophenyl carbonate, or a similar acylating or carbamylating agent, as described in U.S. Pat. No. 8,076,375 to Sefton et al, incorporated herein by this reference.

Still other prodrug systems applicable to indirubin derivatives or analogs include hexanoate conjugates and polymer-agent conjugates as described in United States Patent Application Publication No. 2011/0268658 by Crawford et al., incorporated herein by this reference.

Still other prodrug systems applicable to indirubin derivatives or analogs include the use of prodrugs that are subject to redox activation. This utilizes the large quantities of reductase enzyme present in a hypoxic cell to bioactivate the drug into its cytotoxic form, essentially activating it.

In general, prodrugs can be classified into two major types, based on their cellular sites of bioactivation into the final active drug form, with Type I being those that are bioactivated intracellularly (e.g., anti-viral nucleoside analogs, lipid-lowering statins), and Type II being those that are bioactivated extracellularly, especially in digestive fluids or the systemic circulation (e.g., etoposide phosphate, valganciclovir, fosamprenavir, antibody-gene- or virus-directed enzyme prodrugs [ADEP/GDEP/VDEP] for chemotherapy or immunotherapy). Both types can be further categorized into subtypes, i.e. Type IA, IB and Type IIA, IIB, and IIC based on whether or not the intracellular bioactivating location is also the site of therapeutic action, or the bioactivation occurs in the gastrointestinal (GI) fluids or systemic circulation. Type IA prodrugs include many antimicrobial and chemotherapy agents (e.g., 5-flurouracil). Type IB agents rely on metabolic enzymes, especially in hepatic cells, to bioactivate the prodrugs intracellularly to active drugs. Type II prodrugs are bioactivated extracelluarly, either in the milieu of GI fluids (Type IIA), within the systemic circulation and/or other extracellular fluid compartments (Type IIB), or near therapeutic target tissues/cells (Type IIC), relying on common enzymes such as esterases and phosphatases or target directed enzymes. Importantly, prodrugs can belong to multiple subtypes (i.e., mixed-type). A mixed-type prodrug is one that is bioactivated at multiple sites, either in parallel or sequential steps. Many ADEPs, VDEPs, GDEPs and nanoparticle- or nanocarrier-linked drug moieties can be sequential mixed-type prodrugs. Bioactivation of prodrugs can occur by many reactions, including bioactivation by esterases, hydrolysis, bioactivation by decarboxylases, bioactivation by phosphatases, bioactivation by deacetylases, bioactivation by N-dealkylases, and many other reactions.

When the improvement is made by use of a multiple drug system, the multiple drug system can be, but is not limited to, a multiple drug system selected from the group consisting of:
(a) use of multi-drug resistance inhibitors;
(b) use of specific drug resistance inhibitors;
(c) use of specific inhibitors of selective enzymes;
(d) use of signal transduction inhibitors;
(e) use of repair inhibition; and
(f) use of topoisomerase inhibitors with non-overlapping side effects.

Multi-drug resistance inhibitors are described in U.S. Pat. No. 6,011,069 to Inomata et al., incorporated herein by this reference.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference. PS-341 refers to bortezomib.

Repair inhibition is described in N. M. Martin, "DNA Repair Inhibition and Cancer Therapy," *J. Photochem. Photobiol. B* 63: 162-170 (2001), incorporated herein by this reference.

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:
(a) cytokines;
(b) lymphokines;
(c) therapeutic antibodies;
(d) antisense therapies;
(e) gene therapies;
(f) ribozymes; and
(g) RNA interference.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" in *Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" in *Drug Discovery Handbook* (S. C. Gad, ed., Wiley-Interscience, Hoboken, N.J., 2005), ch. 27, pp. 1278-1283, incorporated herein by this reference.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by use of biotherapeutic resistance modulation, the biotherapeutic resistance modulation can be, but is not limited to, use against tumors resistant to a therapeutic agent or technique selected from the group consisting of:
(a) biological response modifiers;
(b) cytokines;
(c) lymphokines;
(d) therapeutic antibodies;
(e) antisense therapies;
(f) gene therapies;
(g) ribozymes; and
(h) RNA interference.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:
(a) hypoxic cell sensitizers;
(b) radiation sensitizers/protectors;
(c) photosensitizers;
(d) radiation repair inhibitors;
(e) thiol depleters;
(f) vaso-targeted agents;
(g) DNA repair inhibitors;
(h) radioactive seeds;
(i) radionuclides;
(j) radiolabeled antibodies; and
(k) brachytherapy.

Hypoxic cell sensitizers are described in C. C. Ling et al., "The Effect of Hypoxic Cell Sensitizers at Different Irradiation Dose Rates," *Radiation Res.* 109: 396-406 (1987), incorporated herein by this reference. Radiation sensitizers are described in T. S. Lawrence, "Radiation Sensitizers and Targeted Therapies," *Oncology* 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008), incorporated herein by this reference. Photosensitizers are described in R. R. Allison & C. H. Sibata, "Oncologic Photodynamic Therapy Photosensitizers: A Clinical Review," *Photodiagnosis Photodynamic Ther.* 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," *Radiation Res.* 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," *Cancer Res.* 67: 9455-9462 (2007), incorporated herein by this reference.

When the improvement is by use of a novel mechanism of action, the novel mechanism of action can be, but is not limited to, a novel mechanism of action that is a therapeutic interaction with a target or mechanism selected from the group consisting of:
(a) inhibitors of poly-ADP ribose polymerase;
(b) agents that affect vasculature or vasodilation;
(c) oncogenic targeted agents;
(d) signal transduction inhibitors;
(e) EGFR inhibition;
(f) protein kinase C inhibition;
(g) phospholipase C downregulation;
(h) Jun downregulation;
(i) histone genes;
(j) VEGF;
(k) ornithine decarboxylase;
(l) ubiquitin C;
(m) Jun D;
(n) v-Jun;
(o) GPCRs;
(p) protein kinase A;
(q) protein kinases other than protein kinase A;
(r) prostate specific genes;
(s) telomerase; and
(t) histone deacetylase.

EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005), incorporated herein by this reference. Protein kinase C inhibition is described in N. C. Swannie & S. B. Kaye, "Protein Kinase C Inhibitors," *Curr. Oncol. Rep.* 4: 37-46 (2002), incorporated herein by this reference. Phospholipase C downregulation is described in A. M. Martelli et al., "Phosphoinositide Signaling in Nuclei of Friend Cells: Phospholipase C β Downregulation Is Related to Cell Differentiation," *Cancer Res.* 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," *Oncogene* 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," *Proc. Natl. Acad. Sci. USA* 83: 1495-1498 (1986), incorporated herein by this reference. The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," *Surgery* 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," *Cancer Cell* 7: 433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," *Clin. Cancer Res.* 8: 2505-2511 (2002), incorporated herein by this reference. The role of Jun D as a target for therapeutic intervention is described in M. M. Caffarel et al., "JunD Is Involved in the Antiproliferative Effect of $\Delta^9$-Tetrahydrocannibinol on Human Breast Cancer Cells," *Oncogene* 27: 5033-5044 (2008), incorporated herein by this reference. The role of v-Jun as a target for therapeutic intervention is described in M. Gao et al., "Differential and Antagonistic Effects of v-Jun and c-Jun," *Cancer Res.* 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," *Eur. J. Cancer* 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," *Ann. Med.* 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," *Curr. Opin. Hematol.* 9: 322-332 (2002), incorporated herein by this reference.

When the improvement is made by use of selective target cell population therapeutics, the use of selective target cell population therapeutics can be, but is not limited to, a use selected from the group consisting of:

(a) use against radiation sensitive cells;
(b) use against radiation resistant cells;
(c) use against energy depleted cells; and
(d) use against endothelial cells.

As detailed above, a particularly significant activity of indirubin analogs and derivatives, particularly meisoindigo, is the inhibition of the kinase Nek9. Wild-type human Nek9 is a 979-amino-acid protein with the sequence:

(SEQ ID NO: 1)
MSVLGEYERHCDSINSDFGSESGGCGDSSPGPSASQGPRAGGGAAEQEEL

HYIPIRVLGRGAFGEATLYRRTEDDSLVVWKEVDLTRLSEKERRDALNEI

-continued
VILALLQHDNIIAYYNHFMDNTTLLIELEYCNGGNLYDKILRQKDKLFEE

EMVVWYLFQIVSAVSCIHKAGILHRDIKTLNIFLTKANLIKLGDYGLAKK

LNSEYSMAETLVGTPYYMSPELCQGVKYNFKSDIWAVGCVIFELLTLKRT

FDATNPLNLCVKIVQGIRAMEVDSSQYSLELIQMVHSCLDQDPEQRPTAD

ELLDRPLLRKRRREMEEKVTLLNAPTKRPRSSTVTEAPIAVVTSRTSEVY

VWGGGKSTPQKLDVIKSGCSARQVCAGNTHFAVVTVEKELYTWVNMQGGT

KLHGQLGHGDKASYRQPKHVEKLQGKAIRQVSCGDDFTVCVTDEGQLYAF

GSDYYGCMGVDKVAGPEVLEPMQLNFFLSNPVEQVSCGDNHVVVLTRNKE

VYSWGCGEYGRLGLDSEEDYYTPQKVDVPKALIIVAVQCGCDGTFLLTQS

GKVLACGLNEFNKLGLNQCMSGIINHEAYHEVPYTTSFTLAKQLSFYKIR

TIAPGKTHTAAIDERGRLLTFGCNKCGQLGVGNYKKRLGINLLGGPLGGK

QVIRVSCGDEFTIAATDDNHIFAWGNGGNGRLAMTPTERPHGSDICTSWP

RPIFGSLHHVPDLSCRGWHTILIVEKVLNSKTIRSNSSGLSIGTVFQSSS

PGGGGGGGGGEEEDSQQESETPDPSGGFRGTMEADRGMEGLISPTEAMGN

SNGASSSCPGWLRKELENAEFIPMPDSPSPLSAAFSESEKDTLPYEELQG

LKVASEAPLEHKPQVEASSPRLNPAVTCAGKGTPLTPPACACSSLQVEVE

RLQGLVLKCLAEQQKLQQENLQIFTQLQKLNKKLEGGQQVGMHSKGTQTA

KEEMEMDPKPDLDSDSWCLLGTDSCRPSL.

Nek9 is a member of the NIMA family of protein kinases. The NIMA family of protein kinases is named after the *Aspergillus nidulans* protein kinase encoded by the nimA (never in mitosis A) gene. NIMA is required for entry into mitosis and is involved in the control of chromatin condensation, spindle and nuclear envelope organization, and cytokinesis. Eleven protein kinases, Nek1 to Nek11, with a catalytic domain related to NIMA have been identified in the human genome. Nek9 is a 107-kDa polypeptide whose N-terminal catalytic domain is followed by a domain homologous to regulator of chromatin condensation (RCC1). The Nek9 C-terminal coiled coil motif binds to DYNLL/LC8 and this interaction is regulated by Nek9 activity through autophosphorylation. Microinjection of anti-Nek9 antibodies in prophase results in spindle abnormalities and/or chromosomal misalignment. Nek9 co-immunoprecipitates gamma-tubulin and the activated Nek9 localizes to the centrosomes and spindle poles during early mitosis, indicating that active Nek9 has important functions at the microtubular organizing center during cell division. Nek6 and Nek7 can bind strongly to RCC1 domain of Nek9 and are phosphorylated and activated by Nek9 and depletion of either Nek6 or Nek7 leads to defective mitotic progression. It is clear that Nek6, Nek7 and Nek9 contribute to the establishment of the microtubule-based mitotic spindle. Besides spindle tubule formation, It has been reported that Nek9 activation by Polo-like kinase 1 (PLK1) contributed to the phosphorylation of the mitotic kinesin Eg5 that is necessary for subsequent centrosome separation and timely mitosis. In addition, Nek9 phosphorylates NEDD1 which recruits gamma-tubulin to the centrosome to ensure the formation of two dense microtubule asters in cells entering mitosis. These data indicate that Nek9 has important function not only in spindle formation but also in centrosome maturation and separation. Spindle assembly checkpoint (SAC) is a fail-safe mechanism that monitors the fidelity of chromosome segregation in space and time. Until all chromosomes are properly aligned at the spindle equator, the mitotic checkpoint inhibits the anaphase promoting complex/cyclosome (APC/C) that prevents cells from entering anaphase. If the kinetochore-microtubule attachment is not correct, SAC generates the wait-anaphase signal that propagates throughout the cell to inhibit the APC/C. In various human cancers, mitotic checkpoint function is partially compromised, and altered expression or mutations in mitotic checkpoint genes have been shown to be related to chromosome instability (CIN) and aneuploidy, which frequently occurs in malignant cells. Nevertheless, no evidence for checkpoint malfunctions as a direct cause of CIN in tumor cells has been found. However, complete inactivation of the mitotic checkpoint results in gross chromosomal missegregation and is not compatible with cell viability. This has led to the suggestion that inhibition of the mitotic checkpoint could have therapeutic potential in cancer treatment. Moreover, tumor cells that have acquired a decreased checkpoint activity could be more sensitive to mitotic checkpoint inhibition when compared to healthy, checkpoint proficient cells.

Nek9 was found to play an important role in the spindle checkpoint. Nek9 inhibition, through the use of siRNA, induced apoptosis through abnormal mitosis in tumor cells, whereas the hTERT-RPE1 (REP1) normal human retinal pigment epithelium cell line was refractory to abnormal mitosis.

To investigate whether Nek9 inhibition could impair cell proliferation, a growth assay was performed with Caki2 and U1242 cell lines by using two independent Nek9-specific siRNAs. The results showed that the siRNAs did inhibit the production of Nek9 mRNA. In particular, it was observed that mRNA degradation by NEK9#115-siRNA always had a stronger effect than NEK9#72-siRNA. Coincident with the knockdown efficiency, all tested biological properties induced by NEK9#115-siRNA in the observed results were more pronounced than those induced by NEK9#72-siRNA. Immunohistochemical analysis revealed that the fraction of multinuclear cells was increased in Caki2 and U1242 cells. Moreover, micronucleated cells were observed in Caki2 cells, which contained many nuclei.

To analyze the development of abnormal nuclear morphology, live cell imaging was performed after Nek9 knockdown in U1242 cells. Mitosis cells were categorized into three groups; normal mitosis, abnormal mitosis (cytokinesis failure or chromosomes were not aligned in the metaphase plate) and death in mitosis (cells showed blebbing and nuclear fragmentation before attachment onto plate). In cytokinesis failure mitosis, chromosomes were aligned in the metaphase plate, followed by chromosome separation in anaphase. However, furrow ingression was repressed in cytokinesis, resulting in fused daughter cells. These results suggest one of the reasons for the generation of multinuclear cells is that Nek9 knockdown compromised cytokinesis.

In Nek9-siRNA transfected Caki2 cells, it was observed that 33.3% of mitotic cells were unable to undergo normal mitosis. In addition to cytokinesis failure like U1242 cells, more abnormal mitotic cells were observed whose chromosomes could not be aligned correctly at the metaphase plate. After remaining in mitosis for several hours, cells exited from mitosis without cytokinesis, generating micronucleated cells. This data suggests that spindle tubules in Nek9 depletion cells were imprecisely connected to chromosomes and mis-regulated. Moreover, the spindle assembly checkpoint (SAC) complex in NEK9-siRNA transfectants seemed not to function correctly.

In order to explore the effect of Nek9 knockdown on normal cells, RPE1 cells (human retinal pigment cells) were also analyzed. Similar to cancer cells, Nek9 depletion inhibited cellular growth of RPE1 cells. Interestingly, the nuclear shape in the NEK9-siRNA transfectants looked like normal cells, although the number of nuclei was much less than in the control group. Moreover, live cell imaging analysis revealed that normal cells were refractory to abnormal mitosis. The insensitivity of non-malignant RPE1 cells to Nek9 knockdown is not a consequence of insufficient mRNA deletion, as NEK#115 and NEK9#72-siRNA showed 89.75% and 89.66% knockdown, respectively; these values indicated that knockdown was effective. These data suggested that normal cells were less dependent on Nek9 at mitosis and Nek9 inhibitors might be able to kill cancer cells selectively in preference to non-malignant cells. This would provide a new avenue of treatment for malignancies.

It is well established that if all chromosomes are not connected with microtubules precisely, the SAC complex is activated and postpones the onset of anaphase to ensure segregation of the correct number of chromosomes into daughter cells. However, live cell imaging data of Caki2 cells revealed that cells exited from mitotic phase after Nek9 knockdown, even when chromosomes were not aligned in the metaphase plate. This observation suggests that Nek9 inhibition could compromise the functioning of the SAC and allow cells to undergo abnormal mitosis.

First, to investigate whether Nek9 is implicated in the mitotic checkpoint system, the cell cycle was analyzed after nocodazole treatment, which inhibits the metaphase-to-anaphase transition by preventing microtubule polymerization. FCM analysis showed that NC-siRNA transfectants were arrested at G2/M phase by nocodazole treatment. By contrast, NEK9 transfectants did not stop the cell cycle like NC-siRNA transfectants. This data suggests that Nek9-depletion compromised SAC function and forced cells to exit from mitosis.

Immunohistochemical stain analysis was performed to observe morphological change. In an NC-siRNA treated group, a substantial number of typical prometaphase cells with round shape and condensed chromatin in the center were observed. On the other hand, the NEK9-siRNA transfectants contained fewer prometaphase cells and more adherent cells, which have numerous micronuclei. The morphology of micronucleation was clearly different from that of chromatin condensation triggered by apoptosis. The structure of each small nucleus in micronucleated cells was apparent, whereas that in the apoptotic cells was ambiguous.

These results showed that Nek9 knockdown induced cytokinesis failure and incorrect chromosome separation. It is assumed that Nek6 and Nek7 are activated via the C-terminal domain of Nek9 in mitosis. Mouse embryonic fibroblast (MEF) cells derived from Nek7-deficient mice showed cytokinesis failure. Depletion of Nek6 by siRNA also resulted in a significant increase in cells with two or more nuclei. These observations were consistent with prior reports and indicated that the Nek6/7/9 pathway is involved in the cytokinesis process.

In addition, it was found that Nek9 depletion overrode mitotic arrest by nocodazole treatment, indicating that Nek9 function could be included in the SAC system.

It has been reported that overexpression of a kinase-dead Nek9 mutant compromised spindle dynamics and microinjection of anti-Nek9 antibodies disrupted spindle formation. At prometaphase and metaphase, Nek9 localizes at the centrosome. It has previously been reported that Nek9 depletion by siRNA resulted in slower cellular growth due to prolonged retention of the cells in the G1 and S phase. It has been suggested that Nek9 is required for normal cell cycle progression. However, it has also been reported that siRNA-mediated knockdown of Nek9 does not impede cell cycle progression. This discrepancy might be explained by two possibilities. Firstly, cell cycle analysis based only on the amount of DNA is not an accurate method of discrimination between diploid G2/M and tetraploid G1 populations. Live cell imaging is essential to analyze the detailed abnormalities in mitosis. A second possible explanation is due to insufficient knockdown. High knockdown efficiency seems to be necessary to induce apoptosis, probably because small amounts of Nek9 protein were functionally sufficient to rescue severe abnormalities. Indeed, the data described above also indicated that approximately 80% knockdown efficiency was not enough to generate clear cellular growth retardation.

Therefore, the Nek9 protein and/or the NEK9 gene are proposed as a new target for anti-cancer therapy development that would act by inducing interference with normal mitosis and spindle checkpoint control, leading to mitotic catastrophe. Mitotic catastrophe is often characterized by the formation of giant micronucleated cells, which typically reflect the abnormal segregation of chromosomes induced in a p53-independent manner. Mitotic catastrophe is considered to be one of the protective mechanisms reducing cancer incidence, leading to the application of the induction of mitotic catastrophe as a strategy for the treatment of cancer.

It has also been previously been reported that depletion of either Mad2 or BubR1 was able to induce cell death through abnormal mitosis. Mad2 loss effectively inactivates the checkpoint while inducing a checkpoint stress owing to defective microtubule formation, resulting in efficient killing of tumor cells. It has also been reported that inactivation of an essential checkpoint protein, Mps1, induced cell death accompanied by a chromosome segregation error. Additionally, partial reduction of Mad2 or BubR1, which have dual roles in checkpoint activation and chromosome alignment, resulted in sensitivity to taxol; this sensitization was observed only in tumor cells. Partial reduction of Mps1 or BubR1, which have dual roles in checkpoint activation and chromosome alignment, resulted in sensitivity to taxol. The data showed that Nek9 also has a dual function as a regulator of spindle formation and in the mitotic checkpoint, similarly to Mad2, Mps1 and BubR1.

Remarkably, Nek9 depletion did not induce abnormal mitosis in normal cells although cellular growth was impaired. It is supposed that the existence of multiple backup systems for the spindle checkpoint pathway in normal cells makes them resistant to abnormal mitosis. These redundant pathways seem to be lost or compromised in cancer cell lines underlining the potential of spindle checkpoint interfering drugs as an attractive new approach in anti-cancer therapy.

It is considered that the cell cycle of most cancer cells contains defects in the checkpoint system, which allows cancer cells to proliferate indefinitely without normal growth control. To selectively target the abnormal cell cycle machinery in cancer cells is a rational approach for anticancer therapy. The inhibition of NEK9 is therefore proposed as a novel anticancer therapeutic strategy by inducing mitotic catastrophe via impairment of spindle dynamics, cytokinesis and the mitotic checkpoint. A greater understanding of the mitotic progress in normal and cancer cells will improve strategic targeting of cancer cells by Nek9 inhibitors.

Nek9 also has interactions with the human Spt16 and SSRP1 proteins. The human Spt16 and SSRP1 proteins constitute an abundant, nuclear, and heterodimeric complex called FACT. The complex FACT was initially discovered as a chromatin-specific elongation factor that facilitates transcription of chromatin templates in vitro. The exact mechanism by which FACT aids the movement of RNA polymerase II and thus facilitates transcription along nucleosomal DNA is not known. By interacting with histone H2A/H2B dimers, FACT has been postulated to render intranucleosomal histone connections more flexible.

The genes that encode these two FACT polypeptides and, more significantly, the existence of such stable heterodimeric factors are highly conserved among eukaryotes. Homologous heterodimers have been purified and identified from yeast and frog cells. The *Xenopus* DNA unwinding factor (DUF) complex is also composed of Spt16 and SSRP1 homologs. Unlike the mammalian counterpart, DUF was directly implicated in DNA replication, as immunodepletion of this complex led to a reduced ability to replicate exogenously added sperm nuclei or plasmid DNA. However, its ability to alter nucleosomal DNA structure is conserved. Studies on the corresponding Spt16-Pob3 heterodimer in yeast have provided evidence on the pleiotropic nature of this heterodimer as well as its role as a chromatin structure modulator. Mutations in either genes cause various allele-specific defects in transcription initiation and elongation and DNA replication. Additionally, conditional mutants exhibit stalled progression in $G_1$ and S phases, perhaps as the indirect consequence of misregulated processes involving chromatin. Genetic and physical interactions have been observed between Spt16-Pob3 and a substantial number of transcription or replication proteins, including transcription elongator Paf1 complex, histone acetyltransferase complex NuA3, histone deacetylase Rpd3, general transcription factor TFIIE, putative chromatin factors San1 and Chd1, Nhp6, which is a high mobility group protein that forms the SPN complex with a heterodimer, DNA polymerase a, and additional DNA replication factors. These observations link FACT/DUF/Spt16-Pob3 to replication and transcription and, more specifically, to the structural regulation of chromatin, as such an entity serves as template for both processes.

The existing evidence is consistent with the notion that FACT and homologous complexes possess a single central activity that is required for the progression of replication and transcription. However, their roles at multiple steps within these two processes may be mediated by differential coordination with various factors. The potential existence of such an interaction network is substantiated by the aforementioned group of ySpt16-Pob3-interacting proteins, which suggests further interaction partners. Hence, to further delineate the role of human FACT in chromatin-related cellular processes, research efforts have been carried out to delineate the identification and functional characterization of its interacting proteins. By generating monoclonal antibodies directed against SSRP1, and subsequently performing antibody affinity purification, researchers were able to isolate FACT-associated protein complexes from HeLa nuclear extracts. One of the polypeptides identified in these searches is the Nek9 protein.

Nek9 (previously termed Nek8) was originally identified as a β-casein kinase that associates with a putative substrate Bicd2. It was independently identified as a Nek6- and Ran GTPase-binding protein under a different name, Nercc1. Based on kinase domain sequence similarity, Nek9 is a recent addition to the NIMA-like kinase (Nek) family, whose dozen or so members have diverse but relatively unknown functions. In addition to the N-terminal catalytic domain, Nek9 contains a central, RCC1-like, seven-repeats region, followed by a coiled-coil domain. Despite the presence of a nuclear localization signal, previous publications have reported a cytoplasmic localization of this kinase. Furthermore, Nek9 is putatively involved in the microtubule dynamics and has been implicated in the regulation of mitotic progression, as disclosed above.

An in vivo interaction between Nek9 protein and FACT has been identified by immunoaffinity purification. Nuclear extracts were subjected to immunoprecipitation with anti-SSRP1 monoclonal antibodies. The major protein bands of 140 and 90 kDa corresponded to hSpt16 and SSRP1, respectively, as confirmed by Western blot and mass spectrometric analyses. Such affinity purification also recovers a 120-kDa polypeptide, which associates with the FACT heterodimer with a molar ratio of ~1-5. Subsequent spectrometric analysis of this band revealed a sequence match of the identified spectra to the coding sequence of the human Nek9 protein. To further characterize this protein, polyclonal antibodies against different parts of Nek9 were generated and affinity-purified polyclonal antibodies, termed αNek9-M (spanning amino acids 291-559) and αNek9-N (spanning amino acids 1-291). Both antibodies specifically recognized a 120-kDa polypeptide in the HeLa cell extracts as well as in the monoclonal antibody-targeted immunocomplex. Other anti-SSRP1 monoclonal antibodies, whose approximate epitope regions have been mapped by using deletion constructs of SSRP1 were subjected to immunoprecipitation experiments as well.

Nek9 was shown to interact with FACT to form an ~600-kDa complex. Myc-tagged Nek9 was found to bind immobilized FLAG-FACT140 and $His_6$-SSRP1, whereas no interaction between Myc-tagged Nek9 and other similarly tagged proteins was observed. In a gel filtration chromatography procedure, Nek9 eluted with a molecular mass of ~600 kDa. NEK9 and FACT partially co-localize in the interphase nucleus and are similarly free from condensed chromatin but dissociated from each other during chromatin decondensation. Therefore, the subcellular locations of both Nek9 and FACT alter through the cell cycle. Upon autoactivation, Nek9 undergoes a phosphorylation-dependent electrophoretic mobility shift and phosphorylation on amino acid residue $Thr^{210}$. Among Nek family proteins, there is extensive sequence conservation within the kinase domain, especially in the activation loop region. It had previously been demonstrated that Nek9 was able to phosphorylate in vitro the $Thr^{210}$ residue within the activation loop, thus indicating the possible ability of Nek9 to autophosphorylate. To assess whether autophosphorylation indeed occurs on the highly-conserved residue $Thr^{210}$ as well as the relationship between any such phosphorylation and the activity of the kinase, polyclonal antibodies that specifically recognize phosphorylated $Thr^{210}$ were generated. Endogenous, immunoprecipitated Nek9 kinase became activated (i.e., catalyzed the phosphorylation of histone H1) upon preincubation with a high concentration of ATP. The majority of Nek9 underwent the electrophoretic mobility shift only at the high ATP concentration. Phosphorylation on Thr210 accompanies this decrease in mobility, as such a slower-moving form was detectable using the antibody specific for phosphorylated $Thr^{210}$. The specificity of this antibody was confirmed by the lack of immunoreactive signals from the non-shifted species of Nek9. This further suggests that phosphorylation at $Thr^{210}$ was absent or was at low levels for non-phosphorylated Nek9 protein. The FACT-complexed Nek9 protein had similar enzymatic behavior upon kinase activation. The ATP-induced electrophoretic retardation of Nek9 can be attributed to the addition of the negatively-charged phosphate moiety, in view of the fact that treatment with alkaline phosphatase, which removes the phosphate residue by the enzymatic activity of alkaline phosphatase, following kinase autoactivation, abolished the positional shift on the gel. The immunoreactivity of Nek9 toward the antibody specific for phosphorylated $Thr^{210}$ was directly linked to phosphorylation. Additionally, Nek9 phosphorylated at $Thr^{210}$ associates with FACT in a cell-cycle-dependent manner. In the presence of FACT, Nek9 undergoes a marked elevation in phosphorylation at $Thr^{210}$. The level of phosphorylation at $Thr^{210}$ is regulated in a cell-cycle-dependent manner. Although there is a constitutive presence of phosphorylated Nek9 in FACT-Nek9 immunocomplexes throughout different phases of the cell cycle, the levels of association appeared to rise upon release from the $G_1/S$ phase block and then to fall in the M and $G_2$ phases. This may reflect an interphase-specific elevation in the formation of the active phosphorylated Nek9-FACT complex. Additionally, cells harboring Nek9-interfering ds RNA displayed significantly slower cell growth, leading to the conclusion that an adequate level of Nek9 is essential for $G_1/S$ transition and S phase progression. Nek9 is located in the cytoplasm and likely plays significant roles in the regulation of microtubule dynamics and mitosis.

Additionally, Nek9 is activated by the Polo-like kinase Plk1. The cyclin-dependent kinase CDK1 orchestrates the onset of mitosis through the regulation of multiple proteins either directly or in collaboration with a number of helper kinases, including Plk1. Plk1 is involved in the complex mechanism that culminates in CDK1 activation during mitotic entry and is crucial for different mitotic events including the formation of the spindle. The molecular basis for some of Plk1 functions relies on the recognition of previously phosphorylated proteins by the Polo-box domain (PBD) of Plk1, which also targets the kinase to different sites of action such as the centrosomes and centromeres.

The functions of the various members of the NIMA family of protein kinases, which includes Nek9, are still being elucidated. *Aspergillus nidulans* NIMA, the founding member of the family, is necessary for entry into mitosis and has several roles during mitotic progression, including the regulation of chromosome condensation and spindle formation, although it is not clear whether all these functions are shared with its mammalian counterparts. Different Neks have been implicated in the control of the centrosome and microtubule cytoskeleton. However, Nek9, which is ~80% identical to Nek6 and Nek7, is involved in the control of spindle structure and function.

Nek9 is activated at centrosomes during early mitosis, interacts with both Nek6 and Nek7 and directly phosphorylates and activates them. Microinjection of anti-Nek9 antibodies into prophase cells induces prometaphase arrest and in some cases aberrant chromosome segregation, resulting in mitotic catastrophes or aneuploidy, while Nek9 depletion from *Xenopus* meiotic egg extracts results in delayed spindle assembly, reduced number of bipolar spindles and appearance of aberrant microtubule structures. Downregulation of either Nek6 or Nek7 by RNA interference delays cells at metaphase with fragile mitotic spindles and for Nek7 has been shown to result in an increased incidence of multipolar spindle phenotypes. Mice lacking Nek7 die during late embryogenesis or at early postnatal stages, and Nek7 (_/_) cells show increased tendency for chromosomal lagging as well as abnormalities in primary cilia number. Nek6-deficient mice die early during embryogenesis. Thus, Nek9 together with Nek6/7 form a mitotically activated module with key roles during mitotic progression and more specifically spindle organization (Nek6 and Nek7 seem to be functionally equivalent in most instances, thus when adequate the two kinases will be collectively referred to as Nek6/7). Nevertheless, to this date a clear picture of the module activation mechanism, integration with other mitotic signaling systems and precise functions during mitosis has been missing. It has been suggested that Nek9 could be controlling spindle organization in part through the action of Nek6/7 and their ability to phosphorylate the kinesin Eg5 at a site necessary for normal mitotic progression. Recent work has shown that Plk1, in conjunction with CDK1, activates Nek9 early in mitosis, and that downstream of Plk1, Nek9 and Nek6/7 are responsible for centrosome separation during prophase through the control of Eg5 recruitment to centrosomes.

In addition to Thr$^{210}$, described above, Nek9 can be phosphorylated at additional sites, including Ser$^{29}$, Thr$^{333}$, Ser$^{750}$, Ser$^{827}$, Ser$^{869}$, and Thr$^{885}$. A number of these sites conform to an [ST]P sequence, and thus are potential phosphorylation sites for the protein kinase CDK1. This protein kinase has been demonstrated to phosphorylate Nek9 in vitro. Additionally, three potential phosphorylation sites, Ser$^{29}$, Ser$^{750}$, and Ser$^{869}$, conform to an S[S/T]P sequence, a motif that when phosphorylated at the serine or threonine immediately preceding the proline can be recognized by the Plk1 protein-binding domain. Plk1 has been shown to specifically co-immunoprecipitate with Nek9 in mitosis in HeLa cells. This interaction was also detected using the yeast two-hybrid system, and was mapped to the carboxyl-terminal tail of Nek9, where two of the three Nek9 putative PBD-binding sites reside, and to the PBD domain of Plk1. The Nek9-PBD interaction was increased in mitotic extracts and was totally abolished by mutation of Nek9 Ser$^{869}$ to alanine, which is non-phosphorylatable. Mutation of Nek9 Ser$^{29}$ to alanine did not have any effect, consistent with the two-hybrid results above, while mutation of Nek9 Ser$^{750}$ had only a minor effect on the binding. Plk1 was also able to phosphorylate Nek9 in vitro with little or no synergy with CDK1. Specifically, Plk1 was able to modify Thr$^{210}$, in the kinase activation loop, which is required for Nek9 activation. However, CDK1/cyclin B and the unrelated kinase JNK1 were unable to phosphorylate this residue. Phosphorylation of Thr$^{210}$ catalyzed by the kinase Plk1 activated Nek9, as did autophosphorylation of Thr$^{210}$ by Nek9 itself. However, CDK1 and Plk1 are necessary for Nek9 activation in vivo during mitosis. Moreover, Plk1, Nek6, Nek7, Nek9, and the mitotic kinesin are necessary for normal centrosome separation during prophase. This was confirmed by the use of siRNA directed against the 3'-UTR of Nek9 mRNA, which downregulated the level of endogenous Nek9. Additionally, active Nek9 and Nek6 induce centrosome separation in an Eg5-dependent manner. Downregulation of Eg5 almost totally abrogated Nek6- or Nek9-induced centrosome separation, suggesting that Nek6 and Nek9 induce centrosome separation through the regulation of the kinesin Eg5. Active Nek9 and Nek6 can rescue Plk1 but not Eg5 downregulation in prophase centrosome separation. Specifically, Nek9, Nek6 and Nek7 act downstream of Plk1 and upstream of Eg5 during early centrosome separation and suggest that Plk1 inhibition precludes centrosome separation as a result of the failure to activate the Nek9/Nek6/7 module.

Plk1 controls Eg5 phosphorylation at the Nek6 site Ser$^{1033}$, that, together with the CDK1 site Thr$^{926}$, is necessary for prophase centrosome separation and Eg5 recruitment. It was shown that transfection of active Nek9[D346-732] or Nek6 is able to induce ectopic Eg5 accumulation around centrosomes in parallel to centrosome separation even in interphase and that this is accompanied with Eg5 [S1033] phosphorylation. Thus, a physiological correlation exists between Eg5 recruitment and centrosome separation in prophase cells, and activation of the Nek9/Nek6 module is both necessary and sufficient to induce both phenomena in a cell-cycle-independent manner. Significantly, failure to phosphorylate Ser$^{1033}$ of Eg5 results in a delay in prometaphase.

Specifically, the NIMA-family kinases Nek9, Nek6 and Nek7 form a signaling module required for normal spindle assembly and function during mitosis. CDK1 and Plk1 are physiologic activators for Nek9. A two-step activation mechanism for Nek9 has been proposed. In this activation mechanism, CDK1, together with cyclin B1 and perhaps cyclin A, phosphorylates Nek9 at Ser$^{869}$, inducing Plk1 binding and subsequent Plk1 phosphorylation and activation of Nek9. Nek9 activation could directly result from Plk1 phosphorylation of Nek9 at Thr$^{210}$, although conceivably Plk1 phosphorylation of additional sites outside the Nek9 activation loop may also contribute to activation by releasing Nek9 autoinhibition, thus triggering Thr$^{210}$ autophosphorylation. Nek9 colocalizes at prophase centrosomes with active Plk1 and CDK1.

These observations clearly implicate Nek9 as directly involved in mitosis and thus in cell division and proliferation. Therefore, it is important to discover therapeutic agents that can inhibit the activity of Nek9 in order to more effectively treat diseases and conditions characterized by dysregulation of cell division and proliferation, including, but not limited to, malignancies.

A number of Nek9 inhibitors are known in the art. Nek9 inhibitors include, but are not limited to, the agents described below.

U.S. Pat. No. 8,591,943 to Deng et al., incorporated herein by this reference, discloses pyrazolo[1,5-a]pyrimidines, including compounds of Formula (N-I):

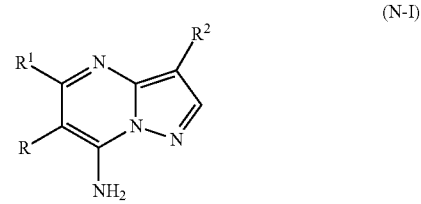

wherein:
(i) R is independently selected from the group consisting of halo, hydroxyl, amino, cyano, hydrogen, —(C$_1$-C$_6$)alkyl, alkoxy, —C(=O)alkyl, heteroaryl, and aryl, wherein each heteroaryl and aryl can be unsubstituted or substituted with one or more alkyl or halo;
(i) R$^1$ is independently selected from the group consisting of heterocycloalkyl, heterocycloalkylalkyl, spiroheterocycloalkyl, heterocyclenyl, —NR$^3$R$^4$, cycloalkyl, heteroaryl, aryl, alkyl, alkynyl, heterocyclenylalkyl, cycloalkylalkyl, heteroarylalkyl, heteroarylalkynyl, spiroheterocycloalkylalkyl, —N-heteroaryl, -alkyl-NH-heterocyclyl and arylalkyl, wherein each heterocycloalkyl, heterocycloalkylalkyl, spiroheterocycloalkyl, heterocyclenyl, cycloalkyl, heteroaryl, aryl, alkyl, alkynyl, heterocyclenylalkyl, cycloalkylalkyl, heteroarylalkyl, heteroarylalkynyl, —N-heteroaryl and arylalkyl can be unsubstituted or substituted with one or more moieties independently selected from the group X;

(iii) X is alkoxy, alkyl, —C(O)alkyl, —C(O)-hydroxyalkyl, —C(O)₂alkyl, —C(O)₂H, hydroxyalkyl, —S(O)₂ alkyl, hydroxyl, heterocycloalkyl, —NH-heterocycloalkyl, -trihaloalkyl, -dihaloalkyl, -monohaloalkyl, —N—S(O)₂-alkyl, —C(O)-heteroaryl, -alkyl-C(O)₂H, -alkyl(CO)N(CH₃)—O—CH₃, -alkyl(CO)-heteroaryl, -alkyl-C(O)—NH₂, amino, heteroaryl, -alkyl-CN, —C(O)₂-arylalkyl, halo, carboxyesteralkyl, —C(O)—NH₂, -alkyl-C(O)₂alkyl, heteroarylalkyl, —C(O)-heteroaryl, —C(O)-alkyl-O-alkyl, -alkyl(CO)NS(O)₂-cycloalkyl, -alkyl(CO)N—S(O)₂—CF₃, —N-alkyl, —SO₂-cycloalkyl, -alkyl(CO)NS(O)₂-alkyl, -alkyl-C(O)—N(alkyl)₂, -alkyl-NS(O)₂-alkyl, alkyl(CO)NS(O)₂-cycloalkyl, —CO—CO₂H, —C(O)₂-alkyl-aryl, —SO₂—CF₃ or —C(O)H, wherein each of heterocycloalkyl, heteroaryl or —C(O)-heteroaryl can be unsubstituted or substituted with one or more alkyl;

(iv) R² is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH₃)₂CN, trifluoromethyl, difluoromethyl, monofluoromethyl, heterocycloalkyl, and arylalkyl;

(v) R³ is cycloalkyl or heteroaryl, wherein each cycloalkyl or heteroaryl can be unsubstituted or substituted with one or more moieties independently selected from the group consisting of X; and (vi) R⁴ is H.

U.S. Pat. No. 8,586,719 to Chan et al., incorporated herein by this reference, discloses triterpenes inhibiting NEK9 gene expression, including carbohydrate-substituted triterpenes.

U.S. Pat. No. 8,389,527 to Fink et al., incorporated herein by this reference, discloses substituted imidazopyridazines, including compounds of Formula (N-II):

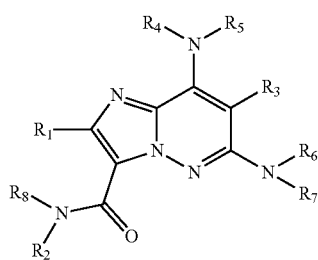

(N-II)

wherein:

(i) R₁ and R₃ are each independently selected from the group consisting of hydrogen, halogen, cyano, and C₁-C₄ alkyl;

(ii) R₂ is selected from substituted or unsubstituted cycloalkyl, substituted or unsubstituted heterocyclyl, substituted or unsubstituted aryl, and substituted or unsubstituted heteroaryl;

(iii) R₄ is selected from hydrogen, substituted or unsubstituted alkyl, —C(=O)alkyl, —S(O₂)alkyl, substituted or unsubstituted cycloalkyl, substituted or unsubstituted heterocyclyl, substituted or unsubstituted aryl, and substituted or unsubstituted heteroaryl;

(iv) R₅ is selected from hydrogen and C₁-C₄ alkyl;

(v) R₆ is selected from substituted or unsubstituted alkyl, substituted or unsubstituted cycloalkyl, substituted or unsubstituted heterocyclyl, substituted or unsubstituted aryl, and substituted or unsubstituted heteroaryl;

(vi) R₇ is selected from hydrogen and C₁-C₄ alkyl; or (vii) R₆ and R₇ together with the nitrogen atom to which they are attached form an optionally substituted 5-, 6-, or 7-membered monocyclic heteroaryl or heterocyclyl ring, or an optionally substituted 7- to 11-membered bicyclic heteroaryl or heterocyclyl ring; and (viii) R₈ is selected from hydrogen and C₁-C₄ alkyl; and provided that if R₂ is a group of Subformula (N-IIa)

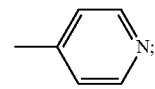

(N-IIa)

R₄ is a group of Subformula (N-IIb);

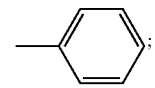

(N-IIb)

R₆ is a group of Subformula (N-IIc);

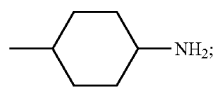

(N-IIc)

then R₃ is not hydrogen.

U.S. Pat. No. 8,354,408 to Bourke et al., incorporated herein by this reference, discloses nitrogen-containing heterocyclic compounds, including compounds of Formula (N-III):

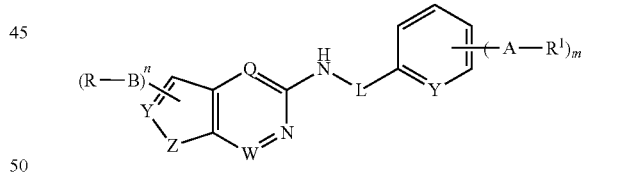

(N-III)

wherein:

(i) Q, W, and Y are each independently selected from the group consisting of N and CR²;

(ii) Z is NR² or S;

(iii) L is absent, CO, SO₂, or substituted or unsubstituted C₁-C₆ alkylene;

(iv) A and B are each absent or substituted or unsubstituted C₁-C₆ alkylene wherein one or more carbon atoms can be optionally replaced with O, CO, NR², NR²CO, CONR², NR²SO₂, S, or S(O)$_n$;

(v) R¹ is independently selected from hydrogen, substituted or unsubstituted C₁-C₆ alkyl, substituted or unsubstituted C₂-C₆ alkenyl, substituted or unsubstituted C₂-C₆ alkynyl, substituted or unsubstituted C₁-C₆ alkoxy, hydroxyl, halogen, CN, NO₂, NR²R³, SO₂R³, SO₂NR²R³, CF₃, OCF₃, NR²SO₂R³, CO₂R³, COSR³, CSR³, COR³, NR², NR²CSR³, CONR²R³, NR²COR³, NR²CONR²R³, SO₃R₃, substituted or unsubstituted $C_3$-$C_8$ cycloalkyl, substituted or unsubstituted aryl, and substituted or unsubstituted heterocyclyl having up to three heteroatoms or heteroatom-containing moieties selected from the group consisting of N, O, S, and $SO_2$;

(vi) R is selected from hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ alkoxy, hydroxyl, halogen, CN, $NO_2$, COR³, CONR²R³, NR²COR³, SO₃R₃, $C_3$-$C_8$ cycloalkyl, aryl, and heterocyclyl having up to three heteroatoms or heteroatom-containing moieties selected from the group consisting of N, O, S, and $SO_2$, each of which may be substituted with up to three substituents independently selected from substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ alkoxy, hydroxyl, $OCF_3$, halogen, cyano, $NO_2$, NR²R³, $SO_2R^3$, $SO_2NR^2R^3$, NR²SO₂R³, CO₂R₃, COR₃, NR²COR³, R²NHCO₂R³, CONR²R³, NR²CONR²R³, and substituted or unsubstituted heterocyclyl having up to three heteroatoms or heteroatom-containing moieties selected from the group consisting of N, O, S, and $SO_2$;

(vii) R² and R³ are each independently selected from hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ alkoxy, cyano, $C_3$-$C_8$ cycloalkyl, substituted or unsubstituted aryl, and substituted or unsubstituted heterocyclyl having up to three heteroatoms or heteroatom-containing moieties selected from the group consisting of N, O, S, and $SO_2$;

(viii) m is 1, 2, or 3; and (ix) n is 1 or 2; and salts, isomers, and prodrugs thereof.

U.S. Pat. No. 8,252,795 to Fink et al., incorporated herein by this reference, discloses imidazopyridazinecarbonitriles, including compounds of Formula (N-IV):

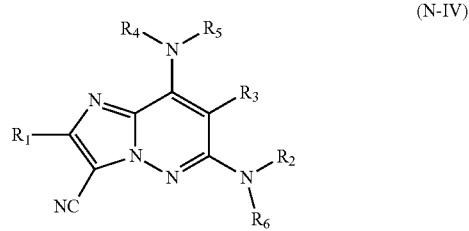

(N-IV)

wherein:

(i) $R_1$ is selected from H, F, Cl, Br, CN, and $C_1$-$C_6$ alkyl;

(ii) $R_2$ is selected from aryl substituted with 0-5 $R_{2a}$ and heteroaryl substituted with 0-5 $R_{2a}$;

(iii) $R2_a$, at each occurrence, is independently selected from H, F, Cl, Br, =O, CN, $NO_2$, —$OR_b$, —$S(O)_pR_c$, —C(=O)$R_d$, —$NR_aR_a$, —($CR2_bR2_c)_rC$(=O)$NR_aR_a$, —$NR_aC$(=O)$R_d$, —$NR_aC$(=O)$OR_b$, —OC(=O)$NR_aR_a$, —$NR_aC$(=O)$NR_aR_a$, —($CR2_bR2_c)_rC$(=O)$OR_b$, —$S(O)_2NR_aR_a$, —$NR_aS(O)_2R_c$, $C_1$-$C_6$ alkyl substituted with 0-5 $R_e$, —($CR_{2b}R_{2b})_r$—($C_3$-$C_6$) carbocyclyl substituted with 0-5 $R_e$, and —($CR_{2b}R_{2b})_r$-heterocyclyl substituted with 0-5 $R_e$;

(iv) $R_{2b}$, at each occurrence, is independently selected from H and $C_1$-$C_6$ alkyl substituted with 0-5 $R_e$;

(v) $R_{2c}$, at each occurrence, is independently selected from H and $C_1$-$C_6$ alkyl substituted with 0-5 $R_e$;

(vi) $R_3$ is selected from H, F, Cl, Br, CN, —$OR_b$, —$NR_aR_a$, —C(=O)$NR_aR_a$, —$NR_aS(O)_2R_c$, —$NR_aC$(=O)$R_d$, —$NR_aC$(=O)$OR_b$, and $C_1$-$C_6$ alkyl substituted with 0-5 $R_e$;

(vii) $R_4$ is selected from H, $C_1$-$C_6$ alkyl substituted with 0-5 $R_e$, —($CR4_bR^4_c)_rOR_b$, —($CR4_bR^4_c)_rS(O)_pR_c$, —($CR4_bR^4_c)_rC$(=O)$R_d$, —($CR4_bR^4_c)_rNR_aR_a$, —($CR4_bR^4_c)_rC$(=O)$NR_aR_a$, —($CR4_bR^4_c)_rNR_aC$(=O)$R_d$, —($CR4_bR^4_c)_rNR_aC$(=O)$OR_b$, —($CR4_bR^4_c)_rOC$(=O)$NR_aR_a$, —($CR4_bR^4_c)_rOC$(=O)$NR_aR_a$, —($CR4_bR^4_c)_rNR_aC$(=O)$NR_aR_a$, —($CR4_bR^4_c)_rC$(=O)$OR_b$, —($CR4_bR^4_c)_rS(O_2)NR_aR_a$, —($CR4_bR^4_c)_rNR_aS(O_2)NR_aR_a$, —($CR4_bR^4_c)_rNR_aS(O_2)R_c$, —($CR4_bR^4_c)_r$—$C_3$-$C_6$ carbocyclyl substituted with 0-5 $R_{4a}$, and —($CR4_bR^4_c)_r$—$C_3$-$C_6$ heterocyclyl substituted with 0-5 $R_{4a}$;

(viii) $R^4_a$, at each occurrence, is independently selected from F, Cl, Br, $C_1$-$C_6$ alkyl substituted with 0-5 $R_e$, $C_2$-$C_6$ alkenyl, $C_2$-$C_6$ alkynyl, $NO_2$, =O, CN, —$SO_3H$, —$S(O)_pR_c$, —$S(O)_2NR_aR_a$, —$NR_aS(O)2R_c$, —$OR_b$, —$NR_aR_a$, —$NR_aC$(=O)$R_d$, —$NR_aC$(=O)$NR_aR_a$, —C(=O)$OR_b$, —C(=O)$OR_d$, —OC(=O)$R_d$, —C(=O)$NR_aR_a$, $C_3$-$C_6$ cycloalkyl, heterocyclyl, and aryl;

(ix) $R^4_b$, at each occurrence, is independently selected from H and $C_1$-$C_6$ alkyl substituted with 0-5 $R_e$;

(x) $R^4_c$, at each occurrence, is independently selected from H and $C_1$-$C_6$ alkyl substituted with 0-5 $R_e$;

(xi) $R_5$ is independently selected from H and $C_1$-$C_6$ alkyl substituted with 0-5 $R_e$;

(xii) $R_6$ is independently selected from H and $C_1$-$C_6$ alkyl substituted with 0-5 $R_e$;

(xiii) $R_a$, at each occurrence, is independently selected from H, CN, $C_1$-$C_6$ alkyl substituted with 0-5 $R_e$, $C_2$-$C_6$ alkenyl substituted with 0-5 $R_e$, $C_2$-$C_6$ alkynyl substituted with 0-5 $R_e$, —$(CH_2)_r$—$C_3$-$C_{10}$ carbocyclyl substituted with 0-5 $R_e$, and —$(CH_2)_r$—$C_3$-$C_{10}$ heterocyclyl substituted with 0-5 $R_e$, or $R_a$ and $R_a$ together with the nitrogen atom to which they are both attached form a heterocyclic ring substituted with 0-5 $R_e$;

(xiv) $R_b$, at each occurrence, is independently selected from H, CN, $C_1$-$C_6$ alkyl substituted with 0-5 $R_e$, $C_2$-$C_6$ alkenyl substituted with 0-5 $R_e$, $C_2$-$C_6$ alkynyl substituted with 0-5 $R_e$, —$(CH_2)_r$—$C_3$-$C_{10}$ carbocyclyl substituted with 0-5 $R_e$, and —$(CH_2)_r$—$C_3$-$C_{10}$ heterocyclyl substituted with 0-5 $R_e$;

(xv) $R_c$, at each occurrence, is independently selected from $C_1$-$C_6$ alkyl substituted with 0-5 $R_e$, $C_2$-$C_6$ alkenyl substituted with 0-5 $R_e$, and $C_2$-$C_6$ alkynyl substituted with 0-5 $R_e$, carbocyclyl, and heterocyclyl;

(xvi) $R_d$, at each occurrence, is independently selected from H, $C_1$-$C_6$ alkyl substituted with 0-5 $R_e$, $C_2$-$C_6$ alkenyl substituted with 0-5 $R_e$, $C_2$-$C_6$ alkynyl substituted with 0-5 $R_e$, —$(CH_2)_r$—$C_3$-$C_{10}$ carbocyclyl substituted with 0-5 $R_e$, and —$(CH_2)_r$—$C_3$-$C_{10}$ heterocyclyl substituted with 0-5 $R_e$;

(xvii) $R_e$, at each occurrence, is independently selected from $C_1$-$C_6$ alkyl substituted with 0-5 $R_f$, $C_2$-$C_6$ alkenyl, $C_2$-$C_6$ alkynyl, —$(CH_2)_r$—$C_3$-$C_6$ cycloalkyl, F, Cl, Br, CN, $NO_2$, =O, $CO_2H$, —$(CH_2)_r$—$OC_1$-$C_5$ alkyl, —$(CH2)_r$OH, SH, and —$(CH2)_rNR_fR_f$;

(xviii) $R_f$, at each occurrence, is independently selected from H, $C_1$-$C_5$ alkyl, $C_3$-$C_6$ cycloalkyl, and phenyl, or $R_f$ and Rf, together with the phenyl ring to which they are both attached, form a heterocyclic ring;

(xix) p, at each occurrence, is independently selected from 0, 1, and 2; and (xx) r, at each occurrence, is independently selected from 0, 1, 2, 3, and 4.

U.S. Pat. No. 8,084,457 to Choidas et al., incorporated herein by this reference, discloses 4,6-disubstituted aminopyridines, including compounds of Formula (N-V):

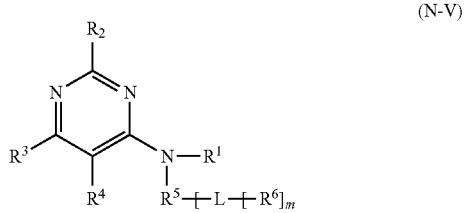
(N-V)

wherein:

(i) $R^1$ is selected from the group consisting of H, linear or branched $C_1$-$C_6$ substituted or unsubstituted alkyl, linear or branched $C_2$-$C_6$ alkenyl, or linear or branched $C_2$-$C_6$ alkynyl;

(ii) $R^2$ and $R^4$ are each independently selected from the group consisting of H, linear or branched $C_1$-$C_6$ substituted or unsubstituted alkyl, linear or branched $C_2$-$C_6$ alkenyl, linear or branched $C_2$-$C_6$ alkynyl, aryl, F, Cl, Br, I, CN, —$NH_2$, or —$NO_2$;

(iii) $R^3$ is selected from the group consisting of F, Cl, Br, I, substituted or unsubstituted aryl, substituted or unsubstituted —O-aryl, substituted or unsubstituted —NH-aryl, substituted or unsubstituted —S-aryl, substituted or unsubstituted aryl, substituted or unsubstituted —O-heterocyclyl, substituted or unsubstituted —NH— heterocyclyl, substituted or unsubstituted —S-heterocyclyl, substituted or unsubstituted —CH=CH-aryl, substituted or unsubstituted heteroaryl, substituted or unsubstituted heterocyclyl, substituted or unsubstituted $C_3$-$C_8$ cycloalkyl, or —NH—$(CH_2)_n$—X, wherein n is 0, 1, 2, 3, 4, 5, or 6 and X is selected from the group consisting of hydroxyl, amino, or substituted or unsubstituted $C_3$-$C_8$ cycloalkyl;

(iv) $R^5$ is selected from the group consisting of substituted or unsubstituted aryl, substituted or unsubstituted heteroaryl, substituted or unsubstituted heterocyclyl, substituted or unsubstituted $C_3$-$C_8$ cycloalkyl, or —NH—(CH2)$_o$—Y, wherein o is 1, 2, 3, 4, 5, or 6 and Y is substituted or unsubstituted aryl, substituted or unsubstituted heteroaryl, substituted or unsubstituted heterocyclyl, substituted or unsubstituted $C_3$-$C_8$ cycloalkyl;

(v) $R^6$ is selected from the group consisting of substituted or unsubstituted $C_1$-$C_8$ alkyl, substituted or unsubstituted aryl, substituted or unsubstituted heteroaryl, substituted or unsubstituted heterocyclyl, substituted pyrrolidinyl, substituted or unsubstituted $C_3$-$C_8$ cycloalkyl, disubstituted cyclohexyl, cyclopentyl, substituted or unsubstituted $C_5$-$C_{12}$ bicycloalkyl, substituted or unsubstituted adamantyl, —$(CH_2)_q$-group, where q is 1, 2, or 3, under the proviso that, if $R^6$ is selected to be a methylene chain —$(CH_2)_q$-group, $R^{17}$ or $R^{19}$ are selected to be a —$(CH_2)_s$-group wherein s is 1, 2, or 3 or a —$(CH_2)_t$-A group wherein t is 1, 2, or 3 and A is O or N, respectively, and $R^6$ and $R^{17}$ or $R^6$ and $R^{17}$ together form a 5- to 8-membered ring system; or $R^6$ is —$(CH_2)_p$—Z, wherein p is 0, 1, 2, 3, 4, 5, or 6 and Z is selected from the group consisting of substituted or unsubstituted aryl, substituted or unsubstituted heteroaryl, substituted or unsubstituted heterocyclyl, —N($R^7R^8$), wherein $R^7$ and $R^8$ are independently selected from H or linear or branched substituted or unsubstituted $C_1$-$C_6$ alkyl, or Z is selected from —$(CR^9R^{10}R^{11})$ wherein $R^9$, $R^{10}$, and $R^{11}$ are independently selected from H, linear or branched substituted or unsubstituted $C_1$-$C_8$ alkyl, or —N($R^{12}R^{13}$) wherein $R^{12}$ and $R^{13}$ are independently selected from H or linear or branched substituted or unsubstituted $C_1$-$C_6$ alkyl; under the proviso that, if Z is —$(CR^9R^{10}R^{11})$, p is 0, 1, 2, 3, 4, 5, or 6; and if Z is selected from substituted or unsubstituted aryl, substituted or unsubstituted heteroaryl, substituted or unsubstituted heterocyclyl, or —N($R^7R^8$), p is 1, 2, 3, 4, 5, or 6;

(vi) L is a group of Subformula (N-V(a)), (N-V(b)), (N-V(c)), (N-V(d)), (N-V(e)), (N-V(f)), (N-V(g)), (N-V(h)), (N-V(i)), (N-V(j)), (N-V(k)), (N-V(l)), or (N-V(m)):

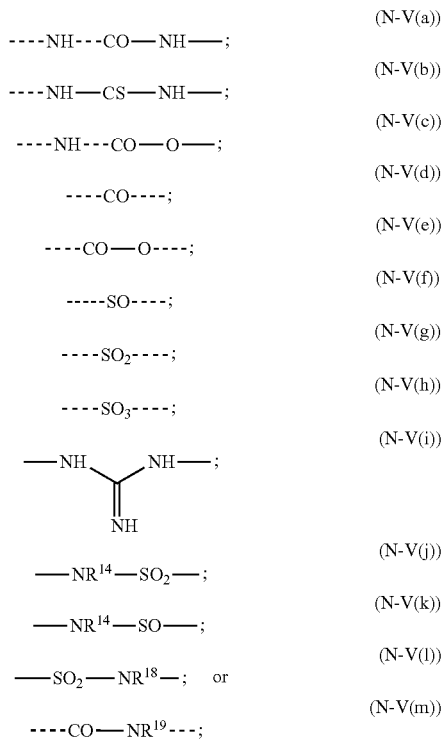

wherein $R^{14}$ is selected from H, linear or branched substituted or unsubstituted $C_1$-$C_6$ alkyl, —$SO_2$—$R^{15}$, wherein $R^{15}$ is linear or branched $C_1$-$C_6$ alkyl, or $R^{14}$ is —$(CH_2)_r$—COO$R^{16}$, wherein r is 0, 1, 2, 3, 4, 5, or 6 and $R^{16}$ is H or linear or branched substituted or unsubstituted $C_1$-$C_6$ alkyl, —$NR^{17}$—CO—, wherein $R^{17}$ is H, linear or branched substituted or unsubstituted $C_1$-$C_6$ alkyl, or a —$(CH_2)_s$-group, wherein s is 1, 2, or 3; and wherein $R^{16}$ and $R^{17}$ both represent a methylene chain group, $R^{16}$ and $R^{17}$ may form together a 5- to 8-membered ring system of Subformula (N-V(n))

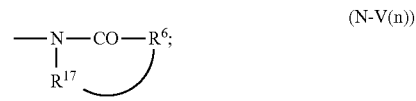
(N-V(n))

$R^{18}$ is H or linear or branched substituted or unsubstituted $C_1$-$C_6$ alkyl, $R^{19}$ is H, linear or branched substituted or unsubstituted $C_1$-$C_6$ alkyl, or a —(CH2)$_t$-A group wherein t is 1, 2, or 3 and A is N or O, and, wherein if $R^6$ is a —(CH2)$_q$-group and $R^{19}$ is or a —$(CH_2)_r$-A group, $R^6$ and $R^{19}$ may form together a 5- to 8-membered ring system of Subformula (N-V(o))

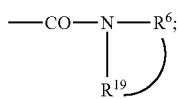

(N-V(o))

and (vii) m is 0 or 1; and stereoisomeric forms and/or pharmaceutically acceptable salts thereof.

U.S. Pat. No. 7,723,336 to Vaccaro et al., incorporated herein by this reference, discloses fused heterocyclic compounds, including $N^6$-(trans-4-aminocyclohexyl)-$N^8$-[4-(ethyloxy)phenyl]imidazo[1,2-b]pyridazine-6,8-diamine, $N^6$-(2-aminoethyl)-$N^8$-(4-(ethyloxy)phenyl)imidazo[1,2-b]pyridazine-6,8-diamine; $N^6$-(4-aminobutyl)-$N^8$-(4-(ethyloxy)phenyl)imidazo[1,2-b]pyridazine-6,8-diamine; 7-chloro-N-(4-(ethyloxy)phenyl)-6-(1-piperazinyl)imidazo[1,2-b]pyridazin-8-amine; $N^6$-(trans-4-aminocyclohexyl)-$N^8$-(4-(methyloxy)phenyl)imidazo[1,2-b]pyridazine-6,8-diamine; $N^6$-(trans-4-aminocyclohexyl)-$N^8$-(3-(ethyloxy)phenyl)imidazo[1,2-b]pyridazine-6,8-diamine; $N^6$-(trans-4-aminocyclohexyl)-$N^8$-phenyl)imidazo[1,2-b]pyridazine-6,8-diamine; $N^6$-(trans-4-aminocyclohexyl)-$N^8$-(3-(methyloxy)phenyl)imidazo[1,2-b]pyridazine-6,8-diamine; $N^6$-(trans-4-aminocyclohexyl)-$N^8$-(3,4-dimethylphenyl)imidazo[1,2-b]pyridazine-6,8-diamine; $N^6$-(trans-4-aminocyclohexyl)-$N^8$-(4-(phenyloxy)phenyl)imidazo[1,2-b]pyridazine-6,8-diamine; $N^6$-(trans-4-aminocyclohexyl)-$N^8$-(4-(butyloxy)phenyl)imidazo[1,2-b]pyridazine-6,8-diamine; $N^6$-(trans-4-aminocyclohexyl)-$N^8$-4-biphenylylimidazo[1,2-b]pyridazine-6,8-diamine; $N^6$-(trans-4-aminocyclohexyl)-$N^8$-(4-methylphenyl)imidazo[1,2-b]pyridazine-6,8-diamine; $N^6$-(trans-4-aminocyclohexyl)-$N^8$-(3,4-bis(methyloxy)phenyl)imidazo[1,2-b]pyridazine-6,8-diamine; $N^6$-(trans-4-aminocyclohexyl)-$N^8$-(4-(phenylmethyl)oxy)phenylimidazo[1,2-b]pyridazine-6,8-diamine; $N^6$-(trans-4-aminocyclohexyl)-$N^8$-(4-(propyloxy)phenyl)imidazol[1,2-b]pyridazine-6,8-diamine; $N^6$-(trans-4-aminocyclohexyl)-$N^8$-pyridin-3-ylimidazo[1,2-b]pyridazine-6,8-diamine; $N^6$-(trans-4-aminocyclohexyl)-$N^8$-(2-methyl-1H-indol-5-yl)imidazo[1,2-b]pyridazine-6,8-diamine; $N^6$-(trans-4-aminocyclohexyl)-$N^8$-methyl-1H-phenylimidazo[1,2-b]pyridazine-6,8-diamine; $N^6$-(trans-4-aminocyclohexyl)-$N^8$-[2-(methyloxy)phenyl]imidazo[1,2-b]pyridazine-6,8-diamine; $N^6$-(trans-4-aminocyclohexyl)-$N^8$-(2-methylphenyl)imidazo[1,2-b]pyridazine-6,8-diamine; $N^6$-(trans-4-aminocyclohexyl)-$N^8$-(2,3-dimethylphenyl)imidazo[1,2-b]pyridazine-6,8-diamine; $N^6$-(trans-4-aminocyclohexyl)-$N^8$-(2,4-dimethylphenyl)imidazo[1,2-b]pyridazine-6,8-diamine; $N^6$-(trans-4-aminocyclohexyl)-$N^8$-(2,5-dimethylphenyl)imidazo[1,2-b]pyridazine-6,8-diamine; $N^6$-(trans-4-aminocyclohexyl)-$N^8$-(3-methylphenyl)imidazo[1,2-b]pyridazine-6,8-diamine; $N^6$-(trans-4-aminocyclohexyl)-$N^8$-(3,5-dimethylphenyl)imidazo[1,2-b]pyridazine-6,8-diamine; $N^6$-(trans-4-aminocyclohexyl)-$N^8$-[3-(dimethylamino)phenyl]imidazo[1,2-b]pyridazine-6,8-diamine; $N^6$-(trans-4-aminocyclohexyl)-$N^8$-(2-methyl-1,3-benzothiazol-6-yl)imidazo[1,2-b]pyridazine-6,8-diamine; $N^6$-(trans-4-aminocyclohexyl)-$N^8$-(2-methyl-1,3-benzothiazol-5-yl)imidazo[1,2-b]pyridazine-6,8-diamine; $N^6$-(trans-4-aminocyclohexyl)-$N^8$-cyclopropylimidazo[1,2-b]pyridazine-6,8-diamine; $N^6$-(trans-4-aminocyclohexyl)-$N^8$-cyclohexylimidazo[1,2-b]pyridazine-6,8-diamine; $N^6$-(trans-4-aminocyclohexyl)-$N^8$-(cyclohexylmethyl)imidazo[1,2-b]pyridazine-6,8-diamine; $N^6$-(trans-4-aminocyclohexyl)-$N^8$-(1-methylethyl)imidazo[1,2-b]pyridazine-6,8-diamine; $N^6$-(trans-4-aminocyclohexyl)-$N^8$-(phenylmethyl)imidazo[1,2-b]pyridazine-6,8-diamine; $N^6$-(trans-4-aminocyclohexyl)-$N^8$-[(2-chlorophenyl)methyl]imidazo[1,2-b]pyridazine-6,8-diamine; $N^6$-(trans-4-aminocyclohexyl)-$N^8$-((4-chlorophenyl)methyl)imidazo[1,2-b]pyridazine-6,8-diamine; $N^6$-(trans-4-aminocyclohexyl)-$N^8$-((4-(methyloxy)phenyl)methylimidazo[1,2-b]pyridazine-6,8-diamine; $N^6$-(trans-4-aminocyclohexyl)-$N^8$-ethylimidazo[1,2-b]pyridazine-6,8-diamine; $N^6$-(trans-4-aminocyclohexyl)-$N^8$-(2-(methyloxy)ethyl)imidazo[1,2-b]pyridazine-6,8-diamine; $N^6$-(trans-4-aminocyclohexyl)-$N^8$-(2-(4-(methyloxy)phenyl)ethyl)imidazo[1,2-b]pyridazine-6,8-diamine; $N^6$-(trans-4-aminocyclohexyl)-$N^8$-2-propen-1-ylimidazo[1,2-b]pyridazine-6,8-diamine; $N^6$-(trans-4-aminocyclohexyl)-$N^8$-(3-methylbutyl)imidazo[1,2-b]pyridazine-6,8-diamine; $N^6$-(trans-4-aminocyclohexyl-$N^8$-propylimidazo[1,2-b]pyridazine-6,8-diamine; $N^6$-(trans-4-aminocyclohexyl-$N^8$-(cyclopropylmethyl)imidazo[1,2-b]pyridazine-6,8-diamine; $N^6$-(trans-4-aminocyclohexyl)-$N^8$-((3-chlorophenyl)methylimidazo[1,2-b]pyridazine-6,8-diamine; 6-(3-amino-1-piperidinyl)-N-(4-(ethyloxy)phenyl)imidazo[1,2-b]pyridazin-8-amine; $N^6$-(3-aminopropyl)-$N^8$-(4-(ethyloxy)phenyl)imidazo[1,2-b]pyridazine-6,8-diamine; $N^6$-(trans-4-aminocyclohexyl)-$N^8$-(2,6-difluorophenyl)imidazo[1,2-b]pyridazine-6,8-diamine; $N^6$-(4-((4-aminocyclohexyl)methyl)cyclohexyl)-$N^8$-(4-(ethyloxy)phenyl)imidazo[1,2-b]pyridazine-6,8-diamine; 2-(1-(8-((4-(ethyloxy)phenyl)amino)imidazo[1,2-b]pyridazin-6-yl)-4-piperidinyl)ethanol; $N^6$-(trans-4-aminocyclohexyl)-$N^8$-1H-indol-5-ylimidazo[1,2-b]pyridazine-6,8-diamine; $N^6$-(trans-4-aminocyclohexyl)-$N^8$-(2-(ethyloxy)phenyl)imidazo[1,2-b]pyridazine-6,8-diamine; 6-(3-amino-1-pyrrolidinyl)-N-(4-(ethyloxy)phenylimidazo[1,2-b]pyridazin-8-amine; $N^6$-(trans-4-aminocyclohexyl)-$N^8$-(2-phenylethyl)imidazo[1,2-b]pyridazine-6,8-diamine; N-(4-(ethyloxy)phenyl)-6-(1-piperazinyl)imidazo[1,2-b]pyridazin-8-amine; $N^6$-(2-(dimethylamino)-ethyl)-$N^8$-(4-(ethyloxy)phenyl)imidazo[1,2-b]pyridazine-6,8-diamine; $N^6$-(4-(ethyloxy)phenyl)-$N^8$-(2-furanylmethyl)imidazo[1,2-b]pyridazine-6,8-diamine; N-(4-(ethyloxy)phenyl)-6-(4-methyl-1,4-diazepan-1-yl)imidazo[1,2-b]pyridazin-8-amine; 2-((6-((trans-4-aminocyclohexyl)amino)imidazo[1,2-b]pyridazin-8-yl)amino)phenol; $N^6$-(trans-4-aminocyclohexyl)-$N^8$-(3-((phenylmethyl)oxy)phenyl)imidazo[1,2-b]pyridazine-6,8-diamine; 3-((6-((trans-4-aminocyclohexylamino)imidazo[1,2-b]pyridazin-8-yl)amino)phenol; 4-((6-((trans-4-aminocyclohexyl)amino)imidazo[1,2-b]pyridazin-8-yl)amino)phenol; $N^6$-(trans-4-aminocyclohexyl)imidazo[1,2-b]pyridazine-6,8-diamine; 3-((6-((trans-4-aminocyclohexyl)amino)imidazo[1,2-b]pyridazin-8-yl)amino)benzonitrile; 4-((6-((trans-4-aminocyclohexyl)amino)imidazo[1,2-b]pyridazin-8-yl)amino)benzonitrile, 3-((6-((trans-4-aminocyclohexyl)amino)imidazo[1,2-b]pyridazin-8-yl)amino)benzoic acid; $N^6$-(trans-4-aminocyclohexyl)-$N^8$-1H-pyrazol-3-ylimidazo[1,2-b]pyridazine-6,8-diamine; 4-((6-((trans-4-aminocyclohexyl)amino)imidazo[1,2-b]pyridazin-8-yl)amino)benzoic acid; 4-((6-((trans-4-aminocyclohexyl)amino)imidazo[1,2-b]pyridazin-8-yl)amino)-N,N-dimethylbenzenesulfonamide; $N^6$-(trans-4-aminocyclohexyl)-$N^8$-(4-(1H-tetrazol-5-yl)phenyl)imidazo[1,2-b]pyridazine-6,8-diamine; $N^6$-(trans-4-(ethylamino)cyclohexyl)-$N^8$-phenylimidazo[1,2-b]pyridazine-6,8-diamine; $N^6$-(trans-4-(methylamino)cyclohexyl)-$N^8$-phenylimidazo[1,2-b]pyridazine-6,8-diamine; $N^6$-(trans-4-aminocyclohexyl)-$N^8$-(2-(phenyloxy)phenyl)imidazo[1,2-b]pyridazine-6,8-diamine; $N^6$-(trans-4-aminocyclohexyl)-$N^8$-(4'-chloro-4-biphenylyl)imidazo[1,2-b]pyridazine-6,8-diamine; $N^6$-(trans-4-aminocyclohexyl)-

N8-(2'-methyl-4-biphenylyl)imidazo[1,2-b]pyridazine-6,8-diamine; N6-(trans-4-aminocyclohexyl)-N8-(3'-chloro-4-biphenylyl)imidazo[1,2-b]pyridazine-6,8-diamine; N6-(trans-4-aminocyclohexyl)-N8-(4-(phenylmethyl)phenyl)imidazo[1,2-b]pyridazine-6,8-diamine; N6-(trans-4-aminocyclohexyl)-N8-(4-(4-morpholinyl)phenyl)imidazo[1,2-b]pyridazine-6,8-diamine; N6-(trans-4-aminocyclohexyl)-N8-(3'-chloro-3-biphenylyl)imidazol[1,2-b]pyridazine-6,8-diamine; N6-(trans-4-aminocyclohexyl)-N8-(4-(1-methylethyl)phenyl)imidazo[1,2-b]pyridazine-6,8-diamine; N6-(trans-4-aminocyclohexyl)-N8-(4-butylphenyl)imidazo[1,2-b]pyridazine-6,8-diamine; N6-(trans-4-aminocyclohexyl)-N8-(5,6,7,8-tetrahydro-1-naphthalenyl)imidazo[1,2-b]pyridazine-6,8-diamine; N6-(trans-4-aminocyclohexyl)-N8-1-naphthalenylimidazo[1,2-b]pyridazine-6,8-diamine; N6-(trans-4-aminocyclohexyl)-N8-(3-(phenylmethyl)phenyl)imidazo[1,2-b]pyridazine-6,8-diamine; N6-(trans-4-aminocyclohexyl)-N8-(4-propylphenyl)imidazo[1,2-b]pyridazine-6,8-diamine; N6-(trans-4-aminocyclohexyl)-N8-(4'-methyl-4-biphenylyl)imidazo[1,2-b]pyridazine-6,8-diamine; N6-(trans-4-aminocyclohexyl)-N8-(3-(1-methylethyl)phenyl)imidazo[1,2-b]pyridazine-6,8-diamine; N6-(trans-4-aminocyclohexyl)-N8-(3-((1-methylethyl)oxy)phenyl)imidazo[1,2-b]pyridazine-6,8-diamine; N6-(trans-4-aminocyclohexyl)-N8-(3,5-bis(methyloxy)phenyl)imidazo[1,2-b]pyridazine-6,8-diamine; trans-N-(8-(6-methyl-3,4-dihydro-1(2H)-quinolinyl)imidazo[1,2-b]pyridazin-6-yl)-1,4-cyclohexanediamine; N6-(trans-4-aminocyclohexyl)-N8-2-naphthalenylimidazo[1,2-b]pyridazine-6,8-diamine; N6-(trans-4-aminocyclohexyl)-N8-(3-(methylsulfanyl)phenyl)imidazo[1,2-b]pyridazine-6,8-diamine; N6-(trans-4-aminocyclohexyl)-N8-(3-ethylphenyl)imidazo[1,2-b]pyridazine-6,8-diamine; N6-(trans-4-aminocyclohexyl)-N8-(4-ethylphenyl)imidazo[1,2-b]pyridazine-6,8-diamine; N6-(trans-4-aminocyclohexyl)-N8-(4-(methylsulfanyl)phenyl)imidazo[1,2-b]pyridazine-6,8-diamine; N6-(trans-4-aminocyclohexyl)-N8-9H-fluoren-2-ylimidazo[1,2-b]pyridazine-6,8-diamine; N6-(trans-4-aminocyclohexyl)-N8-(2-ethylphenyl)imidazo[1,2-b]pyridazine-6,8-diamine; N6-(trans-4-aminocyclohexyl)-N8-(4-cyclohexylphenyl)imidazo[1,2-b]pyridazine-6,8-diamine; N6-(trans-4-aminocyclohexyl)-N8-(4-(1,1-dimethylethyl)phenyl)imidazo[1,2-b]pyridazine-6,8-diamine; N6-(trans-4-aminocyclohexyl)-N8-(3-(phenyloxy)phenylimidazo[1,2-b]pyridazine-6,8-diamine; N6-(trans-4-aminocyclohexyl)-N8-3-biphenylylimidazo[1,2-b]pyridazine-6,8-diamine; N6-(trans-4-aminocyclohexyl)-N8-(4-((1-methylethyl)oxy)phenyl)imidazo[1,2-b]pyridazine-6,8-diamine; N6-(trans-4-aminocyclohexyl)-N8-(2-chlorophenyl)imidazo[1,2-b]pyridazine-6,8-diamine; N6-(trans-4-aminocyclohexyl)-N8-(4-chlorophenyl)imidazo[1,2-b]pyridazine-6,8-diamine; N6-(trans-4-aminocyclohexyl)-N8-(3-chlorophenyl)imidazo[1,2-b]pyridazine-6,8-diamine; N6-(trans-4-aminocyclohexyl)-N8-(4-chloro-1-naphthalenyl)imidazo[1,2-b]pyridazine-6,8-diamine; N6-(trans-4-aminocyclohexyl)-N8-3-quinolinylimidazo[1,2-b]pyridazine-6,8-diamine; N6-(trans-4-aminocyclohexyl)-N8-(3,5-dichlorophenyl)imidazo[1,2-b]pyridazine-6,8-diamine; N6-(trans-4-aminocyclohexyl)-N8-(3-(trifluoromethyl)phenyl)imidazo[1,2-b]pyridazine-6,8-diamine; N6-(trans-4-aminocyclohexyl)-N8-(4-chloro-2-fluorophenyl)imidazo[1,2-b]pyridazine-6,8-diamine; N6-(trans-4-aminocyclohexyl)-N8-(2-fluoro-5-methylphenyl)imidazo[1,2-b]pyridazine-6,8-diamine; N6-(trans-4-aminocyclohexyl)-N8-(4-chloro-3-methylphenyl)imidazo[1,2-b]pyridazine-6,8-diamine; N6-(trans-4-aminocyclohexyl)-N8-(5-phenyl-2-pyridinyl)imidazo[1,2-b]pyridazine-6,8-diamine; N6-(trans-4-aminocyclohexyl)-N8-(3-fluoro-4-methylphenyl)imidazo[1,2-b]pyridazine-6,8-diamine; N6-(trans-4-aminocyclohexyl)-N8-(2-methyl-4-pyridinyl)imidazo[1,2-b]pyridazine-6,8-diamine; N6-(trans-4-aminocyclohexyl)-N8-(4-fluoro-3-methylphenyl)imidazo[1,2-b]pyridazine-6,8-diamine; N6-(trans-4-aminocyclohexyl)-N8-(2-fluoro-4-methylphenyl)imidazo[1,2-b]pyridazine-6,8-diamine; N6-(trans-4-aminocyclohexyl)-N8-(3-((trifluoromethyl)oxy)phenyl)imidazo[1,2-b]pyridazine-6,8-diamine; N6-(trans-4-aminocyclohexyl)-N8-(4-methyl-3-(trifluoromethyl)phenyl)imidazo[1,2-b]pyridazine-6,8-diamine; N6-(trans-4-aminocyclohexyl)-N8-(4-ethyl-2-pyridinyl)imidazo[1,2-b]pyridazine-6,8-diamine; N6-(trans-4-aminocyclohexyl)-N8-(4-(1H-1,2,4-triazol-1-yl)phenyl)imidazo[1,2-b]pyridazine-6,8-diamine; N6-(trans-4-aminocyclohexyl)-N8-(4-(1H-pyrrol-1-yl)phenyl)imidazo[1,2-b]pyridazine-6,8-diamine; N6-(trans-4-aminocyclohexyl)-N8-(4-(4,5-dichloro-1H-imidazol-1-yl)phenyl)imidazo[1,2-b]pyridazine-6,8-diamine; N6-(trans-4-aminocyclohexyl)-N8-(4-(1H-pyrazol-1-yl)phenyl)imidazo[1,2-b]pyridazine-6,8-diamine; N6-(trans-4-aminocyclohexyl)-N8-(4-(3,5-dimethyl-1H-pyrazol-1-yl)phenylimidazo[1,2-b]pyridazine-6,8-diamine; N6-(trans-4-aminocyclohexyl)-N8-(4-(4-methyl-4H-1,2,4-triazol-3-yl)phenyl)imidazo[1,2-b]pyridazine-6,8-diamine; N6-(trans-4-aminocyclohexyl)-N8-(4-(1H-imidazol-1-yl)phenyl)imidazo[1,2-b]pyridazine-6,8-diamine; N6-(trans-4-aminocyclohexyl)-N8-(4-(1-methyl-1H-imidazol-2-yl)phenyl)imidazo[1,2-b]pyridazine-6,8-diamine; N6-(trans-4-aminocyclohexyl)-N8-(4-(2-methyl-1,3-thiazol-4-yl)phenyl)imidazo[1,2-b]pyridazino-6,8-diamine; N6-(trans-4-aminocyclohexyl)-N8-(4-(5-methyl-2-furanyl)phenyl)imidazo[1,2-b]pyridazine-6,8-diamine; N6-(trans-4-aminocyclohexyl)-N8-(4-(2-ethyl-2H-tetrazol-5-yl)phenyl)imidazo[1,2-b]pyridazino-6,8-diamine; 4-((6-((trans-4-aminocyclohexyl)amino)imidazo[1,2-b]pyridazin-8-yl)amino)-3-hydroxy-N,N-dimethylbenzenesulfonamide; N6-(trans-4-aminocyclohexyl)-N8-(2,3-dihydro-1H-inden-5-yl)imidazo[1,2-b]pyridazine-6,8-diamine; 3-((6-((trans-4-aminocyclohexyl)amino)imidazo[1,2-b]pyridazin-8-yl)amino)-N,N-dimethylbenzenesulfonamide; 4-((6-((trans-4-aminocyclohexyl)amino)imidazo[1,2-b]pyridazin-8-yl)amino)-N,N-dimethylbenzamide; N6-(trans-4-((2-chloro-4-pyrimidinyl)amino)cyclohexyl)-N8-phenylimidazo[1,2-b]pyridazine-6,8-diamine; N6-(3-aminocyclopentyl)-N8-phenylimidazo[1,2-b]pyridazine-6,8-diamine; N6-(trans-4-aminocyclohexyl)-N8-(3-(4-morpholinylsulfony-l)phenyl)imidazo[1,2-b]pyridazine-6,8-diamine; 3-((6-((trans-4-aminocyclohexyl)amino)imidazo[1,2-b]pyridazin-8-yl)amino)-N,N-diethylbenzamide 3-((6-((trans-4-aminocyclohexyl)amino)imidazo[1,2-b]pyridazin-8-yl)amino)-N-methyl-N-phenylbenzenesulfonamide; 4-((6-((trans-4-aminocyclohexyl)amino)imidazo[1,2-b]pyridazin-8-yl)amino)-2-hydroxy-N,N-dimethylbenzenesulfonamide N6-(4-aminobicyclo[2.2.2]oct-1-yl)-N8-phenylimidazo[1,2-b]pyridazine-6,8-diamine; N-(4-((6-((trans-4-aminocyclohexyl)amino)imidazo[1,2-b]pyridazin-8-yl)amino)phenyl)methanesulfonamide; N6-(trans-4-aminocyclohexyl)-N8-(4-(3-(dimethylamino)-1-pyrrolidinyl)phenyl)imidazo[1,2-b]pyridazine-6,8-diamine; N6-(trans-4-aminocyclohexyl)-N8-(4-(1-pyrrolidinylsulfonyl)phenyl)imidazo[1,2-b]pyridazine-6,8-diamine; 4-((6-((trans-4-aminocyclohexyl)amino)imidazo[1,2-b]pyridazin-8-yl)amino)benzenesulfonic acid; 4-((6-((trans-4-aminocyclohexyl)amino)imidazo[1,2-b]pyridazin-8-yl)amino)-N,N-diethylbenzenesulfonamide; 4-((6-trans-4-aminocyclohexyl)amino)imidazo[1,2-b]pyridazin-8-yl)amino)-N-propylbenzenesulfonamide; 4-((6-((trans-4- aminocyclohexyl)amino)imidazo[1,2-b]pyridazin-8-yl)amino)-N-ethylbenzenesulfonamide; 4-((6-((trans-4-aminocyclohexyl)amino)imidazo[1,2-b]pyridazin-8-yl)amino)-N-methylbenzenesulfonamide; $N^6$-(trans-4-aminocyclohexyl)-$N^8$-(4-aminophenyl)imidazo[1,2-b]pyridazine-6,8-diamine; 4-((6-((trans-4-aminocyclohexyl)amino)imidazo[1,2-b]pyridazin-8-yl)amino)benzenesulfonamide; 3-((6-((trans-4-aminocyclohexyl)amino)imidazo[1,2-b]pyridazin-8-yl)amino)benzenesulfonamide; 3-((6-((trans-4-aminocyclohexyl)amino)imidazo[1,2-b]pyridazin-8-yl)amino)benzamide; 4-((6-((trans-4-aminocyclohexyl)amino)imidazo[1,2-b]pyridazin-8-yl)amino)benzamide; $N^6$-(trans-4-aminocyclohexyl)-$N^8$-(4-(aminomethyl)phenyl)imidazo[1,2-b]pyridazine-6,8-diamine; 6-((6-((trans-4-aminocyclohexyl)amino)imidazo[1,2-b]pyridazin-8-yl)amino)-1,2-dihydro-3H-indazol-3-one; $N^6$-(trans-4-aminocyclohexyl)-$N^8$-(3-(aminomethyl)phenyl)imidazo[1,2-b]pyridazine-6,8-diamine; $N^6$-(trans-4-aminocyclohexyl)-$N^8$-(2,6-difluorophenyl)imidazo[1,2-b]pyridazine-6,8-diamine; $N^6$-(trans-4-aminocyclohexyl)-7-chloro-$N^8$-[4-(ethyloxy)phenyl]imidazo[1,2-b]pyridazine-6,8-diamine; $N^6$-(3-aminopropyl)-$N^8$-[4-(ethyloxy)phenyl]imidazo[1,2-b]pyridazine-6,8-diamine; $N^6$-(trans-4-aminocyclohexyl)-$N^8$-(2-fluorophenyl)imidazo[1,2-b]pyridazine-6,8-diamine; $N^6$-(trans-4-aminocyclohexyl)-$N^8$-(2,6-difluorophenyl)imidazo[1,2-b]pyridazine-6,8-diamine; $N^6$-(trans-4-aminocyclohexyl)-$N^8$-(2,4-difluorophenyl)imidazo[1,2-b]pyridazine-6,8-diamine; $N^6$-(trans-4-aminocyclohexyl)-$N^8$-(3-fluorophenyl)imidazo[1,2-b]pyridazine-6,8-diamine; $N^6$-(trans-4-aminocyclohexyl)-$N^8$-(4-fluorophenyl)imidazo[1,2-b]pyridazine-6,8-diamine; $N^6$-(trans-4-aminocyclohexyl)-$N^8$-(3,4-difluorophenyl)imidazo[1,2-b]pyridazine-6,8-diamine; $N^6$-(trans-4-aminocyclohexyl)-$N^8$-(2,5-difluorophenyl)imidazo[1,2-b]pyridazine-6,8-diamine; $N^6$-(trans-4-aminocyclohexyl)-$N^8$-(2,3-difluorophenyl)imidazo[1,2-b]pyridazine-6,8-diamine; $N^6$-(trans-4-aminocyclohexyl)-$N^8$-(3,5-difluorophenyl)imidazo[1,2-b]pyridazine-6,8-diamine; $N^6$-(trans-4-aminocyclohexyl)-$N^8$-(3-iodophenyl)imidazo[1,2-b]pyridazine-6,8-diamine; $N^6$-(trans-4-aminocyclohexyl)-$N^8$-[4-(trifluoromethyl)phenyl]imidazo[1,2-b]pyridazine-6,8-diamine; $N^6$-(trans-4-aminocyclohexyl)-$N^8$-pyridin-2-ylimidazo[1,2-b]pyridazine-6,8-diamine; $N^6$-(trans-4-aminocyclohexyl)-$N^8$-(4-methylpyridin-2-yl)imidazo[1,2-b]pyridazine-6,8-diamine; $N^6$-(trans-4-aminocyclohexyl)-$N^8$-(5-methylpyridin-2-ylimidazo[1,2-b]pyridazine-6,8-diamine; $N^6$-(trans-4-aminocyclohexyl)-$N^8$-(4,6-dimethylpyridin-2-yl)imidazo[1,2-b]pyridazine-6,8-diamine; $N^6$-(trans-4-aminocyclohexyl)-$N^8$-pyrimidin-2-ylimidazo[1,2-b]pyridazine-6,8-diamine; $N^6$-(trans-4-aminocyclohexyl)-$N^8$[4-(ethyloxy)phenyl]-7-methylimidazo[1,2-b]pyridazine-6,8-diamine; $N^6$-(trans-4-aminocyclohexyl)-7-ethyl-$N^8$-[4-(ethyloxy)phenyl]imidazo[1,2-b]pyridazine-6,8-diamine; $N^6$-(trans-4-aminocyclohexyl)-7-methyl-$N^8$-phenylimidazo[1,2-b]pyridazine-6,8-diamine; $N^6$-(trans-4-aminocyclohexyl)-$N^8$-(3,4-dimethylphenyl)-7-methylimidazo[1,2-b]pyridazine-6,8-diamine; $N^6$-(trans-4-aminocyclohexyl)-7-methyl-$N^8$-(4-methylphenyl)imidazo[1,2-b]pyridazine-6,8-diamine; $N^6$-(trans-4-aminocyclohexyl)-7-methyl-$N^8$-[3-(methyloxy)phenyl]imidazo[1,2-b]pyridazine-6,8-diamine; $N^6$-(trans-4-aminocyclohexyl)-$N^8$-biphenyl-4-yl-7-methylimidazo[1,2-b]pyridazine-6,8-diamine; $N^6$-(trans-4-aminocyclohexyl)-7-methyl-$N^8$-[4-(propyloxy)phenyl]imidazo[1,2-b]pyridazine-6,8-diamine; 4-((6-((trans-4-aminocyclohexyl)amino)-7-methylimidazo[1,2-b]pyridazin-8-yl)amino)benzoic acid; 4-((6-((4-aminocyclohexyl)amino)-7-methylimidazo[1,2-b]pyridazin-8-yl)amino)-N,N-dimethylbenzenesulfonamide; N-(4-((6-((trans-4-aminocyclohexyl)amino)-7-methylimidazo[1,2-b]pyridazin-8-yl)amino)phenyl)-N-methylacetamide; $N^6$-(trans-4-aminocyclohexyl)-7-ethyl-$N^8$-phenylimidazo[1,2-b]pyridazine-6,8-diamine; $N^6$-(trans-4-aminocyclohexyl)-7-chloro-$N^8$-[4-(ethyloxy)phenyl]imidazo[1,2-b]pyridazine-6,8-diamine; $N^8$-[4-(ethyloxy)phenyl]-$N^6$-piperidin-3-ylimidazo[1,2-b]pyridazine-6,8-diamine; $N^8$-[4-(ethyloxy)phenyl]-$N^6$-pyrrolidin-3-ylimidazo[1,2-b]pyridazine-6,8-diamine; $N^8$-[4-(ethyloxy)phenyl]-$N^6$-piperidin-4-ylimidazo[1,2-b]pyridazine-6,8-diamine; 6-(3-amino-1-piperidinyl)-N-(4-(ethyoxy)phenyl)imidazo[1,2-b]pyridazin-8-amine; $N^8$-(4-(ethyloxy)phenyl))-7-methyl-$N^6$-3-piperidinylimidazo[1,2-b]pyridazine-6,8-diamine; $N^8$-phenyl-$N^6$-3-piperidinylimidazo[1,2-b]pyridazine-6,8-diamine; 6-[(3S)-3-aminopyrrolidin-1-yl]-N-[4-(ethyloxy)phenyl]imidazo[1,2-b]pyridazin-8-amine; $N^2$-(trans-4-aminocyclohexyl)-$N^4$-[4-(ethyloxy)phenyl]pyrazolo[1,5-a][1,3,5]triazine-2,4-diamine; imidazo[2,14][1,2,4]triazine-2,4-diamine; $N^6$-(cis-4-aminocyclohexyl)-$N^8$-[4-(ethyloxy)phenyl]-7-methylimidazo[1,2-b]pyridazine-6,8-diamine; $N^6$-(cis-4-aminocyclohexyl)-$N^8$-(5-methyl-2-pyridinyl)imidazo[1,2-b]pyridazine-6,8-diamine; $N^6$-(cis-4-aminocyclohexyl)-$N^8$-phenylimidazo[1,2-b]pyridazine-6,8-diamine; $N^6$-(cis-4-aminocyclohexyl)-7-methyl-$N^8$-phenylimidazo[1,2-b]pyridazine-6,8-diamine; $N^6$-(cis-4-aminocyclohexyl)-$N^8$-(4-(ethyloxy)phenyl)imidazo[1,2-b]pyridazine-6,8-diamine; $N^6$-(cis-4-aminocyclohexyl)-$N^8$-(3,4-dimethylphenyl)imidazo[1,2-b]pyridazine-6,8-diamine; $N^6$-(cis-4-aminocyclohexyl)-$N^8$-(5-phenyl-2-pyridinyl)imidazo[1,2-b]pyridazine-6,8-diamine; 4-((6-(((cis-4-aminocyclohexyl)amino)imidazo[1,2-b]pyridazin-8-yl)amino)-N,N-dimethylbenzenesulfonamide; $N^6$-(cis-4-aminocyclohexyl)-$N^8$-(4-methylphenyl)imidazo[1,2-b]pyridazine-6,8-diamine; $N^6$-(cis-4-aminocyclohexyl)-$N^8$-(4,6-dimethyl-2-pyridinyl)imidazo[1,2-b]pyridazine-6,8-diamine; $N^6$-(cis-4-aminocyclohexyl)-$N^8$-(4-(1H-pyrazol-1-yl)phenyl)imidazo[1,2-b]pyridazine-6,8-diamine; $N^6$-(cis-4-aminocyclohexyl)-$N^8$-(4-(4-morpholinylcarbonyl)phenyl)imidazo[1,2-b]pyridazine-6,8-diamine; $N^6$-(trans-4-aminocyclohexyl)-7-methyl-$N^8$-(2-methyl-phenyl)imidazo[1,2-b]pyridazine-6,8-diamine; $N^6$-(trans-4-aminocyclohexyl)-$N^8$-(2-fluorophenyl)-7-methylimidazo[1,2-b]pyridazine-6,8-damine; $N^6$-(cis-4-aminocyclohexyl)-7-methyl-$N^8$-(2-methyl phenyl)imidazo[1,2-b]pyridazine-6,8-diamine; $N^6$-(cis-4-aminocyclohexyl)-$N^8$-(2-fluorophenyl)-7-methylimidazo[1,2-b]pyridazine-6,8-diamine; $N^6$-(6-((trans-4-aminocyclohexyl)amino)imidazo[1,2-b]pyridazin-8-yl)benzamide; 1-(6-((trans-4-aminocyclohexyl)amino)imidazo[1,2-b]pyridazin-8-yl)-3-phenylurea; N,N'-bis(4-trans-aminocyclohexyl)imidazo[1,2-b]pyridazine-6,8-diamine; $N^6$-(trans-4-aminocyclohexyl)-$N^8$-(4-ethyloxyphenyl)-7-phenylimidazo[1,2-b]pyridazine-6,8-diamine; $N^6$-(trans-4-aminocyclohexyl)-$N^8$-(phenyl)-7-phenylimidazo[1,2-b]pyridazine-6,8-diamine; $N^6$-(cis-4-aminocyclohexyl)-$N^8$-(4-ethoxyphenyl)-7-phenylimidazo[1,2-b]pyridazine-6,8-diamine; 4-(6-((trans-4-aminocyclohexyl)amino)imidazo[1,2-b]pyridazin-8-yl)amino)-N-(2-(4-pyridinyl)ethyl)benzamide; 4-((6-((trans-4-aminocyclohexyl)amino)imidazo[1,2-b]pyridazin-8-yl)amino)-N-(2-furanylmethyl)benzamide; 4-((6-((trans-4-aminocyclohexyl)amino)imidazo[1,2-b]pyridazin-8-yl)amino)-N-(1H-imidazol-4-ylmethyl)benzamide; 4-((6-((trans-4-aminocyclohexyl)amino)imidazo[1,2-b]pyridazin-8-yl)amino)-N-(3-pyridinylmethyl)benzamide; $N^6$-(trans-4- aminocyclohexyl)-N⁸-(4-((4-phenyl-1-piperidinyl)carbonyl)phenyl)imidazo[1,2-b]pyridazine-6,8-diamine; N⁶-(trans-4-aminocyclohexyl)-N⁸-(4-(1-pyrrolidinylcarbonyl)phenylimidazo[1,2-b]pyridazine-6,8-diamine; N⁶-(trans-4-aminocyclohexyl)-N⁸-(4-(1-piperidinylcarbonyl)phenyl)imidazo[1,2-b]pyridazine-6,8-diamine; 4-((6-((trans-4-aminocyclohexyl)amino)imidazo[1,2-b]pyridazin-8-yl)amino)-N-(phenylmethyl)benzamide; 4-((6-((trans-4-aminocyclohexyl)amino)imidazo[1,2-b]pyridazin-8-yl)amino)-N-(3-(methyloxy)phenyl)benzamide; N⁶-(trans-4-aminocyclohexyl)-N⁸-(4-((3-phenyl-1-pyrrolidinyl)carbonyl)phenyl)imidazo[1,2-b]pyridazine-6,8-diamine; 3-((6-((trans-4-aminocyclohexyl)amino)imidazo[1,2-b]pyridazin-8-yl)amino)-N-phenylbenzamide; 4-((6-((trans-4-aminocyclohexyl)amino)imidazo[1,2-b]pyridazin-8-yl)amino)-N-(2-hydroxyethyl)benzamide; 4-((6-((trans-4-aminocyclohexylamino)imidazo[1,2-b]pyridazin-8-yl)amino)-N-(3-(2-oxo-1-pyrrolidinyl)propyl)benzamide; N⁶-(trans-4-aminocyclohexyl)-N⁸-(4-(4-morpholinylcarbonyl)phenyl)imidazo[1,2-b]pyridazine-6,8-diamine; 4-((6-((trans-4-aminocyclohexyl)amino)imidazo[1,2-b]pyridazin-8-yl)amino)-N-methyl-N-(2-(2-pyridinyl)ethyl)benzamide; 4-((6-((trans-4-aminocyclohexyl)amino)imidazo[1,2-b]pyridazin-8-yl)amino)-N,N-diethylbenzamide; 4-((6-((trans-4-aminocyclohexyl)amino)imidazo[1,2-b]pyridazin-8-yl)amino)-N-cyclopropylbenzamide; 4-((6-((trans-4-aminocyclohexyl)amino)imidazo[1,2-b]pyridazin-8-yl)amino)-N-(cyclohexylmethyl)benzamide; 4-((6-((trans-4-aminocyclohexyl)amino)imidazo[1,2-b]pyridazin-8-yl)amino)-N-3-pyridinylbenzamide; 4-((6-((trans-4-aminocyclohexyl)amino)imidazo[1,2-b]pyridazin-8-yl)amino)-N-(1-methyl-1H-pyrazol-5-yl)benzamide; 4-((6-((trans-4-aminocyclohexyl)amino)imidazo[1,2-b]pyridazin-8-yl)amino)-N-(1-(4-fluorophenyl)-2-oxo-1,2-dihydro-3-pyridinyl)benzamide; 4-((6-((trans-4-aminocyclohexyl)amino)imidazo[1,2-b]pyridazin-8-yl)amino)-N-phenylbenzamide; 4-((6-((trans-4-aminocyclohexyl)amino)imidazo[1,2-b]pyridazin-8-yl)amino)-N-cyclohexylbenzamide; 4-((6-((trans-4-aminocyclohexyl)amino)imidazo[1,2-b]pyridazin-8-yl)amino)-N-(4-pyridinylmethyl)benzamide; 1-(4-((6-((trans-4-aminocyclohexyl)amino)imidazo[1,2-b]pyridazin-8-yl)amino)phenyl)-3-phenylurea; 1-(4-((6-((cis-4-aminocyclohexyl)amino)-7-methylimidazo[1,2-b]pyridazin-8-yl)amino)phenyl)-3-phenylurea; 1-(4-((6-((trans-4-aminocyclohexyl)amino)-7-methylimidazo[1,2-b]pyridazin-8-yl)amino)phenyl)-3-phenylurea; N-(4-((6-((trans-4-aminocyclohexyl)amino)imidazo[1,2-b]pyridazin-8-yl)amino)phenyl)-1-(4-fluorophenyl)-2-oxo-1,2-dihydro-3-pyridinecarboxamide; N-(4-((6-((trans-4-aminocyclohexyl)amino)imidazo[1,2-b]pyridazin-8-yl)amino)-phenyl)-1-(4-fluorophenyl)-2-oxo-1,2-dihydro-3-pyridinecarboxamide; N-(4-((6-((trans-4-aminocyclohexyl)amino)imidazo[1,2-b]pyridazin-8-yl)amino)-2-ethylphenyl)-1-(4-fluorophenyl)-2-oxo-1,2-dihydro-3-pyridinecarboxamide; N-(4-((6-((trans-4-aminocyclohexyl)amino)imidazo[1,2-b]pyridazin-8-yl)amino)phenyl)benzamide; N-(4-((6-((trans-4-aminocyclohexyl)amino)imidazo[1,2-b]pyridazin-8-yl)amino)phenyl)acetamide; 3-((6-((trans-4-aminocyclohexyl)amino)-7-methylimidazo[1,2-b]pyridazin-8-yl)amino)phenol; N-(4-((6-chloroimidazo[1,2-b]pyridazin-8-yl)amino)phenyl)-1-(4-fluorophenyl)-2-oxo-1,2-dihydro-3-pyridinecarboxamide; 1-(4-fluorophenyl)-N-(4-(imidazo[1,2-b]pyridazin-8-ylamino)phenyl)-2-oxo-3-piperidinecarboxamide; 1-(4-fluorophenyl)-N-(4-(imidazo[1,2-b]pyridazin-8-ylamino)phenyl)-2-oxo-1,2-dihydro-3-pyridinecarboxamide; 6-((trans-4-aminocyclohexyl)amino)-8-((4-(ethyloxy)phenyl)amino)imidazo[1,2-b]pyridazine-3-carbonitrile; 6-((trans-4-aminocyclohexyl)amino)-8-(phenylamino)imidazo[1,2-b]pyridazine-3-carbonitrile; 6-((4-trans-aminocyclohexyl)amino)-7-methyl-8-(phenylamino)imidazo[1,2-b]pyridazine-3-carbonitrile; 6-((trans)-4-aminocyclohexylamino)-7-ethyl-8-(phenylamino)imidazo[1,2-b]pyridazine-3-carbonitrile; 6-((trans-4-aminocyclohexyl)amino)-8-anilino-7-isopropylimidazo[1,2-b]pyridazine-3-carbonitrile; N⁶-(trans-4-aminocyclohexyl)-N⁸-(4-(ethyloxy)phenyl)-3-fluoroimidazo[1,2-b]pyridazine-6,8-diamine; N⁶-(trans-4-aminocyclohexyl)-N⁸-(4-(ethyloxy)phenyl)-3-methylimidazo[1,2-b]pyridazine-6,8-diamine; N⁶-(trans-4-aminocyclohexyl)-N⁸-(4-(ethyloxy)phenyl)-2,3-dimethylimidazo[1,2-b]pyridazine-6,8-diamine; N-(6-((trans-4-aminocyclohexyl)amino)imidazo[1,2-b]pyridazin-8-yl)benzenesulfonamide; 6-((trans-4-aminocyclohexyl)oxy)-8-anilinoimidazo[1,2-b]pyridazine-3-carbonitrile; 6-((trans-4-aminocyclohexyl)amino)-8-anilinoimidazo[1,2-b]pyridazine-3-carboxamide; N⁶-(trans-4-aminocyclohexyl)-7-ethyl-N⁸-phenylimidazo[1,2-b]pyridazine-6,8-diamine; N⁶-(trans-4-aminocyclohexyl)-7-ethyl-N⁸-[4-(ethyloxy)phenyl]imidazo[1,2-b]pyridazine-6,8-diamine; N⁶-(trans-4-aminocyclohexyl)-7-benzyl-N⁸-phenylimidazo[1,2-b]pyridazine-6,8-diamine; 3-((6-((trans-4-aminocyclohexyl)amino)-7-isopropylimidazo[1,2-b]pyridazin-8-yl)amino)-N-ethylbenzenesulfonamide; 4-((6-((trans-4-aminocyclohexyl)amino)-7-isopropylimidazo[1,2-b]pyridazin-8-yl)amino)-N-ethylbenzenesulfonamide; 4-((6-((trans-4-aminocyclohexyl)amino)-7-isopropylimidazo[1,2-b]pyridazin-8-yl)amino)-N-phenylbenzamide; N⁶-(trans-4-aminocyclohexyl)-7-isopropyl-N⁸-3-pyridinylimidazo[−1,2-b]pyridazine-6,8-diamine; N⁶-(trans-4-aminocyclohexyl)-N⁸-(3-ethoxyphenyl)-7-isopropylimidazo[1,2-b]pyridazine-6,8-diamine; N⁶-(trans-4-aminocyclohexyl)-N⁸-(4-ethoxyphenyl)-7-isopropyl-imidazo[1,2-b]pyridazine-6,8-diamine; 4-((6-((trans-4-Aminocyclohexyl)amino)-7-isopropylimidazo[1,2-b]pyridazin-8-yl)amino)phenol; N⁶-(trans-4-aminocyclohexyl)-N⁸-(4-(aminomethyl)phenyl)-7-methylimidazo[1,2-b]pyridazine-6,8-diamine; 6-(3-amino-1,2-benzisoxazol-5-yl)-N-phenylimidazo[1,2-b]pyridazin-8-amine; 6-(3-amino-1,2-benzisoxazol-6-yl)-N-phenylimidazo[1,2-b]pyridazin-8-amine; N⁶-(trans-4-aminocyclohexyl)-7-(3-chlorophenyl)-N⁸-phenylimidazo-6,8-diamine; N⁶-(trans-4-aminocyclohexyl)-7-(4-chlorophenyl)-N⁸-phenylimidazo[1,2-b]pyridazine-6,8-diamine 8-anilino-6-((3S)-3-piperidinylamino)imidazo[1,2-b]pyridazine-3-carbonitrile; 3-((6-((trans-4-aminocyclohexyl)amino)-7-isopropylimidazo[1,2-b]pyridazin-8-yl)amino)phenol; N⁶-(trans-4-aminocyclohexyl)-3-cyclopropyl-N⁸-phenylimidazo[1,2-b]pyridazine-6,8-diamine; N⁶-(4-aminocyclohexyl)-N⁸-phenyl-3((E)-2-(4-pyridinyl)vinyl)imidazo[1,2-b]pyridazine-6,8-diamine; N⁶-(trans-4-aminocyclohexyl)-N⁸-phenyl-3-(1-propyn-1-yl)imidazo[1,2-b]pyridazine-6,8-diamine; 6-((trans-4-aminocyclohexyl)amino)-8-anilino-N-4-pyridinylimidazo[1,2-b]pyridazine-3-carboxamide; 6-((4-amino-1-piperidinyl)methyl)-N-phenylimidazo[1,2-b]pyridazin-8-amine; 6-((trans-4-aminocyclohexyl)amino)-8-anilinoimidazo[1,2-b]pyridazine-7-carbonitrile; 8-anilino-6-((3S)-3-piperidinylamino)imidazo[1,2-b]pyridazine-7-carbonitrile; and 4-((6-((trans-4-aminocyclohexyl)amino)-3-cyanoimidazo[1,2-b]pyridazin-8-yl)amino)-N-methylbenzenesulfonamide.

United States Patent Application Publication No. 2014/0005183 by Galatsis et al., incorporated herein by this reference, discloses 4-(substituted amino)-7H-pyrrolo[2,3-d]pyrimidines, including compounds of Formula (N-VI):

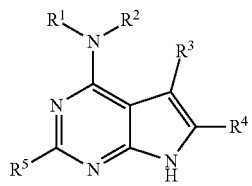

(N-VI)

wherein:

(i) $R^1$ and $R^2$ are each independently hydrogen, $C_1$-$C_6$ alkyl, $C_3$-$C_7$ cycloalkyl, a 4- to 7-membered heterocycloalkyl which contains from one to three heteroatoms selected from N, O, and S, or a 5- to 6-membered heteroaryl which contains one to four heteroatoms selected from N, O, and S; wherein the $C_1$-$C_6$ alkyl, $C_3$-$C_7$ cycloalkyl, 4- to 7-membered heterocycloalkyl, and 5- to 6-membered heteroaryl are optionally substituted with one to three $R^6$; or $R^1$ and $R^2$ taken together with the nitrogen to which they are attached form: (a) a 4- to 7-membered heterocycloalkyl which optionally contains one to two heteroatoms selected from N, O, and S, and optionally contains one double bond; (b) a 6- to 11-membered heterobicycloalkyl which optionally contains one to two additional heteroatoms selected from N, O, and S; or (c) a 6- to 12-membered heterospirocycloalkyl which optionally contains one to two additional heteroatoms selected from N, O, and S, and wherein the structures of (a), (b), or (c) is optionally substituted with one to three $R^7$;

(ii) $R^3$ is phenyl or a 5- to 10-membered heteroaryl which contains one to four heteroatoms selected from N, O, and S, and wherein the phenyl or the 5- to 10-membered heteroaryl are optionally substituted with one to three $R^9$ and wherein the phenyl is optionally fused with a $C_5$-$C_6$ cycloalkyl or a 5- to 6-membered heterocycloalkyl which contains one to three heteroatoms selected from N, O, and S and which is optionally substituted with oxo;

(iii) $R^4$ and $R^5$ are each independently hydrogen or $C_1$-$C_6$ alkyl;

(iv) $R^6$ at each occurrence is selected from $C_1$-$C_3$ alkyl, $C_1$-$C_3$ alkoxy, hydroxyl, halo, —$NR^aR^b$, —$C(O)NR^aR^b$, or a 4- to 7-membered heteroycloalkyl which contains one to three heteroatoms selected from N, O, and S;

(v) $R^7$ at each occurrence is independently selected from halo, hydroxyl, cyano, —$NR^aR^b$, —$C(O)NR^aR^b$, $C_1$-$C_6$ alkyl, $C_1$-$C_6$ alkoxy, phenyl, a 5- to 6-membered heteroaryl containing one to four heteroatoms selected from N, O, or S, or two $R^7$ when attached to the same carbon atom and taken together can be oxo, wherein the $C_1$-$C_6$ alkyl, phenyl, or 5- to 6-membered heteroaryl are optionally substituted with one to three $R^8$;

(vi) $R^8$ at each occurrence is independently hydroxyl, halo, cyano, $C_1$-$C_3$ alkoxy, —$NR^aR^b$, $C_1$-$C_3$ alkyl optionally substituted with one to three halo, $C_3$-$C_7$ cycloalkyl, phenoxy optionally substituted with cyano, or a 5- to 6-membered heteroaryloxy containing one to four heteroatoms selected from N, O, and S and which is optionally substituted with one or two halo or $C_1$-$C_3$ alkyl;

(vii) $R^9$ at each occurrence is independently cyano, halo, hydroxyl, $C_1$-$C_3$ alkyl-S—, carboxyl, —$C(O)NH_2$, —$S(O)_2NH_2$, $C_1$-$C_3$ alkyl optionally substituted with one to three halo or hydroxyl; and (viii) $R^a$ and $R^b$ at each occurrence are each independently hydrogen, $C_1$-$C_6$ alkyl, $C_3$-$C_7$ cycloalkyl, or —$C(O)C_1$-$C_6$ alkyl;

or pharmaceutically acceptable salts thereof.

United States Patent Application Publication No. 2013/0331359 by Yun et al., incorporated herein by this reference, discloses phosphorus-containing-group-substituted quinolines, including: N1-[4-[[7-[3-(diethoxyphosphorylmethylamino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethylamino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(methyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(ethyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(n-propyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(ethyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(methyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(ethyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(n-propyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(diethoxyphosphorylmethyl)(ethyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(acetyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(formyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(propionyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(isopropionyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(cyclopropylformyl(diethoxyphosphorylmethyl)amino)propoxyl]-6-methoxyl-4-quinolyl]oxyl]-3-fluorophenyl]-N1'-(4-fluorophenyl)cyclopropane-1,1-dicarboxamide; N1-[4-[[7-[3-(acetyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(formyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(propionyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(isopropionyl(diethoxyphosphorylmethyl)amino)ethoxyl]-6-methoxyl-4-quinolyl]oxyl]-3-fluorophenyl]-N1'-(4-fluorophenyl)cyclopropane-1,1-dicarboxamide; N1-[4-[[7-[3-(cyclopropylformyl(diethoxyphosphorylmethyl)amino)

ethoxyl]-6-methoxyl-4-quinolyl]oxyl]-3-fluorophenyl]-N1'-(4-fluorophenyl)cyclopropane-1,1-dicarboxamide; N1'-[4-[[7-[3-(aminocarbonyl(diethoxyphosphorylmethyl)amino)propoxyl]-6-methoxyl-4-quinolyl]oxyl]-3-fluorophenyl]-N1-(4-fluorophenyl)cyclopropane-1,1-dicarboxamide; N1'-[4-[[7-[3-(diethoxyphosphorylmethyl)(ethylaminocarbonyl)amino)propoxyl]-6-methoxyl-4-quinolyl]oxyl]-3-fluorophenyl]-N1-(4-fluorophenyl)cyclopropane-1,1-dicarboxamide; N1'-[4-[[7-[3-(diethoxyphosphorylmethyl)(methylaminocarbonyl)amino)propoxyl]-6-methoxyl-4-quinolyl]oxyl]-3-fluorophenyl]-N1-(4-fluorophenyl)cyclopropane-1,1-dicarboxamide; N1'[4-[[7-[3-(diethoxyphosphorylmethyl)(N,N'-dimethylaminocarbonyl)amino)propoxyl]-6-methoxyl-4-quinolyl]oxyl]-3-fluorophenyl]-N1-(4-fluorophenyl)cyclopropane-1,1-dicarboxamide; N1'-[4-[[7-[3-(aminocarbonyl(diethoxyphosphorylmethyl)amino)ethoxyl]-6-methoxyl-4-quinolyl]oxyl]-3-fluorophenyl]-N1-(4-fluorophenyl)cyclopropane-1,1-dicarboxamide; N1'-[4-[[7-[3-(diethoxyphosphorylmethyl)(ethylamino carbonyl)amino)ethoxyl]-6-methoxyl-4-quinolyl]oxyl]-3-fluorophenyl]-N1-(4-fluorophenyl)cyclopropane-1,1-dicarboxamide; N1'-[4-[[7-[3-(diethoxyphosphorylmethyl)(methylaminocarbonyl)amino)ethoxyl]-6-methoxyl-4-quinolyl]oxyl]-3-fluorophenyl]-N1-(4-fluorophenyl)cyclopropane-1,1-dicarboxamide; N1'-[4-[[7-[3-(diethoxyphosphorylmethyl)(N,N'-dimethylaminocarbonyl)amino)ethoxyl]-6-methoxyl-4-quinolyl]oxyl]-3-fluorophenyl]-N1-(4-fluorophenyl)cyclopropane-1,1-dicarboxamide; N1'-[4-[[7-[3-(diethoxyphosphorylmethyl)(methylsulfonyl)amino)propoxyl]-6-methoxyl-4-quinolyl]oxyl]-3-fluorophenyl]-N1-(4-fluorophenyl)cyclopropane-1,1-dicarboxamide; N1'-[4-[[7-[3-(diethoxyphosphorylmethyl)(ethylsulfonyl)amino)propoxyl]-6-methoxyl-4-quinolyl]oxyl]-3-fluorophenyl]-N1-(4-fluorophenyl)cyclopropane-1,1-dicarboxamide; N1-[4-[[6-[3-(diethoxyphosphorylmethylamino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethylamino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(methyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(ethyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(n-propyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(ethyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(methyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(ethyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(n-propyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(diethoxyphosphorylmethyl)(ethyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(acetyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(formyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(propionyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(isopropionyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(cyclopropylformyl(diethoxyphosphorylmethyl)amino)propoxyl]-7-methoxyl-4-quinolyl]oxyl]-3-fluorophenyl]-N1'-(4-fluorophenyl)cyclopropane-1,1-dicarboxamide; N1-[4-[[6-[3-(acetyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(formyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(propionyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(isopropionyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide; N1-[4-[[6-[3-(cyclopropylformyl(diethoxyphosphorylmethyl)amino)ethoxyl]-7-methoxyl-4-quinolyl]oxyl]-3-fluorophenyl]-N1'-(4-fluorophenyl)cyclopropane-1,1-dicarboxamide; N1'-[4-[[6-[3-(amino carbonyl(diethoxyphosphorylmethyl)amino)propoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(ethylaminocarbonyl)amino)propoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(methylaminocarbonyl)amino)propoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(N,N$^1$-dimethylaminocarbonyl)amino)propoxyl]-7-methoxyl-4-quinolyl]oxyl]-3-fluorophenyl]-N1-(4-fluorophenyl)cyclopropane-1,1-dicarboxamide; N1'-[4-[[6-[3-(aminocarbonyl(diethoxyphosphorylmethyl)amino)ethoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(ethylaminocarbonyl)amino)ethoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(methylaminocarbonyl)amino)ethoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(N,N'-dimethylaminocarbonyl)amino)ethoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(methylsulfonyl)amino)propoxyl]-7-methoxyl-4-quinolyl]oxyl]-3-fluorophenyl]-N1-(4-fluorophenyl)cyclopropane-1,1-dicarboxamide; N1'-[4-[[6-[3-(diethoxyphosphorylmethyl)(ethylsulfonyl)amino)propoxyl]-7-methoxyl-4-quinolyl]oxyl]-3-fluorophenyl]-N1-(4-fluorophenyl)cyclopropane-1,1-dicarboxamide; N1-[4-[[7-[[1-(diethoxyphosphorylmethyl)-4-piperidinyl]methoxyl]-6-methoxyl-4-quinolyl]oxyl]-3-fluorophenyl]-N1'-(4-fluorophenyl)cyclopropane-1,1-dicarboxamide; N1-

[4-[[7-[[1-(2-diethoxyphosphorylacetyl)-4-piperidinyl] methoxyl]-6-methoxyl-4-quinolyl]oxyl]-3-fluorophenyl]-N1'-(4-fluorophenyl)cyclopropane-1,1-dicarboxamide; N1-[4-[[6-[[1-(diethoxyphosphorylmethyl)-4-piperidinyl] methoxyl]-7-methoxyl-4-quinolyl]oxyl]-3-fluorophenyl]-N1'-(4-fluorophenyl)cyclopropane-1,1-dicarboxamide; and N1-[4-[[6-[[1-(2-diethoxyphosphorylacetyl)-4-piperidinyl] methoxyl]-7-methoxyl-4-quinolyl]oxyl]-3-fluorophenyl]-N1'-(4-fluorophenyl)cyclopropane-1,1-dicarboxamide.

United States Patent Application Publication No. 2013/0184221 by Panitch et al., incorporated herein by this reference, discloses kinase-inhibiting peptides, including: peptides having an amino acid sequence according to Peptide Formula (1): Q1-Z1-Z2-Z3-Z4-Z5-Z6-Q2 (Peptide Formula (1) wherein Q1 and Q2 are independently absent or present, and wherein if Q1 and Q2 are present, Q1 and Q2 comprise a polypeptide having an amino acid sequence according to Peptide Subformula (1(a)): X1-X2-X3-X4-X5-X6-X7-X8-X9-X10-X11 (Peptide Subformula (1(a))) wherein X1 is any amino acid except K, or is absent; X2 is present or is absent; and when X2 is present, X2 is any amino acid; X3 is any amino acid; X4 is any amino acid; X5 is any basic amino acid; X6 is any amino acid; X7 is any amino acid; X8 is any amino acid; X9 is any amino acid; X10 is any amino acid; X11 is any amino acid, or is absent; and wherein Z1 and Z2 are present; wherein Z3 is present or absent, wherein Z4 is absent or present, but if Z4 is present, Z3 is present, wherein Z5 is absent or present, but if Z5 is present, Z3 and Z4 are present; wherein Z6 is absent or present, but if Z6 is present, Z3, Z4 and Z5 are present; and each of Z1, Z2, Z3, Z4, Z5, and Z6, is a peptide selected from the group consisting of: (a) X1-X2-B1-B2-X3-B3-X4 (Peptide Subformula (1(b))), wherein each of X1, X3 and X4 is a hydrophobic amino acid; X2 is any amino acid; and wherein each of B1, B2 and B3 is a basic amino acid; (b) X1-X2-B1-B2-X3-B3 (Peptide Subformula (1(c))), wherein each of X1 and X3 is a hydrophobic amino acid, X2 is any amino acid; and wherein each of B1, B2, and B3 is a basic amino acid; (c)X1-X2-B1-B2-X3 (Peptide Subformula (1(d))), wherein each of X1 and X3 is a hydrophobic amino acid; X2 is any amino acid; and wherein each of B1 and B2 is a basic amino acid; (d) X1-B1-B2-X2-B3-X3 (Peptide Subformula (1(e))), wherein X1 is any amino acid; each of X2 and X3 is any hydrophobic amino acid, and each of B1, B2, and B3 is a basic amino acid; (e) X1-B1-B2-X2-B3 (Peptide Subformula (1(f))), wherein X1 is a hydrophobic amino acid, H or N; X2 is a hydrophobic amino acid; and each of B1, B2, and B3 is a basic amino acid; (f) X1-B1-B2-X2 (Peptide Subformula (1(g))), wherein X1 is any amino acid; X2 is a hydrophobic amino acid; and each of B1 and B2 is a basic amino acid; (g) X1-X2-B1-B2 (Peptide Subformula (1(h))), wherein X1 is a hydrophobic amino acid, X2 is any amino acid; and each of B1 and B2 is a basic amino acid; (h) X1-X2-B1-X3-X4 (Peptide Subformula (1(i))), wherein each of X1, X3, and X4 is a hydrophobic amino acid; X2 is any amino acid; and B1 is any basic amino acid; (i) X1-B1-X2-X3 (Peptide Subformula (1(j))), wherein X1 is any amino acid; X2 is any amino acid; X3 is a hydrophobic amino acid; and B1 is a basic amino acid; (j) X1-X2-B1-X3 (Peptide Subformula (1(k))), wherein each of X1 and X3 is a hydrophobic amino acid; X2 is any amino acid; and B1 is a basic amino acid; (k) B1-B2-X1-X2-B3-X3 (Peptide Subformula (1(l))), wherein each of X1, X2, and X3 is a hydrophobic amino acid; and each of B1, B2, and B3 is a basic amino acid; (l) B1-B2-X1-X2-B3 (Peptide Subformula (1(m))), wherein each of X1 and X2 is a hydrophobic amino acid; and each of B1, B2, and B3 is a basic amino acid; (m) B1-B2-X1-X2 (Peptide Subformula (1(n))), wherein each of X1 and X2 is a hydrophobic amino acid; and each of B1 and B2 is a basic amino acid; (n) B1-X1-X2-B2-B3-X3 (Peptide Subformula (1(o))), wherein each of X1, X2, and X3 is a hydrophobic amino acid; and each of B1, B2, and B3 is a basic amino acid; (o) B1-X1-X2-B2-B3 (Peptide Subformula (1(p))), wherein each of X1 and X2 is a hydrophobic amino acid, and each of B1, B2, and B3 is a basic amino acid; and (p) B1-X1-X2-B2 (Peptide Subformula (1(q))), wherein each of X1 and X2 is a hydrophobic amino acid; and each of B1 and B2 is any basic amino acid; with the proviso that if Q2 is present, the two amino acids immediately preceding Q2 as part of Z2, Z3, Z4, Z5, or Z6 cannot be KA. Additional peptides include HRRIKAWLKKILALARQLGVAA (SEQ ID NO: 2); WLRRIKAWLRRIKALARQLGVAA (SEQ ID NO: 3); and WLRRIKAWLRRALARQLGVA (SEQ ID NO: 4).

United States Patent Application Publication No. 2013/0090336 by Bourke et al., incorporated herein by this reference, discloses N-containing heterocyclic compounds including a [3,2-d]pyrimidine moiety, including 7-iodo-N-(4-morpholinophenyl)thieno[3,2-d]pyrimidin-2-amine; 7-(4-aminophenyl)-N-(4-morpholinophenyl)thieno[3,2-d]pyrimidin-2-amine; N-(4-(2-(4-morpholinophenylamino)thieno[3,2-d]pyrimidin-7-yl)phenyl)acrylamide; 7-(3-aminophenyl)-N-(4-morpholinophenyl)thieno[3,2-d]pyrimidin-2-amine; N-(3-(2-(4-morpholinophenylamino)thieno[3,2-d]pyrimidin-7-yl)phenyl)acrylamide; N-(4-morpholinophenyl)thieno[3,2-d]pyrimidin-2-amine; methyl 2-(4-morpholinophenylamino)thieno[3,2-d]pyrimidine-7-carboxylate; N-(4-morpholinophenyl)-5H-pyrrolo[3,2-d]pyrimidin-2-amine; 7-(4-amino-3-methoxyphenyl)-N-(4-morpholinophenyl)thieno[3,2-d]pyrimidin-2-amine; 4-(2-(4-morpholinophenylamino)thieno[3,2-d]pyrimidin-7-yl)benzenesulfonamide; N,N-dimethyl-3-(2-(4-morpholinophenylamino)thieno[3,2-d]pyrimidin-7-yl)benzenesulfonamide; 1-ethyl-3-(2-methoxy-4-(2-(4-morpholinophenylamino)thieno[3,2-d]pyrimidin-7-yl)phenyl)urea; N-(4-(2-(4-morpholinophenylamino)thieno[3,2-d]pyrimidin-7-yl)phenyl)methanesulfonamide; 2-methoxy-4-(2-(4-morpholinophenylamino)thieno[3,2-d]pyrimidin-7-yl)phenol; 2-cyano-N-(3-(2-(4-morpholinophenylamino)thieno[3,2-d]pyrimidin-7-yl)phenyl)acetamide; N-(cyanomethyl)-2-(4-morpholinophenylamino)thieno[3,2-d]pyrimidine-7-carboxamide; N-(3-(2-(4-morpholinophenylamino)thieno[3,2-d]pyrimidin-7-yl)phenyl)methanesulfonamide; 1-ethyl-3-(4-(2-(4-morpholinophenylamino)thieno[3,2-d]pyrimidin-7-yl)-2-(trifluoromethoxy)phenyl)urea; N-(3-nitrophenyl)-7-phenylthieno[3,2-d]pyrimidin-2-amine; 7-iodo-N-(3-nitrophenyl)thieno[3,2-d]pyrimidin-2-amine; N1-(7-(2-ethylphenyl)thieno[3,2-d]pyrimidin-2-yl)benzene-1,3-diamine; N-tert-butyl-3-(2-(4-morpholinophenylamino)thieno[3,2-d]pyrimidin-7-yl)benzenesulfonamide; N1-(7-iodothieno[3,2-d]pyrimidin-2-yl)benzene-1,3-diamine 28; 7-(4-amino-3-(trifluoromethoxy)phenyl)-N-(4-morpholinophenyl)thieno[3,2-d]pyrimidin-2-amine; 7-(2-ethylphenyl)-N-(4-morpholinophenyl)thieno[3,2-d]pyrimidin-2-amine; N-(3-(2-(4-morpholinophenylamino)thieno[3,2-d]pyrimidin-7-yl)phenyl)acetamide; N-(cyanomethyl)-N-(3-(2-(4-morpholinophenylamino)thieno[3,2-d]pyrimidin-7-yl)phenyl)methanesulfonamide; N-(cyanomethyl)-N-(4-(2-(4-morpholinophenylamino)thieno[3,2-d]pyrimidin-7-yl)phenyl)methanesulfonamide; N-(3-(5-methyl-2-(4-morpholinophenylamino)-5H-pyrrolo[3,2-d]pyrimidin-7-yl)phenyl)methanesulfonamide; 4-(5-methyl-2-(4-morpholinophenylamino)-5H-pyrrolo[3,2-d]pyrimidin-7- yl)benzenesulfonamide; N-(4-(5-methyl-2-(4-morpholinophenylamino)-5H-pyrrolo[3,2-d]pyrimidin-7-yl)phenyl)methanesulfonamide; 7-iodo-N-(4-morpholinophenyl)-5H-pyrrolo[3,2-d]pyrimidin-2-amine; 7-(2-isopropylphenyl)-N-(4-morpholinophenyl)thieno[3,2-d]pyrimidin-2-amine; 7-bromo-N-(4-morpholinophenyl)thieno[3,2-d]pyrimidin-2-amine; N7-(2-isopropylphenyl)-N2-(4-morpholinophenyl)thieno[3,2-d]pyrimidine-2,7-diamine; N7-(4-isopropylphenyl)-N2-(4-morpholinophenyl)thieno[3,2-d]pyrimidine-2,7-diamine; 7-(5-amino-2-methylphenyl)-N-(4-morpholinophenyl)thieno[3,2-d]pyrimidin-2-amine; N-(cyanomethyl)-4-(2-(4-morpholinophenylamino)thieno[3,2-d]pyrimidin-7-yl)benzamide; 7-iodo-N-(3-morpholinophenyl)thieno[3,2-d]pyrimidin-2-amine; 7-(4-amino-3-nitrophenyl)-N-(4-morpholinophenyl)thieno[3,2-d]pyrimidin-2-amine; 7-(2-methoxypyridin-3-yl)-N-(4-morpholinophenyl)thieno[3,2-d]pyrimidin-2-amine; (3-(7-iodothieno[3,2-d]pyrimidin-2-ylamino)phenyl)methanol; N-tert-butyl-3-(2-(3-morpholinophenylamino)thieno[3,2-d]pyrimidin-7-yl)benzenesulfonamide; N-tert-butyl-3-(2-(3-(hydroxymethyl)phenylamino)thieno[3,2-d]pyrimidin-7-yl)benzenesulfonamide; N-(4-morpholinophenyl)-7-(4-nitrophenylthio)-5H-pyrrolo[3,2-d]pyrimidin-2-amine; N-tert-butyl-3-(2-(3,4,5-trimethoxyphenylamino)thieno[3,2-d]pyrimidin-7-yl)benzenesulfonamide; 7-(4-amino-3-nitrophenyl)-N-(3,4-dimethoxyphenyl)thieno[3,2-d]pyrimidin-2-amine; N-(3,4-dimethoxyphenyl)-7-(2-methoxypyridin-3-yl)thieno[3,2-d]pyrimidin-2-amine; N-tert-butyl-3-(2-(3,4-dimethoxyphenylamino)thieno[3,2-d]pyrimidin-7-yl)benzenesulfonamide; 7-(2-aminopyrimidin-5-yl)-N-(3,4-dimethoxyphenyl)thieno[3,2-d]pyrimidin-2-amine; N-(3,4-dimethoxyphenyl)-7-(2,6-dimethoxypyridin-3-yl)thieno[3,2-d]pyrimidin-2-amine; N-(3,4-dimethoxyphenyl)-7-(2,4-dimethoxypyrimidin-5-yl)thieno[3,2-d]pyrimidin-2-amine; 7-iodo-N-(4-(morpholinomethyl)phenyl)thieno[3,2-d]pyrimidin-2-amine; N-tert-butyl-3-(2-(4-(morpholinomethyl)phenylamino)thieno[3,2-d]pyrimidin-7-yl)benzenesulfonamide; 2-cyano-N-(4-methyl-3-(2-(4-morpholinophenylamino)thieno[3,2-d]pyrimidin-7-yl)phenyl)acetamide; ethyl 3-(2-(4-morpholinophenylamino)thieno[3,2-d]pyrimidin-7-yl)benzoate; 7-bromo-N-(4-(2-(pyrrolidin-1-yl)ethoxy)phenyl)thieno[3,2-d]pyrimidin-2-amine; N-(3-(2-(4-(2-(pyrrolidin-1-yl)ethoxy)phenylamino)thieno[3,2-d]pyrimidin-7-yl)phenyl)acetamide; N-(cyanomethyl)-3-(2-(4-morpholinophenylamino)thieno[3,2-d]pyrimidin-7-yl)benzamide; N-tert-butyl-3-(2-(4-morpholinophenylamino)thieno[3,2-d]pyrimidin-7-yl)benzamide; N-tert-butyl-3-(2-(4-(1-ethylpiperidin-4-yloxy)phenylamino)thieno[3,2-d]pyrimidin-7-yl)benzenesulfonamide; tert-butyl 4-(2-(4-(morpholinomethyl)phenylamino)thieno[3,2-d]pyrimidin-7-yl)-1H-pyrazole-1-carboxylate; 7-bromo-N-(4-((4-ethylpiperazin-1-yl)methyl)phenyl)thieno[3,2-d]pyrimidin-2-amine; N-tert-butyl-3-(2-(4-((4-ethylpiperazin-1-yl)methyl)phenylamino)thieno[3,2-d]pyrimidin-7-yl)benzenesulfonamide; N-(4-((4-ethylpiperazin-1-yl)methyl)phenyl)-7-(1H-pyrazol-4-yl)thieno[3,2-d]pyrimidin-2-amine; N-(cyanomethyl)-3-(2-(4-(morpholinomethyl)phenylamino)thieno[3,2-d]pyrimidin-7-yl)benzamide; N-tert-butyl-3-(2-(4-(2-(pyrrolidin-1-yl)ethoxy)phenylamino)thieno[3,2-d]pyrimidin-7-yl)benzenesulfonamide; tert-butyl pyrrolidin-1-yl)ethoxy)phenylamino)thieno[3,2-d]pyrimidin-7-yl)benzylcarbamate; 3-(2-(4-(2-(pyrrolidin-1-yl)ethoxy)phenylamino)thieno[3,2-d]pyrimidin-7-yl)benzenesulfonamide; 7-(3-chloro-4-fluorophenyl)-N-(4-(2-(pyrrolidin-1-yl)ethoxy)phenyl)thieno[3,2-d]pyrimidin-2-amine; tert-butyl 4-(2-(4-(1-ethylpiperidin-4-yloxy)phenylamino)thieno[3,2-d]pyrimidin-7-yl)-1H-pyrazole-1-carboxylate; 7-(benzo[d][1,3]dioxol-5-yl)-N-(4-(morpholinomethyl)phenyl)thieno[3,2-d]pyrimidin-2-amine; tert-butyl 5-(2-(4-(morpholinomethyl)phenylamino)thieno[3,2-d]pyrimidin-7-yl)-1H-indole-1-carboxylate; 7-(2-aminopyrimidin-5-yl)-N-(4-(morpholinomethyl)phenyl)thieno[3,2-d]pyrimidin-2-amine; tert-butyl 4-(2-(4-(morpholinomethyl)phenylamino)thieno[3,2-d]pyrimidin-7-yl)-5,6-di-hydropyridine-1(2H)-carboxylate; tert-butyl morpholinomethyl)phenylamino)thieno[3,2-d]pyrimidin-7-yl)benzylcarbamate; N-(3-(2-(4-(morpholinomethyl)phenylamino)thieno[3,2-d]pyrimidin-7-yl)phenyl)acetamide; N-(4-(2-(4-(morpholinomethyl)phenylamino)thieno[3,2-d]pyrimidin-7-yl)phenyl)acetamide; N-(3-(2-(4-(morpholinomethyl)phenylamino)thieno[3,2-d]pyrimidin-7-yl)phenyl)methanesulfonamide; 7-(4-(4-methylpiperazin-1-yl)phenyl)-N-(4-(morpholinomethyl)phenyl)thieno[3,2-d]pyrimidin-2-amine; N-(2-methoxy-4-(2-(4-(morpholinomethyl)phenylamino)thieno[3,2-d]pyrimidin-7-yl)phenyl)acetamide; 7-bromo-N-(3,4,5-trimethoxyphenyl)thieno[3,2-d]pyrimidin-2-amine; (3-(2-(3,4,5-trimethoxyphenylamino)thieno[3,2-d]pyrimidin-7-yl)phenyl)methanol; (4-(2-(3,4,5-trimethoxyphenylamino)thieno[3,2-d]pyrimidin-7-yl)phenyl)methanol; (3-(2-(4-morpholinophenylamino)thieno[3,2-d]pyrimidin-7-yl)phenyl)methanol; (4-(2-(4-morpholinophenylamino)thieno[3,2-d]pyrimidin-7-yl)phenyl)methanol; N-(pyrrolidin-1-yl)ethoxy)phenylamino)thieno[3,2-d]pyrimidin-7-yl)benzyl)methanesulfonamide; tert-butyl-morpholinomethyl)phenylamino)thieno[3,2-d]pyrimidin-7-yl)benzylcarbamate; N-(4-(morpholinomethyl)phenyl)-7-(3-(piperazin-1-yl)phenyl)thieno[3,2-d]pyrimidin-2-amine; 7-(6-(2-morpholinoethylamino)pyridin-3-yl)-N-(3,4,5-trimethoxyphenyl)thieno[3,2-d]pyrimidin-2-amine; 7-(2-ethylphenyl)-N-(4-(2-(pyrrolidin-1-yl)ethoxy)phenyl)thieno[3,2-d]pyrimidin-2-amine; 7-(4-(aminomethyl)phenyl)-N-(4-(morpholinomethyl)phenyl)thieno[3,2-d]pyrimidin-2-amine; N-(4-(1-ethylpiperidin-4-yloxy)phenyl)-7-(1H-pyrazol-4-yl)thieno[3,2-d]pyrimidin-2-amine; N-(2,4-dimethoxyphenyl)-7-phenylthieno[3,2-d]pyrimidin-2-amine; 7-bromo-N-(3,4-dimethoxyphenyl)thieno[3,2-d]pyrimidin-2-amine; and N-(3,4-dimethoxyphenyl)-7-phenylthieno[3,2-d]pyrimidin-2-amine.

United States Patent Application Publication No. 2013/0040949 by Gray et al., incorporated herein by this reference, discloses substituted bicyclic compounds of Formula (N-VII):

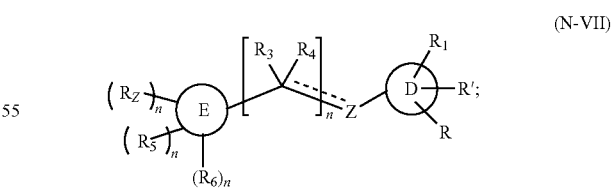

(N-VII)

wherein:
(i) ring D is aryl or heteroaryl;
(ii) R is hydrogen, halo, or -A-B;
(iii) A is $NR_AC(O)$, O, $S(O)_m$, $C(O)$, $C(O)O$, $C(O)NR_A$, $NR_AC(O)NR_A$, or absent;
(iv) B is hydrogen, alkyl, alkoxy, cycloalkyl, or aryl, wherein each of alkyl, alkoxy, cycloalkyl, or aryl is optionally substituted;

(v) $R_1$ is hydroxyl, alkyl, alkoxy, C(O)OR$_A$, C(O)NR$_A$R$_B$, or NR$_A$R$_B$, each of which may be optionally substituted, or hydrogen or halo;

(vi) R' is absent, or R and R', together with the atoms to which they are attached, form a cycloalkyl, heterocycloalkyl, aryl, or heteroaryl ring, each of which is optionally substituted;

(vii) Z is NR$_A$, O, NR$_A$C(O), C(O)NR$_A$, CR$_3$R$_4$, or S(O)$_m$;

(viii) $R_3$ is hydrogen or alkyl;

(ix) $R_4$ is hydrogen, alkyl, or absent, or $R_3$ and $R_4$ together with the carbon to which each is attached form C(O);

(x) ring E is monocyclic or bicyclic heteroaryl;

(xi) $R_z$ is NR$_A$R$_2$;

(xii) $R_2$ is hydrogen, optionally substituted aryl, optionally substituted heteroaryl, optionally substituted heterocycloalkyl, C(O)R$_A$, C(O)OR$_A$, C(O)NR$_A$R$_B$, C(NR$_B$)R$_A$, or C(NR$_B$)OR$_A$;

(xiii) $R_5$ is hydrogen, halo, alkyl, alkoxy, or thioalkoxy;

(xiv) $R_6$ is hydrogen, NR$_A$R$_B$, or OR$_A$;

(xv) each $R_A$ is independently hydrogen, alkyl, alkenyl, cycloalkyl, heterocyclyl, aryl, or heteroaryl, each of which is optionally substituted;

(xvi) each $R_B$ is independently hydrogen, alkyl, alkenyl, cycloalkyl, heterocyclyl, aryl, or heteroaryl, each of which is optionally substituted;

(xvii) or, for each occurrence of NR$_A$R$_B$, $R_A$ and $R_B$ are taken together with the nitrogen atom to which they are attached to form a 3- to 7-membered heterocycloalkyl ring;

(xviii) each m is independently 0, 1, or 2; and (xix) each n is independently 0 or 1.

United States Patent Application Publication No. 2013/0023514 by Markwalder et al., incorporated herein by this reference, discloses substituted pyrrolotriazines, including compounds of Formula (N-VIII):

(N-VIII)

wherein:

(i) $R_1$ is selected from hydrogen, NR$_a$R$_a$, $C_1$-$C_6$ alkyl substituted with 0-5 $R_{1a}$, $C_2$-$C_6$ alkenyl substituted with 0-5 $R_{1a}$, $C_2$-$C_6$ alkynyl substituted with 0-5 $R_{1a}$, —(CHR)$_r$-carbocyclyl substituted with 0-5 $R_{1a}$, or —(CHR)$_r$-heterocyclyl substituted with 0-5 $R_{1a}$;

(ii) $R_{1a}$, at each occurrence, is independently selected from $C_1$-$C_6$ alkyl substituted with 0-5 $R_e$, $C_2$-$C_6$ alkenyl substituted with 0-5 $R_e$, $C_2$-$C_6$ alkynyl substituted with 0-5 $R_e$, $C_1$-$C_6$ haloalkyl, F, Cl, Br, NO$_2$, CN, =O, —(CHR)$_r$OH, —(CHR)$_r$SH, (CHR)$_r$OR$_b$, —(CHR)$_r$S(O)$_p$R$_b$, —(CHR)$_r$C(O)R$_d$, —(CHR)$_r$NR$_a$R$_a$, —(CHR)$_r$C(O)NR$_a$R$_a$, —(CHR)$_r$C(O)NR$_a$NR$_a$R$_a$, —(CHR)$_r$NR$_a$C(O)R$_d$, —(CHR)$_r$NR$_a$C(O)OR$_b$, —(CHR)$_r$NR$_a$C(O)(CRR)$_r$OC(O)NR$_a$R$_a$, —(CHR)$_r$NR$_a$C(O)(CRR)$_r$NR$_a$R$_a$, —(CHR)$_r$NR$_a$C(O)(CRR)$_r$NR$_a$C(O)OR$_d$, —(CHR)$_r$OC(O)NR$_a$R$_a$, —(CHR)$_r$C(O)OR$_d$, —(CHR)$_r$S(O)$_p$NR$_a$R$_a$, —(CHR)$_r$NR$_a$S(O)$_p$R$_b$, —(CHR)$_r$-carbocyclyl substituted with 0-5 $R_e$ and —(CHR)$_r$-heterocyclyl substituted with 0-5 $R_e$;

(iii) $R_2$ is selected from hydrogen and $C_1$-$C_6$ alkyl substituted with 0-3 $R_{ea}$;

(iv) $R_{ea}$ is selected from F, Cl, and Br;

(v) alternatively, $R_1$ and $R_2$ are taken together with the nitrogen atom to which they are attached to form a heterocyclyl substituted with 0-5 $R_{1a}$;

(vi) $R_3$ is selected from aryl substituted with 0-5 $R_{3a}$ and heteroaryl substituted with 0-5 $R_{1a}$;

(vi) $R_{3a}$, at each occurrence, is independently selected from $C_1$-$C_6$ alkyl, $C_2$-$C_6$ alkenyl, $C_2$-$C_6$ alkynyl, $C_1$-$C_6$ haloalkyl, F, Cl, Br, NO$_2$, CN, hydroxyl, sulfhydryl, —OR$_b$, —S(O)$_p$R$_b$, C(O)R$_d$, NR$_a$R$_a$, —C(O)NR$_a$R$_a$, —NR$_a$C(O)R$_d$, —NR$_a$C(O)OR$_b$, —OC(O)NR$_a$R$_a$, —C(O)OR$_d$, —S(O)$_p$NR$_a$R$_a$, or —NR$_a$S(O)$_p$Rb;

(vii) $R_4$ is selected from hydrogen, $C_1$-$C_6$ alkyl, and $C_3$-$C_6$ cycloalkyl;

(viii) $R_a$, at each occurrence, is independently selected from hydrogen, amino, $C_1$-$C_6$ alkyl substituted with 0-3 $R_e$, $C_2$-$C_6$ alkenyl substituted with 0-3 $R_e$, $C_2$-$C_6$ alkynyl substituted with 0-3 $R_e$, $C_1$-$C_6$ haloalkyl, —(CH$_2$)$_r$OH, —(CH$_2$)$_r$-carbocyclyl substituted with 0-3 $R_e$, and —(CH$_2$)$_r$-heterocyclyl substituted with 0-3 $R_e$, or $R_a$ and $R_a$ together with the nitrogen atom to which they are attached form a heterocyclyl substituted with 0-3 $R_e$;

(ix) $R_b$, at each occurrence, is independently selected from $C_1$-$C_6$ alkyl substituted with 0-3 $R_e$, $C_1$-$C_6$ haloalkyl, $C_2$-$C_6$ alkenyl substituted with 0-3 $R_e$, $C_2$-$C_6$ alkynyl substituted with 0-3 $R_e$, —(CH$_2$)$_r$-carbocyclyl substituted with 0-3 $R_e$, and —(CH$_2$)$_r$-heterocyclyl substituted with 0-3 $R_e$;

(x) $R_d$, at each occurrence, is independently selected from hydrogen, $C_1$-$C_6$ alkyl substituted with 0-3 $R_e$, $C_1$-$C_6$ haloalkyl, $C_2$-$C_6$ alkenyl substituted with 0-3 $R_e$, $C_2$-$C_6$ alkynyl substituted with 0-3 $R_e$, —(CH$_2$)$_r$-carbocyclyl substituted with 0-3 $R_e$, and —(CH$_2$)$_r$-heterocyclyl substituted with 0-3 $R_e$;

(xi) $R_e$, at each occurrence, is independently selected from $C_1$-$C_6$ alkyl, $C_2$-$C_6$ alkenyl, $C_2$-$C_6$ alkynyl, —(CH$_2$)$_r$C$_3$-$C_6$ cycloalkyl, F, Cl, Br, CN, NO$_2$, CO$_2$H, =O, —C(O)NR$_f$R$_f$, (CF2)$_r$CF3, —(CH2)$_r$OC$_1$—$C_5$ alkyl, —(CH2)$_r$OH, SH, —(CH2)$_r$SC$_1$—$C_5$ alkyl, —(CH2)$_r$NR$_f$R$_f$, —(CH2)$_r$-phenyl, and (CH2)$_r$-heterocyclyl;

(xii) $R_f$, at each occurrence, is independently selected from hydrogen, $C_1$-$C_5$ alkyl, $C_3$-$C_6$ cycloalkyl, and phenyl;

(xiii) R, at each occurrence, is independently selected from hydrogen, —(CH2)$_r$OH, $C_1$-$C_6$ alkyl, $C_1$-$C_6$ haloalkyl, and —(CH2)$_r$-aryl;

(xiv) p, at each occurrence, is independently selected from 0, 1, and 2;

and (xv) r, at each occurrence, is independently selected from 0, 1, 2, 3, and 4.

United States Patent Application Publication No. 2012/0283241 by Fink et al., incorporated herein by this reference, discloses imidazopyridazinecarbonitriles, including compounds of Formula (N-IX):

(N-IX)

wherein:

(i) $R_1$ is selected from hydrogen, Cl, Br, F, CN, and $C_1$-$C_6$ alkyl;

(ii) $R_2$ is selected from aryl substituted with 0-5 $R_{2a}$ and heteroaryl substituted with 0-5 $R_{2a}$;

(iii) $R_{2a}$, at each occurrence, is independently selected from hydrogen, F, Cl, Br, =O, CN, NO$_2$, —OR$_b$, —S(O)$_p$R$_c$, —C(=O)R$_d$, —NR$_a$R$_a$, —(CR2$_b$R2$_c$)$_r$C(=O)NR$_a$R$_a$, —NR$_a$C(=O)R$_d$, —NR$_a$C(=O)OR$_b$, —OC(=O)NR$_a$R$_a$, —NR$_a$C(=O)NR$_a$R$_a$, —(CR2$_b$R2$_c$)rC(=O)OR$_b$, —S(O)2NR$_a$R$_a$, —NR$_a$S(O)2NR$_a$R$_a$, —NR$_a$S(O)2R$_c$, $C_1$-$C_6$ alkyl substituted with 0-5 R$_e$, —(CR2$_b$R2$_c$)$_r$—$C_3$-$C_6$ carbocyclyl substituted with 0-5 R$_e$, and —(CR2$_b$R2$_c$)$_r$-heterocyclyl substituted with 0-5 R$_e$;

(iv) R2$_b$, at each occurrence, is independently selected from hydrogen and $C_1$-$C_6$ alkyl substituted with 0-5 R$_e$;

(v) R2$_c$, at each occurrence, is independently selected from hydrogen and $C_1$-$C_6$ alkyl substituted with 0-5 R$_e$;

(vi) $R_3$ is selected from H, F, Cl, Br, CN, —OR$_b$, —NR$_a$R$_a$, —C(=O)NR$_a$R$_a$, —NR$_a$S(O)2R$_c$, —NR$_a$C(=O)R$_d$, —NR$_a$C(=O)OR$_b$, and $C_1$-$C_6$ alkyl substituted with 0-5 R$_e$;

(vii) $R_4$ is selected from H, $C_1$-$C_6$ alkyl substituted with 0-5 R$_e$, —(CR4$_b$R$^4_c$)$_r$OR$_b$, —(CR4$_b$R$^4_c$)$_r$S(O)$_p$R$_c$, —(CR4$_b$R$^4_c$)$_r$C(=O)R$_d$, —(CR4$_b$R$^4_c$)$_r$NR$_a$R$_a$, —(CR4$_b$R$^4_c$)$_r$C(=O)NR$_a$R$_a$, —(CR4$_b$R$^4_c$)$_r$NR$_a$C(=O)R$_d$, —(CR4$_b$R$^4_c$)$_r$NR$_a$C(=O)OR$_b$, —(CR4$_b$R$^4_c$)$_r$OC(=O)NR$_a$R$_a$, —(CR4$_b$R$^4_c$)$_r$NR$_a$C(=O)NR$_a$R$_a$, —(CR4$_b$R$^4_c$)$_r$C(=O)OR$_b$, —(CR4$_b$R$^4_c$)$_r$S(O)2NR$_a$R$_a$, —(CR4$_b$R$^4_c$)$_r$NR$_a$S(O)2NR$_a$R$_a$, —(CR4$_b$R$^4_c$)$_r$NR$_a$S(O)2R$_c$, —(CR4$_b$R$^4_c$)$_r$—$C_3$-$C_6$ carbocyclyl substituted with 0-5 R$^4_a$, —(CR4$_b$R$^4_c$)$_r$-heterocyclyl substituted with 0-5 R$^4_a$;

(viii) R$^4_a$, at each occurrence, is independently selected from F, Cl, Br, $C_1$-$C_6$ alkyl substituted with 0-5 R$_e$, $C_2$-$C_6$ alkenyl, $C_2$-$C_6$ alkynyl, NO$_2$, =O, CN, —SO$_3$H, —S(O)$_p$R$_c$, —S(O)$_2$NR$_a$R$_a$, —NR$_a$S(O)$_2$R$_c$, —OR$_b$, —NR$_a$R$_a$, —NR$_a$C(=O)R$_d$, —NR$_a$C(=O)NR$_a$R$_a$, —C(=O)OR$_b$, —C(=O)R$_d$, —OC(=O)R$_d$, —C(=O)NR$_a$R$_a$, $C_3$-$C_6$ cycloalkyl, heterocyclyl, and aryl;

(ix) R$^4_b$, at each occurrence, is independently selected from hydrogen and $C_1$-$C_6$ alkyl substituted with 0-5 R$_e$;

(x) R$^4_c$, at each occurrence, is independently selected from hydrogen and $C_1$-$C_6$ alkyl substituted with 0-5 R$_e$;

(xi) $R_5$ is selected from hydrogen and $C_1$-$C_6$ alkyl substituted with 0-5 R$_e$;

(xii) $R_6$ is selected from hydrogen and $C_1$-$C_6$ alkyl substituted with 0-5 R$_e$;

(xiii) R$_a$, at each occurrence, is independently selected from hydrogen, CN, $C_1$-$C_6$ alkyl substituted with 0-5 R$_e$, $C_2$-$C_6$ alkenyl substituted with 0-5 R$_e$, $C_2$-$C_6$ alkynyl substituted with 0-5 R$_e$, —(CH2)$_r$-$C_3$-$C_{10}$ carbocyclyl substituted with 0-5 R$_e$, and —(CH2)$_r$-heterocyclyl substituted with 0-5 R$_e$; or R$_a$ and R$_a$ together with the nitrogen atom to which they are both attached form a heterocyclic ring substituted with 0-5 R$_e$;

(xiv) R$_b$, at each occurrence, is independently selected from hydrogen, $C_1$-$C_6$ alkyl substituted with 0-5 R$_e$, $C_2$-$C_6$ alkenyl substituted with 0-5 R$_e$, $C_2$-$C_6$ alkynyl substituted with 0-5 R$_e$, —(CH2)$_r$—$C_3$-$C_{10}$ carbocyclyl substituted with 0-5 R$_e$, and —(CH2)$_r$-heterocyclyl substituted with 0-5 R$_e$;

(xv) R, at each occurrence, is independently selected from $C_1$-$C_6$ alkyl substituted with 0-5 R$_e$, $C_2$-$C_6$ alkenyl substituted with 0-5 R$_e$, $C_2$-$C_6$ alkynyl substituted with 0-5 R$_e$, $C_3$-$C_6$ carbocyclyl, and heterocyclyl;

(xvi) R$_d$, at each occurrence, is independently selected from hydrogen, $C_1$-$C_6$ alkyl substituted with 0-5 R$_e$, $C_2$-$C_6$ alkenyl substituted with 0-5 R$_e$, $C_2$-$C_6$ alkynyl substituted with 0-5 R$_e$, —(CH2)$_r$—$C_3$-$C_{10}$ carbocyclyl substituted with 0-5 R$_e$, and —(CH2)$_r$-heterocyclyl substituted with 0-5 R$_e$;

(xvii) R$_e$, at each occurrence, is independently selected from $C_1$-$C_6$ alkyl substituted with 0-5 R$_f$, $C_2$-$C_6$ alkenyl, $C_2$-$C_6$ alkynyl, —(CH2)$_r$—$C_3$-$C_6$ cycloalkyl, F, Cl, Br, CN, NO$_2$, =O, CO$_2$H, —(CH2)$_r$OC$_1$-$C_5$ alkyl, —(CH2)$_r$OH, SH, and —(CH2)$_r$NR$_f$R$_f$;

(xviii) R$_f$, at each occurrence, is independently selected from H, $C_1$-$C_5$ alkyl, $C_3$-$C_6$ cycloalkyl, and phenyl, or R$_f$ and R$_f$ together with the nitrogen atom to which they are both attached form a heterocyclic ring;

(xix) p, at each occurrence, is independently selected from 0, 1, and 2; and (xx) r, at each occurrence, is independently selected from 0, 1, 2, 3, and 4. The compounds include: 6-((3-cyano-4-methylphenyl)amino)-8-(2-pyridinylamino)imidazo[1,2-b]pyridazine-3-carbonitrile; N-(5-((3-cyano-8-(cyclopropylamino)imidazo[1,2-b]pyridazin-6-yl)amino)-2-(trifluoromethoxy)phenyl)acetamide; 3-cyano-5-((3-cyano-8-(cyclopropylamino)imidazo[1,2-b]pyridazin-6-yl)amino)benzenesulfonamide; N-(3-cyano-5-((3-cyano-8-(cyclopropylamino)imidazo[1,2-b]pyridazin-6-yl)amino)phenyl)acetamide; 6-((5-cyano-2-methoxyphenyl)amino)-8-(cyclopropylamino)imidazo[1,2-b]pyridazine-3-carbonitrile; methyl (5-((3-cyano-8-(cyclopropylamino)imidazo[1,2-b]pyridazin-6-yl)amino)-2-methylphenyl)carbamate; 3-((6-((3-acetamido-4-methylphenyl)amino)-3-cyanoimidazo[1,2-b]pyridazin-8-yl)amino)-N-(2-(dimethylamino)ethyl)benzamide; 8-(cyclobutylamino)-6-((3-methoxy-5-(4H-1,2,4-triazol-4-yl)phenyl)amino)imidazo[1,2-b]pyridazine-3-carbonitrile; 6-((1-acetyl-2,3-dihydro-1H-indol-6-yl)amino)-8-(cyclopropylamino)imidazo[1,2-b]pyridazine-3-carbonitrile; 6-((3-cyano-5-((4-methyl-1-piperazinyl)sulfonyl)phenyl)amino)-8-(cyclopropylamino)imidazo[1,2-b]pyridazine-3-carbonitrile; 6-((2-chloro-5-cyano-4-methylphenyl)amino)-8-(2-pyridinylamino)imidazo[1,2-b]pyridazine-3-carbonitrile; 8-(cyclopropylamino)-6-((1,4-dimethyl-2-oxo-1,2-dihydro-7-quinolinyl)amino)imidazo[1,2-b]pyridazine-3-carbonitrile; 3-cyano-5-((3-cyano-8-(cyclopropylamino)imidazo[1,2-b]pyridazin-6-yl)amino)-N-ethylbenzenesulfonamide; 8-(cyclopropylamino)-6-((3-(4-(2-hydroxyethyl)-1-piperazinyl)-5-(4H-1,2,4-triazol-4-yl)phenyl)amino)imidazo[1,2-b]pyridazine-3-carbonitrile; 8-((5-methoxy-2-pyridinyl)amino)-6-((3-methoxy-5-(4H-1,2,4-triazol-4-yl)phenyl)amino)imidazo[1,2-b]pyridazine-3-carbonitrile; 6-((2-chloro-5-cyanophenyl)amino)-8-(cyclopropylamino)imidazo[1,2-b]pyridazine-3-carbonitrile; methyl (3-((3-cyano-8-(cyclopropylamino)imidazo[1,2-b]pyridazin-6-yl)amino)-5-(methylsulfonyl)phenyl)carbamate; 6-((5-cyano-2-methoxyphenyl)amino)-8-(cyclobutylamino)imidazo[1,2-b]pyridazine-3-carbonitrile; 6-((5-cyano-2-methylphenyl)amino)-8-(cyclopropylamino)imidazo[1,2-b]pyridazine-3-carbonitrile; 8-(cyclopropylamino)-6-((3-(2-(dimethylamino)ethoxy)-5-(4H-1,2,4-triazol-4-yl)phenyl)amino)imidazo[1,2-b]pyridazine-3-carbonitrile; 6-((2-chloro-5-cyano-4-methylphenyl)amino)-8-(cyclopropylamino)imidazo[1,2-b]pyridazine-3-carbonitrile; 8-amino-6-((5-cyano-2-methoxyphenyl)amino)imidazo[1,2-b]pyridazine-3-carbonitrile; 8-amino-6-((3-cyano-4-methylphenyl)amino)imidazo[1,2-b]pyridazine-3-carbonitrile; N-(5-((3-cyano-8-(cyclopropylamino)imidazo[1,2-b]pyridazin-6-yl)amino)-2-methylphenyl)acetamide; 6-((2-chloro-5-cyanophenyl)amino)-8-(cyclobutylamino)imidazo[1,2-b]pyridazine-3-carbonitrile; N-(54(3-cyano-8-(cyclopropylamino)imidazo[1,2-b]pyridazin-6-yl)amino)-2,4-difluorophenyl)

acetamide; 6-((4-fluoro-3-(4H-1,2,4-triazol-4-yl)phenyl)amino)-8-((5-methoxy-2-pyridinyl)amino)imidazo[1,2-b]pyridazine-3-carbonitrile; N-(5-((3-cyano-8-((5-(2-hydroxyethoxy)-2-pyridinyl)amino)imidazo[1,2-b]pyridazin-6-yl)amino)-2-methylphenyl)acetamide; N-(5-((3-cyano-8-((5-methoxy-2-pyridinyl)amino)imidazo[1,2-b]pyridazin-6-yl)amino)-2-methylphenyl)acetamide; 8-(cyclopropylamino)-6-((4-(2-(methylamino)ethoxy)-3-(4H-1,2,4-triazol-4-yl)phenyl)amino)imidazo[1,2-b]pyridazine-3-carbonitrile; N-(5-((3-cyano-8-(cyclopropylamino)imidazo[1,2-b]pyridazin-6-yl)amino)-2-methoxyphenyl)acetamide; 6-((5-cyano-2-(2-(4-morpholinyl)ethoxy)phenyl)amino)-8-(cyclopropylamino)imidazo[1,2-b]pyridazine-3-carbonitrile; 8-((2-methoxyethyl)amino)-6-((3-methoxy-5-(4H-1,2,4-triazol-4-yl)phenyl)amino)imidazo[1,2-b]pyridazine-3-carbonitrile; 6-((3-cyano-4-(4-morpholinyl)phenyl)amino)-8-(cyclopropylamino)imidazo[1,2-b]pyridazine-3-carbonitrile; methyl (54(8-amino-3-cyanoimidazo[1,2-b]pyridazin-6-yl)amino)-2-methylphenyl)carbamate; 8-(cyclopropylamino)-6-((3-methoxy-5-(4H-1,2,4-triazol-4-yl)phenyl)amino)imidazo[1,2-b]pyridazine-3-carbonitrile; methyl (5-((3-cyano-8-(cyclopropylamino)imidazo[1,2-b]pyridazin-6-yl)amino)-2,4-difluorophenyl)carbamate; methyl (5-((3-cyano-8-(cyclopropylamino)imidazo[1,2-b]pyridazin-6-yl)amino)-2-fluorophenyl)carbamate; 6-((5-cyano-2-(trifluoromethoxy)phenyl)amino)-8-(cyclopropylamino)imidazo[1,2-b]pyridazine-3-carbonitrile; N-(3-cyano-5-((3-cyano-8-(cyclopropylamino)imidazo[1,2-b]pyridazin-6-yl)amino)phenyl)methanesulfonamide; N-(2-chloro-5-((3-cyano-8-(cyclopropylamino)imidazo[1,2-b]pyridazin-6-yl)amino)phenyl)acetamide; 8-(cyclopropylamino)-6-((4-fluoro-3-(4H-1,2,4-triazol-4-yl)phenyl)amino)imidazo[1,2-b]pyridazine-3-carbonitrile; 8-(cyclopropylamino)-6-((4-(4-morpholinyl)-3-(4H-1,2,4-triazol-4-yl)phenyl)amino)imidazo[1,2-b]pyridazine-3-carbonitrile; 8-(cyclopropylamino)-6-((3-methyl-5-(1H-1,2,4-triazol-1-yl)phenyl)amino)imidazo[1,2-b]pyridazine-3-carbonitrile; 8-(cyclopropylamino)-6-((4-(3-(dimethylamino)propoxy)-3-(4H-1,2,4-triazol-4-yl)phenyl)amino)imidazo[1,2-b]pyridazine-3-carbonitrile; 6-((4-cyano-2-pyridinyl)amino)-8-(cyclopropylamino)imidazo[1,2-b]pyridazine-3-carbonitrile; 3-cyano-5-((3-cyano-8-(cyclopropylamino)imidazo[1,2-b]pyridazin-6-yl)amino)-N-(tetrahydro-2H-pyran-4-yl)benzenesulfonamide; 8-(cyclopropylamino)-6-((2-fluoro-5-(1H-1,2,4-triazol-1-yl)phenyl)amino)imidazo[1,2-b]pyridazine-3-carbonitrile; and N-(3-((3-cyano-8-(cyclopropylamino)imidazo[1,2-b]pyridazin-6-yl)amino)-4-methylphenyl)acetamide.

United States Patent Application Publication No. 2012/0040961 by Gray et al., incorporated herein by this reference, discloses pyrimido-diazepinone compounds, including compounds of Formula (N-X):

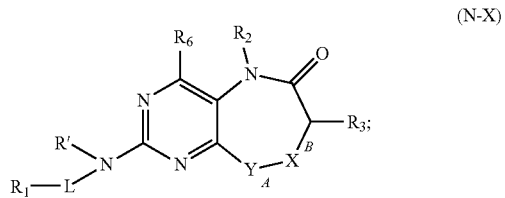

(N-X)

wherein:
(i) X is CHR$_4$, CR$_4$, NH, NR$_4$, or N;
(ii) Y is NR$_5$, N, S, SO, SO$_2$, O, CHR$_5$, or CR$_5$; wherein at least one of X and Y is NH, NR$_4$, NR$_5$, N, S, SO, SO2, or O;
(iii) A is a single bond or double bond;
(iv) B is a single bond or double bond, wherein both A and B are not double bonds;
(v) R' is H or alkyl;
(vi) L is absent, S, SO, SO$_2$, or CO;
(vii) R$_1$ is H, alkyl, alkenyl, alkynyl, each containing 0, 1, 2, or 3 heteroatoms selected from O, S, or N; or R$_1$ is aryl, arylalkyl, heteroaryl, heterocyclyl, or carbocyclyl; wherein R$_1$ may be optionally substituted;
(viii) R$_2$ is hydrogen or optionally substituted alkyl;
(ix) R$_3$ is hydrogen, alkyl, alkenyl, aryl, arylalkyl, heteroaryl, heterocyclyl, or carbocyclyl, each of which may be optionally substituted;
(x) R$_4$ is hydrogen, alkyl, alkenyl, aryl, arylalkyl, heteroaryl, heterocyclyl, or carbocyclyl, each of which may be optionally substituted;
(xi) R$_5$ is hydrogen, alkyl, alkenyl, aryl, arylalkyl, heteroaryl, heterocyclyl, or carbocyclyl, each of which may be optionally substituted;
(xii) or R$_3$ and X, together with the atoms to which they are attached, form a 3-8 membered carbocyclic, aryl, heterocyclic, or heteroaryl; each of which is optionally substituted;
(xiii) or X and Y, together with the atoms to which they are attached, form a 3-8 membered carbocyclyl, aryl, heterocyclyl, or heteroaryl; each of which is optionally substituted; and
(xiv) R$_6$ is hydrogen or optionally substituted alkyl. The compounds include: 9-cyclopentyl-2-(5-(4-hydroxypiperidin-1-yl)pyridin-2-ylamino)-5-methyl-8,9-dihydro-5H-pyrimido[4,5-b][1,4]diazepin-6(7H)-one; 4-(9-cyclopentyl-6-oxo-6,7,8,9-tetrahydro-5H-pyrimido[4,5-b][1,4]diazepin-2-ylamino)-3-methoxy-N-(1-methylpiperidin-4-yl)benzamide, 4-(9-cyclopentyl-5-methyl-6-oxo-6,7,8,9-tetrahydro-5H-pyrimido[4,5-b][1,4]diazepin-2-ylamino)-3-methoxy-N-(1-methylpiperidin-4-yl)benzamide; 4-(9-cyclopentyl-5,8-dimethyl-6-oxo-6,7,8,9-tetrahydro-5H-pyrimido[4,5-b][1,4]diazepin-2-ylamino)-3-methoxy-N-(1-methylpiperidin-4-yl)benzamide; 4-(9-cyclopentyl-5,7-dimethyl-6-oxo-6,7,8,9-tetrahydro-5H-pyrimido[4,5-b][1,4]diazepin-2-ylamino)-3-methoxy-N-(1-methylpiperidin-4-yl)benzamide; 9-cyclopentyl-2-(4-(4-hydroxypiperidin-1-yl)-2-methoxyphenylamino)-5-methyl-8,9-dihydro-5H-pyrimido[4,5-b][1,4]diazepin-6(7H)-one; 9-cyclopentyl-2-(4-((2-hydroxyethyl)(methyl)amino)-2-methoxyphenylamino)-5-methyl-8,9-dihydro-5H-pyrimido[4,5-b][1,4]diazepin-6(7H)-one; 9-cyclopentyl-2-(4-((3-hydroxypropyl)(methyl)amino)-2-methoxyphenylamino)-5-methyl-8,9-dihydro-5H-pyrimido[4,5-b][1,4]diazepin-6(7H)-one; 9-cyclopentyl-2-(4-(4-hydroxy-4-methylpiperidin-1-yl)-2-methoxyphenylamino)-5-methyl-8,9-dihydro-5H-pyrimido[4,5-b][1,4]diazepin-6(7H)-one; 9-cyclopentyl-2-(2-ethoxy-4-(4-hydroxypiperidin-1-yl)phenylamino)-5-methyl-8,9-dihydro-5H-pyrimido[4,5-b][1,4]diazepin-6(7H)-one; 9-cyclopentyl-2-(4-(4-hydroxypiperidin-1-yl)-2-isopropoxyphenylamino)-5-methyl-8,9-dihydro-5H-pyrimido[4,5-b][1,4]diazepin-6(7H)-one; 9-cyclopentyl-2-(4-(4-(2-hydroxyethyl)piperazin-1-yl)-2-methoxyphenylamino)-5-methyl-8,9-dihydro-5H-pyrimido[4,5-b][1,4]diazepin-6(7H)-one; 9-cyclopentyl-2-(2-ethoxy-4-(4-hydroxypiperidin-1-yl)phenylamino)-5-ethyl-8,9-dihydro-5H-pyrimido[4,5-b][1,4]diazepin-6(7H)-one; 9-cyclopentyl-5-ethyl-2-(4-(4-hydroxypiperidin-1-yl)-2-isopropoxyphenylamino)-8,9-dihydro-5H-pyrimido[4,5-b]

[1,4]diazepin-6(7H)-one; 9-cyclopentyl-5-ethyl-2-(5-(4-hydroxypiperidin-1-yl)pyridin-2-ylamino)-8,9-dihydro-5H-pyrimido[4,5-b][1,4]diazepin-6(7H)-one, 9-cyclopentyl-2-(2-methoxy-4-(4-(4-methylpiperazin-1-yl)piperidin-1-yl)phenylamino)-5,8-dimethyl-8,9-dihydro-5H-pyrimido[4,5-b][1,4]diazepin-6(7H)-one; 9-cyclopentyl-2-(2-methoxy-4-(4-(4-methylpiperazin-1-yl)piperidin-1-yl)phenylamino)-8-methyl-8,9-dihydro-5H-pyrimido[4,5-b][1,4]diazepin-6(7H)-one; 9-cyclopentyl-2-(2-methoxy-4-(4-methylpiperazin-1-yl)phenylamino)-5,8-dimethyl-8,9-dihydro-5H-pyrimido[4,5-b][1,4]diazepin-6(7H)-one; 9-cyclopentyl-2-(2-methoxy-4-(4-methylpiperazin-1-yl)phenylamino)-8-methyl-8,9-dihydro-5H-pyrimido[4,5-b][1,4]diazepin-6(7H)-one; 10-cyclopentyl-5-methyl-2-(quinolin-6-ylamino)-6a,7,8,9,9a,10-hexahydrocyclopenta[e]pyrimido[5,4-b][1,4]diazepin-6(5H)-one; 10-cyclopentyl-5-methyl-2-(quinolin-5-ylamino)-6a,7,8,9,9a,10-hexahydrocyclopenta[e]pyrimido[5,4-b][1,4]diazepin-6(5H)-one; 10-cyclopentyl-2-(2-methoxy-4-(4-methylpiperazine-1-carbonyl)phenylamino)-5-methyl-6a,7,8,9,9a,10-hexahydrocyclopenta[e]pyrimido[5,4-b][1,4]diazepin-6(5H)-one; 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxybenzoic acid; 4-(10-cyclopentyl-5-methyl-6-oxo-5,6,6a,7,8,9,9a,10-octahydrocyclopenta[e]pyrimido[5,4-b][1,4]diazepin-2-ylamino)benzamide; 10-cyclopentyl-2-(4-(4-hydroxypiperidine-1-carbonyl)-2-methoxyphenylamino)-5-methyl-6a,7,8,9,9a,10-hexahydrocyclopenta[e]pyrimido[5,4-b][1,4]diazepin-6(5H)-one; 10-cyclopentyl-2-(2-hydroxyethylamino)-5-methyl-6a,7,8,9,9a,10-hexahydrocyclopenta[e]pyrimido[5,4-b][1,4]diazepin-6(5H)-one; 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxybenzamide; 4-(10-cyclopentyl-5-methyl-6-oxo-5,6,6a,7,8,9,9a,10-octahydrocyclopenta[e]pyrimido[5,4-b][1,4]diazepin-2-ylamino)-N-(4-hydroxycyclohexyl)-3-methoxybenzamide; 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxy-N-(1-methylpiperidin-4-yl)benzamide; 10-cyclopentyl-2-(4-hydroxycyclohexylamino)-5-methyl-6a,7,8,9,9a,10-hexahydrocyclopenta[e]pyrimido[5,4-b][1,4]diazepin-6(5H)-one; 10-cyclopentyl-5-methyl-2-(1-methylpiperidin-4-ylamino)-6a,7,8,9,9a,10-hexahydrocyclopenta[e]pyrimido[5,4-b][1,4]diazepin-6(5H)-one; 4-(10-cyclopentyl-5-methyl-6-oxo-5,6,6a,7,8,9,9a,10-octahydrocyclopenta[e]pyrimido[5,4-b][1,4]diazepin-2-ylamino)-N-(2-hydroxyethyl)-3-methoxybenzamide; 10-cyclopentyl-2-(4-(4-hydroxypiperidin-1-yl)-2-methoxyphenylamino)-5-methyl-6a,7,8,9,9a,10-hexahydrocyclopenta[e]pyrimido[5,4-b][1,4]diazepin-6(5H)-one, 10-cyclopentyl-2-(2-methoxy-4-(4-methylpiperazin-1-yl)phenylamino)-5-methyl-6a,7,8,9,9a,10-hexahydrocyclopenta[e]pyrimido[5,4-b][1,4]diazepin-6(5H)-one; 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxy-N-methylbenzamide; 10-cyclopentyl-2-(2-methoxy-4-(4-(4-methylpiperazin-1-yl)piperidin-1-yl)phenylamino)-5-methyl-6a,7,8,9,9a,10-hexahydrocyclopenta[e]pyrimido[5,4-b][1,4]diazepin-6(5H)-one; 6-(10-cyclopentyl-5-methyl-6-oxo-5,6,6a,7,8,9,9a,10-octahydrocyclopenta[e]pyrimido[5,4-b][1,4]diazepin-2-ylamino)-N-methylnicotinamide, 1-(4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxyphenyl)piperidine-4-carboxamide; 10-cyclopentyl-2-(2-isopropoxy-4-(4-(4-methylpiperazin-1-yl)piperidine-1-carbonyl)phenylamino)-5-methyl-6a,7,8,9,9a,10-hexahydrocyclopenta[e]pyrimido[5,4-b][1,4]diazepin-6(5H)-one; 6-(10-cyclopentyl-5-methyl-6-oxo-5,6,6a,7,8,9,9a,10-octahydrocyclopenta[e]pyrimido[5,4-b][1,4]diazepin-2-ylamino)-N-(1-methylpiperidin-4-yl)nicotinamide; 2-(2-methoxy-4-(4-methylpiperazin-1-yl)phenylamino)-5-methyl-7a,8,9,10-tetrahydro-5H-pyrimido[5,4-b]pyrrolo[1,2-d][1,4]diazepin-6(7H)-one; 2-(2-methoxy-4-(4-(4-methylpiperazin-1-yl)phenylamino)-7a,8,9,10-tetrahydro-5H-pyrimido[5,4-b]pyrrolo[1,2-d][1,4]diazepin-6(7H)-one; 2-(2-methoxy-4-(4-(4-methylpiperazin-1-yl)piperidin-1-yl)phenylamino)-5-methyl-7a,8,9,10-tetrahydro-5H-pyrimido[5,4-b]pyrrolo[1,2-d][1,4]diazepin-6(7H)-one; 2-(5-(4-hydroxypiperidin-1-yl)pyridin-2-ylamino)-5-methyl-7a,8,9,10-tetrahydro-5H-pyrimido[5,4-b]pyrrolo[1,2-d][1,4]diazepin-6(7H)-one, 2-(2-ethoxy-4-(4-hydroxypiperidin-1-yl)phenylamino)-5-methyl-7a,8,9,10-tetrahydro-5H-pyrimido[5,4-b]pyrrolo[1,2-d][1,4]diazepin-6(7H)-one; 2-(4-(4-(diethylamino)piperidin-1-yl)-2-isopropoxyphenylamino)-5-methyl-7a,8,9,10-tetrahydro-5H-pyrimido[5,4-b]pyrrolo[1,2-d][1,4]diazepin-6(7H)-one; 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxy-N-(1-methylpiperidin-4-yl)benzamide; 4-(10-cyclopentyl-5-methyl-6-oxo-5,6,6a,7,8,9,9a,10-octahydrocyclopenta[e]pyrimido[5,4-b][1,4]diazepin-2-ylamino)-3-methoxybenzamide; 2-(4-(4-(dimethylamino)piperidin-1-yl)-2-isopropoxyphenylamino)-5-methyl-7a,8,9,10-tetrahydro-5H-pyrimido[5,4-b]pyrrolo[1,2-d][1,4]diazepin-6(7H)-one, 2-(2-methoxy-4-(4-methylpiperazin-1-yl)phenylamino)-5-methyl-9-phenyl-8,9-dihydro-5H-pyrimido[4,5-b][1,4]diazepin-6(7H)-one, 2-(2-methoxy-4-(4-methylpiperazin-1-yl)phenylamino)-9-phenyl-8,9-dihydro-5H-pyrimido[4,5-b][1,4]diazepin-6(7H)-one; 2-(5-(4-hydroxypiperidin-1-yl)pyridin-2-ylamino)-5-methyl-9-phenyl-8,9-dihydro-5H-pyrimido[4,5-b][1,4]diazepin-6(7H)-one; 2-(4-(4-hydroxypiperidin-1-yl)-2-isopropoxyphenylamino)-5-methyl-9-phenyl-8,9-dihydro-5H-pyrimido[4,5-b][1,4]diazepin-6(7H)-one; 2-(2-ethoxy-4-(4-hydroxypiperidin-1-yl)phenylamino)-5-methyl-9-phenyl-8,9-dihydro-5H-pyrimido[4,5-b][1,4]diazepin-6(7H)-one; 2-(2-methoxy-4-(4-methylpiperazin-1-yl)phenylamino)-5,11-dimethyl-5H-benzo[e]pyrimido[5,4-b][1,4]diazepin-6(11H)-one; 2-(2-methoxy-4-(4-methylpiperazin-1-yl)phenylamino)-11-methyl-5H-benzo[e]pyrimido[5,4-b][1,4]diazepin-6(1H)-one; 2-(4-(4-hydroxypiperidin-1-yl)-2-isopropoxyphenylamino)-5,11-dimethyl-5H-benzo[e]pyrimido[5,4-b][1,4]diazepin-6(11H)-one; 2-(2-methoxy-4-(4-(4-methylpiperazin-1-yl)piperidin-1-yl)phenylamino)-5,11-dimethyl-5H-benzo[e]pyrimido[5,4-b][1,4]diazepin-6(11H)-one; 2-(5-(4-hydroxypiperidin-1-yl)pyridin-2-ylamino)-5,11-dimethyl-5H-benzo[e]pyrimido[5,4-b][1,4]diazepin-6(11H)-one; 2-(2-ethoxy-4-(4-hydroxypiperidin-1-yl)phenylamino)-5,11-dimethyl-5H-benzo[e]pyrimido[5,4-b][1,4]diazepin-6(1H)-one; 2-(4-(4-hydroxypiperidin-1-yl)-2-methoxyphenylamino)-5,11-dimethyl-5H-benzo[e]pyrimido[5,4-b][1,4]diazepin-6(11H)-one; 5-ethyl-2-(5-(4-hydroxypiperidin-1-yl)pyridin-2-ylamino)-11-methyl-5H-benzo[e]pyrimido[5,4-b][1,4]diazepin-6(11H)-one; 5-ethyl-2-(4-(4-hydroxypiperidin-1-yl)-2-methoxyphenylamino)-11-methyl-5H-benzo[e]pyrimido[5,4-b][1,4]diazepin-6(11H)-one; 2-(2-ethoxy-4-(4-methylpiperazin-1-yl)phenylamino)-11-methyl-5H-benzo[e]pyrimido[5,4-b][1,4]diazepin-6(11H)-one; 2-(2-isopropoxy-4-(4-methylpiperazin-1-yl)phenylamino)-11-methyl-5H-benzo

[e]pyrimido[5,4-b][1,4]diazepin-6(11H)-one; 11-ethyl-2-(2-methoxy-4-(4-methylpiperazin-1-yl)phenylamino)-5-methyl-5H-benzo[e]pyrimido[5,4-b][1,4]diazepin-6(11H)-one; 11-ethyl-2-(2-methoxy-4-(4-methylpiperazin-1-yl)phenylamino)-5H-benzo[e]pyrimido[5,4-b][1,4]diazepin-6(11H)-one; 2-(2-methoxy-4-(4-methylpiperazin-1-yl)phenylamino)-4,5,11-trimethyl-5H-benzo[e]pyrimido[5,4-b][1,4]diazepin-6(11H)-one; 2-(2-methoxy-4-(4-methylpiperazin-1-yl)phenylamino)-4,11-dimethyl-5H-benzo[e]pyrimido[5,4-b][1,4]diazepin-6(11H)-one; 11-isopropyl-2-(2-methoxy-4-(4-methylpiperazin-1-yl)phenylamino)-5H-benzo[e]pyrimido[5,4-b][1,4]diazepin-6(11H)-one; 11-isopropyl-2-(2-methoxy-4-(4-methylpiperazin-1-yl)phenylamino)-5-methyl-5H-benzo[e]pyrimido[5,4-b][1,4]diazepin-6(11H)-one; 11-cyclopentyl-2-(2-methoxy-4-(4-methylpiperazin-1-yl)phenylamino)-5-methyl-5H-benzo[e]pyrimido[5,4-b][1,4]diazepin-6(11H)-one; 11-cyclopentyl-2-(2-methoxy-4-(4-methylpiperazin-1-yl)phenylamino)-5H-benzo[e]pyrimido[5,4-b][1,4]diazepin-6(11H)-one; 9-fluoro-2-(2-methoxy-4-(4-methylpiperazin-1-yl)phenylamino)-5,11-dimethyl-5H-benzo[e]pyrimido[5,4-b][1,4]diazepin-6(11H)-one; 9-fluoro-2-(2-methoxy-4-(4-methylpiperazin-1-yl)phenylamino)-11-methyl-5H-benzo[e]pyrimido[5,4-b][1,4]diazepin-6(11H)-one; 8-chloro-2-(2-methoxy-4-(4-methylpiperazin-1-yl)phenylamino)-5,11-dimethyl-5H-benzo[e]pyrimido[5,4-b][1,4]diazepin-6(11H)-one; 8-chloro-2-(2-methoxy-4-(4-methylpiperazin-1-yl)phenylamino)-11-methyl-5H-benzo[e]pyrimido[5,4-b][1,4]diazepin-6(11H)-one; 2-(2-methoxy-4-(4-methylpiperazin-1-yl)phenylamino)-8,11-dimethyl-5H-benzo[e]pyrimido[5,4-b][1,4]diazepin-6(11H)-one; 2-(2-methoxy-4-(4-methylpiperazin-1-yl)phenylamino)-5,8,11-trimethyl-5H-benzo[e]pyrimido[5,4-b][1,4]diazepin-6(11H)-one; 2-(2-methoxy-4-(4-methylpiperazin-1-yl)phenylamino)-5,11-dimethyl-5H-pyrido[3,4-e]pyrimido[5,4-b][1,4]diazepin-6(11H)-one; 2-(2-methoxy-4-(4-methylpiperazin-1-yl)phenylamino)-11-methyl-5H-pyrido[3,4-e]pyrimido[5,4-b][1,4]diazepin-6(11H)-one; methyl 4-(5,11-dimethyl-6-oxo-6,11-dihydro-5H-benzo[e]pyrimido[5,4-b][1,4]diazepin-2-ylamino)-3-methoxybenzoate; 2-(2-methoxy-4-(4-methylpiperazine-1-carbonyl)phenylamino)-5,11-dimethyl-5H-benzo[e]pyrimido[5,4-b][1,4]diazepin-6(11H)-one; 2-(2-methoxy-4-(4-(4-methylpiperazin-1-yl)piperidin-1-yl)phenylamino)-5,11-dimethyl-5H-benzo[e]pyrimido[5,4-b][1,4]diazepin-6(11H)-one; 2-(5-(4-hydroxypiperidin-1-yl)pyridin-2-ylamino)-5,11-dimethyl-5H-benzo[e]pyrimido[5,4-b][1,4]diazepin-6(11H)-one; 2-(2-ethoxy-4-(4-hydroxypiperidin-1-yl)phenylamino)-5,11-dimethyl-5H-benzo[e]pyrimido[5,4-b][1,4]diazepin-6(11H)-one; 2-(2-methoxy-4-(4-methylpiperazin-1-yl)phenylamino)-5-methyl-9-phenyl-5H-pyrimido[5,4-e][1,4]diazepin-6(7H)-one; 3-methoxy-4-(5-methyl-6-oxo-9-phenyl-6,7-dihydro-5H-pyrimido[5,4-e][1,4]diazepin-2-ylamino)-N-(1-methylpiperidin-4-yl)benzamide, 4-(9-cyclopentyl-7-ethyl-5-methyl-6-oxo-6,7-dihydro-5H-pyrimido[5,4-e][1,4]diazepin-2-ylamino)-3-hydroxy-N-(1-methylpiperidin-4-yl)benzamide; 4-(7-ethyl-5-methyl-6-oxo-9-phenyl-6,7-dihydro-5H-pyrimido[5,4-e][1,4]diazepin-2-ylamino)-3-methoxy-N-(1-methylpiperidin-4-yl)benzamide; 4-(9-cyclopentyl-5-methyl-6-oxo-6,7-dihydro-5H-pyrimido[5,4-e][1,4]diazepin-2-ylamino)-3-methoxy-N-(1-methylpiperidin-4-yl)benzamide; 9-chloro-2-(2-methoxy-4-(4-methylpiperazin-1-yl)phenylamino)-5,11-dimethyl-5H-benzo[e]pyrimido[5,4-b][1,4]diazepin-6(11H)-one; 11-benzyl-2-(2-methoxy-4-(4-methylpiperazin-1-yl)phenylamino)-5-methyl-5H-benzo[e]pyrimido[5,4-b][1,4]diazepin-6(11H)-one; 11-benzyl-2-(2-methoxy-4-(4-methylpiperazin-1-yl)phenylamino)-5H-benzo[e]pyrimido[5,4-b][1,4]diazepin-6(11H)-one; 4-(5,11-dimethyl-6-oxo-6,11-dihydro-5H-benzo[e]pyrimido[5,4-b][1,4]diazepin-2-ylamino)-3-methoxybenzoic acid; methyl 4-(5,11-dimethyl-6-oxo-6,11-dihydro-5H-benzo[e]pyrimido[5,4-b][1,4]diazepin-2-ylamino)-3-methoxybenzoate; 3-(5,11-dimethyl-6-oxo-6,11-dihydro-5H-benzo[e]pyrimido[5,4-b][1,4]diazepin-2-ylamino)-4-methoxybenzoic acid; 2-(2-methoxy-4-(4-(pyrrolidin-1-yl)piperidine-1-carbonyl)phenylamino)-5,11-dimethyl-5H-benzo[e]pyrimido[5,4-b][1,4]diazepin-6(11H)-one; 2-(2-methoxy-4-(4-(4-methylpiperazin-1-yl)piperidine-1-carbonyl)phenylamino)-5,11-dimethyl-5H-benzo[e]pyrimido[5,4-b][1,4]diazepin-6(11H)-one; 2-(4-(3-(dimethylamino)pyrrolidine-1-carbonyl)-2-methoxyphenylamino)-5,11-dimethyl-5H-benzo[e]pyrimido[5,4-b][1,4]diazepin-6(11H)-one; 4-(5,11-dimethyl-6-oxo-6,11-dihydro-5H-benzo[e]pyrimido[5,4-b][1,4]diazepin-2-ylamino)-3-methoxy-N-(1-methylpiperidin-4-yl)benzamide; 3-(5,11-dimethyl-6-oxo-6,11-dihydro-5H-benzo[e]pyrimido[5,4-b][1,4]diazepin-2-ylamino)-4-methoxy-N-(1-methylpiperidin-4-yl)benzamide; 2-(2-methoxy-5-(4-(4-methylpiperazin-1-yl)piperidine-1-carbonyl)phenylamino)-5,11-dimethyl-5H-benzo[e]pyrimido[5,4-b][1,4]diazepin-6(11H)-one; 2-(5-(3-(dimethylamino)pyrrolidine-1-carbonyl)-2-methoxyphenylamino)-5,11-dimethyl-5H-benzo[e]pyrimido[5,4-b][1,4]diazepin-6(11H)-one; 3-(5,11-dimethyl-6-oxo-6,11-dihydro-5H-benzo[e]pyrimido[5,4-b][1,4]diazepin-2-ylamino)-N-(2-(dimethylamino)ethyl)-4-methoxybenzamide; 2-(4-(4-(2-hydroxyethyl)piperazine-1-carbonyl)-2-methoxyphenylamino)-5,11-dimethyl-5H-benzo[e]pyrimido[5,4-b][1,4]diazepin-6(11H)-one; 2-(2-methoxy-4-(4-methylpiperazin-1-yl)phenylamino)-5-methyl-5H-benzo[e]pyrimido[5,4-b][1,4]diazepin-6(11H)-one; 2-(2-methoxy-4-(4-methylpiperazin-1-yl)phenylamino)-5H-benzo[e]pyrimido[5,4-b][1,4]diazepin-6(11H)-one; 2-(2-methoxy-4-(4-methylpiperazin-1-yl)phenylamino)-5-methylbenzo[f]pyrimido[4,5-b][1,4]thiazepin-6(5H)-one; 2-(2-methoxy-4-(4-methylpiperazin-1-yl)phenylamino)benzo[f]pyrimido[4,5-b][1,4]thiazepin-6(5H)-one; 2-(2-methoxy-4-(4-methylpiperazin-1-yl)phenylamino)benzo[f]pyrimido[4,5-b][1,4]oxazepin-6(5H)-one; and 2-(2-methoxy-4-(4-methylpiperazin-1-yl)phenylamino)-5-methylbenzo[f]pyrimido[4,5-b][1,4]oxazepin-6(5H)-one.

United States Patent Application Publication No. 2011/0230481 by Brzozka et al., incorporated herein by this reference, discloses tetrabromobenzimidazole derivatives, including compounds of Formula (N-XI):

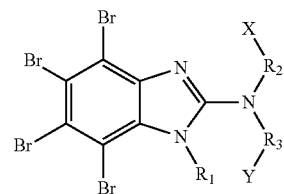

(N-XI)

wherein:

(i) $R_1$ is selected from a group consisting of: hydrogen atom, substituted or unsubstituted alkyl or cycloalkyl, substituted or unsubstituted alkenyl or alkynyl, substituted or unsubstituted aryl, substituted or unsubstituted heteroalkyl or heteroaryl;

(ii) $R_2$ and $R_3$ are independently selected from a group consisting of: hydrogen atom, substituted or unsubstituted hydrocarbon chain, substituted or unsubstituted cycloalkyl, substituted or unsubstituted aryl, substituted or unsubstituted heteroaryl, substituted or unsubstituted heterocycloalkyl;

(iii) X and Y are independently selected from a hydrogen atom, substituted or unsubstituted heteroaryl, guanidinyl, —NH$_2$, —NHR0 or N(R0)$_2$, where R0 represents a substituted or unsubstituted alkyl, aryl or heteroaryl, and wherein X and Y can also represent a substituted or unsubstituted heterocyclic moiety having 3-10 atoms wherein at least one of the ring atoms is nitrogen; or (iv) $R_2$ and $R_3$ are connected to a substituted or unsubstituted heterocycloalkyl; and (v) wherein the following structures are excluded: 2-amino-4,5,6,7-tetrabromo-1H-benzimidazole; 2-methylamino-4,5,6,7-tetrabromo-1H-benzimidazole; 2-dimethylamino-4,5,6,7-tetrabromo-1H-benzimidazole; 2-ethanolamino-4,5,6,7-tetrabromo-1H-benzimidazole; 2-isopropylamino-4,5,6,7-tetrabromo-1H-benzimidazole; 2-(2-hydroxypropylamino)-4,5,6,7-tetrabromo-1H-benzimidazole; 2-(3-hydroxypropylamino)-4,5,6,7-tetrabromo-1H-benzimidazole; 2-(2-dimethylaminoethylamino)-4,5,6, 7-tetrabromo-1H-benzimidazole; 2-dimethylamino-4,5,6,7-tetrabromo-1-methyl-benzimidazole; 2-isopropylamino-4,5, 6,7-tetrabromo-1-methyl-benzimidazole; 2-(methyl(4,5,6,7-tetrabromo-1-methyl-1H-benzo[d]imidazol-2-yl)amino) ethanol; (2-dimethylamino-4,5,6,7-tetrabromobenzoimidazol-1-yl)acetic acid ethyl ester; and (2-dimethylamino-4,5,6,7-tetrabromobenzoimidazol-1-yl) acetic acid.

United States Patent Application Publication No. 2011/0034459 by Adibhatla et al., incorporated herein by this reference, discloses 6,7-dialkoxyquinazoline derivatives, including compounds of Formula (N-XII):

(N-XII)

wherein:
(i) $R^1$ is a group of Subformula (N-XII(a)), (N-XII(b)), or (N-XII(c));

(N-XII(a))

(N-XII(b))

(N-XII(c))

and
(ii) $R^2$ is —CH$_3$ or —CH$_2$CH$_3$.

United States Patent Application Publication No. 2010/0239631 by Bourke et al., incorporated herein by this reference, discloses thiopyrimidines, including compounds of Formula (N-XIII):

(N-XIII)

wherein:
(i) X and Y are independently selected from N and CR$_3$;

(ii) each $R_3$ is independently selected from hydrogen, $C_1$-$C_6$ alkyl, $C_2$-$C_6$ alkenyl, hydroxyl, halogen, nitro, substituted or unsubstituted amino, cyano, nitro, trifluoromethyl, methoxy, trifluoromethoxy, aryl and substituted or unsubstituted 5 or 6 membered heterocyclyl containing 1 to 2 N atoms;

(iii) $R_1$ is selected from hydrogen, $C_1$-$C_6$ alkyl, $C_1$-$C_6$ alkyl-CN, $C_3$-$C_8$ cycloalkyl, $C_1$-$C_6$ alkylene-cycloalkyl, aryl, $C_1$-$C_6$ alkylene-aryl, heterocyclyl and $C_1$-$C_6$ alkylene-heterocyclyl, wherein $C_1$-$C_6$ alkyl, $C_3$-$C_8$ cycloalkyl, heterocyclyl and aryl may be optionally substituted with 1 to 3 substituents selected from R or $R_9$;

(iv) $R_9$ is independently selected from halogen, substituted or unsubstituted $C_1$-$C_6$ alkyl, OH, (O), OCN, substituted or unsubstituted O—$C_1$-$C_6$ alkyl, CN, CF$_3$, CF$_2$CN, SCN, SO$_2$NR$_5$R$_6$, SR$_7$, CHO, CO$_2$R$_7$, COR$_7$, CONR$_5$R$_6$, CONR$_5$R$_7$, NR$_5$COR$_7$, NO$_2$, NR$_5$R$_6$, NR$_5$CN, CH(CN) NR$_5$R$_6$, NR$_5$SO2R$_7$, COCF$_3$, COCH$_2$F, NR$_5$COCOR$_7$, NR$_5$COOR$_7$, NR$_5$CONR$_6$R$_7$, heterocyclyl and CO-heterocyclyl, wherein each heterocyclyl may be optionally substituted with 1 to 4 substituents selected from NH$_2$, CN, OH, CO$_2$R$_7$, CH$_2$CN and 5-membered N-containing heterocyclyl;

(v) R is $C_1$-$C_6$ alkylene-R$_9$, O—$C_1$-$C_6$ alkylene-R$_9$, except when $R_9$ is NR$_5$R$_6$ or O—$C_1$-$C_6$ alkyl, then R is O—$C_2$-$C_6$ alkylene-R$_9$);

(vi) or $R_9$ and R together with the groups to which they are attached form a substituted or unsubstituted 5- or 6-membered N-containing heterocyclyl;

(vii) $R_5$ and $R_6$ are each independently selected from H, $C_1$-$C_6$ alkyl, $C_1$-$C_6$ alkyl-CN, $C_3$-$C_8$ cycloalkyl, aryl, heterocyclyl, substituted or unsubstituted $C_1$-$C_6$ alkylene, cycloalkyl, SO$_2$—$C_1$-$C_6$ alkyl and $C_1$-$C_6$-alkylene-heterocyclyl; or (viii) $R_5$ and $R_6$ together with the nitrogen to which they are attached form a 4-8 membered ring having 1 to 3 heteroatoms independently selected from NR$_8$, 0, S(O)$_m$ wherein m is 0, 1 or 2 and wherein the ring may be optionally substituted with $C_1$-$C_6$ alkyl or NR$_5$R$_6$;

(ix) $R_8$ is selected from H, $C_1$-$C_6$ alkyl, $C_2$-$C_6$ alkylene-OH, $C_2$-$C_6$ alkylene-$NR_5R_6$, $C_3$-$C_8$ cycloalkyl, aryl, heterocyclyl, $C_1$-$C_6$ alkylene-cycloalkyl, $C_1$-$C_6$ alkylene-aryl, $C_1$-$C_6$ alkylene-heterocyclyl and $C_1$-$C_6$-alkyleneCN;

(x) $R_7$ is selected from H, substituted or unsubstituted $C_1$-$C_6$ alkyl, substituted or unsubstituted O—$C_1$-$C_6$ alkyl, substituted or unsubstituted S—$C_1$-$C_6$ alkyl, CNOH, $C_1$-$C_6$-alkylene-CN, substituted or unsubstituted $C_3$-$C_8$ cycloalkyl, substituted or unsubstituted aryl, substituted or unsubstituted heterocyclyl, $C_1$-$C_6$ alkylene-cycloalkyl, $C_1$-$C_6$ alkylene-aryl, $C_1$-$C_6$ alkylene-heterocyclyl, $C_2$-$C_6$ alkenyl, $C_2$-$C_6$ alkynyl, $NR_5R_6$, $C_1$-$C_6$ alkylene-$NR_5R_5$ and $C_1$-$C_6$ alkylene-$OR_5$;

(xi) W is absent, CO, $SO_2$ or C1-C6 alkylene;

(xii) $R_2$ is selected from H, $C_1$-$C_6$ alkyl, $C_3$-$C_8$ cycloalkyl, aryl and heterocyclyl, each of which may be optionally substituted with 1 to 4 substituents selected from R and $R_9$; and (xiii) wherein each alkenyl and alkynyl may be optionally substituted with 1 to 3 substituents independently selected from $C_1$-$C_6$ alkyl, $CO_2R_7$, $CONR_5R_6$, aryl, heterocyclyl, $C_1$-$C_6$ alkylene, OH, and $C_1$-$C_6$ alkylene-$NH_2$.

United States Patent Application Publication No. 2010/0152434 by Peterson, incorporated herein by this reference, discloses kinase-binding nucleosides and derivatives, including compounds of Formula (N-XIV):

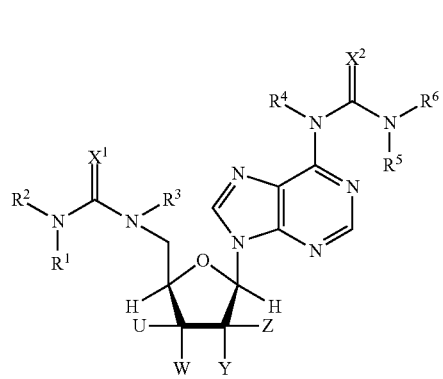

(N-XIV)

wherein:

(i) $R^1$, $R^2$, $R^5$, and $R^6$ are members selected independently from the group consisting of H, HO—, $CH_3O$—, $CH_3$—, $HOCH_2CH_2$—, $HOCH_2CH_2OCH_2CH_2$—, $NH_2CH_2CH_2$—, $R^7NHCH_2CH_2$—, $(R^7)_2NCH_2CH_2$—, $NH_2CH_2CH_2NHCH_2CH_2$—, $R^7NHCH_2CH_2NHCH_2CH_2$—, $(R^7)_2NCH_2CH_2NHCH_2CH_2$—, $R^8CO$—, a mono-, di-, or tricyclic aryl from $C_6$ to $C_{14}$, a mono-, di-, or tri-cyclic aryl from $C_6$ to $C_{14}$ mono-, di-, tri-, or poly-substituted with a member selected independently from the group consisting of F, Cl, Br, I, alkoxy ($R^9O$—), nitro ($NO_2$), nitroso (NO), azido ($N_3$), $C_2$-$C_{12}$ alkyl, $C_2$-$C_{12}$ alkenyl, $C_2$-$C_{12}$ alkynyl, $C_2$-$C_{12}$ acyl; an O, N, or S mono- or bi-cyclic heterocycle having from 2 to 9 carbon atoms, and an O, N, or S mono- or bi-cyclic heterocycle having from 2 to 9 carbon atoms and mono-, di-, tri-, or poly-substituted with a member selected independently from the group consisting of F, Cl, Br, I, alkoxy ($R^9O$—), nitro ($NO_2$), nitroso (NO), azido ($N_3$), $C_2$-$C_{12}$ alkyl, $C_2$-$C_{12}$ alkenyl, $C_2$-$C_{12}$ acyl;

(ii) $R^7$ is $C_1$-$C_5$ alkyl;

(iii) $R^8$ is $H_2N$—, HOHN—, $C_1$-$C_{10}$ alkyl, $C_2$-$C_{10}$ alkenyl, or phenyl;

(iv) $R^9$ is $C_1$-$C_{20}$ alkyl;

(v) $R^3$ and $R^4$ are members selected independently from the group consisting of H, HO—, $CH_3$—, or $CH_3CH_2$—;

(vi) $X^1$ and $X^2$ are members selected independently from the group consisting of O and S;

(vii) U is a member selected from the group consisting of H, HO—, F, $CF_3$—;

(viii) W is a member selected from the group consisting of H, HO—, F, $CF_3$—, $CH_3CH_2O_2CCH_2$—, $CH_3(CH_3O)NCOCH_2$—, $HOCH_2CH_2O$—, $NH_2COCH_2$—, $CH_3NHCOCH_2$—, $(CH_3)_2NCOCH_2$—, $HOCH_2CH_2NHCOCH_2$—, $HSCH_2CH_2NHCOCH_2$—, $R^9O$—, and an O-trialkylsilyl containing 3-16 carbons;

(ix) Y is a member selected from the group consisting of H, HO—, F, $CF_3$—, $HOCH_2CH_2O$—, $R^9O$—, and an O-trialkylsilyl containing 3-16 carbons; and (x) Z is a member selected from the group consisting of H, F, HO—, $CF_3$—, and $R^9O$—.

United States Patent Application Publication No. 2010/0004190 by Chan et al., incorporated herein by this reference, discloses polycyclic kinase inhibitors, including compounds of Formula (N-XV):

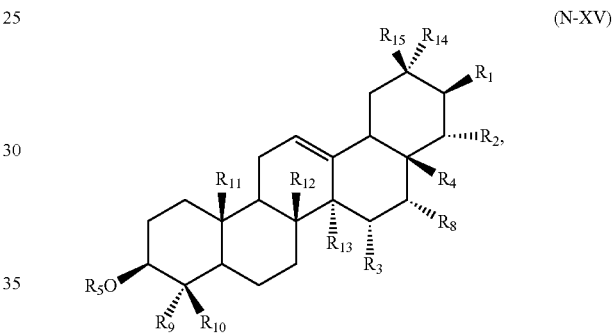

(N-XV)

wherein:

(i) $R_1$ is selected from hydrogen, hydroxyl, O-acetyl, O-angeloyl, O-tigloyl, O-senecioyl, O-alkyl, O-dibenzoyl, O-benzoyl, O-alkanoyl, O-alkenoyl, O-benzoyl-alkyl substituted alkanoyl, O-aryl, O-acyl, O-heterocyclyl, O-heteroaryl and O-sugar moiety, wherein the sugar moiety is substituted with two groups selected from benzoyl, alkanoyl, alkenoyl, benzoyl, alkyl-substituted alkanoyl, aryl, acyl, heterocyclyl, heteroaryl, and derivatives thereof;

(ii) $R_2$ is selected from hydrogen, hydroxyl, O-angeloyl, O-tigloyl, O-senecioyl, O-alkyl, O-dibenzoyl, O-benzoyl, O-alkanoyl, O-alkenoyl, O-benzoyl-alkyl-substituted alkanoyl, O-aryl, O-acyl, O-heterocyclyl, O-heteroaryl, and O-sugar moiety, wherein the sugar moiety is substituted with two groups selected from benzoyl, alkanoyl, alkenoyl, benzoyl alkyl substituted alkanoyl, aryl, acyl, heterocyclyl, heteroaryl, and derivatives thereof;

(iii) $R_4$ is selected from $CH_2R_6$ and $COR_E$, wherein $R_6$ comprises a group selected from hydroxyl, O-angeloyl, O-tigloyl, O-senecioyl, O-alkyl, O-dibenzoyl, O-benzoyl, O-alkanoyl, O-alkenoyl, O-benzoyl-alkyl-substituted alkanoyl, O-aryl, O-acyl, O-heterocylic, O-heteroraryl, and derivatives thereof; or wherein at least one of $R^1$, $R^2$ and $R^6$ is selected from O-angeloyl, O-tigloyl, O-senecioyl, O-dibenzoyl, O-benzoyl, O-alkanoyl, O-alkenoyl, O-benzoyl alkyl substituted alkanoyl, O-aryl, O-acyl, O-heterocyclyl, O-heteroaryl, and derivatives thereof;

(iv) or wherein at least two of $R_1$, $R_2$ and $R_4$ are selected from O-angeloyl, O-tigloyl, O-senecioyl, O-dibenzoyl, O-benzoyl, O-alkanoyl, O-alkenoyl, O-benzoyl alkyl substituted alkanoyl, O-aryl, O-acyl, O-heterocylic, O-heteroaryl, and derivatives thereof, or any of $R_1$, $R_2$ and $R_4$ has two angeloyl, tigloyl, senecioyl, dibenzoyl, benzoyl, alkanoyl, alkenoyl, O-benzoyl alkyl substituted alkanoyl, aryl, acyl, heterocyclyl, heteroaryl, and derivatives thereof;

(v) $R_3$ is H or OH;

(vi) $R_8$ is H or OH;

(vii) $R_5$ is a hydrogen, or sugar moiety(ies) or acid thereof, wherein the sugar moiety(ies) is/are selected from a group consisting of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combination thereof;

(viii) wherein $R_9$, $R_{10}$, $R_{11}$, $R_{12}$, $R_{13}$, $R_{14}$, and $R_{15}$ of the compound are independently selected from $CH_3$, $CH_2OH$, CHO, COOH, COO-alkyl, COO-aryl, COO-heterocyc, COO-heteroaryl, $CH_2$—O-aryl, $CH_2$—O-heterocyclyl, $CH_2$—O-heteroaryl, alkyl, hydroxyl, and acetyl.

United States Patent Application Publication No. 2009/0227533 by Bader et al., incorporated herein by this reference, discloses miRNAs that inhibit the expression of the NEK9 gene.

United States Patent Application Publication No. 2009/0196912 by Eickhoff et al., incorporated herein by this reference, discloses pyridinylamines, including the following compounds: 3,4-difluoro-benzyl)-(5-thiophen-3-yl-pyridin-3-yl)-amine; N-(3-{5-[(benzo[1,3]dioxol-5-ylmethyl)-amino]-pyridin-3-yl}-phenyl)-methanesulfonamide; 3-{5-[(benzo[1,3]dioxol-5-ylmethyl)-amino]-pyridin-3-yl}-phenol; [5-(4-morpholin-4-yl-phenyl)-pyridin-3-yl]-pyridin-3-ylmethyl-amine; 5 N-(2-dimethylamino-ethyl)-3-{5-[(pyridin-3-ylmethyl)-amino]-pyridin-3-yl}-benzamide; (3,4-difluoro-benzyl)-(5-pyrimidin-5-yl-pyridin-3-yl)-amine; (3-chloro-phenyl)-(5-phenethyl-pyridin-3-yl)-amine; N-(2-dimethylamino-ethyl)-3-[5-(4-methoxy-phenylamino)-pyridin-3-yl]-benzamide; 4-(5-phenylamino-pyridin-3-yl)-phenol; [5-(4-methanesulfonyl-phenyl)-pyridin-3-yl]-phenyl-amine; (4-chloro-benzyl)-(5'-methoxy-[3,3']bipyridinyl-5-yl)-amine; 3-[5-(4-chloro-benzylamino)-pyridin-3-yl]-phenol; {4-[5-(3,4-difluoro-benzylamino)-pyridin-3-yl]-phenyl}-methanol; N-(2-dimethylamino-ethyl)-3-{5-[(furan-3-ylmethyl)-amino]-pyridin-3-yl}-benzamide; [5-(4-methanesulfonyl-phenyl)-pyridin-3-yl]-pyridin-3-ylmethyl-amine; (3-bromo-phenyl)-[5-(4-dimethylamino-phenyl)-pyridin-3-yl]-amine; (6'-methoxy-[3,3]bipyridinyl-5-yl)-phenyl-amine; (3-chloro-4-fluoro-phenyl)-[5-(4-dimethylamino-phenyl)-pyridin-3-yl]-amine; (4-diethylamino-benzyl)-[5-(2-methoxy-phenyl)-pyridin-3-yl]-amine; quinolin-3-ylmethyl-(5-quinolin-3-yl-pyridin-3-yl)-amine; {4-[5-(4-chloro-benzylamino)-pyridin-3-yl]-phenyl}-methanol; [3,4']bipyridinyl-5-yl-(3,4-dimethoxy-benzyl)-amine; (3-bromo-phenyl)-(5-quinolin-8-yl-pyridin-3-yl)-amine; N-(2-dimethylamino-ethyl)-3-[5-(3-nitro-phenylamino)-pyridin-3-yl]-benzamide; furan-3-ylmethyl-(5'-methoxy-[3,3]bipyridinyl-5-yl)-amine; N-(2-dimethylamino-ethyl)-4-[5-(3-nitro-phenylamino)-pyridin-3-yl]-benzamide; [3,3']bipyridinyl-5-yl-quinolin-3-ylmethyl-amine; [3,3']bipyridinyl-5-yl-(3,4-dichloro-benzyl)-amine; 4-[5-(4-chloro-benzylamino)-pyridin-3-yl]-phenol; 3-{5-[(naphthalen-2-ylmethyl)-amino]-pyridin-3-yl}-phenol; N-{3-[5-(3,4-difluoro-benzylamino)-pyridin-3-yl]-phenyl}-methanesulfonamide; [3,3]bipyridinyl-5-yl-furan-3-ylmethyl-amine; 4-[5-(3,4-dichloro-benzylamino)-pyridin-3-yl]-phenol; 4-[5-(3,4-dimethoxy-benzylamino)-pyridin-3-yl]-phenol; (3,4-difluoro-benzyl)-(6'-methoxy-[3,3]bipyridinyl-5-yl)-amine; [((E)-5-hex-1-enyl)-pyridin-3-yl]-(3,4,5-trimethoxy-phenyl)-amine; 3-[5-(naphthalen-2-ylamino)-pyridin-3-yl]-phenol; (4-chloro-phenyl)-(5-pyrimidin-5-yl-pyridin-3-yl)-amine; N-{3-[5-(3,4-dichloro-benzylamino)-pyridin-3-yl]-phenyl}-methanesulfonamide; 3-[5-(3,4-dimethoxy-benzylamino)-pyridin-3-yl]-benzamide; 5-bromo-2-{5-[(furan-3-ylmethyl)-amino]-pyridin-3-yl}-indole-1-carboxylic acid tert-butyl ester; [3,3]bipyridinyl-5-yl-pyridin-3-ylmethyl-amine; {2-[5-(3-chloro-phenylamino)-pyridin-3-yl]-phenyl}-methanol; 3-(5-phenylamino-pyridin-3-yl)-benzamide; (4-chloro-phenyl)-(5'-methoxy-[3,3]bipyridinyl-5-yl)-amine; 4-[5-(4-chloro-phenylamino)-pyridin-3-yl]-N-(2-dimethylamino-ethyl)-benzamide; {4-[5-(3-nitro-phenylamino)-pyridin-3-yl]-phenyl}-methanol; (5'-methoxy-[3,3]bipyridinyl-5-yl)-naphthalen-2-ylmethyl-amine; 3-[5-(4-chloro-benzylamino)-pyridin-3-yl]-N-(2-dimethylamino-ethyl)-benzamide; [3,3]bipyridinyl-5-yl-(3,4-difluoro-benzyl)amine; (3,4-difluoro-benzyl)-(5'-methoxy-[3,3]bipyridinyl-5-yl)-amine; 3-[5-(4-trifluoromethoxy-phenylamino)-pyridin-3-yl]-phenol; [5-(3,4-dimethoxy-phenyl)-pyridin-3-yl]-naphthalen-2-yl-amine; N-(2-dimethylamino-ethyl)-3-[5-(naphthalen-2-ylamino)-pyridin-3-yl]-benzamide; (4-chloro-phenyl)-[5-(3-trifluoromethoxy-phenyl)-pyridin-3-yl]-amine; (4-chloro-phenyl)-[5-(2-methoxy-phenyl)-pyridin-3-yl]-amine; 3-{5-[(quinolin-3-ylmethyl)-amino]-pyridin-3-yl}-benzamide; 4-[5-(2,4-dimethoxy-pyrimidin-5-yl)-pyridin-3-ylamino]-benzonitrile; 3-[5-(3,4-dichloro-benzylamino)-pyridin-3-yl]-phenol; [5-(2,4-dimethoxy-pyrimidin-5-yl)-pyridin-3-yl]-(4-isopropyl-phenyl)-amine; (5'-methoxy-[3,3]bipyridinyl-5-yl)-(3-nitro-phenyl)amine; 3-[5-(3-chloro-4-fluoro-phenylamino)-pyridin-3-yl]-benzamide; (3-chloro-4-fluoro-phenyl)-(5-quinolin-3-yl-pyridin-3-yl)-amine; {2-[5-(3-chloro-4-fluoro-phenylamino)-pyridin-3-yl]-phenyl}-methanol; [5-(2,4-dimethoxy-pyrimidin-5-yl)-pyridin-3-yl]-naphthalen-2-yl-amine; (4-chloro-phenyl)-[5-(4-methanesulfonyl-phenyl)-pyridin-3-yl]-amine; N-{3-[5-(4-chloro-phenylamino)-pyridin-3-yl]-phenyl}-acetamide; {2-[5-(4-chloro-phenylamino)-pyridin-3-yl]-phenyl}-methanol; 3-[5-(4-chloro-phenylamino)-pyridin-3-yl]-N-(2-dimethylamino-ethyl)-benzamide; N-(3-{5-[(quinolin-3-ylmethyl)-amino]-pyridin-3-yl}-phenyl)-acetamide; (3,4-difluoro-benzyl)-[5-(3,4-dimethoxy-phenyl)-pyridin-3-yl]amine; [5-(2,4-dimethoxy-pyrimidin-5-yl)-pyridin-3-yl]-furan-3-ylmethyl-amine; {4-[5-(4-chloro-phenylamino)-pyridin-3-yl]-phenyl}-methanol; furan-3-ylmethyl-(6'-methoxy-[3,3]bipyridinyl-5-yl)-amine; N-(2-hydroxy-ethyl)-3-{5-[(pyridin-3-ylmethyl)-amino]-pyridin-3-yl}-benzamide; pyridin-3-ylmethyl-(5-thiophen-3-yl-pyridin-3-yl)-amine; {3-[5-(4-trifluoromethoxy-phenylamino)-pyridin-3-yl]-phenyl}-methanol; {3-[5-(naphthalen-2-ylamino)-pyridin-3-yl]-phenyl}-methanol; (3,4-dichloro-benzyl)-(5'-methoxy-[3,3]bipyridinyl-5-yl)-amine; (3-nitro-phenyl)-(5-thiophen-3-yl-pyridin-3-yl)-amine; (3-chloro-4-fluoro-phenyl)-[5-(2-methoxy-phenyl)-pyridin-3-yl]-amine; 3-[5-(4-chloro-benzylamino)-pyridin-3-yl]-benzamide; (3-chloro-4-fluoro-phenyl)-[5-(2,4-dimethoxy-pyrimidin-5-yl)-pyridin-3-yl]-amine; N-(2-dimethylamino-ethyl)-4-[5-(naphthalen-2-ylamino)-pyridin-3-yl]-benzamide; (5'-methoxy-[3,3]bipyridinyl-5-yl)-(4-trifluoromethoxy-phenyl)-amine; (4-chloro-phenyl)-(6'-methoxy-[3,3]bipyridinyl-5-yl)-amine; [3,4]bipyridinyl-5-yl-naphthalen-2-ylmethyl-amine; [3,4]bipyridinyl-5-yl-(4-chloro-benzyl)amine; benzo[1,3]dioxol-5-ylmethyl-[5-(3,4-dimethoxy-phenyl)-pyridin-3-yl]-amine; (3-{5-[(furan-3-ylmethyl)-amino]-pyridin-3-yl}-phenyl)-methanol; N-{3-[5-(3,4-dimethoxy-benzylamino)- pyridin-3-yl]-phenyl}-acetamide; 3-{5-[(pyridin-3-ylmethyl)-amino]-pyridin-3-yl}-phenol; [5-(3,4-dimethoxy-phenyl)-pyridin-3-yl]-phenyl-amine; (3-chloro-4-fluoro-phenyl)-(5-pyrimidin-5-yl-pyridin-3-yl)-amine; N-{3-[5-(4-chloro-benzylamino)-pyridin-3-yl]-phenyl}-methanesulfonamide; (3,4-dimethoxy-benzyl)-[5-(3,4-dimethoxy-phenyl)-pyridin-3-yl]-amine; 3-{5-[(furan-3-ylmethyl)-amino]-pyridin-3-yl}-N-(2-hydroxy-ethyl)-benzamide; (5-benzo[1,3]dioxol-5-yl-pyridin-3-yl)-furan-3-ylmethyl-amine; (3-bromo-phenyl)-[5-(4-morpholin-4-yl-phenyl)-pyridin-3-yl]-amine; [3,3']bipyridinyl-5-yl-(3-bromo-phenyl)amine; 4-(5-thiophen-3-yl-pyridin-3-ylamino)-benzonitrile; N-(3-{5-[(furan-3-ylmethyl)-amino]-pyridin-3-yl}-phenyl)-methanesulfonamide; (3-bromo-phenyl)-[5-(2-methoxy-phenyl)-pyridin-3-yl]-amine; N-(2-hydroxy-ethyl)-3-[5-(4-methoxy-phenylamino)-pyridin-3-yl]benzamide; 3-[5-(4-chloro-phenylamino)-pyridin-3-yl]-benzamide; N-(3-{5-[(naphthalen-2-ylmethyl)-amino]-pyridin-3-yl}-phenyl)-acetamide; benzo[1,3]dioxol-5-ylmethyl-[3,4]bipyridinyl-5-yl-amine; 5-bromo-2-[5-(3-hydroxy-benzylamino)-pyridin-3-yl]-indole-1-carboxylic acid tert-butyl ester; furan-3-ylmethyl-(5-thiophen-3-yl-pyridin-3-yl)-amine; [3,4]bipyridinyl-5-yl-furan-3-ylmethyl-amine; [5-(3,4-dimethoxy-phenyl)-pyridin-3-yl]-quinolin-3-ylmethyl-amine; N-{3-[5-(4-chloro-benzylamino)-pyridin-3-yl]-phenyl}-acetamide; 3-[5-(3,4-difluoro-benzylamino)-pyridin-3-yl]-phenol; (3-chloro-4-fluoro-phenyl)-(6'-methoxy-[3,3']bipyridinyl-5-yl)-amine; (5'-Methoxy-[3,3']bipyridinyl-5-yl)-(4-methoxy-phenyl)-amine; (4-{5-[(furan-3-ylmethyl)-amino]-pyridin-3-yl}-phenyl)-methanol; 3-[5-(3-chloro-phenylamino)-pyridin-3-yl]-benzamide; N-{3-[5-(4-isopropyl-phenylamino)-pyridin-3-yl]-phenyl}-acetamide; phenyl-(5-quinolin-3-yl-pyridin-3-yl)-amine; 4-(5-Pyrimidin-5-yl-pyridin-3-ylamino)-benzonitrile; (5'-methoxy-[3,3]bipyridinyl-5-yl)-(3,4,5-trimethoxy-phenyl)-amine; (3-chloro-phenyl)-(5-quinolin-8-yl-pyridin-3-yl)-amine; [3,4]bipyridinyl-5-yl-(3,4-dichloro-benzyl)-amine; 3-[5-(3,4-difluoro-benzylamino)-pyridin-3-yl]-benzamide; 3-{5-[(benzo[1,3]dioxol-5-ylmethyl)-amino]-pyridin-3-yl}-benzamide; 4-{5-[(benzo[1,3]dioxol-5-ylmethyl)-amino]-pyridin-3-yl}-phenol; 4-[5-(3,4-difluoro-benzylamino)-pyridin-3-yl]-phenol; (5'-methoxy-[3,3]bipyridinyl-5-yl)-pyridin-3-ylmethyl-amine; (3-bromo-phenyl)-(5'-methoxy-[3,3]bipyridinyl-5-yl)-amine; N-(3-{5-[(benzo[1,3]dioxol-5-ylmethyl)-amino]-pyridin-3-yl}-phenyl)-acetamide; [5-(3,4-dimethoxy-phenyl)-pyridin-3-yl]-(4-isopropyl-phenyl)-amine; N-(2-hydroxy-ethyl)-3-[5-(3-nitro-phenylamino)-pyridin-3-yl]-benzamide; [5-(2,4-dimethoxy-pyrimidin-5-yl)-pyridin-3-yl]-phenyl-amine; 5-bromo-2-{5-[(pyridin-3-ylmethyl)-amino]-pyridin-3-yl}-indole-1-carboxylic acid tert-butyl ester; 3-{5-[(pyridin-3-ylmethyl)-amino]-pyridin-3-yl}-benzamide; (3-bromo-phenyl)-[5-(2,4-dimethoxy-pyrimidin-5-yl)-pyridin-3-yl]-amine; [3-(5-phenylamino-pyridin-3-yl)-phenyl]-methanol; N-{3-[5-(4-methoxy-phenylamino)-pyridin-3-yl]-phenyl}-methanesulfonamide; [3,4]bipyridinyl-5-yl-(3,4-difluoro-benzyl)-amine; N-{3-[5-(3-Nitro-phenylamino)-pyridin-3-yl]-phenyl}-methanesulfonamide; 3-{5-[(Furan-3-ylmethyl)-amino]-pyridin-3-yl}-phenol; 3-[5-(4-isopropyl-phenylamino)-pyridin-3-yl]-phenol; 4-[((E)-5-hex-1-enyl)-pyridin-3-ylamino]-benzonitrile; N-{3-[5-(naphthalen-2-ylamino)-pyridin-3-yl]-phenyl}-acetamide; N-{3-[5-(3,4-difluoro-benzylamino)-pyridin-3-yl]-phenyl}-acetamide; (3-bromo-phenyl)-(5-quinolin-3-yl-pyridin-3-yl)-amine; {4-[5-(3-bromo-phenylamino)-pyridin-3-yl]-phenyl}-methanol; 4-[5-(4-isopropyl-phenylamino)-pyridin-3-yl]-phenol; 3-[5-(4-cyano-phenylamino)-pyridin-3-yl]-N-(2-dimethyl-amino-ethyl)-benzamide; 4-(6'-methoxy-[3,3']bipyridinyl-5-ylamino)-benzonitrile; 3-[5-(naphthalen-2-ylamino)-pyridin-3-yl]-benzamide; 3-[5-(4-methoxy-phenylamino)-pyridin-3-yl]-benzamide; [3,4]bipyridinyl-5-yl-(3-bromo-phenyl)amine; (4-chloro-benzyl)-[5-(3,4-dimethoxy-phenyl)-pyridin-3-yl]-amine; 3-{[5-(2-hydroxymethyl-phenyl)-pyridin-3-ylamino]-methyl}-phenol; [3,3]bipyridinyl-5-yl-(3-nitro-phenyl)amine; N-{3-[5-(3-nitro-phenylamino)-pyridin-3-yl]-phenyl}-acetamide; N-(2-hydroxy-ethyl)-3-(5-phenylamino-pyridin-3-yl)-benzamide; 3-([3,3']bipyridinyl-5-ylaminomethyl)-phenol; 3-{5-[(furan-3-ylmethyl)-amino]-pyridin-3-yl}-benzamide; (6'-methoxy-[3,3]bipyridinyl-5-yl)-(3,4,5-trimethoxy-phenyl)-amine; (3-chloro-4-fluoro-phenyl)-[5-(4-methanesulfonyl-phenyl)-pyridin-3-yl]-amine; N-(3-{5-[(furan-3-ylmethyl)-amino]-pyridin-3-yl}-phenyl)-acetamide; [3,4']bipyridinyl-5-yl-(3-nitro-phenyl)amine; {3-[5-(4-chloro-phenylamino)-pyridin-3-yl]-phenyl}-methanol [3,4]bipyridinyl-5-yl-(3-chloro-phenyl)amine; 3-[5-(3-nitro-phenylamino)-pyridin-3-yl]-benzamide; 3-[5-(4-chloro-phenylamino)-pyridin-3-yl]-phenol; N-{3-[5-(4-chloro-phenylamino)-pyridin-3-yl]-phenyl}-methanesulfonamide; 3-[5-(3-bromo-phenylamino)-pyridin-3-yl]-benzamide; 4-(5'-methoxy-[3,3]bipyridinyl-5-ylamino)-benzonitrile; 3-{[5-(2-methoxy-phenyl)-pyridin-3-ylamino]-methyl}-phenol; 4-[5-(3-chloro-4-fluoro-phenylamino)-pyridin-3-yl]-N-(2-dimethylamino-ethyl)-benzamide; 3-[5-(3-nitro-phenylamino)-pyridin-3-yl]-phenol; {4-[5-(3-chloro-4-fluoro-phenylamino)-pyridin-3-yl]-phenyl}-methanol; 4-{5-[(furan-3-ylmethyl)-amino]-pyridin-3-yl}-phenol; [5-(3,4-dimethoxy-phenyl)-pyridin-3-yl]-furan-3-ylmethyl-amine; 3-[5-(3-bromo-phenylamino)-pyridin-3-yl]-N-(2-hydroxy-ethyl)-benzamide; N-(2-dimethylamino-ethyl)-3-[5-(3,4,5-trimethoxy-phenylamino)-pyridin-3-yl]-benzamide; (3-chloro-4-fluoro-phenyl)-(5'-methoxy-[3,3]bipyridinyl-5-yl)-amine; 3-{[5-(2,4-dimethoxy-pyrimidin-5-yl)-pyridin-3-ylamino]-methyl}-phenol; (5-thiophen-3-yl-pyridin-3-yl)-(3,4,5-trimethoxy-phenyl)amine; N-{3-[5-(4-cyano-phenylamino)-pyridin-3-yl]-phenyl}-methanesulfonamide; N-[3-(5-phenylamino-pyridin-3-yl)-phenyl]-methanesulfonamide; [3,3]bipyridinyl-5-yl-(3-chloro-phenyl)-amine; 4-[5-(3-chloro-4-fluoro-phenylamino)-pyridin-3-yl]-phenol; N-{3-[5-(3-chloro-phenylamino)-pyridin-3-yl]-phenyl}-acetamide; 3-[5-(3,4,5-trimethoxy-phenylamino)-pyridin-3-yl]-benzamide; 3-[5-(3,4,5-trimethoxy-phenylamino)-pyridin-3-yl]-phenol; 3-(5-phenylamino-pyridin-3-yl)-phenol; {3-[5-(3-chloro-4-fluoro-phenylamino)-pyridin-3-yl]-phenyl}-methanol; N-{3-[5-(3-chloro-phenylamino)-pyridin-3-yl]-phenyl}-methanesulfonamide; N-(2-hydroxy-ethyl)-3-[5-(naphthalen-2-ylamino)-pyridin-3-yl]-benzamide; N-[3-(5-phenylamino-pyridin-3-yl)-phenyl]-acetamide; 3-[(5-pyrimidin-5-yl-pyridin-3-ylamino)-methyl]-phenol; N-{3-[5-(3,4,5-trimethoxy-phenylamino)-pyridin-3-yl]-phenyl}-methanesulfonamide; 4-[5-(3-hydroxymethyl-phenyl)-pyridin-3-ylamino]-benzonitrile; 3-[5-(3-chloro-phenylamino)-pyridin-3-yl]-N-(2-hydroxy-ethyl)-benzamide; [5-(3,4-dimethoxy-phenyl)-pyridin-3-yl]-(3-nitro-phenyl)amine; N-{3-[5-(3,4,5-trimethoxy-phenylamino)-pyridin-3-yl]-phenyl}-acetamide; 3-[5-(4-cyano-phenylamino)-pyridin-3-yl]-benzamide; N-(2-dimethylamino-ethyl)-4-[5-(3-hydroxy-benzylamino)-pyridin-3-yl]-benzamide; 4-[5-(4-methanesulfonyl-phenyl)-pyridin-3-ylamino]-benzonitrile; N-{3-[5-(4-trifluoromethoxy-phenylamino)-pyridin-3-yl]-phenyl}-acetamide; N-{3-[5-(4-cyano-phenylamino)-pyridin-3-yl]-phenyl}-acetamide; 3-{[5-(4-methanesulfonyl-phenyl)- pyridin-3-ylamino]-methyl}-phenol; 3-[(6'-methoxy-[3,3']bipyridinyl-5-ylamino)-methyl]-phenol; 3-[5-(3-chloro-4-fluoro-phenylamino)-pyridin-3-yl]-phenol; 3-([3,4']bipyridinyl-5-ylaminomethyl)-phenol; N-{3-[5-(3-chloro-4-fluoro-phenylamino)-pyridin-3-yl]-phenyl}-methanesulfonamide; N-{3-[5-(naphthalen-2-ylamino)-pyridin-3-yl]-phenyl}-methanesulfonamide; 3-{[5-(4-hydroxy-phenyl)-pyridin-3-ylamino]-methyl}-phenol; N-{3-[5-(3-chloro-4-fluoro-phenylamino)-pyridin-3-yl]-phenyl}-acetamide; 3-[(5-benzo[1,3]dioxol-5-yl-pyridin-3-ylamino)-methyl]-phenol; 3-{[5-(3-trifluoromethoxy-phenyl)-pyridin-3-ylamino]-methyl}-phenol; 3-{[5-(3-hydroxymethyl-phenyl)-pyridin-3-ylamino]-methyl}-phenol; 3-[5-(3-hydroxy-benzylamino)-pyridin-3-yl]-N-(2-hydroxy-ethyl)-benzamide; 3-{[5-(4-morpholin-4-yl-phenyl)-pyridin-3-ylamino]-methyl}-phenol; 4-[5-(3-hydroxy-phenyl)-pyridin-3-ylamino]-benzonitrile; 4-[5-(3-nitro-phenylamino)-pyridin-3-yl]-phenol; N-{3-[5-(3-hydroxy-benzylamino)-pyridin-3-yl]-phenyl}-acetamide; 3-[(5'-methoxy-[3,3]bipyridinyl-5-ylamino)-methyl]-phenol; 3-{[5-(3,4-dimethoxy-phenyl)-pyridin-3-ylamino]-methyl}-phenol; N-(2-dimethylamino-ethyl)-3-[5-(3-hydroxy-benzylamino)-pyridin-3-yl]-benzamide; 3-{5-[(3-hydroxybenzyl)amino]pyridin-3-yl}phenol; N-{3-[5-(3-hydroxy-benzylamino)-pyridin-3-yl]-phenyl}-methanesulfonamide; N-{3-[5-(4-methoxy-phenylamino)-pyridin-3-yl]-phenyl}-acetamide; 3-[(5-thiophen-3-yl-pyridin-3-ylamino)-methyl]-phenol; 3-{[5-(4-hydroxymethyl-phenyl)-pyridin-3-ylamino]-methyl}-phenol; 3-[5-(3-hydroxy-benzylamino)-pyridin-3-yl]-benzamide; 2-fluoro-3-[5-(3-hydroxy-benzylamino)-pyridin-3-yl]-phenol; 3-{[5-(3-amino-phenyl)-pyridin-3-ylamino]-methyl}-phenol; 3-{[5-(3-hydroxy-phenyl)-pyridin-3-ylamino]-methyl}-2-methyl-phenol; 3-hydroxy-N-[5-(3-hydroxy-phenyl)-pyridin-3-yl]-benzamide; N-{3-[5-(4-fluoro-phenylamino)-pyridin-3-yl]-phenyl}-acetamide; 3-{[5-(2-fluoro-3-methoxy-phenyl)-pyridin-3-ylamino]-methyl}-phenol; N-{3-[5-(2-fluoro-phenylamino)-pyridin-3-yl]-phenyl}-acetamide; 3-[(5-phenyl-pyridin-3-ylamino)-methyl]-phenol; 3-{[5-(3-methoxy-phenyl)-pyridin-3-ylamino]-methyl}-phenol; N-{3-[5-(2-methoxy-phenylamino)-pyridin-3-yl]-phenyl}-acetamide; 3-{5-[(3-hydroxy-benzyl)methyl-amino]-pyridin-3-yl}-phenol; 5-{[5-(3-hydroxy-phenyl)-pyridin-3-ylamino]-methyl}-benzene-1,3-diol; 3-[5-(3-hydroxy-benzylamino)-pyridin-3-yl]-benzoic acid methyl ester; 3-{5-[2-(3-hydroxy-phenyl)-ethylamino]-pyridin-3-yl}-phenol; 3-[5-(3-amino-benzylamino)-pyridin-3-yl]-phenol; 3-[5-(3-hydroxy-benzylamino)-pyridin-3-yl]-benzoic acid; 5-{[5-(3-hydroxy-phenyl)-pyridin-3-ylamino]-methyl}-2-methyl-phenol; 3-[(5-bromo-pyridin-3-ylamino)-methyl]-phenol; 3-{[5-(2-hydroxy-phenyl)-pyridin-3-ylamino]-methyl}-phenol; N-{3-[5-(methyl-phenyl-amino)-pyridin-3-yl]-phenyl}-acetamide; 2-{[5-(3-hydroxy-phenyl)-pyridin-3-ylamino]-methyl}-phenol; [5-(3-amino-phenyl)-pyridin-3-yl]-phenyl-amine; N-[3-(5-amino-pyridin-3-yl)-phenyl]-acetamide; 3-(5-benzylamino-pyridin-3-yl)-phenol; 3-[5-(2-fluoro-5-methoxy-benzylamino)-pyridin-3-yl]-phenol; 2-(3-hydroxy-phenyl)-N-[5-(3-hydroxy-phenyl)-pyridin-3-yl]-acetamide; 3-(pyridin-3-ylaminomethyl)-phenol; 3-[5-(3-methoxy-benzylamino)-pyridin-3-yl]-phenol; 3-[5-(4-fluoro-3-methoxy-benzylamino)-pyridin-3-yl]-phenol; 3-(5-amino-pyridin-3-yl)-phenol; 3-{5-[(3-methoxy-benzyl)-methyl-amino]-pyridin-3-yl}-phenol; 3-{[5-(3-hydroxy-phenyl)-pyridin-3-ylamino]methyl}-benzoic acid methyl ester; 3-{[5-(3-hydroxy-phenyl)-pyridin-3-ylamino]methyl}-benzoic acid; 3-{[5-(3-hydroxy-phenyl)-pyridin-3-ylamino]methyl}-benzoic acid methyl ester; 3-{[5-(3-hydroxy-phenyl)-pyridin-3-ylamino]-methyl}-benzamide; 3-[5-(3-nitro-benzylamino)-pyridin-3-yl]-phenol; N-[5-(3-hydroxy-phenyl)-pyridin-3-yl]-3-methoxy-4-methyl-benzamide; 3-[5-(3-methoxy-4-methyl-benzylamino)-pyridin-3-yl]-phenol; 3-hydroxy-N-[5-(3-hydroxy-phenyl)-pyridin-3-yl]-2-methyl-benzamide; (3-methoxy-benzyl)-[5-(3-methoxy-benzyl)-pyridin-3-yl]-carbamic acid tert-butyl ester; (3-methoxy-benzyl)-[5-(3-methoxy-benzyl)-pyridin-3-yl]-amine; (3-hydroxy-benzyl)-[5-(3-hydroxy-benzyl)-pyridin-3-yl]-amine; 3-{[5-(3-hydroxy-phenyl)-pyridin-3-ylamino]-methyl}-benzoic acid methyl ester; and (5-phenyl-pyridin-3-yl)-phenyl-amine.

Patent Application Publication No. WO 2005/107760 by Hong et al., incorporated herein by this reference, discloses purine derivatives and analogs of Formula (N-XVI):

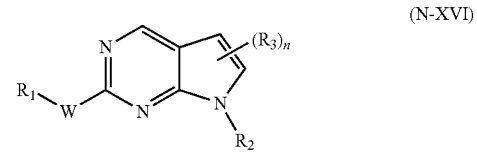

(N-XVI)

wherein:
(i) n is 0, 1, or 2;
(ii) m is 0, 1, 2, or 3;
(iii) W is —NR$_4$—, —S—, —O—, —SO—, and —S(O)$_2$—;
(iv) R$_4$ is hydrogen or C$_1$-C$_6$ alkyl,
(v) R$_1$ is selected from C$_6$-C$_{10}$ aryl-C$_0$-C$_4$ alkyl, C$_5$-C$_{10}$ heteroaryl-C$_0$-C$_4$ alkyl, C$_3$-C$_{12}$ cycloalkyl-C$_0$-C$_4$ alkyl, and C$_3$-C$_8$ heterocycloalkyl-C$_0$-C$_4$ alkyl, wherein any arylalkyl, heteroarylalkyl, cycloalkylalkyl, or heterocycloalkylalkyl group of R$_1$ is optionally substituted by 1 to 3 groups independently selected from halo, nitro, cyano, C$_6$-C$_{10}$ aryl, C$_5$-C$_{10}$ heteroaryl, C$_3$-C$_{12}$ cycloalkyl, C$_3$-C$_8$ heterocycloalkyl, C$_1$-C$_6$ alkyl, C$_1$-C$_6$ alkoxy, halo-substituted C$_1$-C$_6$ alkyl, halo-substituted C$_1$-C$_6$ alkoxy, —XNR$_5$R$_5$, —XNR$_5$XNR$_5$R$_5$, —XNR$_5$XOR$_5$, —XOR$_5$, —XSR$_5$, —XS(O)R$_5$, —XS(O)$_2$R$_5$, —XC(O)NR$_5$R$_5$, —XOXR$_6$, and —XC(O)XR$_6$, wherein X is a bond or C$_1$-C$_6$ alkylene;
(vi) R$_5$ is hydrogen, C$_1$-C$_6$ alkyl, or C$_3$-C$_{12}$ cycloalkyl-C$_0$-C$_4$ alkyl;
(vii) wherein any aryl, heteroaryl, cycloalkyl, or heterocycloalkyl substituent of R$_1$ is further optionally substituted by 1 to 5 groups selected from C$_1$-C$_6$ alkyl and C$_1$-C$_6$ alkoxy;
(viii) R$_2$ is selected from C$_6$-C$_{10}$ aryl-C$_0$-C$_4$ alkyl, C$_5$-C$_{10}$ heteroaryl-C$_0$-C$_4$ alkyl, C$_3$-C$_{12}$ cycloalkyl-C$_0$-C$_4$ alkyl, and C$_3$-C$_8$ heterocycloalkyl-C$_0$-C$_4$ alkyl, wherein any arylalkyl, heteroarylalkyl, cycloalkylalkyl, or heterocycloalkylalkyl group of R$_2$ is optionally substituted by 1 to 3 groups independently selected from halo, nitro, cyano, C$_1$-C$_6$ alkyl, C$_1$-C$_6$ alkenyl, C$_1$-C$_6$ alkynyl, C$_1$-C$_6$ alkoxy, halo-substituted C$_1$-C$_6$ alkyl, halo-substituted C$_1$-C$_6$ alkoxy, C$_3$-C$_8$ heteroaryl-C$_0$-C$_4$ alkyl, —XNR$_5$R$_5$, —XOR$_5$, —XSR$_5$, —XS(0)R$_5$, —XS(O)$_2$R$_5$, —XSNR$_5$R$_5$, —XS(O)NR$_5$R$_5$, —XS(O)$_2$NR$_5$R$_5$, —XC(O)OR$_5$, —XOC(O)OR$_5$, —XC(O)R$_5$, —XC(O)NR$_5$XR$_5$R$_5$, —XC(O)NR$_5$R$_5$, —XC(O)NR$_5$XC(O)OR$_5$, —XC(O)NR$_5$XNR$_5$C(O)R$_5$, —XC(O)NR$_5$XOR$_5$, —XNR$_5$XNR$_5$C(O)OR$_5$, —XC(O)NR$_5$XOR$_5$, —XO(O)N(XOR$_5$)$_2$, —XNR$_5$C(O)R$_5$, —XC(O)NR$_5$R$_6$, —XC(O)R$_6$, —XR$_7$, —XR$_6$, and —XO(O)NR$_5$X1R$_7$, wherein X is a bond or $C_1$-$C_6$ alkylene; $R_5$ is selected from hydrogen, $C_1$-$C_6$ alkyl, and $C_3$-$C_{12}$ cycloalkyl-$C_0$-$C_4$ alkyl; and $R_7$ is cyano;

(ix) $R_3$ is selected from halo, hydroxy, —XSR$_5$, —XS(O) R$_5$, —XS(O)$_2$R$_5$, —XC(O)R$_5$, and —XO(O)OR$_5$, wherein X is a bond or $C_1$-$C_6$ alkylene and $R_5$ is selected from hydrogen, $C_1$-$C_6$ alkyl, and $C_3$-$C_{12}$ cycloalkyl-$C_0$-$C_4$ alkyl; and (x) the N-oxide derivatives, prodrug derivatives, protected derivatives, individual isomers and mixtures of isomers thereof;

and the pharmaceutically acceptable salts thereof.

PCT Patent Application Publication No. WO 2011/126882 by Gelber et al., incorporated herein by this reference, discloses therapeutic peptides with Nek9-inhibitory activity, including analogs and derivatives of SGRPP-MIVWFNRPFLIAVSHTHGQTILFMAKVINPVGA (SEQ ID NO: 5).

PCT Patent Application Publication No. WO 2013/148864 by Gudkov et al., incorporated herein by this reference, discloses curaxins and derivatives thereof, including compounds of Formula (N-XVII):

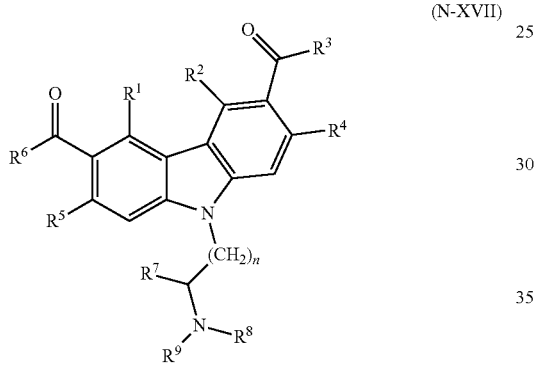

(N-XVII)

wherein:

(i) each of $R^1$, $R^2$, $R^3$, $R^4$, $R^5$, $R^6$, $R^7$, $R^8$, and $R^9$ are independently hydrogen, hydroxyl, or alkyl; and (ii) n is 0, 1, 2, 3, 4, or 5.

PCT Patent Application Publication No. WO 2009/032694 by Gray et al., incorporated herein by this reference, discloses pyrimidine, pyrrolopyridine, and pyrazolopyrimidine derivatives, including compounds of Formula (N-XVIII):

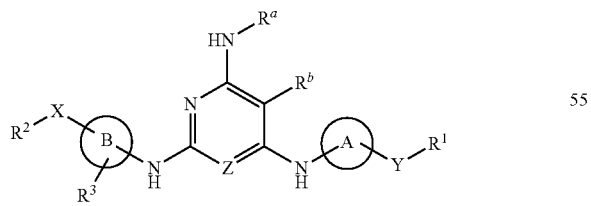

(N-XVIII)

wherein:

(i) Z is N or CH;

(ii) A is aryl or heteroaryl optionally substituted with one or more $R^4$ groups;

(iii) B is phenyl when Z is N; or B is phenyl, pyrazolyl or thiazolyl when Z is CH; wherein B is optionally substituted with one or more $R^4$ groups;

(iv) Y is —SO$_2$—, —SO$_2$NH—, —NH—SO$_2$—, —NH—C(O)—, —C(O)—NH—, —O—, or NR$_2$;

(v) each occurrence of X is independently NH, O, or S;

(vi) $R^1$ is H, $C_1$-$C_6$ alkyl, halo-($C_1$-$C_6$ alkyl), $C_1$-$C_6$ cycloalkyl, halo-($C_1$-$C_6$ cycloalkyl), heterocyclyl, heterocyclyl-($C_1$-$C_6$ alkyl), aryl, aryl-($C_1$-$C_6$ alkyl), heteroaryl, or heteroaryl-($C_1$-$C_6$ alkyl);

(vii) $R^2$ is H, $C_1$-$C_6$ alkyl, halo-($C_1$-$C_6$ alkyl), $C_1$-$C_6$ cycloalkyl, halo-($C_1$-$C_6$ cycloalkyl), heterocyclyl, heterocyclyl-($C_1$-$C_6$ alkyl), aryl, aryl-($C_1$-$C_6$ alkyl), heteroaryl, or heteroaryl-($C_1$-$C_6$ alkyl);

(viii) $R^3$ is $R^4$, —CO—$R^5$, or a moiety of Subformula (N-XVIII(a)), (N-XVIII(b)), (N-XVIII(c)), (N-XVIII(d)), (N-XVIII(e)), (N-XVIII(f)), (N-XVIII(g)), (N-XVIII(h)), (N-XVIII(i)), (N-XVIII(j)), (N-XVIII(k)), or (N-XVIII(l))

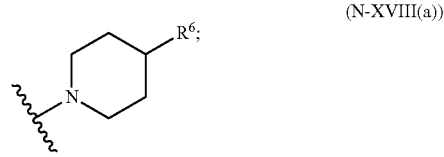

(N-XVIII(a))

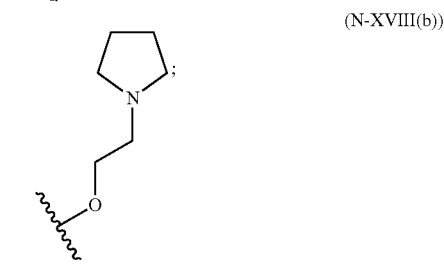

(N-XVIII(b))

(N-XVIII(c))

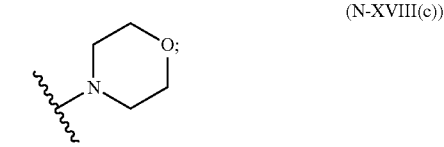

(N-XVIII(d))

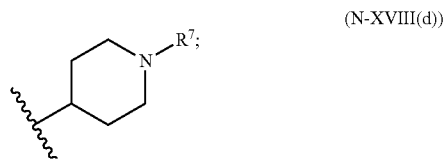

(N-XVIII(e))

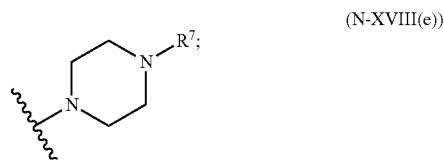

(N-XVIII(f))

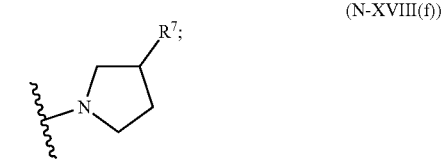

(N-XVIII(g))

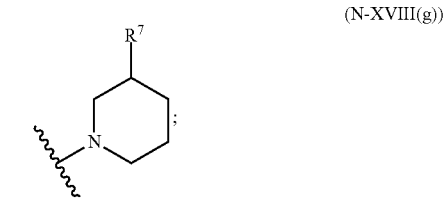

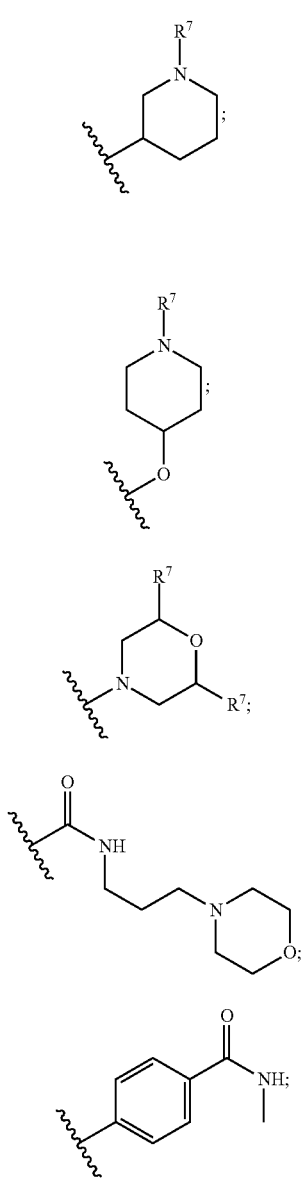
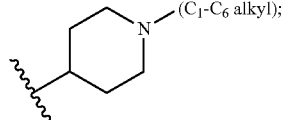
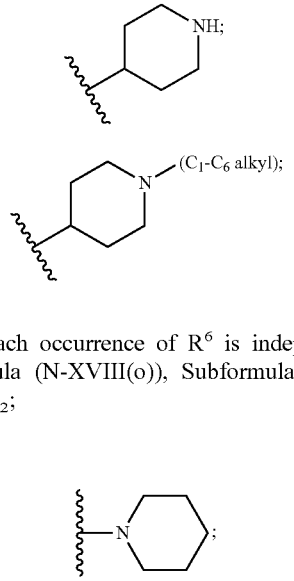
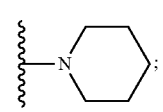

(ix) $R^a$ is hydrogen and $R^b$ is halogen, or $R^a$ and $R^b$, taken together with the atoms to which they are bound form: (i) a pyrazolo ring fused to the pyrimidine ring when Z is N or (ii) a pyrrolo ring fused to the pyrimidine ring when Z is CH, the pyrazolo or pyrrolo ring optionally bearing one or two $R^4$ groups;

(x) each occurrence of $R^4$ is independently halogen, $C_1$-$C_6$ alkyl, halo-($C_1$-$C_6$ alkyl), $C_1$-$C_6$ cycloalkyl, halo-($C_1$-$C_6$ cycloalkyl), heterocyclyl, heterocyclyl-($C_1$-$C_6$ alkyl), aryl, aryl-($C_1$-$C_6$ alkyl), heteroaryl, heteroaryl-($C_1$-$C_6$ alkyl), ($C_1$-$C_6$) alkoxy, ($C_1$-$C_6$) alkylthio, hydroxyl, nitro, azido, cyano, acyloxy, carboxy, ester, carbamoyl, carboxamide, ureido, amidino, guanidine, sulfonyl, sulphonylamino, or aminosulfonyl;

(xi) each occurrence of $R^5$ is independently ($C_1$-$C_6$) alkoxy, a moiety of Subformula (N-XVIII(m)), hydroxy, a moiety of Subformula (N-XVIII(a)), a moiety of Subformula (N-XVIII(n)), dialkylamino, or —$NR^7$;

(xii) each occurrence of $R^6$ is independently hydroxy, Subformula (N-XVIII(o)), Subformula (N-XVIII)(d)), or —$CONH_2$;

(xiii) each occurrence of $R^7$ is independently hydrogen, ($C_1$-$C_6$) alkyl, ($C_1$-$C_6$) alkoxy, hydroxyl, or ($C_1$-$C_6$) hydroxyalkyl;

with the provisos that:

(a) when Z is N, B is phenyl, and —X—$R^2$ is —NH—$R^2$, then —X—$R^2$ is bound in the meta or para position on the phenyl group and $R^3$ and $R^4$, if present on B, are not bound to the meta or para position and are not —$COR^5$, $C_1$-$C_6$ alkyl, halo-($C_1$-$C_6$ alkyl), $C_3$-$C_6$ cycloalkyl, halo-($C_3$-$C_6$ cycloalkyl), heterocyclyl, heterocyclyl-($C_1$-$C_6$ alkyl), aryl, aryl-($C_1$-$C_6$ alkyl), heteroaryl, heteroaryl-($C_1$-$C_6$ alkyl), $C_1$-$C_6$ alkoxy, $C_1$-$C_6$ alkylthio, cyano, acyloxy, carboxyl, ester, carbamoyl, carboxamide, or amidino;

(b) when Z is N, B is phenyl, and —X—$R^2$ is not —NH—$R^2$, then $R^3$ is bound to the meta or para position and is a moiety of Subformula (XIX(a)), (XIX(c)), (XIX(e)), (XIX(f)), (XIX(g)), or (XIX(j)), or if $R^3$ and $R^4$, if present on B, are each bound to the meta or para position and are independently nitro, azido, ureido, guanidine, sulphonylamino; and (c) when Z is CH, and $R^a$ and $R^b$ are taken together with the atoms to which they are bound to form a pyrrolo ring fused to the pyridine ring, then: (1) —X—$R^2$ is not isopropoxy bound to the ortho position and $R^3$ or $R^4$, if present on B, is methyl, ethyl, methoxy, ethoxy, chloro or bromo any of which is bound to the ortho position; or (2) $R^3$ is bound to the meta or para position and is a moiety of Subformula (XIX(b)), (XIX(i)), (XIX(k)), or (XIX(l)) or $R^3$ or $R^4$, if present on B, are each bound to the meta or para position and are independently $C_1$-$C_6$ alkoxy, $C_1$-$C_6$ alkylthio, hydroxyl, nitro, azido, cyano, acyloxy, carboxy, ester, carbamoyl, carboxamide, ureido, amidino, guanidine, sulfonyl, sulphonylamino, aminosulfonyl; —CO—$R^5$, or phenyl substituted with aminosulfonyl, amino, alkynyl or carboxamide.

PCT Patent Application Publication No. WO 2009/017795 by Ajami et al., incorporated herein by this reference, discloses indazole compounds of Formulas (N-XIX) or (N-XX)

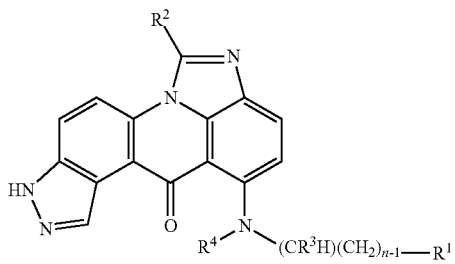
(N-XIX)

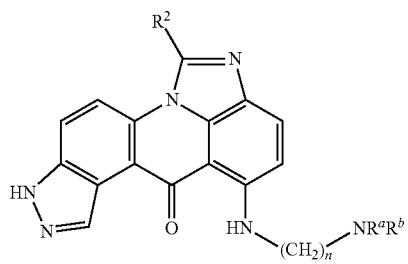
(N-XX)

wherein, for both compounds of Formula (N-XIX) and (N-XX):

(i) $R^1$ is hydrogen or $NR^aR^b$;

(ii) $R^a$ and $R^b$, independently, are hydrogen or an optionally substituted alkyl, or $R^a$ and $R^b$, taken together with the nitrogen to which they are attached, are attached, form a non-aromatic heterocycle, optionally substituted at one or more substitutable carbon atoms with methyl, hydroxyl, or methoxy, and optionally N'-substituted with $C_1$-$C_4$ alkyl or $C_1$-$C_4$ alkyl substituted with —$NR^cR^d$;

(iii) $R^c$ and $R^d$ are independently hydrogen, methyl, or ethyl;

(iv) $R^2$ is hydrogen or $C_1$-$C_4$ alkyl;

(v) $R^3$ is hydrogen or $C_1$-$C_4$ alkyl;

(vi) $R^4$ is hydrogen or $C_1$-$C_4$ alkyl; and (vii) n is 2, 3, 4, or 5.

PCT Patent Application Publication No. WO 2011/153553 by Garske et al., incorporated herein by this reference, discloses electrophilic Nek9 inhibitors of Formula (N-XXI), (N-XXII), or (N-XXIII):

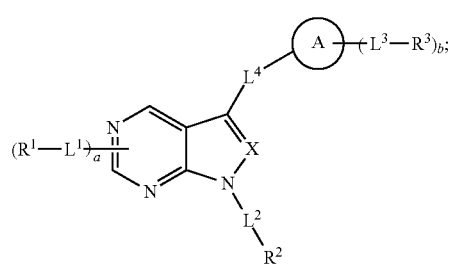
(N-XXI)

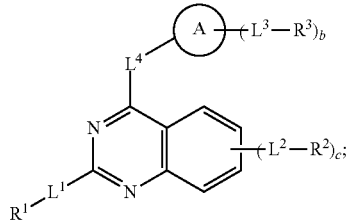
(N-XXII)

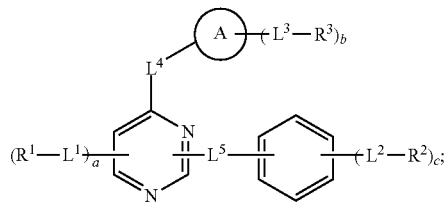
(N-XXIII)

wherein, for compounds of Formula (N-XXI), (N-XXII), and (N-XXIII):

(i) X is =N— or =C($L^6$-$R^6$)—;

(ii) Ring A is, in each instance, independently selected from cycloalkyl, heterocycloalkyl, aryl, or heteroaryl;

(iii) $L^1$, $L^2$, $L^3$, $L^4$, $L^5$, and $L^6$ are, in each instance, independently selected from a bond, —C(O)—, —C(O)N($R^7$)—, —C(O)O—, —S(O)$_g$—, —S(O)$_2$N($R^7$)—, —O—, —$NR^7$—, —N($R^7$)C(O)N($R^8$)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, wherein g is 0, 1, or 2;

(iv) $R^1$, $R^2$, $R^3$, $R^4$, $R^5$, $R^6$, $R^7$, and $R^8$ are, in each instance, independently selected from hydrogen, halogen, cyano, hydroxyl, amino, carboxyl, —$CONH_2$, nitro, sulfhydryl, —$SO_2Cl$, —$SO_3H$, —$SO_4H$, —$SO_2NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

(v) a is 0, 1, or 2;

(vi) b is 0, 1, 2, 3, 4, or 5; and (vii) c is 0, 1, 2, 3, or 4.

PCT Patent Application Publication No. WO 2013/006758 by Kahne et al., incorporated herein by this reference, discloses diphosphate mimetics, including compounds of Formula (N-XXIV):

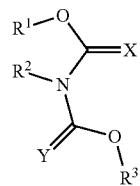
(N-XXIV)

wherein:

(i) X is O or S;

(ii) Y is O or S;

(iii) $R^1$ and $R^2$ are independently optionally substituted alkyl, optionally substituted alkenyl, optionally substituted alkynyl, optionally substituted carbocyclyl, optionally substituted heterocyclyl, optionally substituted aryl, or optionally substituted heteroaryl, or $R^1$ and $R^2$ are taken together to form a 5-membered oxazolidin-2-one ring or a 6-membered 1,3-oxazinan-2-one ring, wherein the ring is optionally substituted or fused to an optionally substituted carbocyclyl, optionally substituted heterocyclyl, optionally substituted aryl, or optionally substituted heteroaryl ring; and (iv) $R^3$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

PCT Patent Application Publication No. WO 2013/074986 by Baker, incorporated herein by this reference, discloses compounds of Formula (N-XXV):

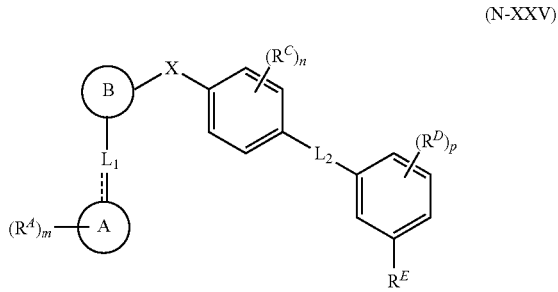

(N-XXV)

wherein:

(i) Ring A is a carbocyclic, heterocyclic, heteroaryl, or aryl ring;

(ii) each instance of $R^A$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1}$, $-N(R^{A1})_2$, and $-SR^{A1}$, wherein each occurrence of $R^{A1}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{A1}$ groups are joined to form an optionally substituted heterocyclic ring; m is 0, 1, 2, 3, or 4;

(iii) Ring B is a moiety of Subformula (N-XXV(a))

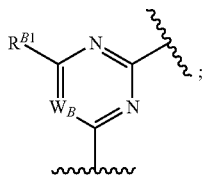

(N-XXV(a))

(iv) $R^{B1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^B1a$, $-N(R^{B1a})_2$, and $-SR^{B1a}$, wherein each occurrence of $R^{B1a}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{B1a}$ groups are joined to form an optionally substituted heterocyclic ring;

(v) $W_B$ is N or $CR^{B2}$, wherein $R^{B2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{B2a}$, $-N(R^{B2a})_2$, and $-SR^{B2a}$, wherein each occurrence of $R^{B2a}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{B2a}$ groups are joined to form an optionally substituted heterocyclic ring;

(vi) optionally wherein $R^{B1}$ and $R^{B2}$ are joined to form an optionally substituted carbocyclyl, optionally substituted heterocyclyl, optionally substituted heteroaryl, or optionally substituted aryl ring;

(vii) L is a bond directly attaching Ring A to Ring B; or L is $=C(R^{L1a})-$, $-O-$, $-S-$, $-NR^{L1b}-$, $-N(R^{L1b})C(=O)-$, $-C(=O)NR^{L1b}-$, $-SC(=O)-$, $-C(=O)S-$, $-OC(=O)-$, $-C(=O)O-$, $NR^{L1b}C(=S)-$, $-C(=S)NR^{L1b}-$, trans-$CH=CH-$, cis-$CH=CH-$, $-S(=O)_2O-$, $-OS(=O)_2-$, $-S(=O)_2NR^{L1b}$, $-NR^{L1b}S(=O)_2-$, or an optionally substituted $C_1$-$C_4$ hydrocarbon chain, optionally wherein one methylene unit of the hydrocarbon chain is replaced with $=C(R^{L1a})-$, $-O-$, $-S-$, $-NR^{L1b}-$, $-N(R^{L1b})C(=O)-$, $-C(=O)NR^{L1b}-$, $-SC(=O)-$, $-C(=O)S-$, $-OC(=O)-$, $-C(=O)O-$, $NR^{L1b}C(=S)-$, $-C(=S)NR^{L1b}-$, trans-$CH=CH-$, cis-$CH=CH-$, $-S(=O)_2O-$, $-OS(=O)_2-$, $-S(=O)2NR^{L1b}$, or $-NR^{L1b}S(=O)_2-$; wherein $R^{L1a}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, cyano, or nitro, and $R^{L1b}$ is hydrogen, $C_1$-$C_6$ alkyl, or a nitrogen protecting group;

(viii) ≈ represents a single or double bond;

(ix) X is an optionally substituted $C_1$-$C_4$ hydrocarbon chain, optionally wherein one or more carbon units of the hydrocarbon chain is replaced with $-O-$, $-S-$, or $-NR^x-$, where $R^x$ is hydrogen, $C_1$-$C_6$ alkyl, or a nitrogen protecting group;

(x) $L_2$ is a bond, $-O-$, $-S-$, $-NR^{L2a}-$, $-N(R^{L2a})C(=O)-$, $-C(=O)NR^{L2a}-$, $-SC(=O)-$, $-C(=O)S-$, $-OC(=O)-$, $-C(=O)O-$, $NR^{L2a}C(=S)-$, $-C(=S)NR^{L2a}-$, trans-$CR^{L2b}=CR^{L2b}-$, cis-$CR^{L2b}=CR^{L2b}-$, $-C≡C-$, $-OC(R^{L2})_2$, $-C(R^{L2b})_2O$, $-NR^{L2a}C(R^{L2b})_2-$, $-C(R^{L2b})_2NR^{L2a}-$, $SC(R^{L2b})_2-$, $-C(R^{L2b})_2S-$, $-S(=O)_2O-$, $-OS(=O)_2-$, $-S(=O)_2NR^{L2a}-$, $-NR^{L2a}S(=O)_2-$, or an optionally substituted $C_1$-$C_4$ hydrocarbon chain, optionally wherein one methylene unit of the hydrocarbon chain is replaced with $-O-$, $-S-$, $-NR^{L2a}-$, $-N(R^{L2a})C(=O)-$, $-C(=O)NR^{L2a}-$, $-SC(=O)-$, $-C(=O)S-$, $-OC(=O)-$, $-C(=O)O-$, $NR^{L2a}C(=S)-$, $-C(=S)NR^{L2a}-$, trans-$CR^{L2b}=CR^{L2b}-$, cis-$CR^{L2b}=CR^{L2b}-$, $-C≡C-$, $-S(=O)_2O-$, $-OS(=O)_2-$, $-S$ (=O)$_2$NR$^{L2a}$, or —NR$^{L2a}$S(=O)$_2$—; wherein L$^{2a}$ is hydrogen, C$_1$-C$_6$ alkyl, or a nitrogen protecting group, and wherein each occurrence of L$^{2b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L2b}$ groups are joined to form an optionally substituted carbocyclic or optionally substituted heterocyclic ring;

(xi) each instance of R$^C$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{C1}$, —N(R$^{C1}$)$_2$, and —SR$^{C1}$, wherein each occurrence of R$^{C1}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two R$^{C1}$ groups are joined to form an optionally substituted heterocyclic ring;

(xii) n is 0, 1, 2, 3, or 4;

(xiii) each instance of R$^D$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$)$_2$, and —SR$^{D1}$, wherein each occurrence of R$^{D1}$ is independently selected from the group consisting of hydrogen, acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two R$^{D1}$ groups are joined to form an optionally substituted heterocyclic ring;

(xiv) p is 0, 1, 2, 3, or 4;

(xv) R$^E$ is a moiety of Subformula (N-XXV(b)), (N-XXV(c)), (N-XXV(d)), (N-XXV(e)), (N-XXV(f)), (N-XXV(g)), (N-XXV(h)), (N-XXV(i)), (N-XXV(j)), (N-XXV(k)), (N-XXV(l)), (N-XXV(m)), (N-XXV(n)), (N-XXV(o)), (N-XXV(p)), (N-XXV(q)), or (N-XXV(r)), depicted below in sequence:

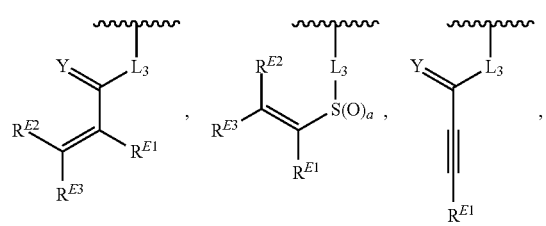

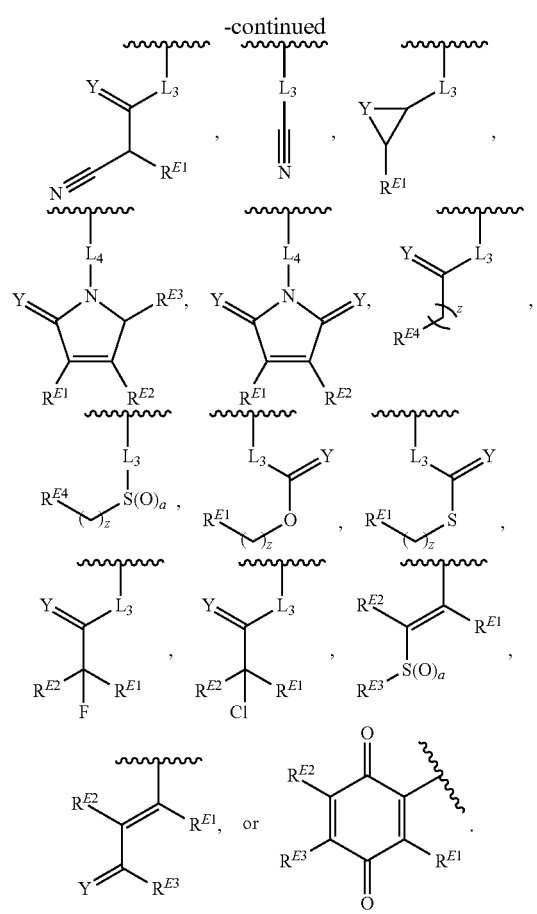

wherein:

(xvi) L$_3$ is a bond, —O—, —S—, —NR$^{L3a}$—, —N(R$^{L3a}$)C(=O)—, —C(=O)NR$^{L3a}$—, —SC(=O)—, —C(=O)S—, —OC(=O)—, —C(=O)O—, NR$^{L3a}$C(=S)—, —C(=S)NR$^{L3a}$—, trans-trans-CR$^{L3b}$=CR$^{L3b}$—, cis-CR$^{L3b}$=CR$^{L3b}$—, —C=C—, —OC(R$^{L3b}$)$_2$—, —C(R$^{L3b}$)$_2$O—, —NR$^{L3a}$C(R$^{L3b}$)$_2$—, —C(R$^{L3b}$)$_2$NR$^{L3a}$—, SC(R$^{L3b}$)$_2$—, —C(R$^{L3b}$)$_2$S—, —S(=O)$_2$O—, —OS(=O)$_2$—, —S(=O)2NR$^{L3a}$, —NR$^{L3a}$S(=O)$_2$—, or an optionally substituted C$_1$-C$_4$ hydrocarbon chain, optionally wherein one methylene unit of the hydrocarbon chain is replaced with —O—, —S—, —NR$^{L3a}$—, —N(R$^{L3a}$)C(=O)—, —C(=O)NR$^{L3a}$—, —SC(=O)—, —C(=O)S—, —OC(=O)—, —C(=O)O—, NR$^{L3a}$C(=S)—, —C(=S)NR$^{L3a}$—, trans-CR$^{L3b}$=CR$^{L3b}$—, cis-CR$^{L3b}$=CR$^{L3b}$—, —S(=O)$_2$O—, —OS(=O)$_2$—, —S(=O)2NR$^{L3a}$, or —NR$^{L3a}$S(=O)$_2$—; wherein L$^{3a}$ is hydrogen, C$_1$-C$_6$ alkyl, or a nitrogen protecting group, and wherein each occurrence of L$^{3b}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{L3b}$ groups are joined to form an optionally substituted carbocyclic or optionally substituted heterocyclic ring;

(xvii) L$_4$ is a bond or an optionally substituted C$_1$-C$_4$ hydrocarbon chain;

(xviii) R$^{E1}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E1a}$, —CH$_2$N(R$^{E1a}$)2, —CH$_2$SR$^{E1a}$, —OR$^{E1a}$, —N(R$^{E1a}$)$_2$, and —SR$^{E1a}$, wherein each occurrence of R$^{E1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E1a}$ groups are joined to form an optionally substituted heterocyclic ring;

(xix) R$^{E2}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E2a}$, —CH$_2$N(R$^{E2a}$)2, —CH$_2$SR$^{E2a}$, —OR$^{E2a}$, —N(R$^{E2a}$)$_2$, and —SR$^{E2a}$, wherein each occurrence of R$^{E2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E2a}$ groups are joined to form an optionally substituted heterocyclic ring;

(xx) R$^{E3}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^{E3a}$, —CH$_2$N(R$^{E3a}$)2, —CH$_2$SR$^{E3a}$, —OR$^{E3a}$, —N(R$^{E3a}$)$_2$, and —SR$^{E3a}$, wherein each occurrence of R$^{E3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{E3a}$ groups are joined to form an optionally substituted heterocyclic ring;

(xxi) optionally wherein R$^{E1}$ and R$^{E3}$ or R$^{E2}$ and R$^{E3}$ or R$^{E1}$ and R$^{E2}$ are joined to form an optionally substituted carbocyclic or optionally substituted heterocyclic ring;

(xxii) R$^{E4}$ is a leaving group;

(xxiii) Y is 0, S, or NR$^{E5}$, wherein R$^{E5}$ is hydrogen, C$_1$-C$_6$ alkyl, or a nitrogen protecting group;

(xxiv) a is 1 or 2; and (xxv) z is 0, 1, 2, 3, 4, 5, or 6.

PCT Patent Application Publication No. WO 2012/158843 by Taunton et al., incorporated herein by this reference, discloses compounds of Formula (N-XXVI)

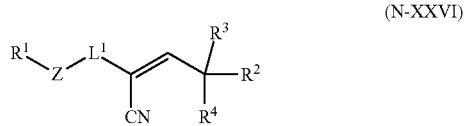

(N-XXVI)

wherein:

(i) R$^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

(ii) Z is a bond, —O—, —N(R$^a$)—, —S—, —SO—, —SO$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;

(iii) R$^a$ is hydrogen or unsubstituted alkyl;

(iv) L$^1$ is a bond, —C(O)—, —N(L$^2$R$^5$)C(O)—, —OC(O)—, —S(O), —(0L$^2$R$^5$)OP(O)—, —N(L$^2$R$^5$)SO$_2$—, —(N(L$^2$R$^5$))NP(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, a moiety of Subformula (N-XXVI(a)) or Subformula (N-XXVI(b))

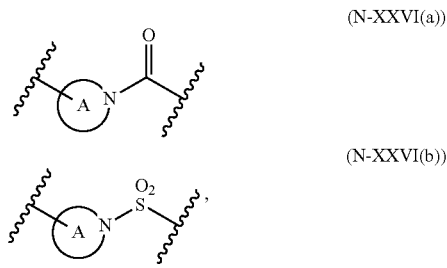

wherein A is substituted or unsubstituted heterocycloalkylene or substituted or unsubstituted heteroarylene;

(v) n is 0, 1 or 2;

(vi) L$^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

(vii) R$^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

(viii) R$^2$ and R$^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or R$^2$ and R$^3$ are optionally joined together to form a substituted or unsubstituted cycloalkyl, substituted or unsubstituted heterocycloalkyl, substituted or unsubstituted aryl, or substituted or unsubstituted heteroaryl;

(ix) R$^4$ is independently hydrogen, —NR$^{4A}$R$^{4B}$, —OR$^{4A}$, —SR$^{4A}$, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and (x) R$^{4A}$ and R$^{4B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

PCT Patent Application Publication No. WO 2012/109075 by Ibrahim et al., incorporated herein by this reference, discloses 1H-pyrrolo-[2,3b]pyridine compounds of Formula (N-XXVII)

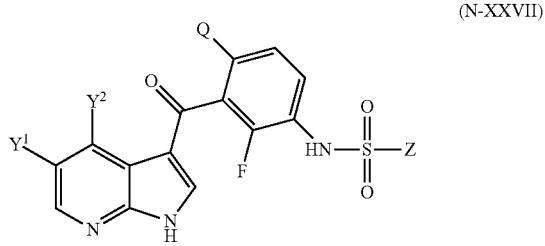

(N-XXVII)

wherein:

(i) $Y^1$ is selected from the group consisting of cyano, halogen, hydroxyl, optionally substituted $C_1$-$C_6$ alkyl, optionally substituted $C_1$-$C_6$ alkoxy, optionally substituted $C_3$-$C_6$ cycloalkyl, optionally substituted $C_1$-$C_6$ haloalkyl, optionally substituted $C_1$-$C_6$ haloalkoxy, optionally substituted aryl and optionally substituted heteroaryl; optionally wherein the two adjacent substituents on the aryl or heteroaryl ring together with the atoms to which they are attached form an optionally substituted 5- or 6-membered ring having from 0 to 3 additional heteroatoms selected from N, O or S;

(ii) $Y^2$ is hydrogen, halogen, cyano, hydroxyl, $C_1$-$C_6$ alkyl, $C_1$-$C_6$ alkoxy, $C_1$-$C_6$ haloalkyl, $C_1$-$C_6$ haloalkoxy, aryl, arylalkyl, heteroaryl, heteroarylalkyl, $C_3$-$C_8$ cycloalkyl-$C_0$-$C_4$ alkyl, or $(R^2)(R^3)N$—, wherein $R^2$ and $R^3$ are each independently selected from the group consisting of hydrogen, $C_1$-$C_6$ alkyl, $C_1$-$C_6$ alkoxy, aryl, arylalkyl, heteroaryl, heteroarylalkyl, $C_3$-$C_8$ cycloalkyl-$C_0$-$C_4$ alkyl, heterocycloalkyl and heterocycloalkyl-$C_1$-$C_4$ alkyl; or $R^2$ and $R^3$ taken together with the nitrogen atom to which they are attached form a 3- to 8-membered ring having from 0-2 additional heteroatoms as ring members selected from N, O, or S; and $Y^2$ is optionally substituted with one to three moieties each independently selected from $R^c$;

(iii) Q is selected from hydrogen, F, Cl, or methyl;

(iv) Z is —$N(R^4)(R^5)$ or —$C(R^6)(R^7)(R^8)$, wherein $R^4$ and $R^5$ are each independently selected from the group consisting of hydrogen, optionally substituted $C_1$-$C_6$ alkyl, optionally substituted $C_3$-$C_8$ cycloalkyl, optionally substituted heterocycloalkyl, optionally substituted heterocycloalkylalkyl, optionally substituted aryl, optionally substituted arylalkyl, optionally substituted heteroaryl, or optionally substituted heteroarylalkyl, or $R^4$ and $R^5$ taken together with the nitrogen atom to which they are attached form a 4- to 8-membered ring having from 0 to 2 additional heteroatoms as ring members selected from N, O, and S, wherein the 4- to 8-membered ring is optionally substituted;

(v) $R^6$, $R^7$ and $R^8$ are each independently hydrogen, optionally substituted $C_1$-$C_6$ alkyl, optionally substituted $C_1$-$C_6$ haloalkyl, optionally substituted $C_1$-$C_6$ haloalkoxy, optionally substituted $C_3$-$C_8$ cycloalkyl, optionally substituted $C_3$-$C_8$ cycloalkylalkyl, optionally substituted aryl, optionally substituted arylalkyl, optionally substituted heterocycloalkyl, optionally substituted heterocycloalkylalkyl, optionally substituted heteroaryl, optionally substituted heteroarylalkyl or —$X^2R^9$, wherein $X^2$ is —Ne, O or S;

(vi) $R^{10}$ is hydrogen, $C_1$-$C_6$ alkyl, or aryl;

(vii) $R^9$ is hydrogen, $C_1$-$C_6$ alkyl, $C_1$-$C_6$ haloalkyl, $C_1$-$C_6$ haloalkoxy, $C_3$-$C_8$ cycloalkylalkyl, aryl, arylalkyl, heteroaryl, or heteroarylalkyl, where $R^9$ is optionally substituted with 1 to 3 $R^e$ substituents; or (viii) any two of the $R^6$, $R^7$, and $R^8$ groups taken together with the carbon atom to which they are attached form a 3- to 8-membered optionally substituted non-aromatic ring having from 0 to 2 heteroatoms selected from N, O, or S; provided that, at each occurrence, at least two of the $R^6$, $R^7$, and $R^8$ groups are not simultaneously hydrogen, and with the provisos that: (i) when $Y^1$ is halogen, methyl, cyano, —OMe, or 2-methoxypyrimidin-5-yl, Z is other than dimethylamino, diethylamino, 1-pyrrolidine, 1-piperidinyl, 4-morpholinyl, isopropyl, —$CH(CH_3)(CH_2CH_3)$, —$CH(CH_3)(CH_2CH_2CH_3)$, cyclobutyl, cyclopentyl, or cyclohexyl; and (ii) when $Y^1$ is 1-methyl-4-pyrazolyl, 3-methylsulfonylphenyl or 3-methylsulfonylaminophenyl, Z is other than cyclopropyl, cyclobutyl, cyclopentyl or cyclohexyl.

PCT Patent Application Publication No. WO 2013/147711 by Nacro et al., incorporated herein by this reference, discloses bicyclic heterocyclic derivatives, including compounds of Formula (N-XXVIII):

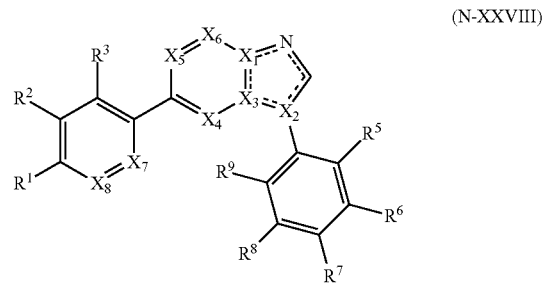

(N-XXVIII)

wherein:

(i) $X_1$, $X_2$, and $X_3$ are independently nitrogen or carbon;

(ii) $X_4$, $X_5$, and $X_6$ are independently nitrogen or $CR^4$; wherein at least one of $X_1$, $X_2$, $X_3$, $X_4$, $X_5$, and $X_6$ is nitrogen;

(iii) $X_7$ is nitrogen or $CR^{10}$;

(iv) ---- is a single or double bond, as required by valency;

(v) $R^1$, $R^2$, $R^3$, $R^5$, $R^6$, $R^7$, $R^8$, $R^9$, $R^{10}$, and $R^{11}$ are independently hydrogen, halogen, optionally substituted alkyl, optionally substituted aryl, optionally substituted carbocyclyl, optionally substituted heteroaryl, optionally substituted heterocyclyl, cyano, —SR, —$N(R)_2$, nitro, —$C(O)R$, —$CO_2R$, —$C(O)N(R)_2$, —$S(O)R$, —$SO_2R$, —$SO_2N(R)_2$, —$OC(O)R$, —$NRC(O)R$, —$NRSO_2R$, or —$NRC(O)N(R)_2$;

(vi) each R is independently hydrogen, optionally substituted $C_1$-$C_6$ alkyl, optionally substituted aryl, optionally substituted carbocyclyl, optionally substituted heteroaryl, or optionally substituted heterocyclyl, or two R groups on the same nitrogen atom may be taken together to form an optionally substituted heterocyclyl moiety;

(vii) each $R^4$ is independently hydrogen, halogen, or optionally substituted $C_1$-$C_6$ alkyl; and (viii) $R^1$ and $R^2$, $R^2$ and $R^3$, $R^3$ and $R^4$, $R^1$ and $R^{11}$, $R^{10}$ and $R^{11}$, $R^5$ and $R^6$, $R^6$ and $R^7$, $R^7$ and $R^8$, or $R^8$ and $R^9$ may be optionally taken together to form an optionally substituted 5-membered or 6-membered carbocyclyl, aryl, heterocyclyl, or heteroaryl ring.

For these Nek9 inhibitors, the compounds described above also include pharmaceutically acceptable analogues, congeners, bioisosteres, hydrolysis products, metabolites, precursors, and prodrugs thereof. For compounds having one or more chiral centers, the compounds include all possible stereoisomers including enantiomers and/or diastereomers unless it can be shown that one or more specific stereoisomers lack pharmacological activity.

Additionally, the kinases Mad2, BubR1, and Mps1 interact with Nek9 and inhibitors of one or more of those kinases can promote inhibition of the activity of Nek9 in this complex regulatory network. Inhibitors of Mad2 are disclosed in the following United States patents, all of which are incorporated herein by this reference: U.S. Pat. No. 8,629,118 to Pellman; U.S. Pat. No. 8,586,297 to Pagano et al.; U.S. Pat. No. 8,470,798 to Tagaki et al.; U.S. Pat. No. 8,399,659 to Claiborne et al.; U.S. Pat. No. 8,354,386 to Lee et al.; U.S. Pat. No. 7,718,648 to Claiborne et al.; and U.S. Pat. No. 7,572,784 to Claiborne et al. Inhibitors of BubR1 are disclosed in the following United States patents, all of which are incorporated herein by this reference: U.S. Pat. No. 8,026,355 to Hansen et al.; U.S. Pat. No. 7,943,629 to Luecking et al.; U.S. Pat. No. 7,897,568 to Jia et al.; and U.S. Pat. No. 7,781,580 to Lee et al. Inhibitors of Mps1 are disclosed in the following United States patents, all of which are incorporated herein by this reference: U.S. Pat. No. 8,551,980 to Schulze et al.; U.S. Pat. No. 8,541,576 to Casucelli et al.; U.S. Pat. No. 8,513,241 to Cervi et al.; U.S. Pat. No. 8,394,802 to Mirizzi et al.; U.S. Pat. No. 8,207,165 to Cervi et al.; U.S. Pat. No. 8,106,069 to Salom et al.; U.S. Pat. No. 6,593,098 to Yen et al.; and U.S. Pat. No. 5,972,640 to Drubin et al.

In another alternative, the derivative or analog of meisoindigo, including one of Alternatives (1)-(486) above, can be used together with an agent that inhibits Nek9 expression, such as by suppressing transcription of the NEK9 gene. These agents include, but are not limited to, short interfering RNA (sRNA), microRNA (miRNA), synthetic hairpin RNA (shRNA), antisense nucleic acids, and complementary DNA (cDNA). Other agents that can inhibit expression by suppressing transcription of the NEK9 gene are known in the art and are disclosed in PCT Application Publication No. 2011/070150 by Ullrich et al., including precursors of sRNA or miRNA, oligonucleotide aptamers, ribozymes, polypeptides binding to target structures, including antibodies or peptidic aptamers, and low-molecular-weight organic molecules. The use of siRNAs for inhibiting the expression of the NEK9 gene is also disclosed in PCT Patent Application Publication No. 2006/128063 by Gao et al., incorporated herein by this reference. RNA interference is the process whereby the introduction of double stranded RNA into a cell inhibits the expression of a gene corresponding to its own sequence. RNAi is usually described as a post-transcriptional gene-silencing (PTGS) mechanism in which double stranded RNA triggers degradation of homologous messenger RNA in the cytoplasm. The siRNAs bind to a ribonuclease complex called RNA-induced silencing complex (RISC) that guides the small dsRNAs to its homologous mRNA target. Consequently, RISC cuts the mRNA approximately in the middle of the region paired with the antisense sRNA, after which the mRNA is further degraded.

When antibodies are used, such antibodies can be polyclonal or monoclonal. As used herein in this context, the term "monoclonal antibodies" includes, but is not limited to, chimeric antibodies, humanized antibodies, antibody fragments such as scFv fragments, diabodies, heavy chain antibodies (HcAbs), and single-domain antibodies (sdAbs). Such monoclonal antibodies are not necessarily produced as the result of cell fusion between B cells and myeloma cells, and can be produced in other eukaryotic cells or even bacterial cells according to methods known in the art. General techniques of antibody engineering are described in C. A. K. Borrebaeck, "Antibody Engineering" (2d ed., Oxford University Press, New York, 1995), incorporated herein by this reference.

Screening methods for Nek9 inhibitors are described in United States Patent Application Publication No. 2011/0229484 by Baumert et al., incorporated herein by this reference. A variety of assay protocols and detection techniques are well known in the art and can easily be adapted for this purpose by one skilled in the art. Such methods include, but are not limited to, high-throughput assays (e.g., microarray technology, phage display technology) and in vitro and in vivo cellular and tissue assays. One alternative comprises incubating a biological system, which expresses (or can express) Nek9, with a candidate compound under conditions and for a time sufficient for the candidate compound to modulate the kinase activity; and measuring the activity of the kinase. Candidate compounds that decrease the activity of the kinase are identified as kinase inhibitors. In certain embodiments, a method according to the invention more specifically includes incubating a biological system, which expresses (or can express) Nek9 with a candidate compound under conditions and for a time sufficient for the candidate compound to modulate the activity of the kinase, thereby obtaining a test system; incubating the biological system under the same conditions and for the same time absent the candidate compound, thereby obtaining a control system; measuring in the test system, at least one factor that is representative of the activity of the Nek9 kinase; measuring that factor in the control system; comparing the factor measured in the test system and the control system; and determining that the candidate compound inhibits the activity of the kinase if the factor measured in the test system is less than or greater than the factor measured in the control system. Other methods are known in the art.

Accordingly, the following compositions and methods are within the scope of the present invention: (1) compositions and methods employing a derivative or analog of meisoindigo, including one of Alternatives (1)-(486) above, together with an Nek9 inhibitor; (2) compositions and methods employing a derivative or analog of meisoindigo, including one of Alternatives (1)-(486) above, together with an anti-Nek9 antibody; (3) compositions and methods employing a derivative or analog of meisoindigo, including one of Alternatives (1)-(486) above, together with an agent that inhibits Nek9 expression; and (4) compositions and methods employing a derivative or analog of meisoindigo, including one of Alternatives (1)-(486) above, together with an inhibitor of at least one of Mad2, BubR1, and Mps1.

Another class of agents that can be used together with derivatives or analogs of meisoindigo and Nek9 inhibitors or other agents inhibiting the expression of Nek9 are histone deactylase inhibitors ("HDAC inhibitors"). Suitable HDAC inhibitors are disclosed in PCT Patent Application Publication No. WO 2013/040286 by Chen et al., incorporated herein by this reference, and include compounds of Formula (H-I):

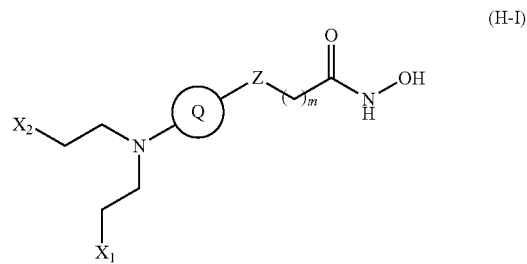

wherein:

(i) m is 5, 6, 7, 8, 9, 10, 11, 12, 13, 14, 15, or 16;

(ii) Z is absent, $C(R_aR_b)$, O, S, C(O), $N(R_a)$, $SO_2$, OC(O), C(O)O, $OSO_2$, $S(O_2)O$, C(O)S, SC(O), C(O)C(O), $C(O)N(R_a)$, $N(R_a)C(O)$, $S(O_2)N(R_a)$, $N(R_a)S(O_2)$, $OC(O)N(R_a)$, $N(R_a)C(O)O$, $N(R_a)C(O)S$, or $N(R_a)C(O)N(R_b)$, in which each of IR, and $R_b$, independently, is H, alkyl, alkenyl, or alkynyl;

(iii) $X_1$ and $X_2$ independently, is halo or $OSO_2R_c$, in which $R_c$ is alkyl, alkenyl, or alkynyl; and (iv) Q is cycloalkyl, heterocycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —C═NH, cyano, alkyl-Rd, $OR_d$, $OC(O)R_d$, $OC(O)OR_d$, $OC(O)SR_d$, $SR_d$, $C(O)R_d$, $C(O)OR_d$, $C(O)SR_d$, $C(O)NR_eR_f$, $SOR_d$, $SO_2R_d$, $NR_eR_f$, or $N(R_e)C(O)R_f$ in which each of $R_d$, $R_e$, and $R_f$, independently, is H, alkyl, alkenyl, alkynyl, cycloalkyl, heterocycloalkyl, aryl, heteroaryl, halo, cyano, amine, nitro, hydroxy, or alkoxy.

Other HDAC inhibitors are known in the art, and are disclosed in U.S. Pat. No. 8,648,092 to Lee et al., incorporated herein by this reference, which discloses imidazo[1,2-a]pyridine derivatives; U.S. Pat. No. 8,637,547 to Davidson et al., incorporated herein by this reference, which discloses cyclopentyl (2S)-cyclohexyl[({6-[3-(hydroxyamino)-3-oxopropyl]pyridin-3-yl}methyl)amino]acetate; U.S. Pat. No. 8,614,223 to van Duzer et al., incorporated herein by this reference, which discloses pyrimidine hydroxy amide compounds; U.S. Pat. No. 8,609,678 to van Duzer et al., incorporated herein by this reference, which discloses reverse amide compounds including a zinc chelator group; U.S. Pat. No. 8,603,521 to Loury et al., incorporated herein by this reference, which discloses N-hydroxy-4-{2-[3-(N,N-dimethylaminomethyl)benzofuran-2-ylcarbonylamino]ethoxy}-benzamide; U.S. Pat. No. 8,598,168 to Moradei et al., incorporated herein by this reference, which discloses ortho-aminobenzamides; U.S. Pat. No. 8,592,444 by Varasi et al., incorporated herein by this reference, which discloses spirocyclic derivatives; U.S. Pat. No. 8,592,441 to Verdonck et al., incorporated herein by this reference, which discloses substituted indolyl alkylamino derivatives; U.S. Pat. No. 8,557,825 to Van Emelen et al., incorporated herein by this reference, which discloses sulfonyl derivatives; U.S. Pat. No. 8,546,588 by Blackburn et al., incorporated herein by this reference, which discloses substituted hydroxamic acids; U.S. Pat. No. 8,524,711 to Angibaud et al., incorporated herein by this reference, which discloses substituted amino compounds; U.S. Pat. No. 8,513,237 to Van Emelen et al., incorporated herein by this reference, which discloses sulfonylamino derivatives; U.S. Pat. No. 8,501,737 to Van Emelen, incorporated herein by this reference, which discloses piperazinyl, piperidinyl, and morpholinyl derivatives; U.S. Pat. No. 8,492,401 to Oalmann et al., incorporated herein by this reference, which discloses thiazolopyridine derivatives; U.S. Pat. No. 8,491,927 to Epner et al., incorporated herein by this reference, which discloses entinostat, panobinostat, vorinostat, and romedepsin; and U.S. Pat. No. 8,476,255 by Rajgopal et al., incorporated herein by this reference, which discloses stilbene-like compounds. Other histone deacetylase inhibitors are known in the art.

Accordingly, the following compositions and methods are within the scope of the present invention: (1) compositions and methods employing a derivative or analog of meisoindigo, including one of Alternatives (1)-(486) above, together with an HDAC inhibitor; (2) compositions and methods employing a derivative or analog of meisoindigo, including one of Alternatives (1)-(486) above, together with an HDAC inhibitor and an Nek9 inhibitor; (3) compositions and methods employing a derivative or analog of meisoindigo, including one of Alternatives (1)-(486) above, together with an HDAC inhibitor and an anti-Nek9 antibody; (4) compositions and methods employing a derivative or analog of meisoindigo, including one of Alternatives (1)-(486) above, together with an HDAC inhibitor and an agent that inhibits Nek9 expression; and (4) compositions and methods employing a derivative or analog of meisoindigo, including one of Alternatives (1)-(486) above, together with an HDAC inhibitor and an inhibitor of at least one of Mad2, BubR1, and Mps1.

Another aspect of the present invention is a composition to improve the efficacy and/or reduce the side effects of suboptimally administered drug therapy comprising an alternative selected from the group consisting of:

(i) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;

(ii) a composition comprising:
  (a) a therapeutically effective quantity of a therapeutic agent, a modified therapeutic agent or a derivative, analog, or prodrug of a therapeutic agent or modified therapeutic agent; and
  (b) at least one additional therapeutic agent, therapeutic agent subject to chemosensitization, therapeutic agent subject to chemopotentiation, diluent, excipient, solvent system, or drug delivery system, wherein the composition possesses increased therapeutic efficacy or reduced side effects as compared with an unmodified therapeutic agent;

(iii) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;

(iv) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and (v) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent.

Typically, the composition possesses increased efficacy or reduced side effects for cancer therapy. Typically, the unmodified therapeutic agent is indirubin, an analog of indirubin, or a derivative of indirubin or of an analog of indirubin, as described above. In another alternative, the therapeutically active agent is an agent selected from the group consisting of Alternatives (1)-(486), the modified therapeutic agent is a modification of an agent selected from the group consisting of Alternatives (1)-(486), and the derivative, analog, or prodrug is a derivative, analog, or prodrug of an agent selected from the group consisting of Alternatives (1)-(486) or of a modification of an agent selected from the group consisting of Alternatives (1)-(486). Alternatives (1)-(486) are described above. Typically, the unmodified therapeutic agent is meisoindigo, and, where the composition includes a modified therapeutic agent, the modified therapeutic agent is typically a modification of meisoindigo.

In one alternative, the composition comprises a drug combination comprising:

(i) indirubin, an analog of indirubin, or a derivative of indirubin or of an analog of indirubin; and (ii) an additional therapeutic agent selected from the group consisting of:
 (a) topoisomerase inhibitors;
 (b) fraudulent nucleosides;
 (c) fraudulent nucleotides;
 (d) thymidylate synthetase inhibitors;
 (e) signal transduction inhibitors;
 (f) cisplatin or platinum analogs;
 (g) alkylating agents;
 (h) anti-tubulin agents;
 (i) antimetabolites;
 (j) berberine;
 (k) apigenin;
 (l) amonafide;
 (m) colchicine or an analog thereof;
 (n) genistein;
 (o) etoposide;
 (p) cytarabine;
 (q) a camptothecin;
 (r) a vinca alkaloid;
 (s) 5-fluorouracil;
 (t) curcumin;
 (u) an NF-κB inhibitor;
 (v) rosmarinic acid;
 (w) mitoguazone;
 (x) tetandrine;
 (y) an antineoplastic agent not metabolized by cytochrome P450 CYP 1A2 or CYP 2C19;
 (z) a biological therapy;
 (aa) a tyrosine kinase inhibitor;
 (ab) all-trans-retinoic acid;
 (ac) an arsenical;
 (ad) hydroxyurea;
 (ae) thioguanine;
 (af) mercaptopurine;
 (ag) homoharringtonine;
 (ah) oridonin;
 (aj) uracil mustard;
 (ak) nilotinib;
 (al) dasatinib;
 (am) lonidamine;
 (an) 5-azacytidine;
 (ao) thalidomide or an analog thereof;
 (ap) an EGFR inhibitor such as erlotinib, afatinib, lapatinib, or dacomitinib;
 (aq) a gold salt such as aurothiomalate or aurothioglucose;
 (ar) dibromodulcitol;
 (as) dianhydrogalactitol;
 (at) decitabine; and
 (au) a proteasome inhibitor.

In this alternative, when the additional therapeutic agent is an alkylating agent, the alkylating agent can be, but is not limited to, an alkylating agent selected from the group consisting of BCNU, BCNU wafers, CCNU, bendamustine (Treanda), and temozolimide (Temodar).

In another alternative, the composition comprises:

(i) indirubin, an analog of indirubin, or a derivative of indirubin or of an analog of indirubin; and (ii) a therapeutic agent subject to chemosensitization selected from the group consisting of:
 (a) topoisomerase inhibitors;
 (b) fraudulent nucleosides;
 (c) fraudulent nucleotides;
 (d) thymidylate synthetase inhibitors;
 (e) signal transduction inhibitors;
 (f) cisplatin or platinum analogs;
 (g) alkylating agents;
 (h) anti-tubulin agents;
 (i) antimetabolites;
 (j) berberine;
 (k) apigenin;
 (l) amonafide;
 (m) vinca alkaloids;
 (n) 5-fluorouracil;
 (o) curcumin;
 (p) NF-κB inhibitors;
 (q) rosmarinic acid;
 (r) mitoguazone;
 (s) tetrandrine; and
 (t) a proteasome inhibitor.

In still another alternative, the composition comprises:

(i) indirubin, an analog of indirubin, or a derivative of indirubin or of an analog of indirubin; and (ii) a therapeutic agent subject to chemopotentiation selected from the group consisting of:
 (a) topoisomerase inhibitors;
 (b) fraudulent nucleosides;
 (c) fraudulent nucleotides;
 (d) thymidylate synthetase inhibitors;
 (e) signal transduction inhibitors;
 (f) cisplatin or platinum analogs;
 (g) alkylating agents;
 (h) anti-tubulin agents;
 (i) antimetabolites;
 (j) berberine;
 (k) apigenin;
 (l) amonafide;
 (m) vinca alkaloids;
 (n) 5-fluorouracil;
 (o) curcumin;
 (p) NF-κB inhibitors;
 (q) rosmarinic acid;
 (r) mitoguazone;
 (s) tetrandrine;
 (t) biotherapeutics; and
 (u) a proteasome inhibitor.

wherein the indirubin, an analog of indirubin, or a derivative of indirubin or of an analog of indirubin acts as a chemopotentiator.

In this alternative, wherein the additional therapeutic agent is a biotherapeutic, the biotherapeutic can be, but is not limited to, a biotherapeutic selected from the group consisting of Avastin, Herceptin, Rituxan, and Erbitux.

In yet another alternative, the therapeutic agent is indirubin, an analog of indirubin, or a derivative of indirubin or of an analog of indirubin and the indirubin, an analog of indirubin, or a derivative of indirubin or of an analog of indirubin is subjected to a bulk drug product improvement, wherein the bulk drug product improvement is selected from the group consisting of:
 (a) salt formation;
 (b) preparation as a homogeneous crystal structure;
 (c) preparation as a pure isomer;
 (d) increased purity;
 (e) preparation with lower residual solvent content; and
 (f) preparation with lower residual heavy metal content.

In still another alternative, the therapeutic agent is indirubin, an analog of indirubin, or a derivative of indirubin or of an analog of indirubin and the composition comprises a diluent, wherein the diluent is selected from the group consisting of:
 (a) an emulsion;
 (b) dimethylsulfoxide (DMSO);
 (c) N-methylformamide (NMF)
 (d) DMF;
 (e) ethanol;
 (f) benzyl alcohol;
 (g) dextrose-containing water for injection;
 (h) Cremophor;
 (i) cyclodextrin; and
 (j) PEG.

In still another alternative, the therapeutic agent is indirubin, an analog of indirubin, or a derivative of indirubin or of an analog of indirubin and the composition comprises a solvent system, wherein the solvent system is selected from the group consisting of:
 (a) an emulsion;
 (b) dimethylsulfoxide (DMSO);
 (c) N-methylformamide (NMF)
 (d) DMF;
 (e) ethanol;
 (f) benzyl alcohol;
 (g) dextrose-containing water for injection;
 (h) Cremophor;
 (i) cyclodextrin; and
 (j) PEG.

In yet another alternative, the therapeutic agent is indirubin, an analog of indirubin, or a derivative of indirubin or of an analog of indirubin and the composition comprises an excipient, wherein the excipient is selected from the group consisting of:
 (a) mannitol;
 (b) albumin;
 (c) EDTA;
 (d) sodium bisulfite;
 (e) benzyl alcohol;
 (f) a carbonate buffer;
 (g) a phosphate buffer; and
 (h) methylcellulose.

In still another alternative, the therapeutic agent is indirubin, an analog of indirubin, or a derivative of indirubin or of an analog of indirubin and the indirubin, an analog of indirubin, or a derivative of indirubin or of an analog of indirubin is incorporated into a dosage form selected from the group consisting of:
 (a) tablets;
 (b) capsules;
 (c) topical gels;
 (d) topical creams;
 (e) patches;
 (f) suppositories; and
 (g) lyophilized dosage fills.

In yet another alternative, the therapeutic agent is indirubin, an analog of indirubin, or a derivative of indirubin or of an analog of indirubin and the indirubin, an analog of indirubin, or a derivative of indirubin or of an analog of indirubin is incorporated into a dosage kit and packaging selected from the group consisting of amber vials to protect from light and stoppers with specialized coatings to improve shelf-life stability.

In still another alternative, the therapeutic agent is indirubin, an analog of indirubin, or a derivative of indirubin or of an analog of indirubin and the composition comprises a drug delivery system selected from the group consisting of:
 (a) nanocrystals;
 (b) bioerodible polymers;
 (c) liposomes;
 (d) slow release injectable gels; and
 (e) microspheres.

In still another alternative, the therapeutic agent is indirubin, an analog of indirubin, or a derivative of indirubin or of an analog of indirubin and the indirubin, an analog of indirubin, or a derivative of indirubin or of an analog of indirubin is present in the composition in a drug conjugate form selected from the group consisting of:
 (a) a polymer system;
 (b) polylactides;
 (c) polyglycolides;
 (d) amino acids;
 (e) peptides; and
 (f) multivalent linkers.

In yet another alternative, the therapeutic agent is a modified indirubin, an analog of indirubin, or a derivative of indirubin or of an analog of indirubin and the modification is selected from the group consisting of:
 (a) alteration of side chains to increase or decrease lipophilicity;
 (b) addition of an additional chemical functionality to alter a property selected from the group consisting of reactivity, electron affinity, and binding capacity; and
 (c) alteration of salt form.

In still another alternative, the therapeutic agent is indirubin, an analog of indirubin, or a derivative of indirubin or of an analog of indirubin and the indirubin, an analog of indirubin, or a derivative of indirubin or of an analog of indirubin is in the form of a prodrug system, wherein the prodrug system is selected from the group consisting of:
 (a) the use of enzyme sensitive esters;
 (b) the use of dimers;
 (c) the use of Schiff bases;
 (d) the use of pyridoxal complexes;
 (e) the use of caffeine complexes;
 (f) the use of N-substituted carbohydrate derivatives;
 (g) the use of Mannich N-oxides;
 (h) the use of products of reaction with an acylating or carbamylating agent;
 (i) the use of hexanoate conjugates;
 (j) the use of polymer-agent conjugates; and
 (k) the use of prodrugs that are subject to redox activation.

In yet another alternative, the therapeutic agent is indirubin, an analog of indirubin, or a derivative of indirubin or of an analog of indirubin and the composition further comprises at least one additional therapeutic agent to form a multiple drug system, wherein the at least one additional therapeutic agent is selected from the group consisting of:
(a) an inhibitor of multi-drug resistance;
(b) a specific drug resistance inhibitor;
(c) a specific inhibitor of a selective enzyme;
(d) a signal transduction inhibitor;
(e) an inhibitor of a repair enzyme; and
(f) a topoisomerase inhibitor with non-overlapping side effects.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992), all of which are incorporated herein by this reference.

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg.

Plasma concentrations in the subjects may be between about 100 μM to about 1000 μM. In some embodiments, the plasma concentration may be between about 200 μM to about 800 μM. In other embodiments, the concentration is about 300 μM to about 600 μM. In still other embodiments the plasma concentration may be between about 400 to about 800 μM. Administration of prodrugs is typically dosed at weight levels which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-α-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated, as described above.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 to Nardella, U.S. Pat. No. 6,921,722 to Nardella, U.S. Pat. No. 7,314,886 to Chao et al., and U.S. Pat. No. 7,446,122 to Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

For administration of meisoindigo in patients with acute myelogenous leukemia (AML), the initial dosage can be one of: (i) 50 m.g. b.i.d. for 28 days; (ii) 75 mg b.i.d. for 28 days; (iii) 100 mg b.i.d. for 28 days; or (iv) 125 mg b.i.d. for 28 days. The meisoindigo is typically provided at 25 mg and 50 mg dosage strengths in soft gel capsules. The meisoindigo can be administered orally, twice daily, once in the morning immediately after breakfast and once in the evening immediately after dinner. The capsules are swallowed whole with a glass of water. The capsules should not be chewed or crushed.

The use of meisoindigo is particularly indicated for patients who meet the following criteria: (i) male or female patients 18 years of age or over with AML, acute lymphocytic leukemia (ALL), or high-risk myelodysplastic syndrome (MDS) (IPSS≥Int-2), who are unsuitable for treatment with standard chemotherapy regimens, e.g., elderly (≥70 years of age), poor risk (e.g., adverse risk karyotype), or who have failed up to three lines of therapy; this can include patients with secondary AML; (ii) life expectancy of greater than 3 months in relation to diseases other than AML, ALL, or MDS; (iii) ECOG performance status 0-3; (iv) adequate hepatic function as defined by bilirubin≤1.5× the upper limit of normal (ULN) and aspartate aminotransferase (AST) and alanine aminotransferase (ALT)≤2.5× ULN; (v) adequate renal function, with serum creatinine ≤1.5×ULN; (vi) no uncontrolled active infection; and (vii) hydroxyurea ceased 48 hours prior to initial administration of meisoindigo.

Doses can be escalated to the maximum dose if no dose-limiting toxicities are seen at a higher dose.

Specifically, meisoindigo induces apoptosis via suppression of Bcl-2 and also induces cell cycle arrest via the upregulation of negative cell cycle regulators p21 and p27.

Meisoindigo can be used together with G-CSF for the treatment or prevention of severe neutropenic infection requiring intravenous antibiotics. Meisoindigo can also be used together with antifungal agents such as voriconazole; azole antifungals might have some effect on higher meisoindigo exposures, so that dosage adjustment can be required when meisoindigo is administered together with azole antifungal agents.

The invention is illustrated by the following Examples. These Examples are included for illustrative purposes only and are not intended to limit the invention.

EXAMPLE 1

Synthesis of Meisoindigo

Prior Process

To synthesis meisoindigo, typically, add equal molar amount of 2-hydroxyindole and N-methyl-indolinyl-diketone, glacial acetic acid (2.0 L of glacial acetic acid for one mole of the reaction substances), and hydrochloric acid (concentrated, 6.67 ml of HCl for one mole of the reaction substances) into three-neck flask, heat to 70-80° C., stir for 2 h, cool to room temperature. Bulk brown crystal precipitates are then formed. Filter, and sequentially wash with glacial acetic acid, dH2O, and ethanol. The melting point is measured. It should be between 235-237° C. Filter, and sequentially wash with glacial acetic acid, dH2O, and ethanol. Melt point is measured. It should be between 235-237° C.

Newly Developed Process

An outline of the process is shown in Table 1.

TABLE 1

| Reaction solution* | Reaction Conditions | Purification Process |
|---|---|---|
| Acetic acid (15 v) Conc. HCl (0.05 v) | 70-80° C. for 3 hrs | Cool to 25-30° C., filter, wash with acetic acid (5 v), water (10 v) and then ethanol (10 v) |

The asterisk (*) indicates that oxindole (1 equivalent) and N-methylisatin (1 equivalent) were added to the reaction solution.

The characterization of the reaction was as follows: Reaction mass: SM1 (0.45%), SM2 (8.7%), drug content (73%). Solid: purity (99.9%), SM1 (0.03%), unknown (RRT 0.86, 0.09%). Yield: 51%. Both 5-g and 50-g scales yield solid at 99.88% purity Only acetic acid (5 v) used in purification process for a 10-g batch yielded solid at 99.95%.

Effect of Process Parameters
Reaction Temperature

The reaction was carried out as described above with acetic acid and concentrated HCl except that the reaction temperature was controlled at 50-55° C. or 100-110° C., purified with acetic acid (5 v). Results are shown in Table 2.

TABLE 2

| Scale | Reaction Temperature | Reaction Time | Mass content, % | Solid content, % |
|---|---|---|---|---|
| 10 g | 100-110° C. | 1 h | 53 | 99.82 |
| 10 g | 50-55° C. | 5 h | 65 | 99.91 |
|  |  | 6 h | 77 |  |
|  |  | 7 h | 73 |  |
| 25 g | 50-55° C. | 4 h | 59 | 99.1 |
|  |  | 5 h | 63 |  |
|  |  | 6 h | 64 |  |

Reaction Process: Effect of Acetic Acid

Results with varying volumes of acetic acid are shown in Table 3. The same reaction conditions were used as for Table 1 except for the amount of acetic acid. The solid was washed with acetic acid (5 v) and water (10 v). The above-purified solid was washed with ethanol (10 v) to get 96.3% pure compound.

TABLE 3

|  |  |  | Drug Content (%) |  |
|---|---|---|---|---|
| Acetic Acid | Reaction Time | Reaction Mass | Crude Solid | Note |
| 25 v | 3 h | 57 | 99.6 |  |
| 15 v | 3 h | 73 | 99.9 |  |
| 10 v | 3 h | 84 | 99.8 | (intermediate) |
| (Intermediate only used) |  |  |  | 31% |
|  |  |  |  | 16% |
| 7.5 v + water (7.5 v) | 29 | 39 | 95.1 | 18% |
|  | 68 | 56 |  |  |
|  | 76 | 58 |  |  |
| 5 v | 3 h | 71 | 79.6 |  |
|  |  |  | 84.8 |  |

Effect of Concentrated HCl (Presence/Absence or Using Other Acids)

These results are shown in Table 4. The same reaction conditions were used as for Table 1 except for the amount of hydrochloric acid (in some cases, indicated by the superscript[2], the concentrated hydrochloric acid was replaced by a catalytic amount of sulfuric acid or trifluoroacetic acid). In the experiment indicated by the superscript[3], acetic acid was reduced from 15 v to 7.5 v with additional 7.5 v of water.

TABLE 4

|  |  |  | Drug Content (%) |  |
|---|---|---|---|---|
| Acetic Acid[1] | Reaction Time | Reaction Mass | Crude Solid | Note |
| 25 v | 3 h | 57 | 99.6 |  |
| 15 v | 3 h | 73 | 99.9 |  |
| 10 v | 3 h | 84 | 99.8 | (intermediate) |
| (Intermediate only used) |  |  |  | 31% |
|  |  |  |  | 16% |
| 7.5 v + water (7.5 v) | 29 | 39 | 95.1 | 18% |
|  | 68 | 56 |  |  |
|  | 76 | 58 |  |  |
| 5 v | 3 h | 71 | 79.6[2] |  |
|  |  |  | 84.8[3] |  |

Effect of HCl Concentration

The effect of varying HCl concentration is shown in Tables 5, 6, 7, and 8. In Table 5, superscript[5] indicates that acetic acid/concentrated HCl was replaced with various concentrations of HCl. Acetic acid (5 v) was added after 46 hours to the reaction solution. Tables 6 and 7 show the effect of several solvents used for the purification process. Table 8 shows the results of varying purification processes of the solid from an 8N HCl process.

TABLE 5

| 8N HCl (15 v) | 6 h | 51 | 96.4[5] | |
|---|---|---|---|---|
| 10-g scale | 10 h | 96 | | |
| 8N HCl (15 v) | 4 h | 68 | 97.2[5] | SM-2 |
| 50-g scale | 6 h | 92 | | |
| | 8 h | 96 | | |
| | 10 h | 95 | | |
| 8N HCl (15 v) | 10 h | 93.3 | 96.3 | 2.1 |
| 10-g scale | 12 h | 93.3 | | 2.0 |
| | 14 h | 93.8 | | 1.8 |
| 8N HCl (15 v) | 10 h | | (wet) | Yield |
| 100-g scale | | | 94.4 | 96% |

TABLE 6

| Solvent | Temperature/time | Followed by | Purity |
|---|---|---|---|
| Ethanol (10 v) | 70-75° C. for 1 h | 25-30° C. for 1 h | 98.5% |
| Ethyl acetate (10 v) | 65-70° C. for 1 h | 25-30° C. for 1 h | 97.0% |
| IPA (5 v) | 70-75° C. for 1 h | 25-30° C. for 1 h | 98.5% |
| Acetone (5 v) | 55-60° C. for 1 h | 25-30° C. for 1 h | 97.2% |
| Acetic acid (5 v) | 70-75° C. for 1 h | 25-30° C. for 1 h | 98.8% |

TABLE 7

| Solvent (15 v) | Temperature/time | Followed by | Purity |
|---|---|---|---|
| Acetic acid | 70-75° C. for 1 h | 25-30° C. for 1 h | 98.94% |
| 50% HOAc in EtOH | 70-75° C. for 1 h | 25-30° C. for 1 h | 99.48% |

TABLE 8

| Scale | Solvent (15 v) | 70-75° C. | 25-30° C. | Purity |
|---|---|---|---|---|
| 10-g | Acetic acid | 1 h | 1 h | 99.6% |
| | 50% HOAc in EtOH | 1 h | 1 h | 99.85% |
| 50-g | 50% HOAc in EtOH | 1 h | 1 h | |
| | 50% HOAc in EtOH | — | 3 h | |

Effect of Variation of N-Methylisatin Equivalents

The effect of varying the quantity of N-methylisatin is shown in Table 9.

TABLE 9

| | | Drug Content (%) | | |
|---|---|---|---|---|
| Scale | Reaction Time | Reaction Mass | Crude Solid | N-Methylisatin equ. |
| 50 g | 3 h | 73 | 99.9 | 1 |
| 10 g | 3 h | 66 | 99.95 | 0.9 |
| 10 g | 3 h | 58 | 99.2% | 1.2 |

Modification of the Process for GMP Manufacturing

Reaction material with 8N HCl had HCl fumes during filtration. Therefore the process was modified using acetic acid and 8N HCl at 1:1 ratio (5v), heated at 70-80° C. for 6 hours followed by recrystallization with ethanol or methanol yielding drug with purity of 99.7% and 99.45%, respectively.

10-g scale lot yielded 63% and 50-g scale yielded 67.5% with purity of 99.37% and impurity profile of 50-g scale (Lot B502/08) as described below. If the HCl was reduced to catalytic amount, the yield was reduced to 44%, about 50% conversion after 8 hrs. Results are shown in Table 10. Table 11 shows the effect of reaction time on impurity profiles. Table 12 shows purity and yield for several batches. For the results shown in Table 12, superscript[1] indicates that, to improve the thickness of reaction mass, volume was increased; the reaction was completed in 2 hours; superscript[2] indicates that purity was determined in the crude material; and superscript[3] indicates that the purity in crude material was 99.6%, purified material was 99.9% using ethanol volume of 6 v of wet material.

TABLE 10

| RRT | Crude | Purified with MeOH |
|---|---|---|
| 0.45 | 0.04 | 0.01 (KSM-1) |
| 0.59 | — | — (intermediate) |
| 0.87 | 0.25 | 0.09 |
| 0.91 | 0.11 | 0.02 |
| 0.96 | 0.35 | 0.17 |

TABLE 11

| RT | RRT | 2 h | 3 h | 4 h | 5 h | 6 h | 7 h | Crude |
|---|---|---|---|---|---|---|---|---|
| 7.2 | 0.45 | 5.71 | 4.99 | 4.76 | 4.57 | 4.76 | 5.1 | 0.04 |
| 8.75 | 0.54 | 0.37 | 0.51 | 0.74 | 0.85 | 1.03 | 1.39 | 0.03 |
| 11.26 | 0.70 | 0.8 | 0.74 | 0.68 | 0.68 | 0.73 | 0.77 | 0.02 |
| 11.86 | 0.74 | 4.08 | 3.77 | 3.59 | 3.6 | 3.8 | 4.12 | 0.09 |
| 12.42 | 0.77 | 0.89 | 0.81 | 0.79 | 0.75 | 0.82 | 0.8 | 0.02 |
| 14.02 | 0.87 | 5.94 | 5.67 | 5.41 | 5.52 | 5.71 | 6.46 | 0.25 |
| 14.19 | 0.88 | 6.32 | 5.79 | 5.78 | 5.53 | 5.86 | 6.42 | 0.16 |
| 14.63 | 0.91 | 2.42 | 2.31 | 2.4 | 2.32 | 2.54 | 2.89 | 0.11 |
| 15.4 | 0.96 | 0.1 | 0.2 | 0.21 | 0.27 | 0.34 | 0.46 | 0.35 |
| 16.12 | 1.00 | 71.57 | 73.26 | 73.84 | 73.74 | 72.02 | 68.59 | 98.66 |

TABLE 12

| Lot B502 | Scale | HOAc:8N HCl | % Purity | Yield |
|---|---|---|---|---|
| 08 | 50 g | 1:1, 5 V each | 99.37 | 68% |
| 10 | 100 g | 1:1, 5 V each | 99.06 | 75% |
| 12 | 50 g | 1:1, 7.5 V each[1] | 99.73[2] | 79% |
| 13 | 100 g | 1:1, 7.5 V each | 99.90[3] | 80% |

Preparation of Intermediate Reference Material

As shown in the study of the effect of HCl concentration, it was shown that a significant amount (82%) of intermediate was formed after reaction in 1N HCl for 48 hours with drug content of 11.5% in the crude solid. This intermediate was not stable and degraded upon storage at room temperature. A second reaction with crude solid containing 75.2% intermediate and 21.1% drug was purified to prepare the intermediate reference material.

EXAMPLE 2

Effect of Meisoindigo on Viability of Cancer Cell Lines

FIG. 1 shows the viability of the AML cell line MV 4-11 (FLT-3 ITD) after meisoindigo treatments. Viability at 48 hours is shown by (♦); viability at 24 hours is shown by (■). Results are shown for a control, 1% DMSO without meisoindigo, 0.1 μM meisoindigo, 1 μM meisoindigo, 10 μM meisoindigo, and 100 μM meisoindigo.

FIG. 2 shows the viability of a number of myeloid cell lines in terms of the percentage of viable cells after 24 hours of treatment with meisoindigo. Results are shown for a control, 1% DMSO without meisoindigo, 0.1 µM meisoindigo, 1 µM meisoindigo, 10 µM meisoindigo, and 100 µM meisoindigo.

FIG. 3 shows the viability of a number of additional myeloid cell lines in terms of the percentage of viable cells after 24 hours of treatment with meisoindigo. Results are shown for a control, 1% DMSO without meisoindigo, 0.1 µM meisoindigo, 1 µM meisoindigo, 10 µM meisoindigo, and 100 µM meisoindigo.

FIG. 4 shows the targeting of kinases by meisoindigo.

FIG. 5 shows the overall survival with meisoindigo, alone and with hydroxyurea, in chronic myelogenous leukemia, together with the results for busulfan.

These results indicate that meisoindigo is effective in killing a number of malignant cell lines, particularly AML cell lines.

EXAMPLE 3

Effect of Meisoindigo on Kinases

To determine the effect of meisoindigo on a large number of kinases, including Nek9, a scanning procedure was performed with a large number of human kinases to determine the inhibition of these kinases by meisoindigo.

The scanning procedure is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag. This procedure is described in T. A. Carter et al., "Inhibition of Drug-Resistant Mutants of ABL, KIT, and EGF Receptor Kinases," *Proc. Natl. Acad. Sci. USA* 102: 11011-11016 (2005), incorporated herein by this reference.

Kinase assays were carried out as follows: For most assays, kinase-tagged T7 phage strains were grown in parallel in 24-well blocks in an *Escherichia coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 µm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40×stocks in 100% DMSO and directly diluted into the assay. All reactions were performed in polypropylene 384-well plates in a final volume of 0.04 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

The compounds were screened at the requested concentrations, and results for primary screen binding interactions were reported as "% Ctrl," where lower numbers indicate stronger hits (i.e., an increased degree of inhibition of kinase activity) as follows (Equation (1)):

$$\left(\frac{\text{test compound signal} - \text{positive control signal}}{\text{negative control signal} - \text{positive control signal}}\right) \times 100 \quad (1)$$

wherein: "test compound signal" is the signal for the test compound (meisoindigo); "positive control signal" is a control compound (0% Ctrl); and "negative control signal" is DMSO (100% Ctrl).

The selectivity score (S) is a quantitative measure of compound selectivity. It is calculated by dividing the number of kinases that bind to the compound by the total number of distinct kinases tested, excluding mutant variants. Specifically, S(35)=(number of non-mutant kinases with % Ctrl <35)/(number of non-mutant kinases tested); S(10)=(number of non-mutant kinases with % Ctrl <10)/(number of non-mutant kinases tested); and S(1)=(number of non-mutant kinases with % Ctrl <1)/(number of non-mutant kinases tested).

The results for screening of meisoindigo with a large number of kinases is shown in FIG. 6. FIG. 6, shown as FIG. 6A, FIG. 6B, FIG. 6C, FIG. 6D, FIG. 6E, FIG. 6F, FIG. 6G, FIG. 6H, FIG. 6I, and FIG. 6A, is a table showing the results of a screen for kinase inhibition by meisoindigo, wherein meisoindigo shows significant inhibition of the kinase Nek9. FIG. 6A shows results for AAK1 to CDK7. FIG. 6B shows results for ADCK3 to DADK1. FIG. 6C shows results for DAPK2 to GAK. FIG. 6D shows results for EGFR(L858R, T790M) to JAK1(JH2DOMAIN-PSEUDOKINASE). FIG. 6E shows results for JAK2(JH1 DOMAIN-CATALYTIC) to MYLK2. FIG. 6F shows results for LYN to PAK6. FIG. 6G shows results for PAK7 to RIPK5. FIG. 6H shows results from PIK3A (M1043I) to SRPK1. FIG. 6I shows results for SRPK2 to TNK1. FIG. 6J shows results for TNK2 to ZAK.

The selectivity score for meisoindigo is shown in Table 13.

TABLE 13

| Compound Name | Selectivity Score Type | Number of Hits | Number of Non-Mutant Kinases | Screening Concentration, nm | Selectivity Score |
|---|---|---|---|---|---|
| Meisoindigo | S(35) | 1 | 385 | 50000 | 0.003 |
| Meisoindigo | S(10) | 0 | 385 | 50000 | 0 |
| Meisoindigo | S(1) | 0 | 385 | 50000 | 0 |

Advantages of the Invention

The present invention provides more effective and efficient methods of using therapeutic drugs that have previously been evaluated for treatment of a number of diseases and conditions, especially hyperproliferative disorders, but whose evaluations resulted in a premature conclusion of lack of sufficient efficacy or of occurrence of side effects sufficient to prevent the use of the therapeutic drug. Such more effective and efficient methods of therapeutic drugs will improve efficacy, prevent or reduce the occurrence of significant side effects, and will identify categories of patients and situations in which such drugs can be effectively employed. These therapeutic drugs include, but are not limited to, indirubin, an analog of indirubin, or a derivative of indirubin or of an analog of indirubin, in particular, meisoindigo.

Methods according to the present invention possess industrial applicability for the preparation of a medicament for the treatment of a number of diseases and conditions, especially hyperproliferative diseases, and possess industrial applicability as pharmaceutical compositions.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method of treating a disease or condition treatable by administration of a Nek9 inhibitor to a subject in need thereof comprising administration of an effective quantity of a therapeutically active agent, wherein the disease or condition treatable by administration of the Nek9 inhibitor is selected from the group consisting of acute promyelocytic leukemia, acute lymphoblastic leukemia, and myelodysplastic syndrome, and wherein the therapeutically active agent is selected from the group consisting of meisoindigo and the salts, solvates, and prodrugs thereof.

2. The method of claim 1 wherein the therapeutically active agent is meisoindigo.

* * * * *

SEQUENCE LISTING

<160> NUMBER OF SEQ ID NOS: 5

<210> SEQ ID NO 1
<211> LENGTH: 979
<212> TYPE: PRT
<213> ORGANISM: Homo sapiens

<400> SEQUENCE: 1

Met Ser Val Leu Gly Glu Tyr Glu Arg His Cys Asp Ser Ile Asn Ser
1               5                   10                  15

Asp Phe Gly Ser Glu Ser Gly Gly Cys Gly Asp Ser Ser Pro Gly Pro
            20                  25                  30

Ser Ala Ser Gln Gly Pro Arg Ala Gly Gly Gly Ala Ala Glu Gln Glu
        35                  40                  45

Glu Leu His Tyr Ile Pro Ile Arg Val Leu Gly Arg Gly Ala Phe Gly
    50                  55                  60

Glu Ala Thr Leu Tyr Arg Arg Thr Glu Asp Asp Ser Leu Val Val Trp
65                  70                  75                  80

Lys Glu Val Asp Leu Thr Arg Leu Ser Glu Lys Glu Arg Arg Asp Ala
                85                  90                  95

Leu Asn Glu Ile Val Ile Leu Ala Leu Leu Gln His Asp Asn Ile Ile
            100                 105                 110

Ala Tyr Tyr Asn His Phe Met Asp Asn Thr Thr Leu Leu Ile Glu Leu
        115                 120                 125

Glu Tyr Cys Asn Gly Gly Asn Leu Tyr Asp Lys Ile Leu Arg Gln Lys
    130                 135                 140

Asp Lys Leu Phe Glu Glu Glu Met Val Val Trp Tyr Leu Phe Gln Ile
145                 150                 155                 160

-continued

```
Val Ser Ala Val Ser Cys Ile His Lys Ala Gly Ile Leu His Arg Asp
            165                 170                 175
Ile Lys Thr Leu Asn Ile Phe Leu Thr Lys Ala Asn Leu Ile Lys Leu
            180                 185                 190
Gly Asp Tyr Gly Leu Ala Lys Lys Leu Asn Ser Glu Tyr Ser Met Ala
            195                 200                 205
Glu Thr Leu Val Gly Thr Pro Tyr Tyr Met Ser Pro Glu Leu Cys Gln
            210                 215                 220
Gly Val Lys Tyr Asn Phe Lys Ser Asp Ile Trp Ala Val Gly Cys Val
225                 230                 235                 240
Ile Phe Glu Leu Leu Thr Leu Lys Arg Thr Phe Asp Ala Thr Asn Pro
            245                 250                 255
Leu Asn Leu Cys Val Lys Ile Val Gln Gly Ile Arg Ala Met Glu Val
            260                 265                 270
Asp Ser Ser Gln Tyr Ser Leu Glu Leu Ile Gln Met Val His Ser Cys
            275                 280                 285
Leu Asp Gln Asp Pro Glu Gln Arg Pro Thr Ala Asp Glu Leu Leu Asp
            290                 295                 300
Arg Pro Leu Leu Arg Lys Arg Arg Glu Met Glu Glu Lys Val Thr
305                 310                 315                 320
Leu Leu Asn Ala Pro Thr Lys Arg Pro Arg Ser Ser Thr Val Thr Glu
            325                 330                 335
Ala Pro Ile Ala Val Val Thr Ser Arg Thr Ser Glu Val Tyr Val Trp
            340                 345                 350
Gly Gly Gly Lys Ser Thr Pro Gln Lys Leu Asp Val Ile Lys Ser Gly
            355                 360                 365
Cys Ser Ala Arg Gln Val Cys Ala Gly Asn Thr His Phe Ala Val Val
            370                 375                 380
Thr Val Glu Lys Glu Leu Tyr Thr Trp Val Asn Met Gln Gly Gly Thr
385                 390                 395                 400
Lys Leu His Gly Gln Leu Gly His Gly Asp Lys Ala Ser Tyr Arg Gln
            405                 410                 415
Pro Lys His Val Glu Lys Leu Gln Gly Lys Ala Ile Arg Gln Val Ser
            420                 425                 430
Cys Gly Asp Asp Phe Thr Val Cys Val Thr Asp Glu Gly Gln Leu Tyr
            435                 440                 445
Ala Phe Gly Ser Asp Tyr Tyr Gly Cys Met Gly Val Asp Lys Val Ala
            450                 455                 460
Gly Pro Glu Val Leu Glu Pro Met Gln Leu Asn Phe Phe Leu Ser Asn
465                 470                 475                 480
Pro Val Glu Gln Val Ser Cys Gly Asp Asn His Val Val Leu Thr
            485                 490                 495
Arg Asn Lys Glu Val Tyr Ser Trp Gly Cys Gly Glu Tyr Gly Arg Leu
            500                 505                 510
Gly Leu Asp Ser Glu Glu Asp Tyr Tyr Thr Pro Gln Lys Val Asp Val
            515                 520                 525
Pro Lys Ala Leu Ile Ile Val Ala Val Gln Cys Gly Cys Asp Gly Thr
            530                 535                 540
Phe Leu Leu Thr Gln Ser Gly Lys Val Leu Ala Cys Gly Leu Asn Glu
545                 550                 555                 560
Phe Asn Lys Leu Gly Leu Asn Gln Cys Met Ser Gly Ile Ile Asn His
            565                 570                 575
Glu Ala Tyr His Glu Val Pro Tyr Thr Thr Ser Phe Thr Leu Ala Lys
```

```
                580             585             590
Gln Leu Ser Phe Tyr Lys Ile Arg Thr Ile Ala Pro Gly Lys Thr His
            595                 600             605
Thr Ala Ala Ile Asp Glu Arg Gly Arg Leu Leu Thr Phe Gly Cys Asn
            610                 615                 620
Lys Cys Gly Gln Leu Gly Val Gly Asn Tyr Lys Lys Arg Leu Gly Ile
625                 630                 635                 640
Asn Leu Leu Gly Gly Pro Leu Gly Gly Lys Gln Val Ile Arg Val Ser
                645                 650                 655
Cys Gly Asp Glu Phe Thr Ile Ala Ala Thr Asp Asp Asn His Ile Phe
                660                 665                 670
Ala Trp Gly Asn Gly Gly Asn Gly Arg Leu Ala Met Thr Pro Thr Glu
                675                 680                 685
Arg Pro His Gly Ser Asp Ile Cys Thr Ser Trp Pro Arg Pro Ile Phe
            690                 695                 700
Gly Ser Leu His His Val Pro Asp Leu Ser Cys Arg Gly Trp His Thr
705                 710                 715                 720
Ile Leu Ile Val Glu Lys Val Leu Asn Ser Lys Thr Ile Arg Ser Asn
                725                 730                 735
Ser Ser Gly Leu Ser Ile Gly Thr Val Phe Gln Ser Ser Pro Gly
                740                 745             750
Gly Gly Gly Gly Gly Gly Gly Glu Glu Glu Asp Ser Gln Gln Glu
            755                 760                 765
Ser Glu Thr Pro Asp Pro Ser Gly Gly Phe Arg Gly Thr Met Glu Ala
            770                 775                 780
Asp Arg Gly Met Glu Gly Leu Ile Ser Pro Thr Glu Ala Met Gly Asn
785                 790                 795                 800
Ser Asn Gly Ala Ser Ser Cys Pro Gly Trp Leu Arg Lys Glu Leu
                805                 810                 815
Glu Asn Ala Glu Phe Ile Pro Met Pro Asp Ser Pro Ser Pro Leu Ser
                820                 825                 830
Ala Ala Phe Ser Glu Ser Glu Lys Asp Thr Leu Pro Tyr Glu Glu Leu
                835                 840                 845
Gln Gly Leu Lys Val Ala Ser Glu Ala Pro Leu Glu His Lys Pro Gln
            850                 855                 860
Val Glu Ala Ser Ser Pro Arg Leu Asn Pro Ala Val Thr Cys Ala Gly
865                 870                 875                 880
Lys Gly Thr Pro Leu Thr Pro Pro Ala Cys Ala Cys Ser Ser Leu Gln
                885                 890                 895
Val Glu Val Glu Arg Leu Gln Gly Leu Val Leu Lys Cys Leu Ala Glu
                900                 905                 910
Gln Gln Lys Leu Gln Gln Glu Asn Leu Gln Ile Phe Thr Gln Leu Gln
            915                 920                 925
Lys Leu Asn Lys Lys Leu Glu Gly Gly Gln Gln Val Gly Met His Ser
            930                 935                 940
Lys Gly Thr Gln Thr Ala Lys Glu Glu Met Glu Met Asp Pro Lys Pro
945                 950                 955                 960
Asp Leu Asp Ser Asp Ser Trp Cys Leu Leu Gly Thr Asp Ser Cys Arg
                965                 970                 975
Pro Ser Leu

<210> SEQ ID NO 2
<211> LENGTH: 22
```

```
<212> TYPE: PRT
<213> ORGANISM: Artificial Sequence
<220> FEATURE:
<223> OTHER INFORMATION: Artificial sequence for kinase-inhibiting
      peptide

<400> SEQUENCE: 2

His Arg Arg Ile Lys Ala Trp Leu Lys Lys Ile Leu Ala Leu Ala Arg
1               5                   10                  15

Gln Leu Gly Val Ala Ala
            20

<210> SEQ ID NO 3
<211> LENGTH: 23
<212> TYPE: PRT
<213> ORGANISM: Artificial Sequence
<220> FEATURE:
<223> OTHER INFORMATION: Artificial sequence kinase-inhibiting peptide

<400> SEQUENCE: 3

Trp Leu Arg Arg Ile Lys Ala Trp Leu Arg Arg Ile Lys Ala Leu Ala
1               5                   10                  15

Arg Gln Leu Gly Val Ala Ala
            20

<210> SEQ ID NO 4
<211> LENGTH: 20
<212> TYPE: PRT
<213> ORGANISM: Artificial Sequence
<220> FEATURE:
<223> OTHER INFORMATION: Artificial sequence kinase-inhibiting peptide

<400> SEQUENCE: 4

Trp Leu Arg Arg Ile Lys Ala Trp Leu Arg Arg Ala Leu Ala Arg Gln
1               5                   10                  15

Leu Gly Val Ala
            20

<210> SEQ ID NO 5
<211> LENGTH: 38
<212> TYPE: PRT
<213> ORGANISM: Artificial Sequence
<220> FEATURE:
<223> OTHER INFORMATION: Artificial sequence Nek9-inhibiting peptide

<400> SEQUENCE: 5

Ser Gly Arg Pro Pro Met Ile Val Trp Phe Asn Arg Pro Phe Leu Ile
1               5                   10                  15

Ala Val Ser His Thr His Gly Gln Thr Ile Leu Phe Met Ala Lys Val
            20                  25                  30

Ile Asn Pro Val Gly Ala
            35
```